United States Patent
Wan et al.

(10) Patent No.: US 8,871,928 B2
(45) Date of Patent: Oct. 28, 2014

(54) TRICYCLIC COMPOUNDS, PREPARATION METHODS, AND THEIR USES

(75) Inventors: Zehong Wan, Shanghai (CN); Xiaomin Zhang, Shanghai (CN); Zhaolong Tong, Shanghai (CN); Kai Long, Shanghai (CN); Sarah E. Dowdell, Media, PA (US); Eric Steven Manas, Lafayette Hill, PA (US); Krista Beaver Goodman, Wayne, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/825,034

(22) PCT Filed: Sep. 20, 2011

(86) PCT No.: PCT/CN2011/001597
§ 371 (c)(1),
(2), (4) Date: Mar. 19, 2013

(87) PCT Pub. No.: WO2012/037782
PCT Pub. Date: Mar. 29, 2012

(65) Prior Publication Data
US 2013/0178488 A1    Jul. 11, 2013

(30) Foreign Application Priority Data
Sep. 20, 2010 (WO) ............... PCT/CN2010/077154

(51) Int. Cl.
*C07D 471/00* (2006.01)
*C07D 487/00* (2006.01)
*C07D 471/04* (2006.01)

(52) U.S. Cl.
CPC .................................. *C07D 471/04* (2013.01)
USPC ......................................................... 544/252

(58) Field of Classification Search
None
See application file for complete search history.

(56) References Cited

FOREIGN PATENT DOCUMENTS

| JP | 2011088847 | 5/2011 |
| WO | WO9845293 | 10/1998 |
| WO | WO2005007092 | 1/2005 |
| WO | WO2005007092 A1 * | 1/2005 |
| WO | WO 2005007092 A2 * | 1/2005 |

* cited by examiner

*Primary Examiner* — Dennis Heyer
*Assistant Examiner* — Daniel M Podgorski
(74) *Attorney, Agent, or Firm* — Fang Qian

(57) ABSTRACT

The present invention relates to novel compounds that inhibit Lp-PLA$_2$ activity, processes for their preparation, to compositions containing them and to their use in the treatment of diseases associated with the activity of Lp-PLA$_2$, for example atherosclerosis, Alzheimer's disease, and/or diabetic macular edema.

15 Claims, No Drawings

TRICYCLIC COMPOUNDS, PREPARATION METHODS, AND THEIR USES

This application is a 371 of International Application No. PCT/CN2011/001597, filed 20 Sep. 2011, which claims the benefit of Application No. PCT/CN2010/077154, filed 20 Sep. 2010.

FIELD OF THE INVENTION

The present invention relates to novel tricyclic compounds, processes for their preparation, intermediates useful in their preparation, pharmaceutical compositions containing them, and their use in therapy for the treatment of diseases or conditions mediated by Lp-PLA$_2$.

BACKGROUND OF THE INVENTION

Lipoprotein-associated phospholipase A$_2$ (Lp-PLA$_2$) is, previously known as platelet-activating factor acetylhydrolase (PAF-AH), a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules during the oxidation of LDL. (See Zalewski A, et al., *Arterioscler. Thromb. Vasc. Biol.*, 25, 5, 923-31 (2005)). Lp-PLA$_2$ hydrolyzes the sn-2 ester of the oxidized phosphatidylcholines to give lipid mediators, lyso-phosphatidylcholine (lysoPC) and oxidized nonesterified fatty acids (NEFAs). It has been observed that lysoPC and NEFAs elicit inflammatory responses. (See Zalewski A, et al. (2005)).

Research data has indicated that LysoPC promotes atherosclerotic plaque development, which can ultimately lead to the formation of a necrotic core. (See Wilensky et al., *Current Opinion in Lipidology*, 20, 415-420 (2009)). Further, the effect of Lp-PLA$_2$ inhibitors on atherosclerotic plaque composition was demonstrated in a diabetic and hypercholesterolemic porcine model of accelerated coronary atherosclerosis. (See Wilensky et al., *Nature Medicine*, 10, 1015-1016 (2008)). Therefore, it has also been postulated that Lp-PLA$_2$ inhibitors may be used to treat atherosclerosis.

Additionally, studies have shown that the level of Lp-PLA$_2$ is an independent risk factor in coronary artery disease. (See Packard et al, *N. Engl. J. Med.*, 343, 1148-1155 (2000)). Thus, it was believed that Lp-PLA$_2$ inhibitor can be beneficial to treat disease that exhibit vascular dysfunction, for example, diabetes, hypertension, angina pectoris and/or after ischaemia and reperfusion.

It has been reported that high Lp-PLA$_2$ activity is associated with high risk of dementia, including Alzheimer's disease (AD) (See Van Oijen, et al. *Annals of Neurology*, 59,139 (2006)). Higher level of oxidized LDL has also been observed in AD patients (See Kassner et al. *Current Alzheimer Research*, 5, 358-366 (2008); Dildar, et al., *Alzheimer Dis Assoc Disord*, 24, April-June (2010); Sinem, et al. *Current Alzheimer Research*, 7, 463-469 (2010)). Further, research data has shown that neuroinflammation are present in AD patients and multiple cytotoxic inflammatory cytokines are up-regulated in AD patients. (See Colangelo, et al., *Journal of Neuroscience Research*, 70, 462-473 (2002); Wyss-Coray, *Nature Medicine*, 12, September (2006)). Research has shown that LysoPC function as a pro-inflammatory factor inducing multiple cytotoxic inflammatory cytokine release (See Shi, et al. *Atherosclerosis*, 191, 54-62 (2007)). Therefore, it has been believed that the inhibitors of Lp-PLA$_2$ can be used to treat AD by inhibiting activity of Lp-PLA$_2$ and reducing lysoPC production.

In addition, the treatment of an Lp-PLA$_2$ inhibitor on a diabetic and hypercholesterolemia swine model demonstrated that the blood-brain-barrier leakage and the brain amyloid beta protein (Aβ) burden, the pathological hallmarks of Alzheimer's disease, were reduced. (See U.S. Patent Application Publication No. 2008/0279846). This observation suggested that Lp-PLA$_2$ inhibitors have a therapeutic effects on Alzheimer's disease. The restoration of blood-brain-barrier leakage also suggests that Lp-PLA$_2$ inhibitors will be beneficial to vascular dementia treatment.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See Perry, *Acta Neuropathol*, 120, 277-286 (2010)). As discussed above, Lp-PLA$_2$ inhibitors can reduce inflammation, for example, reducing multiple cytokine release by suppressing lysoPC production. (See Shi, et al. *Atherosclerosis* 191, 54-62 (2007)). Thus, it has been believed that Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (Wilensky et al, 2009). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-LA$_2$ and the association between localized inflammatory processes and diabetic retinopathy, it is postulated that Lp-PLA$_2$ can be used to treat diabetic eye disease.

Glaucoma and age-related macular degeneration (AMD) are retina neurodegenerative diseases. Studies suggested that inflammation, including TNF-alpha signaling, may play an important role in the pathogenesis of glaucoma and AMD (See Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention provides compounds of Formula (I) or pharmaceutically acceptable salts thereof:

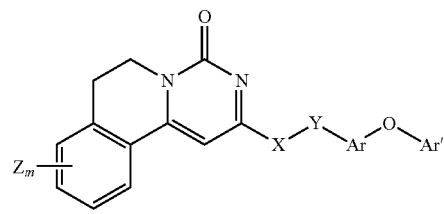

wherein:
Z is selected from the group consisting of C$_1$-C$_3$alkyl, —O—(C$_1$-C$_3$alkyl) and halo;
m is 0, 1, 2 or 3;

X is O, S, NH or —N—($C_1$-$C_3$alkyl);

Y is —$(CH_2)_n$—, wherein n is 0, 1, 2, or 3;

Ar is phenyl or heteroaryl, either of which is optionally substituted with one or more substituents selected from the group consisting of CN, halo, $C_1$-$C_3$alkyl, $C_{1-3}$alkoxy and $C_1$-$C_3$haloalkyl; and Ar' is phenyl or heteroaryl, either of which is optionally substituted with one or more substituents selected from the group consisting of CN, halo, $C_1$-$C_3$alkyl, $C_{1-3}$alkoxy and $C_1$-$C_3$haloalkyl.

This invention also provides pharmaceutical compositions comprising a compound of present invention and pharmaceutically acceptable carriers.

The invention also provides methods of treating a disease associated with the activity of Lp-$PLA_2$, which comprises treating a subject in need thereof with a therapeutically effective amount of an inhibitor of Lp-$PLA_2$. The disease may be associated with the increased involvement of monocytes, macrophages or lymphocytes; with the formation of lysophosphatidylcholine and oxidized free fatty acids; with lipid oxidation in conjunction with Lp-$PLA_2$ activity; or with endothelial dysfunction.

This invention also provides methods of treating a disease by inhibiting Lp-$PLA_2$ activity. Exemplary disease includes, but is not limited to, neurodegeneration disease (e.g., Alzheimer's disease, vascular dementia), atherosclerosis, stroke, metabolic bone disorder (e.g., bone marrow abnormalities), dyslipidemia, Paget's diseases, type II diseases, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD) and multiple sclerosis. The methods comprise administering a safe and effective amount of a compound of this invention to a subject in need thereof. It is not intended that the present invention to be limited to any particular stage of the disease (e.g. early or advanced).

This invention also provides methods of treating Alzheimer's disease. The methods comprise administering to a subject in need thereof a safe and effective amount of a compound of this invention.

This invention also provides methods of decreasing beta amyloid (also referred to as "Aβ") accumulation in the brain of a subject. The methods comprise administering to a subject in need thereof a pharmaceutical composition comprising a safe and effective amount of a compound of the present invention. In certain embodiment, the beta amyloid is Abeta-42.

This invention also provides methods for treating eye diseases and disorders by administering a compound of this invention. In certain embodiment, this invention provides methods of treating macular edema, which comprises administering to the subject a safe and effective amount of a compound of this invention. In certain embodiment, the macular edema is associated with diabetic eye disease, for example, diabetic retinopathy. In one embodiment, the macular edema is associated with posterior uveitis.

This invention also provides the use of a compound of this invention for manufacturing a medicament for treating diseases described herein.

This invention also provides a compound described herein for use in carrying out methods of treatment described herein.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. Definitions

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

The term "neurodegeneration disease" as used herein refers to a varied assortment of central nervous system disorders characterized by gradual and progressive loss of neural tissue and/or neural tissue function. A neurodegeneration disease is a class of neurological disorder or disease where the neurological disease is characterized by a gradual and progressive loss of neural tissue, and/or altered neurological function, typically reduced neurological function as a result of a gradual and progressive loss of neural tissue. In one embodiment, the neurodegeneration diseases described herein are neurodegeneration diseases or disorders where there is an abnormal blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

The term "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyrus), vascular dementia due to hemorrhagic lesions, small vessel disease (including, e.g. vascular dementia due to lacunar lesions and Binswanger disease), and mixed Alzheimer's Disease with vascular dementia.

The phrase "blood-brain barrier" or "BBB" are used interchangeably herein, and are used to refer to the permeability barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

The phrase "metabolic bone disease" as used herein refers to a varied assortment of bone diseases and disorders characterized by gradual and progressive loss of bone tissue. Metabolic bone diseases described herein are metabolic bone diseases whereby there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteoid synthesis.

The term "osteoporosis" refers to conditions which mineral and/or bone matrix are decreased and/or bone mass is reduced.

"Alkyl" refers to a monovalent, saturated hydrocarbon chain having a specified number of carbon atoms. For example, $C_1$-$C_6$ alkyl refers to an alkyl group having from 1 to 6 carbon atoms. In still other embodiments, alkyl groups contain 1 to 2, 3, 4, or 5 carbon atoms. Alkyl groups may be optionally substituted with one or more substituent as defined herein. Alkyl groups may be straight or branched. In one embodiment, branched alkyl groups may have one, two, or three branches. Exemplary alkyl includes, but is not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

"Alkoxy" refers to the group —O-alkyl. In one embodiment, alkoxyl groups contain 1 to 2, 3, 4, or 5 carbon atoms. Exemplary alkoxy groups include, but are not limited to, methoxy, ethoxy and propoxy.

"Halogen" refers to fluorine (F), chlorine (Cl), bromine (Br), or iodine (I). "Halo" refers to the halogen radicals: fluoro (—F), chloro (—Cl), bromo (—Br), and iodo (—I).

"Haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms. Exemplary haloalkyl groups include, but are not limited to, chloromethyl, bromoethyl, trifluoromethyl, dichloromethyl.

"Heteroaryl" refers to a monocyclic aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems having 5, 6 or 7 member atoms. In some embodiments, heteroaryl groups are monocyclic ring system having 6 member atoms. In other embodiments, heteroaryl group have one or two nitrogen atom as member atoms. Examples of heteroaryl include, but are not limited to, pyrrolyl, pyrazolyl, pyridinyl and pyrimidinyl.

"Optionally substituted" indicates that a group, such as alkyl, alkenyl, alkynyl, aryl (for example phenyl), cycloalkyl, cycloalkenyl, heterocycloalkyl, or heteroaryl, may be unsubstituted, or the group may be substituted with one or more substituent as defined.

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, halo, hydroxyl, amino, amide, —SH, cyano, nitro, thioalkyl, carboxylic acid, —NH—C(=NH)—NH$_2$, alkyl, alkenyl, alkynyl, alkoxyl, aryl, heteroaryl, cycloalkyl, heterocycloalkyl, in which alkyl, alkenyl, alkynyl, alkoxyl, aryl, heteroaryl, cycloalkyl, thioalkyl and heterocycloalkyl may be further substituted. Suitable substituents are defined herein for each substituted or optionally substituted group.

As used herein, "treat", "treating" or "treatment" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, and/or (4) to slow the progression of the condition or one or more of the biological manifestations of the condition.

As used herein, "subject" means a mammalian subject (e.g., dog, cat, horse, cow, sheep, goat, monkey, etc.), and particularly human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, compounds of Formula I and pharmaceutically acceptable salts thereof:

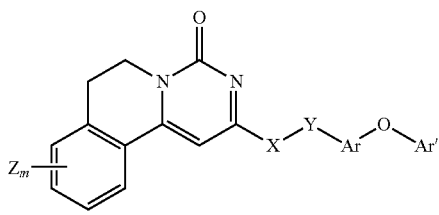

wherein:
- Z is selected from the group consisting of $C_1$-$C_3$alkyl, —O—($C_1$-$C_3$alkyl) and halo;
- m is 0, 1, 2 or 3;
- X is O, S, NH or —N—($C_1$-$C_3$alkyl),
- Y is —$(CH_2)_n$—, wherein n is 0, 1, 2 or 3;
- Ar is phenyl or heteroaryl, either of which is optionally substituted with one or more substituents selected from the group consisting of CN, halo, $C_1$-$C_3$alkyl, $C_{1-3}$alkoxy and $C_1$-$C_3$haloalkyl; and
- Ar' is phenyl or heteroaryl, either of which is optionally substituted with one or more substituents selected from the group consisting of CN, halo, $C_1$-$C_3$alkyl, $C_{1-3}$alkoxy and $C_1$-$C_3$haloalkyl.

In one embodiment, this invention provides compounds of Formula (I), wherein Z is —$OCH_3$, or pharmaceutically acceptable salts thereof. In certain embodiment, this invention provides compounds of Formula (I), wherein Z is F or Cl, or pharmaceutically acceptable salts thereof. In one embodiment, this invention provides compounds of Formula (I), wherein Z is —$CH_3$, or pharmaceutically acceptable salts thereof.

In one embodiment, this invention also relates to compounds of any of the above embodiments, wherein m is 0 or 1 or pharmaceutically acceptable salts thereof. Further, in certain embodiment, this invention provides compounds of any of the above embodiments, wherein X is —O—, or pharmaceutically acceptable salts thereof. In one embodiment, this invention provides compounds of any of the above embodiments, wherein X is NH or $NCH_3$, or pharmaceutically acceptable salts thereof. In certain embodiment, this invention provides compounds of any of the above embodiments, wherein Y is —$CH_2$— or —$CH_2$—$CH_2$—, or pharmaceutically acceptable salts thereof.

Further, in one embodiment, this invention provides compounds of any of the above embodiments, wherein Ar is phenyl, which is optionally substituted with one or more substituents selected from the groups consisting of CN, $CF_3$ and halo, or pharmaceutically acceptable salts thereof. In certain embodiment, this invention provides compounds of any of the above embodiments, wherein Ar is phenyl, which is optionally substituted with one or more substituents selected from the groups consisting of CN, $CF_3$ and F, or pharmaceutically acceptable salts thereof.

In one embodiment, this invention provides compounds of any of the above embodiments, wherein Ar is pyridinyl which is optionally substituted with one or more substituents selected from the groups consisting of CN and halo, or pharmaceutically acceptable salts thereof. In certain embodiments, this invention provides compounds of any of the above embodiments, wherein Ar' is phenyl, pyridinyl or pyrimidinyl, which is optionally substituted with one or more substituents selected from the group consisting of $CH_3$, halo and $CF_3$, or pharmaceutically acceptable salts thereof.

This invention also provides compounds of Formula (IA) and pharmaceutically acceptable salts thereof:

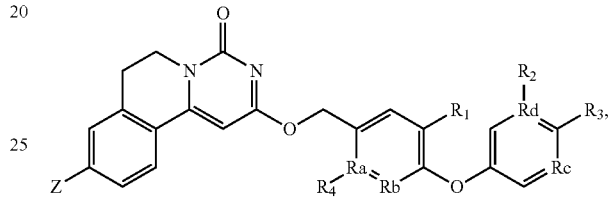

Formula (IA)

wherein,
- Z is $OCH_3$, Me or F;
- each occurrence of $R_a$ and $R_d$ is independently C or N;
- each occurrence of $R_b$ and $R_c$ is independently CH or N;
- each occurrence of $R_1$, $R_2$, $R_3$ and $R_4$ is independently selected from the groups consisting of H, CN, $CF_3$ and halo; and
- when $R_a$ is N, $R_4$ is absent, when $R_d$ is N, $R_2$ is absent.

In one embodiment, this invention provides compounds of Formula (IA), wherein Z is —$OCH_3$. In other embodiment, this invention provides compounds of any of the above embodiments related to Formula (IA), wherein $R_a$ and $R_d$ are C and $R_b$ and $R_c$ are CH. In one embodiment, this invention provides compounds of any of the above embodiments related to Formula (IA), wherein at least one of $R_1$ and $R_4$ is CN or F. In other embodiment, this invention provides compounds of any of the above embodiments related to Formula (IA), wherein at least one of $R_2$ and $R_3$ is $CF_3$ or CN.

A further aspect of the invention provides compounds of formula (II) and pharmaceutically acceptable salts thereof:

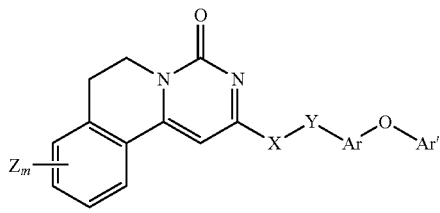

or a salt thereof wherein:
- Z is $C_1$-$C_6$alkyl, —$OR^1$, halo, or —$NR^5R^6$;
- m is 0-4;
- X is O and Y is absent; or
- X is O, S, NH or —$NR^5$ and Y is $CH_2$ or —$CH_2CH_2$—; or
- X is $CH_2$ and Y is O, S, NH or —$NR^S$;

Ar is phenyl or heteroaryl, either of which is unsubstituted or substituted by one or more of CN, halo, $C_1$-$C_6$alkyl, $C_1$-$C_6$alkoxy, or halo-substituted$C_1$-$C_6$alkyl;

Ar' is phenyl or heteroaryl, either of which is unsubstituted or substituted by one or more of CN, halo, $C_1$-$C_6$alkyl, $C_1$-$C_6$alkoxy, or halo-substituted$C_{1-6}$alkyl;

$R^1$ is H, $C_1$-$C_6$alkyl, or $R^{10}$(O)C wherein;

any carbon of an $R^{10}$ or $C_1$-$C_6$alkyl group is unsubstituted or substituted by 1, 2 or 3 groups selected from the group consisting of, halo, $-OR^{10}$, $-NR^5R^6$, oxo, cyano, $-C(O)R^{10}$, $-C(O)OR^{10}$, $-CONR^5R^6$, $-N(R^5)C(O)R^{10}$, $-N(R^5)C(O)OR^{10}$, $-OC(O)NR^5R^6$, $-N(R^5)C(O)NR^5R^6$—$N(R)SO_2R^{10}$, $C_2$-$C_{10}$alkenyl, $C_2$-$C_{10}$alkynyl, $C_3$-$C_6$cycloalkyl, $C_3$-$C_6$heterocycloalkyl, aryl, $C_1$-$C_6$alkyl-aryl, heteroaryl and $C_1$-$C_6$alkyl-heteroaryl;

$R^5$ and $R^6$ is each independently selected from the group consisting of hydrogen, $C_1$-$C_{10}$alkyl, $C_3$-$C_8$cycloalkyl, $C_3$-$C_8$cycloalkyl-$C_1$-$C_{10}$alkyl, $C_3$-$C_8$heterocycloalkyl, $C_3$-$C_8$heterocycloalkyl-$C_1$-$C_{10}$alkyl, aryl, aryl-$C_1$-$C_{10}$alkyl, heteroaryl, heteroaryl-$C_1$-$C_{10}$alkyl, $-C(O)C_1$-$C_4$alkyl, $-C(O)C_3$-$C_6$cycloalkyl, $-C(O)C_3$-$C_6$heterocycloalkyl, $-C(O)$aryl, $-C(O)$heteroaryl; and $R^{10}$ is selected from the group consisting of hydrogen, $C_1$-$C_{10}$alkyl, $C_2$-$C_{10}$alkenyl, $C_2$-$C_{10}$alkynyl, $-C(O)C_1$-$C_4$alkyl, $-C(O)$aryl, $-C(O)$heteroaryl, $-C(O)C_3$-$C_6$cycloalkyl, $-C(O)C_3$-$C_6$heterocycloalkyl, $C_3$-$C_8$cycloalkyl, $C_3$-$C_8$heterocycloalkyl, $C_6$-$C_{14}$aryl, aryl-$C_1$-$C_{10}$alkyl, heteroaryl and heteroaryl-$C_1$-$C_{10}$alkyl.

The compounds of Formula (I), Formula (IA), Formula (II) or pharmaceutically acceptable salts thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I), Formula (IA), Formula (II) or pharmaceutically acceptable salts thereof as mixtures with isomers thereof in which one or more chiral centers are inverted. Likewise, it is understood that the compounds of Formula (I), Formula (IA), Formula (II) or pharmaceutically acceptable salts thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I), Formula (IA), Formula (II) or pharmaceutically acceptable salts thereof, as well as any wholly or partially equilibrated mixtures thereof. The present invention also includes the individual isomers of the compounds of Formula (I), Formula (IA), Formula (II) or pharmaceutically acceptable salts thereof as well as mixtures with isomers thereof in which one or more chiral centers are inverted. It is to be understood that the present invention includes all combinations and subsets of the particular groups defined hereinabove.

Certain compounds described herein may contain one or more chiral atoms, or may otherwise be capable of existing as enantiomers. The compounds of the present invention include mixtures of enantiomers as well as purified enantiomers or enantiomerically enriched mixtures. Also included within the scope of the invention are the individual isomers of the compounds of the present invention as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the compounds described herein are included within the scope of the compounds of the present invention. The different isomeric forms may be separated or resolved one from the other by conventional methods, or any given isomer may be obtained by conventional synthetic methods or by stereospecific or asymmetric syntheses.

The invention also includes various deuterated forms of compounds of Formula (I), Formula (IA), Formula (II) or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), Formula (IA), Formula (II) or pharmaceutically acceptable salts thereof. Commercially available deuterated starting materials may be employed in the preparation of deuterated forms of compounds of Formula (I), Formula (IA), Formula (II) or pharmaceutically acceptable salts thereof, or they may be synthesized using conventional techniques employing deuterated reagents (e.g. lithium aluminum deuteride).

In addition to the free base form of the compounds described herein, the salt form of the compounds is also within the scope of the present invention. The pharmaceutically-acceptable salts may be prepared in situ during the final isolation and purification of the compound, or by separately reacting the purified compound in its free acid or free base form with a suitable base or acid, respectively.

In one embodiment, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

C. Synthesis of Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

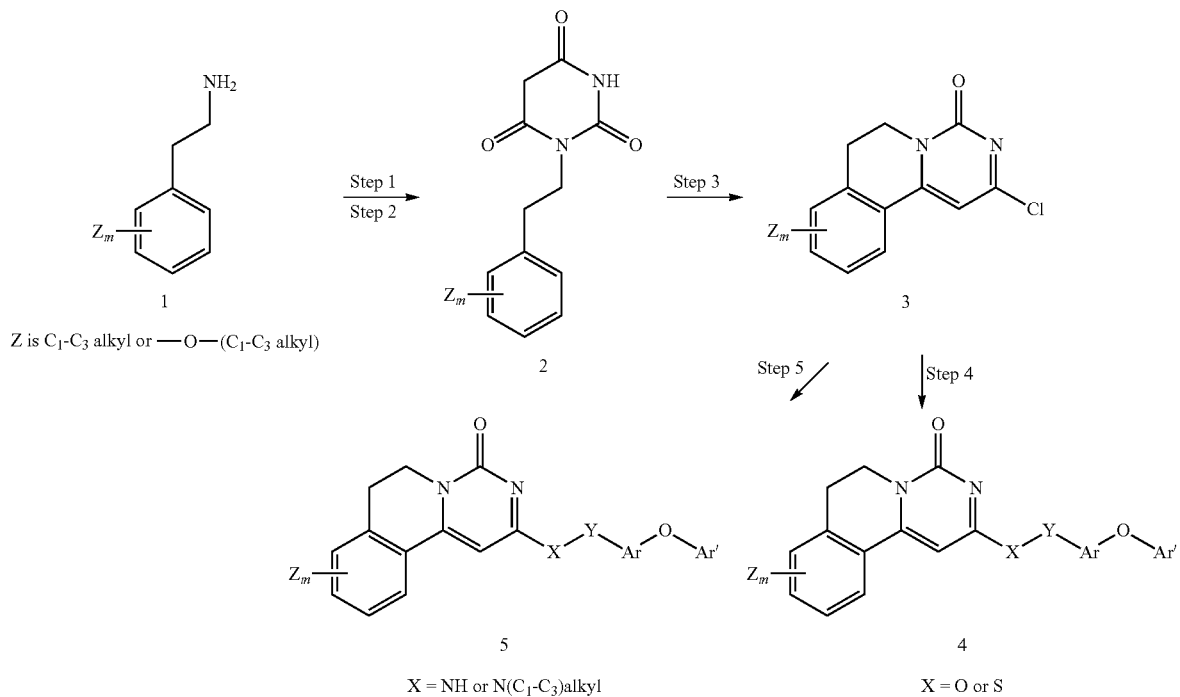

General Experimental Scheme 1 provides an exemplary synthesis for preparing compounds 4 and 5. In the general experimental scheme 1, m, Y, Ar, Ar' are defined as in Formula (I). Step (1) is carried out by reacting compound 1 with appropriate reagents such as KOCN and HCl solution under a suitable temperature such as the reflux temperature of the solvent system to provide 1-(3-methoxyphenethyl)urea intermediates. Step (2) is a cyclization reaction using appropriate reagents such as $CH_2(CO_2Et)_2$ and NaOEt in a suitable solvent or a mixture of solvents such as EtOH at a suitable temperature such as the reflux temperature of the solvent system to afford compound 2. Step (3) is carried out by reacting compound 2 with suitable reagents such as $POCl_3$ at an appropriate temperature such as 120° C. to provide compound 3. Step (4) is carried out by reacting compound 3 with suitable reagents such as Ar'—O—Ar—Y—XH in the presence of a suitable base such as sodium hydride in a suitable solvent or a mixture of solvents such as tetrahydrofuran (THF) at suitable temperature such as room temperature to provide final compound 4. Step (5) is carried out by reacting compound 3 with suitable reagents such as Ar'—O—Ar—Y—XH, in the presence of a suitable base such as $K_2CO_3$ in a suitable solvent or a mixture of solvents such as dimethylformamide (DMF) under a suitable temperature such as 50° C. to provide final compound 5.

General Experimental Scheme 2

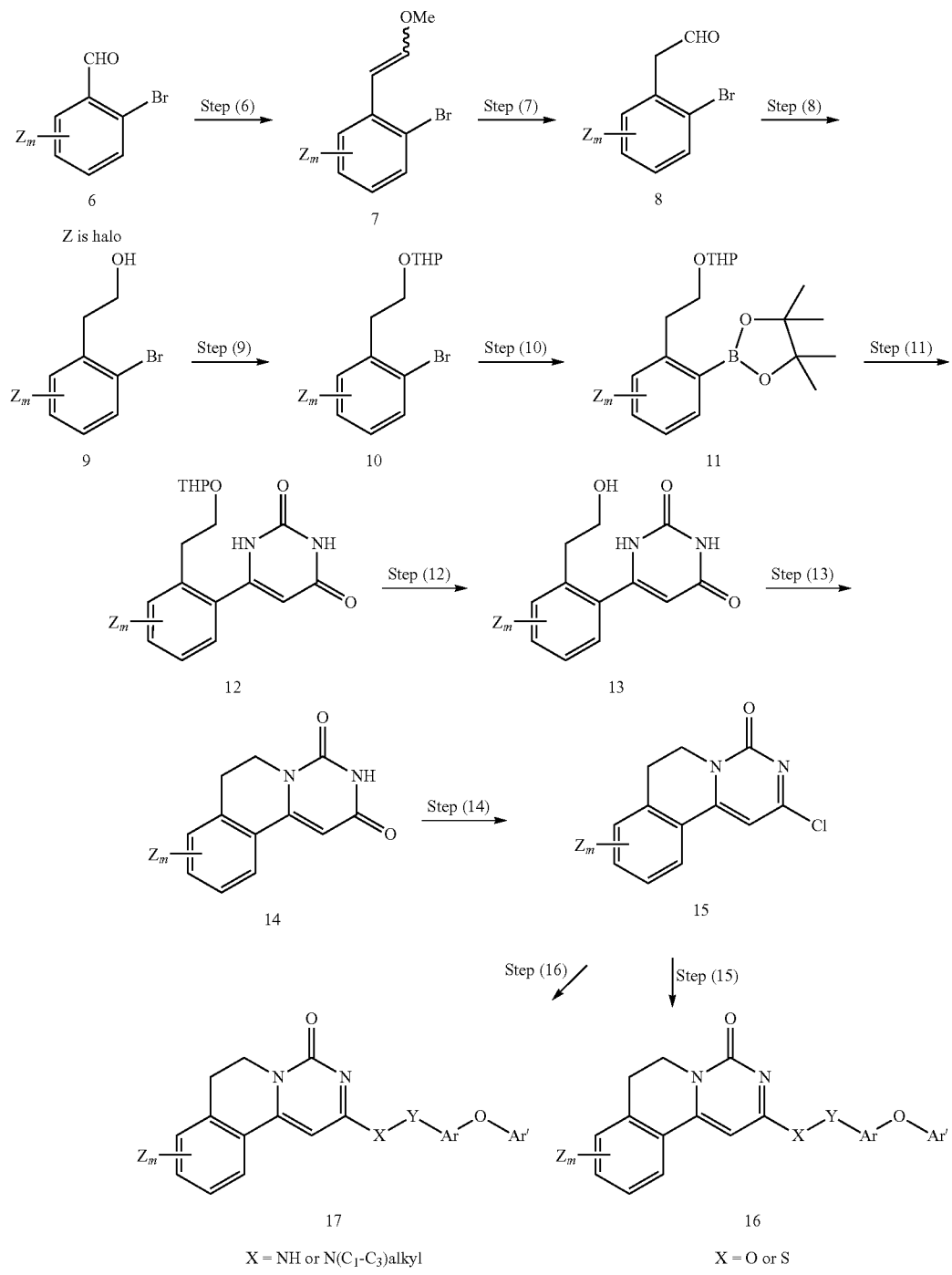

General Experimental Scheme 2 provides an exemplary synthesis for preparing compounds 16 and 17. In the General Experimental Scheme 2, m, Y, Ar and Ar' are as defined in Formula (I). Step (6) is a Wittig reaction by reacting compound 6 with a suitable Wittig reagent such as $Ph_3PCH_2OMe$, in the presence of a suitable base such as $KO^tBu$ in a suitable solvent or a mixture of solvents such as tetrahydrofuran (THF) under a suitable temperature such as room temperature to provide compound 7. Step (7) is carried out by using suitable reagents such as HCl solution in a suitable solvent or a mixture of solvents such as THF at a suitable temperature such as room temperature to provide compound 8. Step (8) is carried out by reacting compound 8 with suitable reagents such as $NaBH_4$ under an appropriate temperature such as 0° C. to provide compound 9. Step (9) is carried out by reacting compound 9 with appropriate reagents such as 3,4-dihydro-2H-pyran and p-toluenesulfonic acid (TsOH) in a suitable solvent or a mixture of solvents such as $CHCl_3$ under a suitable temperature such as room temperature to provide compound 10. Step (10) is carried out by reacting compound 10 with an appropriate catalyst such as Pd(dppf)Cl$_2$ in the presence of a suitable base such as KOAc in a suitable solvent or a mixture of solvents such as a solvent system of 1,4-dioxane and water under a suitable temperature such as 100° C. to give the compound 11. Step (11) is carried out by reacting compound 10 with an appropriate catalyst such as Pd(dppf)Cl$_2$ and in the presence of a suitable base such as KOAc in a suitable solvent or a mixture of solvents such as 1,4-dioxane and water under a suitable temperature such as 100° C. to give the compound 12. Step (12) is carried out by reacting compound 12 in the presence of suitable reagents such as TsOH in a suitable solvent or a mixture of solvents such as methanol at a suitable temperature such as room temperature to provide compound 13. Step (13) is carried out by reacting compound 13 with suitable reagents such as methanesulfonyl chloride and triethyl amine at a suitable temperature such as room temperature to give compound 14. Step (14) is carried out by reacting compound 14 with a suitable reagents such as phosphoryl trichloride at a suitable temperature such as 100° C. to provide compound 15. Step (15) is carried out by reacting compound 15 with suitable reagents such as Ar'—O—Ar—Y—XH in the presence of a suitable base such as sodium hydride in a suitable solvent or a mixture of solvents such as THF at a suitable temperature such as room temperature to provide compound 16. Step (16) is carried out by reacting compound 15 with a suitable reagents such as Ar'—O—Ar—Y—XH, in the presence of suitable base such as K$_2$CO$_3$ in a suitable solvent or a mixture of solvents such as dimethylformamide (DMF) under 50° C. to provide compound 17.

General Experimental Procedures

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or recrystallisation using suitable solvents. Chromatographic methods known to the skilled person include column chromatography, flash chromatography, HPLC (high performance liquid chromatography), and MDAP (mass directed autopreparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5u C18 (2) 100 A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a prepacked SiO$_2$ column, a detector with UV wavelength at 254 nm and mixed solvents.

The terms "CombiFlash", "Biotage®", "Biotage® 75" and "Biotage® SP4" when used herein refer to commercially available automated purification systems using pre-packed silica gel cartridges.

Final compounds were characterized with LCMS (conditions listed below) or NMR. $^1$H-NMR spectra were recorded using a Bruker Avance 400 MHz spectrometer. CDCl$_3$ is deuteriochloroform, DMSO-d$_6$ is hexadeuteriodimethylsulfoxide, and CD$_3$OD (or MeOD) is tetradeuteriomethanol. Chemical shifts are reported in parts per million (δ) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on instruments, using electrospray (ES) ionization techniques. All temperatures are reported in degrees Celsius. All other abbreviations are as described in the ACS Style Guide (American Chemical Society, Washington, D.C., 1986).

LCMS Conditions:
1) Acidic conditions:
Mobile phase: water containing 0.05% TFA/0.05% acetonitrile
Column: Agilent SB-C18 4.6×30 mm-1.8 microns
Detection: MS and photodiode array detector (PDA)
2) Basic conditions:
Mobile phase: water containing 10 mmol NH$_4$HCO$_3$/acetonitrile
Column: XBridge™ C18 4.6×50 mm-3.5 microns
Detection: MS and photodiode array detector (PDA)
MDAP Conditions:
1) Acidic conditions:
Instrument: Waters instrument
Column: Sunfire Prep C18 column (5 um, 19×50 mm)
Mobile phase: water containing 0.05% TFA/acetonitrile.
2) Basic conditions:
Instrumnet: Waters instrument
Column: Xbridge Prep C18 column (5 um, 19×50 mm)
Mobile phase: water containing 0.04% ammonia/acetonitrile.

Abbreviations and Resource Sources

The following abbreviations and resources are used herein below:
ISCO system—Teledyne ISCO (http://www.isco.com/html/seFlashChromatography.html)
r.t/rt/RT—Room Temperature
ACN—Acetonitrile
9-BBN—9-Borabicyclo[3.3.1]nonane
DAST—Diethylaminosulfur trifluoride
DCM—Dichloromethane
DIBAL-H—Diisobutylaluminium hydride.
DMA—N,N-Dimethylacetamide
DME—1,2-Dimethoxyethane
DMF—Dimethylformamide
DMSO—dimethyl sulfoxide
DMAP—4-Dimethylaminopyridine
EA—Ethyl acetate
EtOH—Ethanol
FC—Flash chromatography
MDAP—Mass-Directed Autopreparation
MsCl—Methanesulfonyl chloride NBS—N-bromosuccinamide
NIS—N-iodosuccinimide
NMP—N-methyl-2-pyrrolidone
TEA—Triethylamine
TFA—Trifluoro acetic acid
THF—Tetrahydrofuran
TMSCL—Trimethylsilyl chloride
TsOH—Trimethylsilyl chloride
PE—Petroleum ether
DIBAL-H—Diisobutylaluminum hydride
9-BBN—9-borabicyclo[3,3,1]nonane

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.
Nomenclature
ChemBioDraw Ultra, or MDL ISIS/Draw 2.5 SP1

Intermediates

D1 N-{2-[3-(Methyloxy)phenyl]ethyl}urea

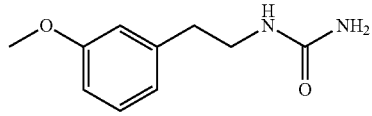

To a solution of 2-(3-methoxy-phenyl)-ethylamine (15 g, 0.10 mol) in H$_2$O (50 mL) was added potassium cyanate (KCNO) (8.1 g, 0.10 mol) and HCl (10 mL) in H$_2$O (50 mL). The reaction mixture was refluxed overnight, then cooled to 0° C. and filtered. The filtrated cake was washed with cold water (50 mL) and dried to afford the title product as a white solid (15 g).

LC-MS (ESI): m/z 195 [M+H]$^+$; 0.77 min (ret time).

D2 1-{2-[3-(Methyloxy)phenyl]ethyl}-2,4,6(1H,3H,5H)-pyrimidinetrione

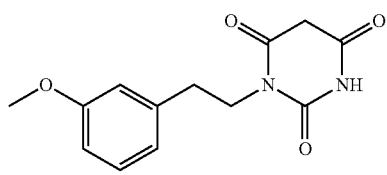 [SMILES: COc1cccc(CCN2C(=O)CC(=O)NC2=O)c1]

To a solution of [2-(3-methoxy-phenyl)-ethyl]-urea (27 g, 0.14 mol) in anhydrous EtOH (300 mL) was added malonic acid diethyl ester (27 g, 0.17 mol) and EtONa (28 g, 0.42 mol). The reaction mixture was refluxed overnight, then concentrated to 150 mL, diluted with water (150 mL), adjusted to pH about 6.0 with 5 M HCl solution and filtered. The filtrated cake was washed with water (150 mL) and dried to afford the title product as a yellow solid (24.0 g, 65.9%).

$^1$HNMR (DMSO, 400 MHz) δ: 7.19 (t, 1H), 6.77 (d, 3 H), 3.84(t, 2 H), 3.71(s, 3 H), 3.61(s, 2 H), 2.70(t, 2 H).

D3 2-Chloro-9-(methyloxy)-6,7-dihydro-4H-pyrimido[6,1-a]isoquinolin-4-one

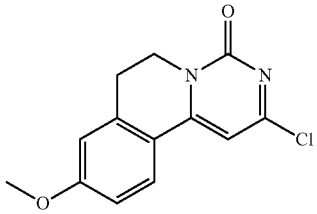 [SMILES: COc1ccc2c(c1)CCn1c-2cc(Cl)nc1=O]

A mixture of 1-{2-[3-(Methyloxy)phenyl]ethyl}-2,4,6 (1H,3H,5H)-pyrimidinetrione (10.0 g, 38.2 mmol) in POCl$_3$ (150 mL) was heated at 120° C. overnight, then concentrated to 50 mL under vacuum, poured into 300 mL ice water slowly, adjusted to pH=6.0 with 5 M NaOH solution and extracted with dichloromethane three times (300 mL×3). Combined organic parts were dried over anhydrous Na$_2$SO$_4$, filtered and concentrated. Purification via column chromatography on silica gel (dichloromethane/methanol=100/1 to 50/1) afforded the title product as a yellow solid (5.5 g, 55%).

$^1$H NMR (400 MHz, CDCl$_3$) δ: 7.62 (d, 1 H), 6.87 (d, 1 H), 6.72 (s, 1 H), 6.61 (s, 1 H), 4.17 (t, 2 H), 3.82 (s, 3 H), 2.95 (t, 2 H).

D4
5-Bromo-2-(3-(trifluoromethyl)phenoxy)benzonitrile

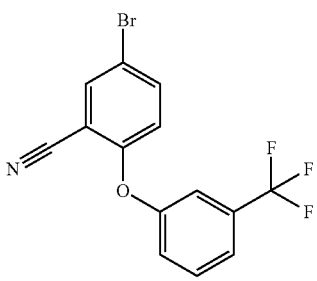 [SMILES: N#Cc1cc(Br)ccc1Oc1cccc(C(F)(F)F)c1]

A mixture of 5-bromo-2-fluorobenzonitrile (1.00 g, 5.00 mmol), 3-(trifluoromethyl)phenol (1.05 g, 6.50 mmol) and potassium carbonate (2.07 g, 15.0 mmol) in dimethyl sulfoxide (DMSO) (10 mL) was heated at 100° C. overnight. Purification via Biotage (C18) system afforded the title product (1.0 g).

D5 5-(4,4,5,5-Tetramethyl-1,3,2-dioxaborolan-2-yl)-2-(3 (trifluoromethyl)phenoxy)benzonitrile

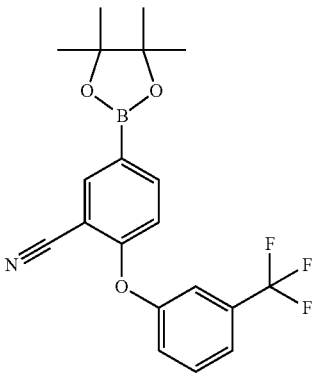 [SMILES: CC1(C)OB(c2ccc(Oc3cccc(C(F)(F)F)c3)c(C#N)c2)OC1(C)C]

A mixture of 5-bromo-2-{[3-(trifluoromethyl)phenyl]oxy}benzonitrile (200 mg, 0.585 mmol), Pinacoboronic ester (163 mg, 0.643 mmol), PdCl$_2$ (dppf)-CH$_2$Cl$_2$ adduct (23.9 mg, 0.0290 mmol) and potassium acetate (172 mg, 1.75 mmol) in N,N-dimethylformamide (DMF) (5 mL) was bubbled with argon and heated at 80° C. for 2 h, then concentrated. Simple purification via ISCO system afforded the title product (200 mg), which was used without further purification.

D6 5-Hydroxy-2-(3-(trifluoromethyl)phenoxy)benzonitrile

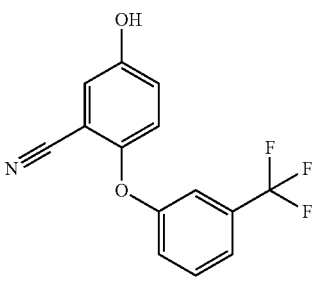 [SMILES: N#Cc1cc(O)ccc1Oc1cccc(C(F)(F)F)c1]

To a solution of 5-(4,4,5,5-tetramethyl-1,3,2-dioxaborolan-2-yl)-2-{[3-(trifluoromethyl)phenyl]oxy}benzonitrile (200 mg, 0.514 mmol) in 1,4-dioxane (10 mL) was added dropwise H$_2$O$_2$ (0.157 mL, 5.14 mmol) at 0° C. The reaction mixture was stirred at r.t for 3 h, then quenched with saturated sodium sulfite solution and concentrated. Purification via ISCO system afforded the desired product (75 mg) as a white solid.

D7 1-Chloro-4-(4-nitrophenoxy)-2-(trifluoromethyl)benzene

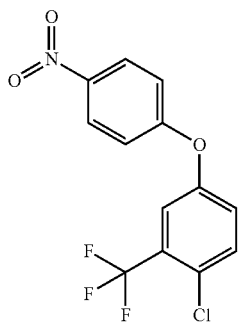 [SMILES: O=[N+]([O-])c1ccc(Oc2ccc(Cl)c(C(F)(F)F)c2)cc1]

To a mixture of 4-chloro-3-(trifluoromethyl)phenol (1.00 g, 5.09 mmol), 1-fluoro-4-nitrobenzene (0.718 g, 5.09 mmol) and potassium carbonate (2.11 g, 15.3 mmol) in dimethyl sulfoxide (DMSO) (25 mL) was heated at 100° C. overnight, then diluted with ethyl acetate (200 mL) and water (200 mL). The separated aqueous part was extracted with ethy acetate (100 mL) twice. Combined organic parts were washed with water then brine, dried over sodium sulfate and concentrated. Purification via ISCO system afforded the desired product (800 mg) as a white solid.

D8 4-(4-Chloro-3-(trifluoromethyl)phenoxy)aniline

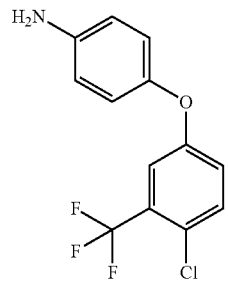 [SMILES: Nc1ccc(Oc2ccc(Cl)c(C(F)(F)F)c2)cc1]

To a solution of 1-chloro-4-[(4-nitrophenyl)oxy]-2-(trifluoromethyl)benzene (20 mg, 0.063 mmol) in Methanol (20 mL) was added raney nickel (7.39 mg, 0.126 mmol). The reaction mixture was stirred at rt until the starting material was converted completely, then filtered and concentrated. The residue was directly used into next step without further purification.

LC-MS (ESI): m/z 288 [M+H]$^+$; 2.69 min (ret time).

D9 4-(4-Chloro-3-(trifluoromethyl)phenoxy)phenol

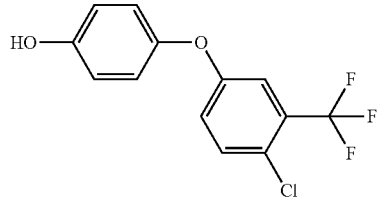 [SMILES: Oc1ccc(Oc2ccc(Cl)c(C(F)(F)F)c2)cc1]

To a solution of 4-{[4-chloro-3-(trifluoromethyl)phenyl]oxy}aniline (380 mg, 1.32 mmol) in water (20 mL) was added hydrochloric acid (0.401 mL, 13.2 mmol) at 0° C., then a solution of sodium nitrite (100 mg, 1.45 mmol) in water (5 mL) was added. The reaction mixture turned brown, was stirred further for 1 h, then poured into boiling solution of water (15 mL) and sulfuric acid (15.0 mL, 281 mmol) and refluxed for 1 h. The resulting mixture was extracted with ethyl acetate (30 mL) twice. Combined organic parts were washed with water then brine, dried over sodium sulfate and concentrated. Purification via ISCO system afforded the desired product (80 mg) as a white solid.

$^1$H NMR (CDCl$_3$, 400 MHz) δ: 9.46 (s, 1 H), 7.59 (d, J=8.8 Hz, 1 H), 7.23 (d, J=2.8 Hz, 1 H), 7.10 (d, J=2.8 Hz, 1 H), 7.09 (dd, J$_1$=8.8 Hz & J$_2$=2.8 Hz, 1 H), 6.91 (d, J=9.4 Hz, 2 H), 6.76 (d, J=9.4 Hz, 2 H).

D10 2-Chloro-4-{[4-chloro-3-(trifluoromethyl)phenyl]oxy}benzaldehyde

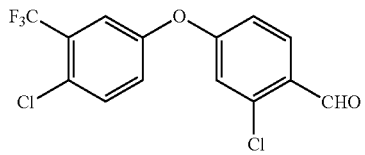

A mixture of 2-chloro-4-fluorobenzaldehyde (500 mg, 3.15 mmol), 4-chloro-3-(trifluoromethyl)phenol (620 mg, 3.15 mmol) and potassium carbonate (1.31 g, 9.46 mmol) in dimethyl sulfoxide (5 mL) was stirred at 100° C. overnight, then cooled to rt and diluted with ethyl acetate (30 mL) and water (30 mL). The separated aqueous layer was extracted with ethyl acetate (30 mL) twice. Combined organic layers were washed with water and brine, dried over sodium sulfate, filtered and concentrated. Purification via ISCO system (petroleum ether/ethyl acetate=4/1) afforded the title product as a pale white solid (890 mg, 80%).

D11 (2-Chloro-4-{[4-chloro-3-(trifluoromethyl)phenyl]oxy}phenyl)methanol

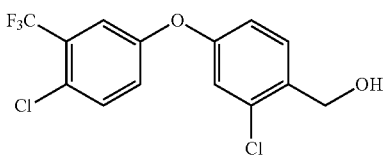 [SMILES: OCc1ccc(Oc2ccc(Cl)c(C(F)(F)F)c2)cc1Cl]

To a solution of 2-chloro-4-{[4-chloro-3-(trifluoromethyl)phenyl]oxy}benzaldehyde (150 mg, 0.448 mmol) in methanol (5 mL) was added sodium borohydride (18.6 mg, 0.492 mmol) at 0° C. The reaction mixture was stirred at rt for 30 min, then quenched with acetone and concentrated. Purification via ISCO system (petroleum ether/ethyl acetate=1/1) afforded the title product (120 mg, 76%) as a colorless oil.
LC-MS (ESI): m/z 563 [M+H]$^+$; 4.25 min (ret time).

D12 4-{[4-Chloro-3-(trifluoromethyl)phenyl]oxy}-2-(trifluoromethyl)be-nzaldehyde

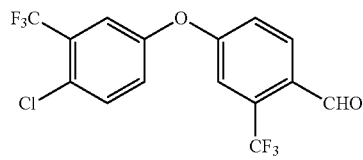

The title compound was prepared by a procedure similar to that described for D10 starting from 4-fluoro-2-(trifluoromethyl)benzaldehyde and 4-chloro-3-(trifluoromet-hyl)phenol.

D13 [4-{[4-Chloro-3-(trifluoromethyl)phenyl]oxy}-2-(trifluoromethyl)phenyl]methanol

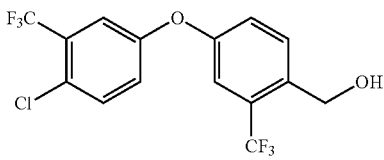 [SMILES: OCc1ccc(Oc2ccc(Cl)c(C(F)(F)F)c2)cc1C(F)(F)F]

The title compound was prepared by a procedure similar to that described for D11 starting from 4-{[4-chloro-3-(trifluoromethyl)phenyl]oxy}-2-(trifluoromethyl)benzal-dehyde.

D14 2-(Trifluoromethyl)-4-{[3-(trifluoromethyl)phenyl]oxy}benzaldehyde

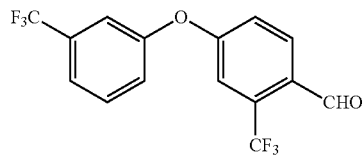

The title compound was prepared by a procedure similar to that described for D10 starting from 4-fluoro-2-(trifluoromethyl)benzaldehyde and 3-(trifluoromethyl)phenol.

D15 (2-(Trifluoromethyl)-4-{[3-(trifluoromethyl)phenyl]oxy}phenyl)methanol

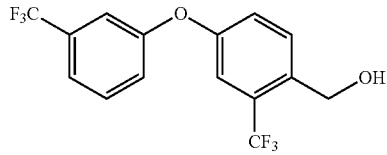 [SMILES: OCc1ccc(Oc2cccc(C(F)(F)F)c2)cc1C(F)(F)F]

The title compound was prepared by a procedure similar to that described for D11 starting from 2-(trifluoromethyl)-4-{[3-(trifluoromethyl)phenyl]oxy}benzaldehyde.

D16 2-Chloro-4-{[3-(trifluoromethyl)phenyl]oxy}benzaldehyde

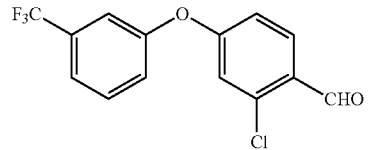 [SMILES: O=Cc1ccc(Oc2cccc(C(F)(F)F)c2)cc1Cl]

The title compound was prepared by a procedure similar to that described for D10 starting from 2-chloro-4-fluorobenzaldehyde and 3-(trifluoromethyl)phenol.

D17 (2-Chloro-4-{[3-(trifluoromethyl)phenyl]oxy}phenyl)methanol

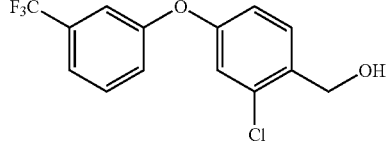 [SMILES: OCc1ccc(Oc2cccc(C(F)(F)F)c2)cc1Cl]

The title compound was prepared by a procedure similar to that described for D11 starting from 2-chloro-4-{[3-(trifluoromethyl)phenyl]oxy}benzaldehyde.

D18 5-{[4-Chloro-3-(trifluoromethyl)phenyl]oxy}-2-formylbenzonitrile

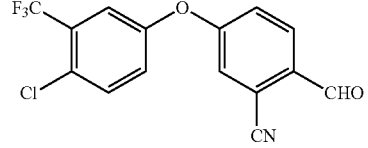 [SMILES: N#Cc1cc(Oc2ccc(Cl)c(C(F)(F)F)c2)ccc1C=O]

To a solution of 4-chloro-3-trifluoromethyl-phenol (3.2 g, 16.3 mmol) in acetonitrile (80 mL) was added 2-fluoro-5-formyl-benzonitrile (2.43 g, 16.3 mmol) and Cs$_2$CO$_3$ (5.89 g, 18.0 mmol). The reaction mixture was stirred at r.t. for 5 h, filtered and concentrated. Purification via flash chromatography on silica gel (petroleum ether/ethyl acetate=10/1 to 3/1) afforded the desired product (4.6 g, 86.8%).

$^1$H NMR (CDCl$_3$, 400 MHz) δ: 9.89 (s, 1 H), 8.16 (d, J=2.0 Hz, 1 H), 7.98 (dd, J$_1$=8.4 Hz & J$_2$=2.0 Hz, 1 H), 7.55 (d, J=8.4 Hz, 1 H), 7.43 (d, J=2.8 Hz, 1 H), 7.21 (dd, J$_1$=8.8 Hz & J$_2$=2.8 Hz, 1 H), 6.89 (d, J=8.4 Hz, 1 H)

D19 5-{[4-Chloro-3-(trifluoromethyl)phenyl]oxy}-2-(hydroxymethyl)benzoni-trile

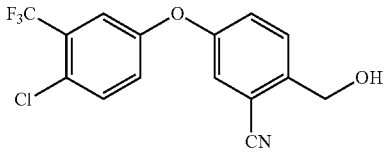 [SMILES: N#Cc1cc(Oc2ccc(Cl)c(C(F)(F)F)c2)ccc1CO]

The title compound was prepared by a procedure similar to that described for D11 starting from 5-{[4-chloro-3-(trifluoromethyl)phenyl]oxy}-2-formylbenzonitrile.

D20 5-Formyl-2-{[3-(trifluoromethyl)phenyl]oxy}benzonitrile

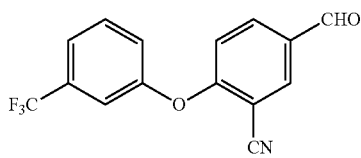 [SMILES: N#Cc1cc(C=O)ccc1Oc1cccc(C(F)(F)F)c1]

The title compound was prepared by a procedure similar to that described for D10 starting from 3-trifluoromethyl-phenol and 2-Fluoro-5-formyl-benzonitrile.

$^1$H NMR (400 MHz, CDCl$_3$) δ: 9.95 (s, 1 H), 8.22 (s, 2 H), 8.02 (d, J=8.8 Hz, 1 H), 7.64 (m, 2 H), 7.35 (m, 1 H), 6.94 (d, J=8.8 Hz, 1 H).

D21 5-(Hydroxymethyl)-2-{[3-(trifluoromethyl)phenyl]oxy}benzonitrile

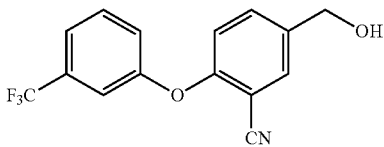 [SMILES: N#Cc1cc(CO)ccc1Oc1cccc(C(F)(F)F)c1]

The title compound was prepared by a procedure similar to that described for D11 starting from 5-formyl-2-(3-trifluoromethyl-phenoxy)-benzonitrile.

$^1$H NMR (400 MHz, CDCl$_3$) δ: 7.72 (s, 1 H), 7.5 (m, 3 H), 7.32 (s, 1 H), 7.25 (s, 1 H), 6.92 (d, J=8.8 Hz, 1 H), 4.72 (s, 2 H).

D22 6-{[3-(Trifluoromethyl)phenyl]oxy}-3-pyridinecarbaldehyde

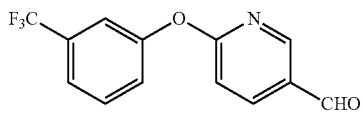 [SMILES: O=Cc1ccc(Oc2cccc(C(F)(F)F)c2)nc1]

The title compound was prepared by a procedure similar to that described for D10 starting from 6-chloro-3-pyridinecarbaldehyde and 3-(trifluoromethyl)phenol.

D23 (6-{[3-(Trifluoromethyl)phenyl]oxy}-3-pyridinyl)methanol

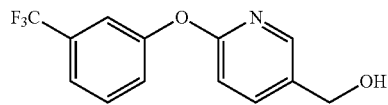 [SMILES: OCc1ccc(Oc2cccc(C(F)(F)F)c2)nc1]

The title compound was prepared by a procedure similar to that described for D11 starting from 6-{[3-(trifluoromethyl)phenyl]oxy}-3-pyridinecarbaldehyde.

D24 5-(Chloromethyl)-2-{[3-(trifluoromethyl)phenyl]oxy}benzonitrile

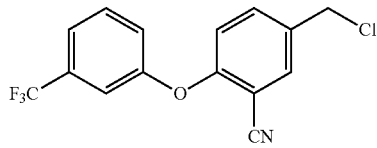 [SMILES: N#Cc1cc(CCl)ccc1Oc1cccc(C(F)(F)F)c1]

To a solution of 5-hydroxymethyl-2-(3-trifluoromethyl-phenoxy)-benzonitrile (20 g, 68.2 mmol) in toluene (200 mL) was added SOCl$_2$ (5.4 mL, 75.1 mmol), the reaction solution was stirred at rt for overnight, then diluted with water (100 mL). Separated organic layer was dried over Na$_2$SO$_4$, filtered and concentrated. Purification via recrystallization with petroleum ether (100 mL) afforded the title product (12.9 g, 50%).

$^1$H NMR (400 MHz, CDCl$_3$) δ: 7.75 (s, 1 H), 7.55 (m, 3 H), 7.35 (s, 1 H), 7.28 (s, 1 H), 6.88 (d, J=8.4 Hz, 1 H), 4.57 (s, 2 H).

D25 S-[(3-Cyano-4-{[3-(trifluoromethyl)phenyl]oxy}phenyl)methyl]ethanethioate

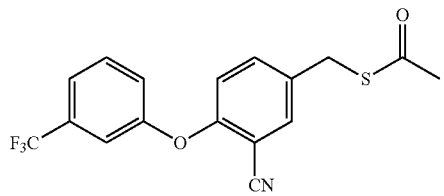 [SMILES: CC(=O)SCc1ccc(Oc2cccc(C(F)(F)F)c2)c(C#N)c1]

A mixture of 5-(chloromethyl)-2-{[3-(trifluoromethyl)phenyl]oxy}benzonitrile (1.00 g, 3.21 mmol) and potassium thioacetate (0.403 g, 3.53 mmol) in N,N-dimethylformamide (10 mL) was stirred at rt for 2 h, then quenched with water and diluted with ethyl acetate (200 mL), washed with water for three times (60 mL×3) and concentrated. Purification via ISCO system (ethyl acetate/petroleum ether=1/10) afforded the desired product as a yellow oil.

D26 5-(Mercaptomethyl)-2-{[3-(trifluoromethyl)phenyl]oxy}benzonitrile

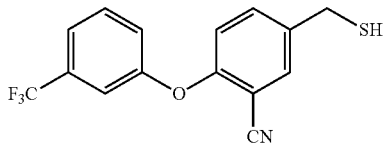

A mixture of S-[(3-cyano-4-{[3 (trifluoromethyl)phenyl]oxy}phenyl)methyl]ethanethioate (650 mg, 1.85 mmol) in methanol (2.5 mL) and water (5 mL) and $K_2CO_3$ (511 mg, 3.70 mmol) was stirred at rt for 48 h and concentrated. The residue was dissolved indichloromethane (120 mL), then washed with water for three times (40 mL×3), dried over $Na_2SO_4$ and concentrated. Purification via ISCO system (petroleum ether/ethyl acetate=10/1 to 5/1) afforded the desired product as a colorless oil.

D27 4-(4-Chloro-3-(trifluoromethyl)phenoxy)benzaldehyde

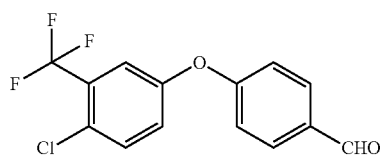 [SMILES: O=Cc1ccc(Oc2ccc(Cl)c(C(F)(F)F)c2)cc1]

The title compound was prepared by a procedure similar to that described for D10 starting from 4-chloro-3-trifluoromethyl-phenol and 4-fluoro-benzaldehyde.

LC-MS (ESI): m/z 300 [M]+; 1.34 min (ret time).

D28 1-Chloro-4-(4-(difluoromethyl)phenoxy)-2-(trifluoromethyl)benzene

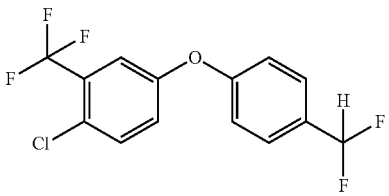 [SMILES: FC(F)c1ccc(Oc2ccc(Cl)c(C(F)(F)F)c2)cc1]

To a solution of 4-(4-chloro-3-trifluoromethyl-phenoxy)-benzaldehyde (2.50 g, 8.30 mmol) in DCM (40 mL) was added DAST (2.68 g, 16.7 mmol) dropwise at 0° C. slowly. The reaction mixture was stirred at rt for overnight, then diluted $H_2O$ (50 mL) and extracted with DCM for two times (40 mL×2). Combined organic parts were washed with brine, dried over sodium sulfate, filtered and concentrated. Purification via ISCO system (petroleum ether/ethyl acetate=5/1) afforded the title product (2.0 g) as a yellow solid.

$^1$H NMR (400 MHz, CDCl$_3$) δ: 7.52 (d, J=8.8 Hz, 1 H), 7.47 (d, J=8.8 Hz, 1 H), 7.36 (s, 1 H), 7.25 (s, 1 H), 7.12 (m, 1 H), 7.09 (m, 2 H), 6.65 (t, J=56.8 Hz, 1 H).

D29 1-Chloro-4-(4-(chlorodifluoromethyl)phenoxy)-2-(trifluoromethyl)benzene

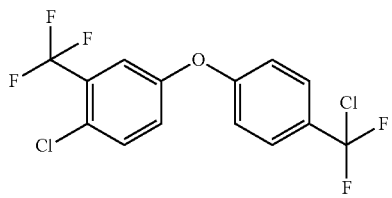 [SMILES: FC(F)(F)c1cc(Oc2ccc(C(F)(F)Cl)cc2)ccc1Cl]

To a solution of 1-chloro-4-(4-difluoromethyl-phenoxy)-2-trifluoromethyl-benzene (2.0 g, 6.21 mmol) in $CCl_4$ (30 mL) was bubbled $Cl_2$. The reaction mixture was stirred under $Cl_2$ and tungsten light for 6 h, then concentrated. Purification via prep-TLC (petroleum ether/ethyl acetate=10/1) afforded the title product (1.1 g) as a yellow oil $^1$H NMR (400 MHz, CDCl$_3$) δ: 7.62 (d, J=7.2 Hz, 2 H), 7.48 (d, J=7.2 Hz, 1 H), 7.39 (s, 1 H), 7.15 (d, J=8.8 Hz, 1 H), 7.06 (t, J=10 Hz, 2 H).

D30 3-Cyano-4-(3-(trifluoromethyl)phenoxy)benzoic acid

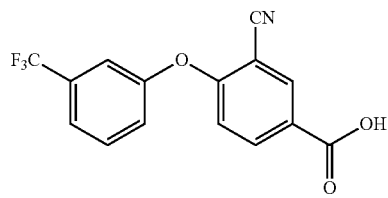 [SMILES: N#Cc1cc(C(=O)O)ccc1Oc1cccc(C(F)(F)F)c1]

A mixture of 5-[chloro(difluoro)methyl]-2-{[3-(trifluoromethyl)phenyl]oxy}benzonitrile (506 mg, 1.46 mmol) and silver nitrate (321 mg, 1.89 mmol) in acetonitrile (5 mL) and water (7 mL) was sealed in a microwave vial and irradiated with a microwave at 150° C. for 45 min, then extraced with ethyl acetate (100 mL) and washed with water for three times (50 mL×3) and concentrated. Purification via ISCO system (ethyl acetate/petroleum ether=1/5 to 1/2) afforded the title product (300 mg) as a pale yellow solid.

D31 1-Chloro-4-[(4-ethenylhenyl)oxy]-2-(trifluoromethyl)benzene

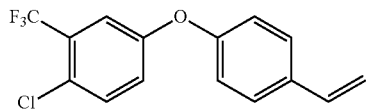 [SMILES: C=Cc1ccc(Oc2ccc(Cl)c(C(F)(F)F)c2)cc1]

The title compound was prepared by a procedure similar to that described for D78 starting from 4-{[4-chloro-3-(trifluoromethyl)phenyl]oxy}benzaldehyde.

D32 2-(4-{[4-Chloro-3-(trifluoromethyl)phenyl]oxy}phenyl)ethanol

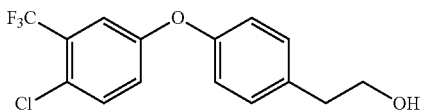 [SMILES: OCCc1ccc(Oc2ccc(Cl)c(C(F)(F)F)c2)cc1]

The title compound was prepared by a procedure similar to that described for D79 starting from 4-chloro-3-(trifluoromethyl)phenyl 4-ethenylphenyl ether.

D33
4-(4-Chloro-3-(trifluoromethyl)phenoxy)benzoic acid

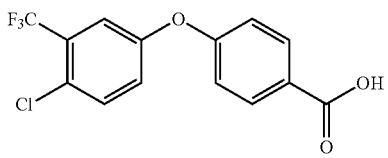 [SMILES: O=C(O)c1ccc(Oc2ccc(Cl)c(C(F)(F)F)c2)cc1]

The title compound was prepared by a procedure similar to that described for D30 starting from chloro-4-({4-[chloro(difluoro)methyl]phenyl}oxy)-2-(trifluoromethyl)benzene.

D34 3-(Methyloxy)-4-{[3-(trifluoromethyl)phenyl]oxy}benzaldehyde

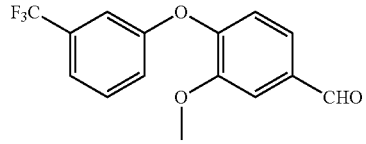 [SMILES: COc1cc(C=O)ccc1Oc1cccc(C(F)(F)F)c1]

The title compound was prepared by a procedure similar to that described for D10 starting from 4-fluoro-3-(methyloxy)benzaldehyde and 3-(trifluoromethyl)phenol.

D35 (3-(Methyloxy)-4-{[3-(trifluoromethyl)phenyl]oxy}phenyl)methanol

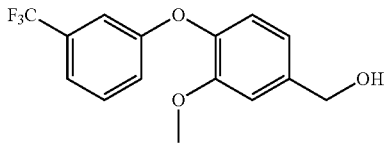 [SMILES: COc1cc(CO)ccc1Oc1cccc(C(F)(F)F)c1]

The title compound was prepared by a procedure similar to that described for D11 starting from 3-(methyloxy)-4-{[3-(trifluoromethyl)phenyl]oxy}benzaldehyde.

D36 3-Methyl-4-{[3-(trifluoromethyl)phenyl]oxy}benzaldehyde

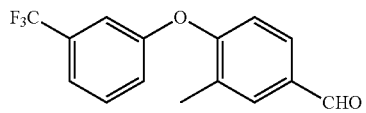 [SMILES: Cc1cc(C=O)ccc1Oc1cccc(C(F)(F)F)c1]

The title compound was prepared by a procedure similar to that described for D10 starting from 4-fluoro-3-methylbenzaldehyde and 3-(trifluoromethyl)phenol.

D37 (3-Methyl-4-{[3-(trifluoromethyl)phenyl]oxy}phenyl)methanol

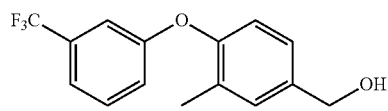

The title compound was prepared by a procedure similar to that described for D11 starting from 3-methyl-4-{[3-(trifluoromethyl)phenyl]oxy}benzaldehyde.

D38 3-(Trifluoromethyl)-4-{[3-(trifluoromethyl)phenyl]oxy}benzaldehyde

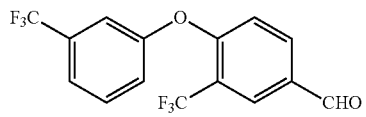 [SMILES: O=Cc1ccc(Oc2cccc(C(F)(F)F)c2)c(C(F)(F)F)c1]

The title compound was prepared by a procedure similar to that described for D10 starting from 4-fluoro-3-(trifluoromethyl)benzaldehyde and 3-(trifluoromethyl)phenol.

D39 (3-(Trifluoromethyl)-4-{[3-(trifluoromethyl)phenyl]oxy}phenyl)methanol

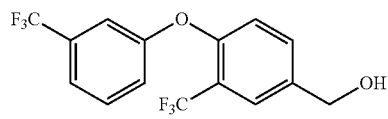

The title compound was prepared by a procedure similar to that described for D11 starting from 3-(trifluoromethyl)-4-{[3-(trifluoromethyl)phenyl]oxy}benzaldehyde.

D40 2-{[4-Fluoro-3-(trifluoromethyl)phenyl]oxy}-5-formylbenzonitrile

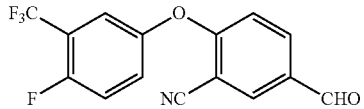 [SMILES: N#Cc1cc(C=O)ccc1Oc1ccc(F)c(C(F)(F)F)c1]

To a solution of 4-fluoro-3-trifluoromethyl-phenol (3.5 g, 20 mmol) in acetonitrile (80 mL) was added 2-fluoro-5-formyl-benzonitrile (2.9 g, 20 mmol) and $Cs_2CO_3$ (7.00 g, 21.4 mmol). The reaction mixture was stirred at rt for overnight, filtered and concentrated. Purification via flash chromatography on silica gel (petroleum ether/ethyl acetate=10/1 to 3/1) afforded the desired product (5.2 g, 86.4%).

$^1$H NMR (CDCl$_3$, 400 MHz,) δ: 9.95 (s, 1 H), 8.22 (s, 1 H), 8.02 (d, J=8.8 Hz, 1 H), 7.43 (m, 1 H), 7.35 (m, 2 H), 6.92 (d, J=8.8 Hz, 1 H).

D41 2-{[4-Fluoro-3-(trifluoromethyl)phenyl]oxy}-5-(hydroxymethyl)benzoni-trile

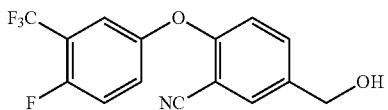 [SMILES: N#Cc1cc(CO)ccc1Oc1ccc(F)c(C(F)(F)F)c1]

The title compound was prepared by a procedure similar to that described for D11 starting from 2-{[4-fluoro-3-(trifluoromethyl)phenyl]oxy}-5-formylbenzonitrile.

D42 2-{[4-Chloro-3-(trifluoromethyl)phenyl]oxy}-5-ethenylbenzonitrile

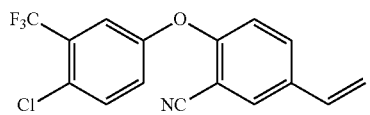 [SMILES: C=Cc1ccc(Oc2ccc(Cl)c(C(F)(F)F)c2)c(C#N)c1]

The title compound was prepared by a procedure similar to that described for D78 starting from 2-{[4-chloro-3-(trifluoromethyl)phenyl]oxy}-5-formylbenzonrile.

D43 2-{[4-Chloro-3-(trifluoromethyl)phenyl]oxy}-5-(2-hydroxyethyl)benzoni-trile

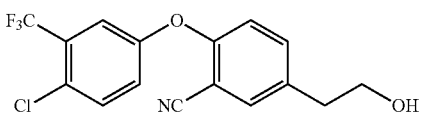 [SMILES: N#Cc1cc(CCO)ccc1Oc1ccc(Cl)c(C(F)(F)F)c1]

The title compound was prepared by a procedure similar to that described for D79 starting from 2-{[4-chloro-3-(trifluoromethyl)phenyl]oxy}-5-ethenylbenzonitrile.

D44 3-Bromo-4-(3-(trifluoromethyl)phenoxy)benzaldehyde

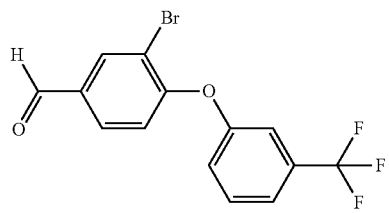 [SMILES: O=Cc1ccc(Oc2cccc(C(F)(F)F)c2)c(Br)c1]

The title compound was prepared by a procedure similar to that described for D10 starting from 3-bromo-4-fluorobenzaldehyde and 3-(trifluoromethyl)phenol.

D45 (3-Bromo-4-(3-(trifluoromethyl)phenoxy)phenyl)methanol

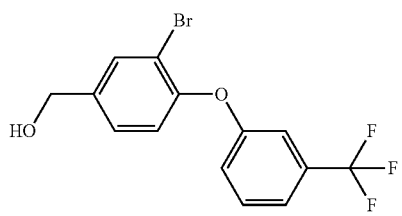 [SMILES: OCc1ccc(Oc2cccc(C(F)(F)F)c2)c(Br)c1]

To a solution of 3-bromo-4-{[3-(trifluoromethyl)phenyl]oxy}benzaldehyde (500 mg, 1.45 mmol) in methanol (10 mL) was added sodium borohydride (54.8 mg, 1.45 mmol) at 0° C. The reaction mixture was stirred at r.t for 15 min, then quenched with acetone and concentrated. Purification via ISCO system (petroleum ether/ethyl acetate=1/1) afforded the desired product (400 mg) as a lear oil.

D46 3-Chloro-4-(3-(trifluoromethyl)phenoxy)benzaldehyde

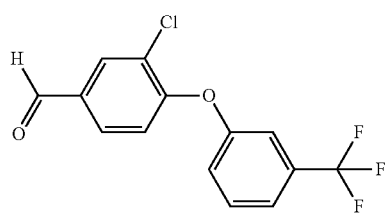

The title compound was prepared by a procedure similar to that described for D10 starting from 3-chloro-4-fluorobenzaldehyde and 3-(trifluoromethyl)phenol.

D47 (3-Chloro-4-(3-(trifluoromethyl)phenoxy)phenyl)methanol

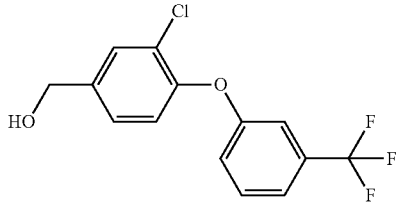

The title compound was prepared by a procedure similar to that described for D11 starting from 3-chloro-4-{[3-(trifluoromethyl)phenyl]oxy}benzaldehyde.

D48 5-{[3-(Trifluoromethyl)phenyl]oxy}-2-pyridinecarbaldehyde

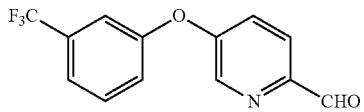 [SMILES: O=Cc1ccc(Oc2cccc(C(F)(F)F)c2)cn1]

The title compound was prepared by a procedure similar to that described for D10 starting from 3-(trifluoromethyl)phenol and 5-chloro-2-pyridinecarbaldehyde.

D49 (5-{[3-(Trifluoromethyl)phenyl]oxy}-2-pyridinyl)methanol

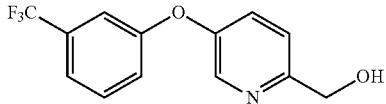 [SMILES: OCc1ccc(Oc2cccc(C(F)(F)F)c2)cn1]

The title compound was prepared by a procedure similar to that described for D11 starting from 5-{[3-(trifluoromethyl)phenyl]oxy}-2-pyridinecarbaldehyde.

D50 5-Hydroxy-2-methylbenzonitrile

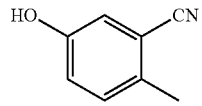

To a solution of $H_2SO_4$ (25 mL, conc.) in $H_2O$ (50 mL) was added 5-amino-2-methyl-benzonitrile (4.13 g, 31.0 mmol). Crashed ice (40 g) was added. Then, a solution of $NaNO_2$ (2.59 g, 37.0 mmol) in $H_2O$ (25 mL) was added dropwise below 5° C. Five minutes later, cold water (25 mL), urea (281 mg, 4.70 mmol) and ice (25 g) were added sequencely. The reaction mixture was added into a refluxed solution of $Na_2SO_4$ (23.7 g, 167 mmol) and $H_2SO_4$ (50 mL, conc.) in $H_2O$ (25 mL). The resulting mixture was refluxed for 2 h, then extracted with ethyl acetate for three times (200 mL×3). Combined organic parts were dried over $Na_2SO_4$, filtered and concentrated. Purification via ISCO system (petroleum ether/ethyl acetate=30/1 to 10/1) afforded the title product (2.9 g).

D51 2-Methyl-5-{[3-(trifluoromethyl)phenyl]oxy}benzonitrile

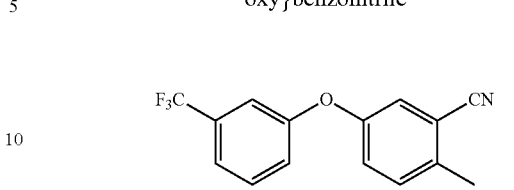

To a solution of 5-hydroxy-2-methyl-benzonitrile (2.0 g, 15 mmol) in DCM (50 mL) were added 3-(trifluoromethyl)phenylboronic acid (5.7 g, 30 mmol), $Et_3N$ (7.60 g, 10.5 mmol) and $Cu(OAc)_2$ (2.7 g, 15 mmol) and 4 A molecular sieve (1.5 g). The reaction mixture was stirred at room temperature overnight, then filtered through a pad of celite and concentrated. Purification via flash chromatography on silica gel (petroleum ether/ethyl acetate=100/1 to 30/1) afforded the title product (2.9 g).
$^1H$ NMR δ: 7.43 (m, 1 H), 7.35 (m, 1 H), 7.24 (m, 1 H), 7.18 (m, 2 H), 7.08 (m, 2 H), 2.47 (s, 3 H).

D52 2-(Dibromomethyl)-5-(3-(trifluoromethyl)phenoxy)benzonitrile

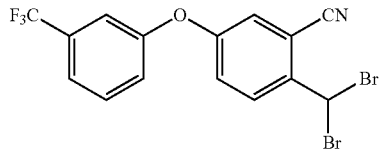 [SMILES: N#Cc1cc(Oc2cccc(C(F)(F)F)c2)ccc1C(Br)Br]

To a mixture of 2-methyl-5-{[3-(trifluoromethyl)phenyl]oxy}benzonitrile (1.10 g, 3.97 mmol), diphenylperoxyanhydride (0.192 g, 0.794 mmol) in $CCl_4$ (15 mL) was added NBS (2.12 g, 11.9 mmol). The reaction mixture was stirred at 85° C. for 7 h, then concentrated, diluted with ethyl acetate (200 mL), washed with water for three times (60 mL×3) and reconcentrated to afford the desired product as a yellow solid, which was used directly for next transformation without further purification.

D53 2-Formyl-5-(3-(trifluoromethyl)phenoxy)benzonitrile

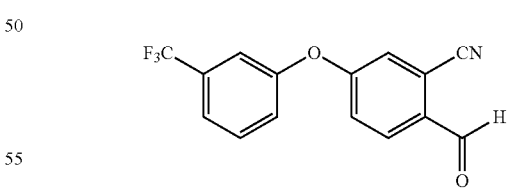

To a mixture of 2-(dibromomethyl)-5-{[3-(trifluoromethyl)phenyl]oxy}benzonitrile (1.50 g, 3.45 mmol), silver nitrate (1.76 g, 10.3 mmol) in acetonitrile (10 mL) was added water (30 mL). The reaction mixture was stirred at 110° C. for 1 h, then concentrated, diluted with ethyl acetate (200 mL), washed with water for three times (60 mL×3) and reconcentrated to afford the title product as a yellow solid, which was used directly for next transformation without further purification.
LC-MS (ESI): m/z 292 [M+H]$^+$; 3.47 min (ret time).

D54 2-(Hydroxymethyl)-5-(3-(trifluoromethyl)phenoxy)benzonitrile

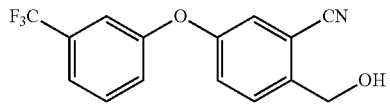

The title compound was prepared by a procedure similar to that described for D11 starting from 2-formyl-5-{[3-(trifluoromethyl)phenyl]oxy}benzonitrile.

LC-MS (ESI): m/z 294 [M+H]$^+$; 2.38 min (ret time).

D55 5-(4-Chloro-3-(trifluoromethyl)phenoxy)picolinonitrile

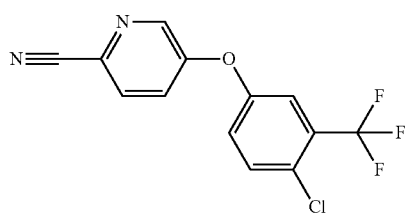

The title compound was prepared by a procedure similar to that described for D10 starting from 5-fluoro-2-pyridinecarbonitrile and 4-chloro-3-(trifluorom-ethyl)phenol.

LC-MS (ESI): m/z 299 [M+H]$^+$; 3.59 min (ret time)

D56 5-(4-Chloro-3-(trifluoromethyl)phenoxy)picolinaldehyde

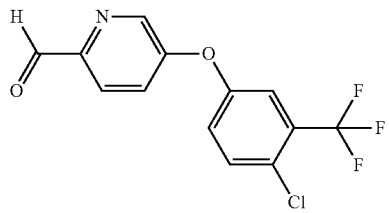 [SMILES: O=Cc1ccc(Oc2ccc(Cl)c(C(F)(F)F)c2)cn1]

To a solution of 5-{[4-chloro-3-(trifluoromethyl)phenyl]oxy}-2-pyridinecarbonitrile (1.0 g, 3.35 mmol) in tetrahydrofuran (THF) (20 mL) was added dropwise DIBAL-H (6.70 mL, 6.70 mmol) at −78° C. The reaction mixture was stirred at −78° C. for 1 h, then quenched with 1 M HCl solution and concentrated. Purification via ISCO system afforded the title product (350 mg) as a white solid.

LC-MS (ESI): m/z 302 [M+H]$^+$; 3.42 min (ret time).

D57 (5-(4-Chloro-3-(trifluoromethyl)phenoxy)pyridin-2-yl)methanol

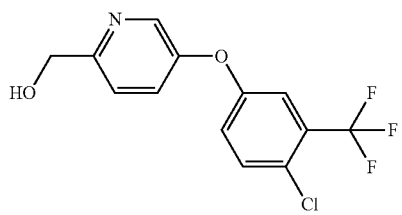 [SMILES: OCc1ccc(Oc2ccc(Cl)c(C(F)(F)F)c2)cn1]

The title compound was prepared by a procedure similar to that described for D11 starting from 5-{[4-chloro-3-(trifluoromethyl)phenyl]oxy}-2-pyridinec-arbaldehyde.

LC-MS (ESI): m/z 304 [M+H]$^+$; 2.68 min (ret time).

D58 2-Hydroxy-5-iodobenzonitrile

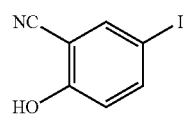

To a solution of 2-hydroxy-benzonitrile (47.6 g, 0.400 mmol) in CH$_3$CN (500 mL) was added CF$_3$SO$_3$H (40 mL) dropwise at 0° C. The reaction mixture was stirred at 0° C. for 20 min, then NIS (108 g, 0.48 mmol) was added. The mixture was stirred at room temperature overnight, then concentrated, diluted with H$_2$OO (300 mL) and extracted with EA (300 mL*3). Combined organic parts were dried over sodium sulfate, filtered and reconcentrated. Purification via column chromatography on silica gel (petroleum ether/ethyl acetate=5/1) afforded the title product (80 g) as a white solid.

$^1$H NMR (400 MHz, CDCl$_3$) δ: 7.78 (s, 1 H), 7.70 (d, J=8.4 Hz, 1 H), 6.77 (d, J=8.8 Hz, 1H).

D59 5-Iodo-2-((5-(trifluoromethyl)pyridin-2-yl)oxy)benzonitrile

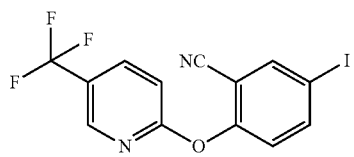 [SMILES: N#Cc1cc(I)ccc1Oc1ccc(C(F)(F)F)cn1]

To a solution of 2-hydroxy-5-iodo-benzonitrile (80.0 g, 0.328 mol) and 2-chloro-5-tri fluoromethyl-pyridine (60.0 g, 0.328 mol) in DMF (500 ml) was added K$_2$CO$_3$ (91.0 g, 0.656 mol). The reaction mixture was refluxed overnight, then filtered and concentrated. Purification via column chromatography on silica gel (petroleum ether/ethyl acetate=10/1) afforded the title product (120 g) as a white solid.

¹H NMR (400 MHz, CDCl₃) δ: 8.38 (s, 1 H), 8.01 (m, 2H), 7.95 (d, J=8.0 Hz, 1 H), 7.22 (d, J=8.4 Hz, 1 H), 8.08 (d, J=8.8 Hz, 1 H), 7.68 (s, 1 H).

D60 Methyl 3-cyano-4-((5-(trifluoromethyl)pyridin-2-yl)xy)benzoate

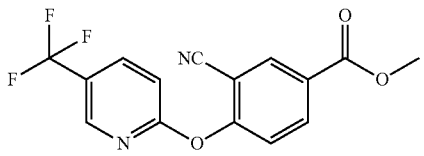 [SMILES: COC(=O)c1ccc(Oc2ccc(C(F)(F)F)cn2)c(C#N)c1]

To a solution of 5-iodo-2-(5-trifluoromethyl-pyridin-2-yloxy)-benzonitrile (110 g, 0.29 mol) in MeOH (1500 mL) and DMF (400 mL) was added Pd(dppf)Cl₂ (20 g). The mixture was stirred in autoclave (10 L) at 100° C. under CO (1 MPa) for 72 hours. MeOH and DMF was removed in vacuo, the crude product was purified by column chromatography on silica gel (PE:EA=20:1 to 10:1) to afford 3-cyano-4-(5-trifluoromethyl-pyridin-2-yloxy)-benzoic acid methyl ester as a yellow oil (45 g, 48.2%).

¹H NMR (400 MHz, CDCl₃) δ: 8.39 (s, 1H), 8.29 (d, J=8.8 Hz, 1H), 8.01 (d, J=8.8 Hz, 1H), 7.40 (d, J=8.8 Hz, 1H), 7.27 (d, J=8.4 Hz, 1H), 3.94 (s, 3H).

D61 5-(Hydroxymethyl)-2-((5-(trifluoromethyl)pyridin-2-yl)oxy)benzonitrile

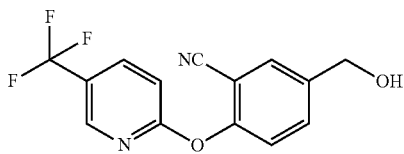 [SMILES: N#Cc1cc(CO)ccc1Oc1ccc(C(F)(F)F)cn1]

To a solution of 3-cyano-4-(5-trifluoromethyl-pyridin-2-yloxy)-benzoic acid methyl ester (23 g, 0.070 mol) in anhydrous THF (200 mL) was added portionwise LiAlH₄ (4.07 g, 0.11 mmol) at -78° C. The reaction mixture was warmed to -55° C. slowly and stirred for 20 mins, diluted with water (3 mL 0.16 mmol, slow addition), filtered and concentrated. Purification via column chromatography on silica gel (petroleum ether/ethyl acetate=10/1 to 5/1) afforded the title product (12.5 g) as a colorless oil.

¹H NMR (400 MHz, CDCl₃) δ: 8.37 (s, 1 H), 7.98 (d, J=8.8 Hz, 1 H), 7.72 (s, 1 H), 7.64 (d, J=8.4 Hz, 1 H), 7.29 (d, J=8.8 Hz, 1 H), 7.19 (d, J=8.4 Hz, 1 H).

D62 5-Formyl-2-{[6-(trifluoromethyl)-3-pyridinyl]oxy}benzonitrile

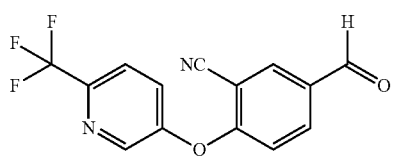 [SMILES: N#Cc1cc(C=O)ccc1Oc1ccc(C(F)(F)F)nc1]

To a solution of 2-fluoro-5-formylbenzonitrile (1.371 g, 9.20 mmol) and 6-(trifluoromethyl)-3-pyridinol (1.5 g, 9.20 mmol) in DMF (10 mL) was added potassium carbonate (3.81 g, 27.6 mmol). The reaction mixture was stirred at 60° C. for overnight. The resultant mixture was filtrated and the filtrate was purified via Biotage-C18 at afford the title compound as pale solids (2.4 g, 7.80 mmol, 85% yield).

LC-MS (ESI): m/z 293[M+H]⁺, 2.97 min (ret time).

D63 5-(Hydroxymethyl)-2-{[6-(trifluoromethyl)-3-pyridinyl]oxy}benzonitrile

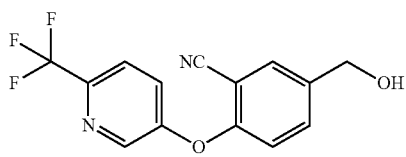 [SMILES: N#Cc1cc(CO)ccc1Oc1ccc(C(F)(F)F)nc1]

To the solution of 5-formyl-2-{[6-(trifluoromethyl)-3-pyridinyl]oxy}benzonitrile (180 mg, 0.616 mmol) in methanol (20 mL) at 0° C. was added sodium borohydride (25 mg, 0.661 mmol) and the resultant solution was stirred at room temperature for 30 min. This mixture was quenched by acetone and concentrated in vacuum.

The residue was purified via ISCO (DCM: MeOH=20:1) to afford the title compound as a clear oil (170 mg, 0.578 mmol, 94% yield).

LC-MS (ESI): m/z 295[M+H]⁺, 2.68 min (ret time).

D64 5-(4-Chloro-3-(trifluoromethyl)phenoxy)picolinonitrile

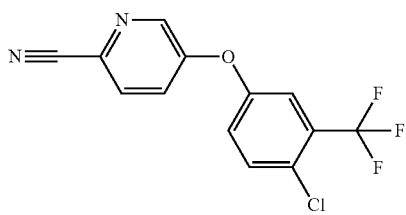 [SMILES: N#Cc1ccc(Oc2ccc(Cl)c(C(F)(F)F)c2)cn1]

The title compound was prepared by a procedure similar to that described for D10 starting from 5-fluoro-2-pyridinecarbonitrile and 4-chloro-3-(trifluorom-ethyl)phenol.

LC-MS (ESI): m/z 299 [M+H]⁺; 3.59 min (ret time)

D65 5-(4-Chloro-3-(trifluoromethyl)phenoxy)picolinaldehyde

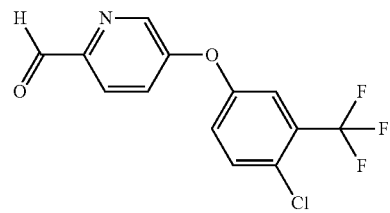 [SMILES: O=Cc1ccc(Oc2ccc(Cl)c(C(F)(F)F)c2)cn1]

To a solution of 5-{[4-chloro-3-(trifluoromethyl)phenyl]oxy}-2-pyridinecarbonitrile (1.0 g, 3.35 mmol) in THF (20 mL) was added dropwise DIBAL-H (6.70 mL, 6.70 mmol) at −78° C. The reaction mixture was stirred at −78° C. for 1 h, then quenched with 1 M HCl solution and concentrated. Purification via ISCO system afforded the title product (350 mg) as a white solid.

LC-MS (ESI): m/z 302 [M+H]$^+$; 3.42 min (ret time).

D66 (5-(4-Chloro-3-(trifluoromethyl)phenoxy)pyridin-2-yl)methanol

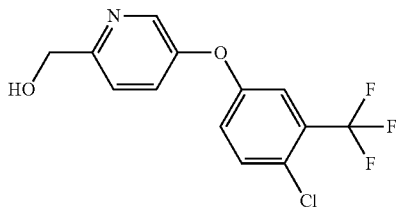 [SMILES: OCc1ccc(Oc2ccc(Cl)c(C(F)(F)F)c2)cn1]

The title compound was prepared by a procedure similar to that described for D11 starting from 5-{[4-chloro-3-(trifluoromethyl)phenyl]oxy}-2-pyridinec-arbaldehyde.

LC-MS (ESI): m/z 304 [M+H]$^+$; 2.68 min (ret time).

D67 6-(4-Chloro-3-(trifluoromethyl)phenoxy)-5-fluoronicotinaldehyde

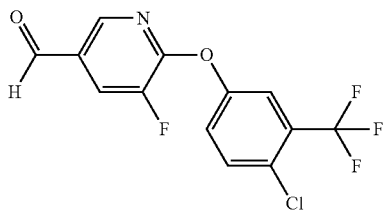 [SMILES: O=Cc1cnc(Oc2ccc(Cl)c(C(F)(F)F)c2)c(F)c1]

The title compound was prepared by a procedure similar to that described for D10 starting from 6-chloro-5-fluoro-3-pyridinecarbaldehyde and 4-chloro-3-(trifluorom-ethyl)phenol.

LC-MS (ESI): m/z 320 [M+H]$^+$; 3.56 min (ret time).

D68 (6-(4-Chloro-3-(trifluoromethyl)phenoxy)-5-fluoropyridin-3-yl)methanol

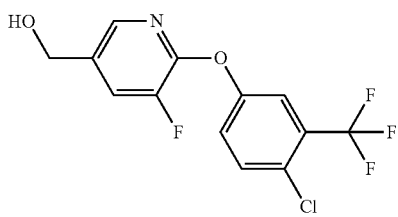 [SMILES: OCc1cnc(Oc2ccc(Cl)c(C(F)(F)F)c2)c(F)c1]

The title compound was prepared by a procedure similar to that described for D11 starting from 6-{[4-chloro-3-(trifluoromethyl)phenyl]oxy}-5-fluoro-3-pyridinecarb-aldehyde.

LC-MS (ESI): m/z 322 [M+H]$^+$; 3.26 min (ret time).

D69 5-Fluoro-6-(3-(trifluoromethyl)phenoxy)nicotinaldehyde

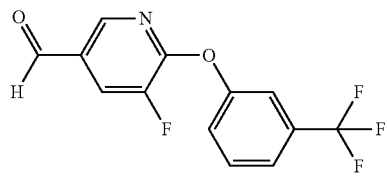 [SMILES: O=Cc1cnc(Oc2cccc(C(F)(F)F)c2)c(F)c1]

The title compound was prepared by a procedure similar to that described for D10 starting from 6-chloro-5-fluoro-3-pyridinecarbaldehyde and 3-(trifluor-omethyl)phenol.

LC-MS (ESI): m/z 286 [M+H]$^+$; 3.40 min (ret time).

D70 (5-Fluoro-6-(3-(trifluoromethyl)phenoxy)pyridin-3-yl methanol

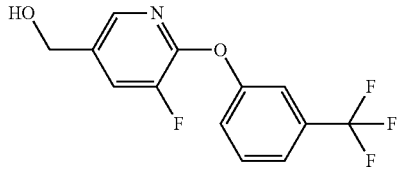 [SMILES: OCc1cnc(Oc2cccc(C(F)(F)F)c2)c(F)c1]

The title compound was prepared by a procedure similar to that described for D11 starting from 5-fluoro-6-{[3-(trifluoromethyl)phenyl]oxy}-3-pyridinecarbaldehyde.

LC-MS (ESI): m/z 288 [M+H]$^+$; 3.05 min (ret time).

D71 5-Fluoro-6-(4-fluoro-3-(trifluoromethyl)phenoxy)nicotinaldehyde

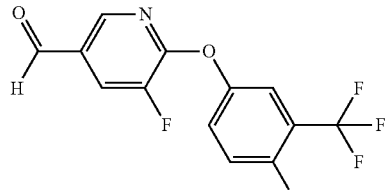

The title compound was prepared by a procedure similar to that described for D10 starting from 6-chloro-5-fluoro-3-pyridinecarbaldehyde and 4-fluoro-3-(trifluoromethyl)phenol.

LC-MS (ESI): m/z 304 [M+H]$^+$; 3.42 min (ret time).

D72 (5-Fluoro-6-(4-fluoro-3-(trifluoromethyl)phenoxy)pyridin-3-yl)methanol

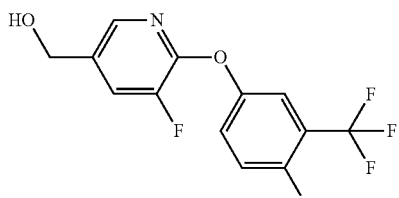

The title compound was prepared by a procedure similar to that described for D11 starting from 5-fluoro-6-{[4-fluoro-3-(trifluoromethyl)phenyl]oxy}-3-pyridinecar-baldehyde.

LC-MS (ESI): m/z 306 [M+H]$^+$; 3.07 min (ret time).

D73
2-((5-Chloropyridin-3-yl)oxy)-5-formylbenzonitrile

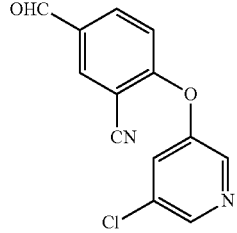 [SMILES: N#Cc1cc(C=O)ccc1Oc1cncc(Cl)c1]

To a solution of 2-fluoro-5-formylbenzonitrile (1.2 g, 8 mmol) and 5-chloro-3-pyridinol (1.04 g, 1 eq) in DMF 60 ml was added K$_2$CO$_3$ (2.78 g, 2 eq). The resultant solution was warmed up to 100° C. for 2 hours. Solvent was evaporated, Etheyl acetate (30 ml) and water (30 ml) were added. The organic layer was separated and dried over Na$_2$SO$_4$. Separation via ISCO (Petrolium ether:ethyl acetate=5:1) then afforded the title compound (2.06 g).

LC-MS (ESI): m/z 259 [M+H]$^+$. NMR: 9.97(1H, S), 8.56 (1H, d), 8.43(1H, d), 8.25(1H, d), 8.05-8.08(1H, dd), 7.54 (1H, d), 7.01(1H, d).

D74 2-((5-Chloropyridin-3-yl)oxy)-5-(hydroxymethyl)benzonitrile

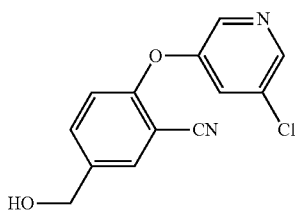 [SMILES: N#Cc1cc(CO)ccc1Oc1cncc(Cl)c1]

The title compound was prepared by a procedure similar to that described for D11 starting from 2-[(5-chloro-3-pyridinyl)oxy]-5-formylbenzonitrile.

LC-MS (ESI): m/z 487 [M+H]$^+$; 3.36 min (ret time).

D75 5-(Aminomethyl)-2-((5-chloropyridin-3-yl)oxy)benzonitrile

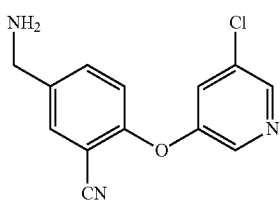 [SMILES: N#Cc1cc(CN)ccc1Oc1cncc(Cl)c1]

The title compound was prepared by a procedure similar to that described for D77 starting with 2-[(5-chloro-3-pyridinyl) oxy]-5-formylbenzonitrile

D76 4-((5-Chloropyridin-3-yl)oxy)benzaldehyde

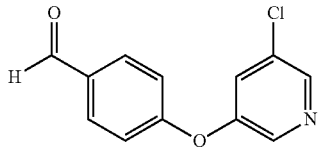 [SMILES: O=Cc1ccc(Oc2cncc(Cl)c2)cc1]

To a solution of 4-fluorobenzaldehyde (1.5 g) and 5-chloro-3-pyridinol (1.566 g) in DMF (50 mL) was added K$_2$CO$_3$ (3.34 g). The reaction mixture was stirred at 100° C. for 2 overnight, then concentrated, diluted with ethy acetate (30 mL), then washed with water for three times (15 mL×3), dried over Na$_2$SO$_4$, filtered and reconcentrated. Purification via ISCO system (petroleum ether/ethyl acetate=2/1) afforded the title product (2.46 g).

$^1$H NMR (CDCl$_3$, 400 MHz,) δ: 9.98 (s, 1 H), 8.44 (d, 1 H), 8.36 (d, 1 H), 7.92-7.94 (dd, 2H), 7.41(dd, 1H), 7.13-7.15(dd, 1H).

D77
(4-((5-Chloropyridin-3-yl)oxy)phenyl)methanamine

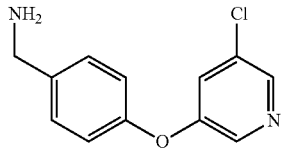 [SMILES: NCc1ccc(Oc2cncc(Cl)c2)cc1]

To a solution of 4-[(5-chloro-3-pyridinyl)oxy]benzaldehyde (175 mg, 0.75 mmol) in EtOH (10 mL) were added hydroxylamine hydrochloride (75.0 mg, 1.45 eq) and sodium acetate (93.0 mg, 1.52 eq). The reaction mixture was stirred at 70° C. until the starting material was consumed up, then washed with dichloromethane for three times (10 mL×3) and brine (15 mL). Combined organic parts were concentrated and dissolved in glacial AcOH (3 mL). Then powdered Zn (196 mg, 4 eq) was added. The reaction mixture was stirred overnight, then filtered through celite, neutralized with saturated solution of Na$_2$CO$_3$ to pH>8 and extracted with ethyl acetate. Combined organic parts were dried over Na$_2$SO$_4$, filtered and concentrated to give the crude product, which was directly used into next step without purification.

LC-MS (ESI): m/z 235 [M+H]$^+$; 1.91 min (ret time).

D78 2-((5-(Trifluoromethyl)pyridin-2-yl)oxy)-5-vinylbenzonitrile

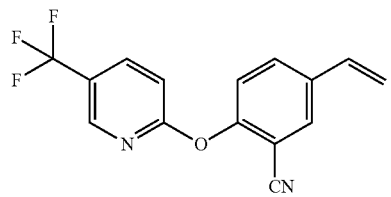 [SMILES: C=Cc1ccc(Oc2ccc(C(F)(F)F)cn2)c(C#N)c1]

To a solution of methyl(triphenyl)phosphonium bromide (1.08 g, 3.01 mmol) in THF (20 mL) was added dropwise BuLi (1.80 mL, 2.87 mmol) at 0° C. The suspension turned yellow and clear. After 30 min at 0° C., 5-formyl-2-{[5-(trifluoromethyl)-2-pyridinyl]oxy}benzonitrile (0.800 g, 2.74 mmol) in THF (5 mL) was added dropwise. The reaction mixture was warmed up to rt and stirred further for 2 h, then quenched with saturated ammonium chloride solution and concentrated. The residue was dissolved into ethyl acetate (100 mL), washed with water then brine, dried over sodium sulfate, filtered and concentrated. Purification via ISCO system afforded the title product (500 mg).

LC-MS (ESI): m/z 291 [M+H]$^+$; 3.64 min (ret time).

D79 5-(2-Hydroxyethyl)-2-(trifluoromethyl)pyridin-2-yl)oxy)benzonitrile

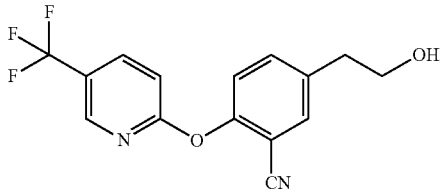 [SMILES: N#Cc1cc(CCO)ccc1Oc1ccc(C(F)(F)F)cn1]

To a solution of 5-ethenyl-2-{[5-(trifluoromethyl)-2-pyridinyl]oxy}benzonitrile (0.350 g, 1.21 mmol) in THF (20 mL) was added dropwise 9-BBN (3.62 mL, 1.81 mmol) at 0° C. Stirring was kept overnight at r.t., solution of sodium hydroxide (2.41 mL, 7.24 mmol), then hydrogen peroxide (0.185 mL, 1.809 mmol) was added at 0° C. The reaction mixture was heated at 50° C. for 2 h, quenched with NaHSO₃ solution and concentrated. Purification via ISCO system afforded the title product (100 mg).

LC-MS (ESI): m/z 309 [M+H]⁺; 2.91 min (ret time).

D80 2-(4-Chloro-3-(trifluoromethyl)phenoxy)-5-formylbenzonitrile

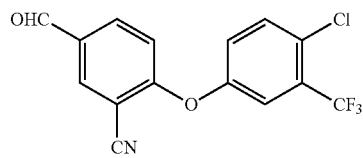 [SMILES: N#Cc1cc(C=O)ccc1Oc1ccc(Cl)c(C(F)(F)F)c1]

To a solution of 4-chloro-3-(trifluoromethyl)phenol (7.5 g, 38 mmol) and 2-fluoro-5-formylbenzonitrile (5.7 g, 38 mmol) in MeCN (100 mL) was added Cs₂CO₃ (15 g, 46 mmol). The reaction mixture was stirred at rt for overnight, then filtered through a pad of celite and concentrated. Purification via flash chromatography on silica gel (petroleum ether/ethyl acetate=10/1 to 3/1) afforded the title product.

$^1$H NMR (400 MHz, CDCl₃) δ: 9.95 (s, 1 H), 8.22 (d, J=2Hz, 1 H), 8.03 (dd, J₁=2 Hz, J₂=8.8 Hz, 1 H), 7.60 (d, J=8.8 Hz, 1 H), 7.48 (d, J=2.8 Hz, 1 H), 7.26 (dd, J₁=2.8 Hz, J₂=8.4 Hz, 1 H), 6.94 (d, J=8.4 Hz, 1 H).

D81 5-(Aminomethyl)-2-(4-chloro-3-(trifluoromethyl)$_p$ henoxy)benzonitrile

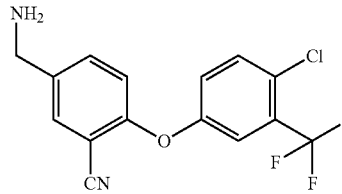

The title compound was prepared by a procedure similar to that described for D77 starting from 2-{[4-chloro-3-(trifluoromethyl)phenyl]oxy}-5-formylbenzonitrile.

D82 5-Hydroxynicotinonitrile

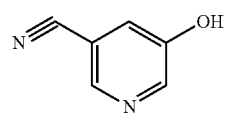

To a solution of 5-bromo-pyridin-3-ol (15.0 g, 86.2 mmol) in DMF (150 mL) was added CuCN (9.30 g, 109 mmol). The reaction mixture was refluxed for 24 h, then concentrated. The crude product was used for the next step without further purification.

D83 5-(2-Cyano-4-formylphenoxy)nicotinonitrile

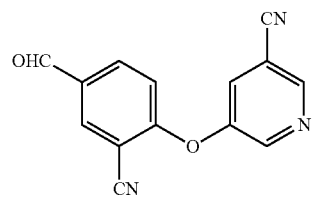 [SMILES: N#Cc1cncc(Oc2ccc(C=O)cc2C#N)c1]

To a stirring solution of 5-hydroxy-nicotinonitrile (8.00 g, 66.7 mmol) and 2-fluoro-5-formylbenzonitrile (10.0 g, 66.7 mmol) in CH₃CN (200 mL) was added Cs₂CO₃ (26 g, 80 mmol), the reaction mixture was stirred at room temperature for 3 days, filtered and concentrated.

Purification via column chromatography on silica gel (petroleum ether/ethyl acetate=8/1 to 2/1) afforded the title product (5.0 g) as a yellow solid $^1$H NMR (400 MHz, CDCl₃) δ: 9.93 (s, 1 H), 8.76 (s, 1 H), 8.67 (s, 1 H), 8.21 (s, 1 H), 8.05 (d, J=8.8 Hz, 1 H), 7.68 (s, 1 H), 6.99 (d, J=8.8 Hz, 1 H).

D84 5-(2-Cyano-4-(hydroxymethyl)phenoxy)nicotinonitrile

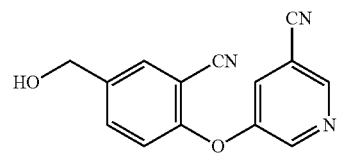 [SMILES: N#Cc1cncc(Oc2ccc(CO)cc2C#N)c1]

The title compound was prepared by a procedure similar to that described for D11 starting from 5-[(2-cyano-4-formylphenyl)oxy]-3-pyridinecarbonitrile.

LC-MS (ESI): m/z 252 [M+H]⁺; 2.60 min (ret time)

D85 (4-(4-Methyl-1H-imidazol-1-yl)phenyl)methanol

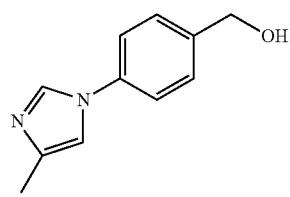

A mixture of 4-methyl-1H-imidazole (1.00 g, 12.2 mmol), 4-fluorobenzaldehyde (1.51 g, 12.2 mmol) and solid $Na_2CO_3$ (2.58 g, 24.4 mmol) in 1,2-dimethoxyethane (DME) (10 mL) and water (10.0 mL) was sealed in a microwave vial and irradiated with a microwave using initial high to 150° C. for 3 h, then diluted with water (10 mL) and extracted with ethyl acetate. Combined organic parts were dried over anhydrous $Na_2SO_4$, filtered and concentrated. The residue was redissolved in ethanol (25 mL) and stirred in an ice-water bath. Then $NaBH_4$ (0.461 g, 12.2 mmol) was added in portions. The reaction mixture was stirred for 1 h, then quenched with saturated ammouina chloride solution and solvent was removed. The residue was extracted with ethyl acetate. Combined organic parts were dried over anhydrous $Na_2SO_4$, filtered and concentrtated. Purification via ISCO system (gradient eluent up to 0-5% methanol in $CH_2Cl_2$; 40 g silica gel column) afforded the title product (0.647 g) as a white solid.

$^1$H NMR ($CDCl_3$, 400 MHz,) δ: 7.63 (s, 1 H), 7.39 (d, J=8.0 Hz, 2 H), 7.26 (d, J=8.0 Hz, 2 H), 6.92 (s, 1 H), 4.68 (s, 2 H), 2.22 (s, 3 H)

D86 2-((5-Chloropyridin-3-yl)oxy)-5-((methylamino)methyl)benzonitrile

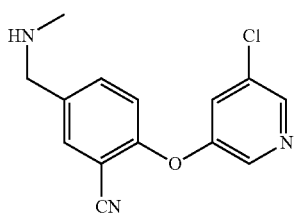 [SMILES: CNCc1ccc(Oc2cncc(Cl)c2)c(C#N)c1]

To a solution of 2-[(5-chloro-3-pyridinyl)oxy]-5-formyl-benzonitrile (100 mg, 0.387 mmol) in dichloromethane (4 mL) were added methylamine hydrochloride (52.0 mg, 0.773 mmol) and sodium acetate (63 mg, 0.773 mmol). After 0.5 h, sodium triacetoxyborohydride (164 mg, 2 eq) and 1 drop of HOAc were added. The reaction mixture was stirred for 1 h, diluted with saturated $NaHCO_3$ and extracted with dichloromethane for three times (5 mL×3). Combined organic parts were dried over $Na_2SO_4$, filtered and concentrated. Purification via ISCO system (dichloromethane/methanol=10/1) afforded the title product (50 mg).

LC-MS (ESI): m/z 274 [M+H]$^+$; 1.93 min (ret time)

D87 5-Formyl-2-((5-(trifluoromethyl)pyridin-3-yl)oxy)benzonitrile

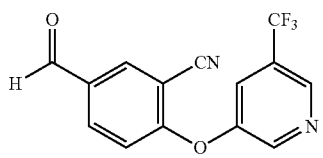 [SMILES: N#Cc1cc(C=O)ccc1Oc1cncc(C(F)(F)F)c1]

To a solution of phenyl-methanol (15.1 g, 0.14 mol) in THF (190 mL) was added NaH (5.6 g, 0.14 mol) at 0° C. The mixture was stirred at 0° C. for 30 min, the solvent was removed in vacuo, then a solution of 3-chloro-5-trifluoromethyl-pyridine (17 g, 0.093 mol) in DMSO (200 mL) was added to the mixture above. The resulting mixture was stirred at 130° C. overnight. Then $H_2O$ (200 mL) was added in. The mixture was extracted with EtOAc (200 mL×3). The combined organic layer was washed with brine, dried over sodium sulfate and purified by column chromatography on silica gel (hexane:EtOAc=100:1 to 50:1) to afford 3-benzyloxy-5-trifluoromethyl-pyridine as a yellow oil (20 g, 85%).

$^1$H NMR (400 MHz, $CDCl_3$) δ: 8.46 (s, 1H), 8.42 (s, 1H), 7.42(s, 1H), 7.15-7.38 (m, 5H), 5.08(s, 2H).

To a solution of 3-benzyloxy-5-trifluoromethyl-pyridine (8 g, 0.032 mol) in MeOH (160 mL) was added Pd/C (4 g, with water <1%). The mixture was stirred at 50° C. under $H_2$ (55 Psi) for 48 hours. The reaction mixture was filtered and the filtrate was concentrated under reduced pressure to afford 5-trifluoromethyl-pyridin-3-ol as a white solid (3.6 g, 69.9%).

$^1$H NMR (400 MHz, $CD_3OD$) δ: 8.33 (d, J=2.4 Hz, 1H), 8.31 (s, 1H), 7.43 (s, 1H).

To a stirring solution of 5-trifluoromethyl-pyridin-3-ol (3.6 g, 0.022 mol) and 2-fluoro-5-formyl-benzonitrile (3.0 g, 0.022 mol) in $CH_3CN$ (60 ml) was added $Cs_2CO_3$ (8.6 g, 0.026 mol), the reaction mixture was stirred at RT overnight. The reaction mixture was filtered and the filtrate was concentrated under reduced pressure to remove $CH_3CN$. The crude product was purified by column chromatography on silica gel (hexane:EtOAc=10:1 to 3:1) to afford 5-formyl-2-(5-trifluoromethyl-pyridin-3-yloxy)-benzonitrile as a white solid (5.1 g, 76%).

$^1$H NMR (400 MHz, $CDCl_3$) δ: 9.92 (s, 1H), 8.79 (s, 1H), 8.66 (d, J=2.4 Hz, 1H), 8.20(d, J=1.6 Hz, 1H), 8.02 (d, J=8.8 Hz, 1H), 7.67 (s, 1H), 6.94 (d, J=8.8 Hz, 1H).

D88 5-(Hydroxymethyl)-2-((5-(trifluoromethyl)pyridin-3-yl)oxy)benzonitrile

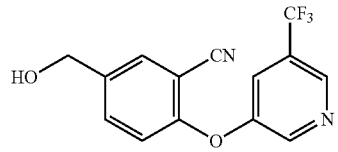

To a solution of 5-formyl-2-{[5-(trifluoromethyl)-3-pyridinyl]oxy}benzonitrile (300 mg, 1.03 mmol) in ethanol (10 mL) was added $NaBH_4$ (58.3 mg, 1.54 mmol). The reaction mixture was stirred for 1 h at room temperature, then quenched with aq. $NH_4Cl$, diluted with ethyl acetate (200 mL), washed with water (50 mL×3) then brine and concentrated. Purification via ISCO system (EtOAc/PEethyl acetate/petroleum ether=1/2, 1/1) afforded the desired product as a pale yellow oil.

LC-MS (ESI): m/z 295 [M+H]$^+$; 2.62 min (ret time)

D89 2-(4-Chloro-3-(trifluoromethyl)phenoxy)-5-formylbenzonitrile

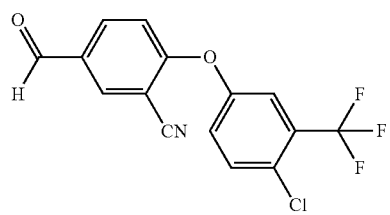 [SMILES: N#Cc1cc(C=O)ccc1Oc1ccc(Cl)c(C(F)(F)F)c1]

The title compound was prepared by a procedure similar to that described for D10 starting from 2-fluoro-5-formylbenzonitrile and 4-chloro-3-(trifluoromethyl)phenol.

D90 2-(3-Chloro-4-(trifluoromethyl)phenoxy)-5-((methylamino)methyl)be-nzonitrile

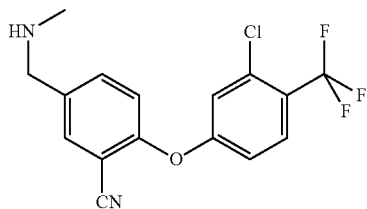 [SMILES: CNCc1ccc(Oc2ccc(C(F)(F)F)c(Cl)c2)c(C#N)c1]

The title compound was prepared by a procedure similar to that described for D77 starting from 2-{[3-chloro-4-(trifluoromethyl)phenyl]oxy}-5-formylbenzonitrile.
LC-MS (ESI): m/z 341 [M+H]$^+$; 2.70 min (ret time)

D91 4-(3-(trifluoromethyl)phenoxy)benzaldehyde

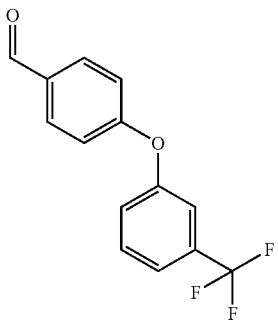 [SMILES: O=Cc1ccc(Oc2cccc(C(F)(F)F)c2)cc1]

To a solution of 4-fluorobenzaldehyde (306 mg, 2.47 mmol) in DMF (10 mL) was added 3-(trifluoromethyl)phenol (400 mg, 2.47 mmol) and K$_2$CO$_3$ (682 mg, 4.94 mmol). The reaction solution was warm up to 100° C. for 2, then concentrated, diluted with water (10 mL) and extracted with ethyl acetate (10 mL×3). Combined organic parts were dried over Na$_2$SO$_4$, filtered and concentrated. The crude product was used into next step directly.
LC-MS (ESI): m/z 267 [M+H]$^+$; 3.60 min (ret time).

D92 (4-(3-(trifluoromethyl)phenoxy)phenyl)methanol

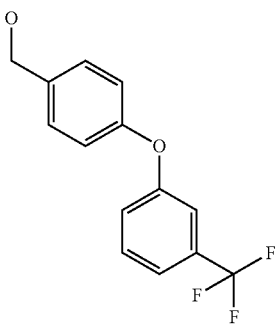 [SMILES: OCc1ccc(Oc2cccc(C(F)(F)F)c2)cc1]

To a solution of 4-{[3-(trifluoromethyl)phenyl]oxy}benzaldehyde (657 mg, 2.47 mmol) in EtOH (20 mL) at 0° C. added slowly NaBH$_4$ (9.00 mg, 2.47 mmol). The reaction solution was stirred for 1.5 h, then quenched with water (5 mL), extracted with ethyl acetate (20 mL). Combined organic parts were dried over Na$_2$SO$_4$, filtered and concentrated. Purification via ISCO system (petroleum ether/ethyl acetate=3/1) afforded the title product.
LC-MS (ESI): m/z 251 [M–H$_2$O+H]$^+$; 3.25 min (ret time).

D93 3,5-difluoro-4-(3-(trifluoromethyl)phenoxy)benzonitrile

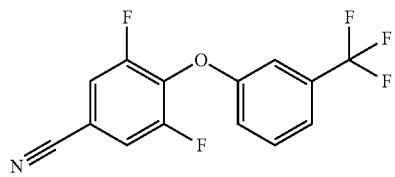 [SMILES: N#Cc1cc(F)c(Oc2cccc(C(F)(F)F)c2)c(F)c1]

The title compound was prepared by a procedure similar to that described for D91 starting from 3,4,5-Trifluorobenzonitrile and 3-(Trifluoromethyl)phenol.
LC-MS (ESI): m/z 300 [M+H]$^+$; 3.74 min (ret time).

D94 (3,5-difluoro-4-(3-(trifluoromethyl)phenoxy)phenyl)methanamine

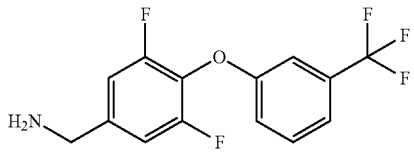 [SMILES: NCc1cc(F)c(Oc2cccc(C(F)(F)F)c2)c(F)c1]

To a solution of 3,5-Difluoro-4-{[3-(trifluoromethyl)phenyl]oxy}benzonitrile (1.57 g, 5.25 mmol) in Tetrahydrofuran (THF) (16 mL) was added dropwise borane solution in THF (15.0 mL, 15.0 mmol) at 0° C. The reaction mixture was refluxed for 3 h, then quenched with HCl (6.0 M, 4.0 mL, 24 mmol), basified with 1M NaOH solution, diluted with water and extracted with dichloromethane. Combined organic parts were dried over Na$_2$SO$_4$, filtered and concentrated. Purification via ISCO system afforded the title product as a colorless liquid.
LC-MS (ESI): m/z 267 [M+H]$^+$; 3.60 min (ret time).

D95 3-fluoro-4-(3-(trifluoromethyl)phenoxy)benzonitrile

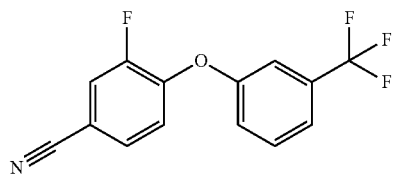 [SMILES: N#Cc1ccc(Oc2cccc(C(F)(F)F)c2)c(F)c1]

The title compound was prepared by a procedure similar to that described for D91 starting from 3,4-Difluorobenzonitrile and 3-(Trifluoromethyl)phenol.

D96 (3-fluoro-4-(3-(trifluoromethyl)phenoxy)phenyl)methanamine

The title compound was prepared by a procedure similar to that described for D94 starting from 3-fluoro-4-(3-(trifluoromethyl)phenoxy)benzonitrile.

D97 3-fluoro-4-(3-(trifluoromethyl)phenoxy)benzaldehyde

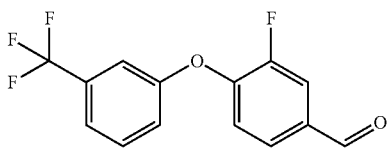 [SMILES: O=Cc1ccc(Oc2cccc(C(F)(F)F)c2)c(F)c1]

The title compound was prepared by a procedure similar to that described for D91 starting from 3,4-Difluorobenzaldehyde.
LC-MS (ESI): m/z 285 [M+H]$^+$; 3.59 min (ret time).

D98 (3-fluoro-4-(3-(trifluoromethyl)phenoxy)phenyl)methanol

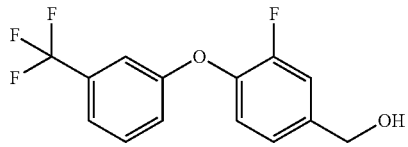 [SMILES: OCc1ccc(Oc2cccc(C(F)(F)F)c2)c(F)c1]

The title compound was prepared by a procedure similar to that described for D92 starting from 3-Fluoro-4-{[3-(trifluoromethyl)phenyl]oxy}benzaldehyde.
LC-MS (ESI): m/z 269 [M−H$_2$O+H]$^+$; 3.32 min (ret time).

D99 1-chloro-4-(4-nitrophenoxy)-2-(trifluoromethyl)benzene

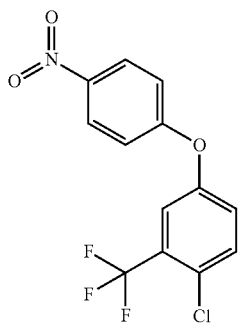 [SMILES: O=[N+]([O-])c1ccc(Oc2ccc(Cl)c(C(F)(F)F)c2)cc1]

The title compound was prepared by a procedure similar to that described for D91 starting from 4-chloro-3-(trifluoromethyl)phenol and 1-fluoro-4-nitrobenzene.
LC-MS (ESI): m/z 318 [M+H]$^+$; 3.92 min (ret time).

D100 4-(4-chloro-3-(trifluoromethyl)phenoxy)aniline

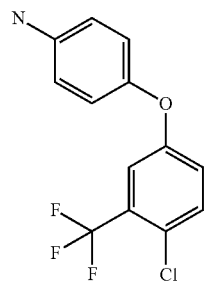 [SMILES: Nc1ccc(Oc2ccc(Cl)c(C(F)(F)F)c2)cc1]

To a solution of 1-chloro-4-[(4-nitrophenyl)oxy]-2-(trifluoromethyl)benzene (20 mg, 0.063 mmol) in Methanol (20 mL) was added Raney Nickel (7.39 mg, 0.126 mmol). When the starting material was converted completely by LCMS, The reaction mixture was flitered and concentrated to get the crude, which was used into next step.
LC-MS (ESI): m/z 288 [M+H]$^+$; 2.69 min (ret time).

D101 4-(4-chloro-3-(trifluoromethyl)phenoxy)phenol

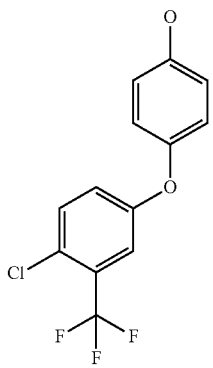 [SMILES: Oc1ccc(Oc2ccc(Cl)c(C(F)(F)F)c2)cc1]

To a suspension of 4-{[4-chloro-3-(trifluoromethyl)phenyl]oxy}aniline (380 mg, 1.32 mmol) in Water (20 mL) were added hydrochloric acid (0.401 mL, 13.2 mmol) and a solution of sodium nitrite (100 mg, 1.45 mmol) in water (5 mL) at 0° C. The reation mixture was stirred for 1 h, then poured into a boiling solution of water (15 mL) and sulfuric acid (15 mL, 281 mmol). The solution was refluxed for 1 h, then cooled to room temperature and extracted with ethyl acetate (30 mL×2). Combined the organic parts were washed with water and brine, dried over sodium sulfate, filtered and concentrated. Purification via ISCO system afforded the title product as a white solid.

D102 6-methoxy-1-methyl-3,4-dihydroisoquinoline

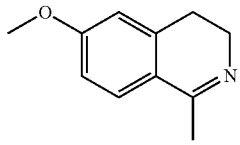

To a solution of N-{2-[3-(methyloxy)phenyl]ethyl}acetamide (12.8 g, 66.1 mmol) in dry Dichloromethane (DCM) (20 mL) was added POCl₃ (24.6 mL, 264 mmol). The reaction mixture was refluxed for 2 h, then diluted with H₂O, basified with a solution of 5% NH₄OH and extracted with CH₂Cl₂. Separated organic part was washed with water, dried over anhydrous Na₂SO₄, filtered and concentrated. Purification via ISCO system (dichloromethane/methanol=97/3) afforded the title product.

LC-MS (ESI): m/z 176 [M+H]$^+$; 1.52 min (ret time).

D103 2-(2,2-dimethyl-4,6-dioxo-1,3-dioxan-5-ylidene)-2-hydroxyethyl acetate

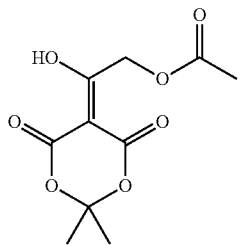 [SMILES: CC(=O)OCC(O)=C1C(=O)OC(C)(C)OC1=O]

A mixture of (acetyloxy)acetic acid (4.5 g, 38.1 mmol) and DCC (9.28 g, 45.0 mmol) in Dichloromethane (DCM) (20 mL) was stirred for 30 min with ice bath. Then 2,2-dimethyl-1,3-dioxane-4,6-dione (5.40 g, 37.5 mmol) and dimethylaminopyridine (11.4 g, 94.0 mmol) were added. The reaction mixture was stirred at room temp over one day, then filtered and extracted with dichloromethane. Combined dichloromethane parts were washed with 1 N HCl (100 mL*2), then water (100 mL) and brine (100 mL), dried over anhydrous sodium sulfate, filtered and concentrated. The crude was washed with MeOH (5 mL) to give the title product as a white silid.

D104 (9-methoxy-4-oxo-6,7-dihydro-4H-pyrido[2,1-a]isoquinolin-2-yl)methyl acetate

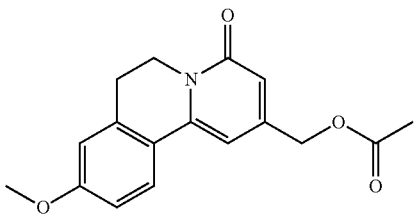 [SMILES: COc1ccc2c(c1)CCn1c-2cc(COC(C)=O)cc1=O]

A mixture of 1-methyl-6-(methyloxy)-3,4-dihydroisoquinoline (500 mg, 2.85 mmol), 2-(2,2-dimethyl-4,6-dioxo-1,3-dioxan-5-ylidene)-2-hydroxyethyl acetate (2090 mg, 8.56 mmol) and trifluoroacetic acid (0.220 mL, 2.85 mmol) in 1,2-dichloroethane was sealed in a microwave via and irradiated with a microwave in Biotage Initiator using initial high to 160° C. for 30 min, then concentrated. Purification via ISCO system with dichloroethane/methanol=97/3 afforded the desired product as a yellow oil.

LC-MS (ESI): m/z 300 [M+H]$^+$; 2.63 min (ret time).

D105 2-(hydroxymethyl)-9-methoxy-6,7-dihydro-4H-pyrido[2,1-a]isoquinolin-4-one

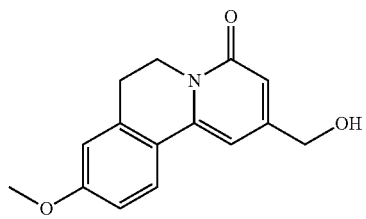 [SMILES: COc1ccc2c(c1)CCn1c-2cc(CO)cc1=O]

To a solution of [9-(methyloxy)-4-oxo-6,7-dihydro-4H-pyrido[2,1-a]isoquinolin-2-yl]methyl acetate (20 mg, 0.067 mmol) in methanol (2.0 mL) and water (2.0 mL) was added NaOH (8.02 mg, 0.200 mmol). The reaction mixture was stirred at room temp. for 3 h, then concentrated to remove solvent and extracted with dichloromethane. Combined organic parts were dried over anhydrous Na₂SO₄, filtered and concentrated. The residue was used into next step without purification.

LC-MS (ESI): m/z 258 [M+H]$^+$; 2.13 min (ret time).

D106 1-chloro-4-(4-nitrophenoxy)-2-(trifluoromethyl)benzene

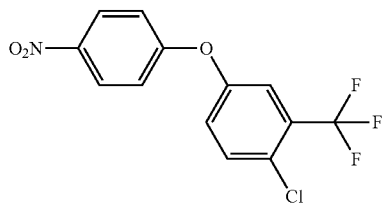 [SMILES: O=[N+]([O-])c1ccc(Oc2ccc(Cl)c(C(F)(F)F)c2)cc1]

The title compound was prepared by a procedure similar to that described for D100 starting from 4-chloro-3-(trifluoromethyl)phenol and 1-fluoro-4-nitrobenzene

D107 2-(4-chloro-3-(trifluoromethyl)phenoxy)-5-formylbenzonitrile

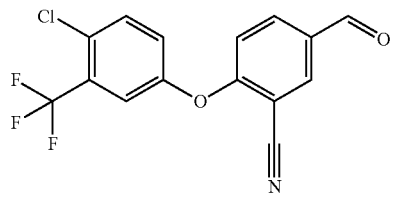 [SMILES: N#Cc1cc(C=O)ccc1Oc1ccc(Cl)c(C(F)(F)F)c1]

The title compound was prepared by a procedure similar to that described for D91 starting from 4-chloro-3-trifluoromethyl-phenol, Cs₂CO₃ and 2-fluoro-5-formyl-benzonitrile in acetonitrile.

¹H NMR (CDCl₃, 400 MHz,) δ: 9.89 (1 H, s), 8.16 (1 H, d, J=2.0 Hz), 7.98 (1 H, dd, J₁-8.4 Hz & J₂=2.0 Hz), 7.55 (1 H, d, J=8.4 Hz), 7.43 (1 H, d, J=2.8 Hz), 7.21 (1 H, dd, J₁=8.8 Hz & J₂=2.8 Hz), 6.89 (1 H, d, J=8.4 Hz).

D108 2-(4-chloro-3-(trifluoromethyl)phenoxy)-5-(hydroxymethyl)benzonitrile

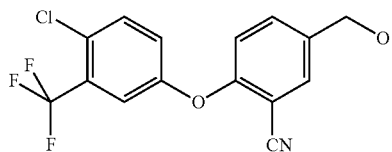 [SMILES: N#Cc1cc(CO)ccc1Oc1ccc(Cl)c(C(F)(F)F)c1]

The title compound was prepared by a procedure similar to that described for D92 starting from 2-(4-chloro-3-(trifluoromethyl)phenoxy)-5-formylbenzonitrile LC-MS (ESI): m/z 310 [M–H₂O+H]⁺; 3.28 min (ret time).

D109
2-(3-(trifluoromethyl)phenoxy)-5-vinylbenzonitrile

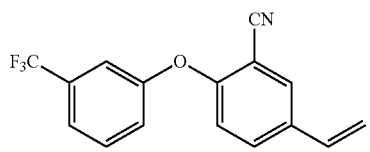 [SMILES: C=Cc1ccc(Oc2cccc(C(F)(F)F)c2)c(C#N)c1]

The title compound was prepared by a procedure similar to that described for D78 starting from methyltriphenoxyphosphonium iodide.

LC-MS (ESI): m/z 308 [M+H]⁺; 3.18 min (ret time).

D110 5-(2-hydroxyethyl)-2-(3-(trifluoromethyl)phenoxy)benzonitrile

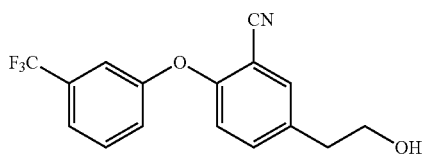 [SMILES: N#Cc1cc(CCO)ccc1Oc1cccc(C(F)(F)F)c1]

The title compound was prepared by a procedure similar to that described for D79 starting from 5-ethenyl-2-{[3-(trifluoromethyl)phenyl]oxy}benzonitrile LC-MS (ESI): m/z 308 [M+H]⁺; 3.18 min (ret time).

D111 1-chloro-4-(4-(chloromethyl)phenoxy)-2-(trifluoromethyl)benzene

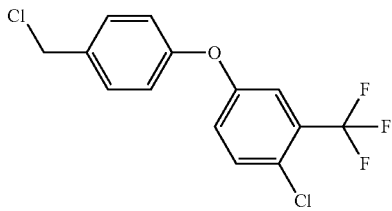 [SMILES: FC(F)(F)c1cc(Oc2ccc(CCl)cc2)ccc1Cl]

The title compound was prepared by a procedure similar to that described for D24 starting from (4-{[4-chloro-3-(trifluoromethyl)phenyl]oxy}phenyl)methanol.

D112 N-(3-methoxyphenethyl)acetamide

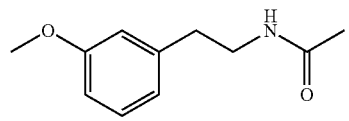

To a solution of {2-[3-(methyloxy)phenyl]ethyl}amine (10.0 g, 66.1 mmol) and pyridine (16.1 mL, 198 mmol) in Dichloromethane (20 mL) was added dropwise acetyl chloride (7.79 g, 99.0 mmol) during 15 min under nitrogen at 0° C. The reaction mixture was stirred at room temp., then diluted with dichloromethane, washed with 1N HCl, water and brine. Separated organic part was dried over anhydrous Na₂SO₄, filtered and concentrated. Purification via ISCO system (dichloromethane/methanol=20/1) afforded the title product.

LC-MS (ESI): m/z 194 [M+H]⁺; 2.07 min (ret time).

D113 2-hydroxy-9-methoxy-6,7-dihydro-4H-pyrido[2,1-a]isoquinolin-4-one

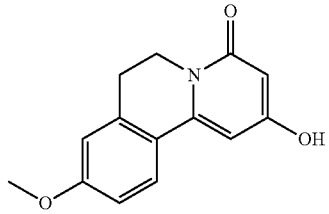 [SMILES: COc1ccc2c(c1)CCn1c-2cc(O)cc1=O]

A mixture of 1-methyl-6-(methyloxy)-3,4-dihydroisoquinoline (1.50 g, 8.56 mmol) and dimethyl propanedioate (5.65 g, 42.8 mmol) in N-Methyl-2-pyrrolidone (15 mL) was sealed in a microwave vial and irradiated in Biotage Initiator using initial high to 200° C. for 20 min, then diluted with water and extracted with ethyl acetate. Combined organic parts were dried over Na₂SO₄, filtered and concentrated. Purification via Biotage (5%-95%=acetonitrile/water; reverse phase column) afforded the title product.

LC-MS (ESI): m/z 244 [M+H]⁺; 2.20 min (ret time).

D114 5-(difluoromethyl)-2-(3-(trifluoromethyl)phenoxy)benzonitrile

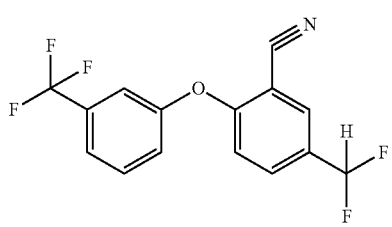 [SMILES: N#Cc1cc(C(F)F)ccc1Oc1cccc(C(F)(F)F)c1]

The title compound was prepared by a procedure similar to that described for D28 starting from 5-formyl-2-(3-trifluoromethyl-phenoxy)-benzonitrile.

$^1$H NMR (400 MHz, CDCl$_3$) δ: 7.78 (s, 1H), 7.58 (d, J=8.8 Hz, 1H), 7.49 (m, 2H), 7.31 (s, 1H), 7.24 (d, J=7.6 Hz, 1H), 6.89 (d, J=8.8 Hz, 1H), 6.58 (t, J=56 Hz, 1H).

D115 5-(chlorodifluoromethyl)-2-(3-(trifluoromethyl)phenoxy)benzonitrile

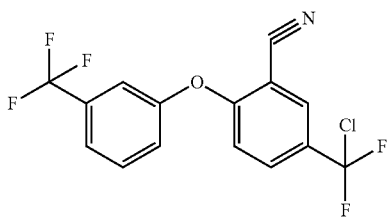 [SMILES: N#Cc1cc(C(F)(F)Cl)ccc1Oc1cccc(C(F)(F)F)c1]

The title compound was prepared by a procedure similar to that described for D29 starting from 5-difluoromethyl-2-(3-trifluoromethyl-phenoxy)-benzonitrile.

$^1$H NMR (400 MHz, CDCl$_3$) δ: 7.97 (s, 1 H), 7.75 (d, J=9.2 Hz, 1 H), 7.60 (m, 2 H), 7.40 (s, 1 H), 7.32 (d, J=7.2 Hz, 1 H), 6.92 (d, J=9.2 Hz, 1 H).

D116 5-(chloromethyl)-2-(3-(trifluoromethyl)phenoxy)benzonitrile

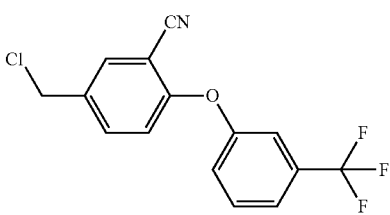 [SMILES: N#Cc1cc(CCl)ccc1Oc1cccc(C(F)(F)F)c1]

To a solution of 5-Hydroxymethyl-2-(3-trifluoromethyl-phenoxy)-benzonitrile (20.0 g, 68.2 mmol) in toluene (200 mL) was added SOCl$_2$ (5.40 mL, 75.1 mmol). The reaction solution was stirred at room temperature overnight, then diluted with H$_2$O (100 mL). Separated organic part was dried over Na$_2$SO$_4$, filtered, concentrated and recrystallized with petroleum ether (100 mL) to give the title product.

$^1$H NMR (400 MHz, CDCl$_3$) δ: 7.75 (s, 1 H), 7.55 (m, 3 H), 7.35(s, 1 H), 7.28 (s, 1 H), 6.88 (d, J=8.4 Hz, 1H), 4.57 (s, 2H).

D117 5-bromo-2-(4-chloro-3-(trifluoromethyl)phenoxy)benzonitrile

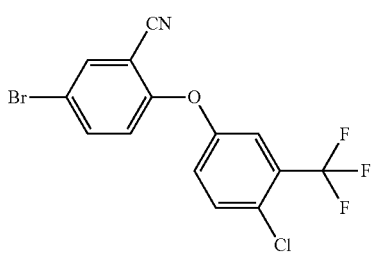 [SMILES: N#Cc1cc(Br)ccc1Oc1ccc(Cl)c(C(F)(F)F)c1]

The title compound was prepared by a procedure similar to that described for D4 starting from 5-bromo-2-fluorobenzonitrile and 3-(trifluoromethyl)-4-chlorophenol.

D118 2-(4-chloro-3-(trifluoromethyl)phenoxy)-5-hydroxybenzonitrile

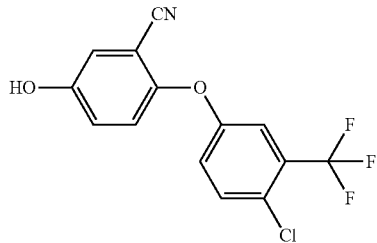 [SMILES: N#Cc1cc(O)ccc1Oc1ccc(Cl)c(C(F)(F)F)c1]

The title compound was prepared by a procedure similar to that described for D5 and D6 starting from 5-bromo-2-{[3-(trifluoromethyl)phenyl]oxy}benzonitrile.

D119 2-(4-(4-chloro-3-(trifluoromethyl)phenoxy)benzyl)isoindoline-1,3-dione

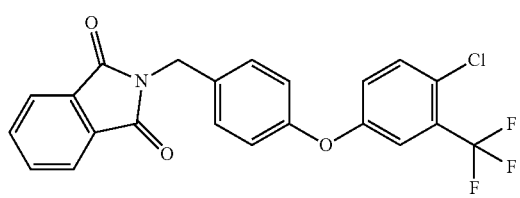 [SMILES: O=C1c2ccccc2C(=O)N1Cc1ccc(Oc2ccc(Cl)c(C(F)(F)F)c2)cc1]

A mixture of 1-chloro-4-{[4-(chloromethyl)phenyl]oxy}-2-(trifluoromethyl)benzene (580 mg, 1.81 mmol), pyridine (1.46 mL, 18.1 mmol), phthalimide, potassium (669 mg, 3.61 mmol) and 18-crown-6 (47.7 mg, 0.181 mmol) in Tetrahydrofuran (15 mL) was stirred at room temperature under N$_2$ overnight, then concentrated, diluted with water and extracted with dichloromethane (10 mL×3). Combined organic parts were washed with brine, dried over MgSO$_4$, filtered and concentrated to give the crude product.

LC-MS (ESI): m/z 432 [M+H]$^+$; 4.17 min (ret time).

D120 (4-(4-chloro-3-(trifluoromethyl)phenoxy)phenyl)methanamine

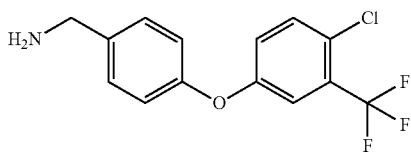 [SMILES: NCc1ccc(Oc2ccc(Cl)c(C(F)(F)F)c2)cc1]

A mixture of 2-[(4-{[4-chloro-3-(trifluoromethyl)phenyl]oxy}phenyl)methyl]-1H-isoindole-1,3(2H)-dione (0.777 g, 1.80 mmol) and hydrazine (2.12 g, 36.0 mmol) in ethanol (15 mL) was stirred at room temperature under N$_2$ overnight, then filtered, acidified with 1N HCl (50 mL) and extracted with dichloromethane (50 mL*2). The aqueous part was neutralized to pH=11 with 2 N NaOH and extracted with dichloromethane (50 mL*2). Combined organic parts were washed with brine, dried over Na$_2$SO$_4$, filtered and concentrated. Purification via Biotage system (5%-95% MeCN/H$_2$O; reverse phase column) afforded the desired product as a yellow solid.

LC-MS (ESI): m/z 285 [M−NH$_3$+H]$^+$; 2.72 min (ret time).

D121 5-((1,3-dioxoisoindolin-2-yl)methyl)-2-(3-(trifluoromethyl)phenoxy)benzonitrile

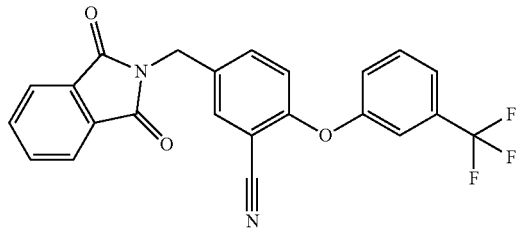 [SMILES: N#Cc1cc(CN2C(=O)c3ccccc3C2=O)ccc1Oc1cccc(C(F)(F)F)c1]

The title compound was prepared by a procedure similar to that described for D119 starting from 5-(chloromethyl)-2-{[3-(trifluoromethyl)phenyl]oxy}benzonitrile.

D122 5-(aminomethyl)-2-(3-(trifluoromethyl)phenoxy)benzonitrile

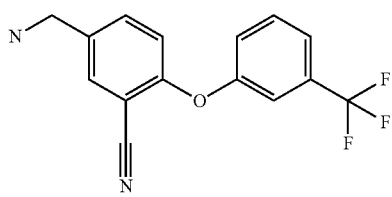 [SMILES: N#Cc1cc(CN)ccc1Oc1cccc(C(F)(F)F)c1]

The title compound was prepared by a procedure similar to that described for D120 starting from 5-((1,3-dioxoisoindolin-2-yl)methyl)-2-(3-(trifluoromethyl)phenoxy)benzonitrile.

LC-MS (ESI): m/z 276[M–NH$_3$+H]$^+$; 2.46 min (ret time).

D123 9-methoxy-4-oxo-6,7-dihydro-4H-pyrido[2,1-a]isoquinolin-2-yl trifluoromethanesulfonate

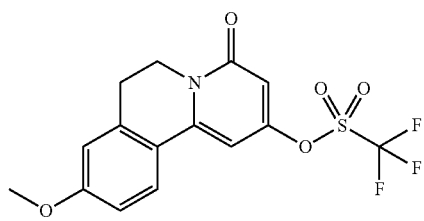 [SMILES: COc1ccc2c(c1)CCn1c-2cc(OS(=O)(=O)C(F)(F)F)cc1=O]

To a solution of 2-hydroxy-9-(methyloxy)-6,7-dihydro-4H-pyrido[2,1-a]isoquinolin-4-one (300 mg, 1.23 mmol) and 1,1,1-trifluoro-N-phenyl-N—[(trifluoromethyl)sulfonyl]methanesulfonamide (441 mg, 1.23 mmol) in Dichloromethane (10 mL) was added triethylamine (0.344 mL, 2.47 mmol). The reaction solution was stirred at room temp. under N$_2$ overnight, then diluted with water, extracted with ethyl acetate. Combined organic parts were dried over Na$_2$SO$_4$, filtered and concentrated Purification via Biotage system (5%-95% acetonitrile/water; reverse phase column) afforded the desired product as a yellow solid.

LC-MS (ESI): m/z 376[M+H]$^+$; 3.31 min (ret time).

D124 5-(2-cyano-4-((methylamino)methyl)phenoxy)nicotinonitrile

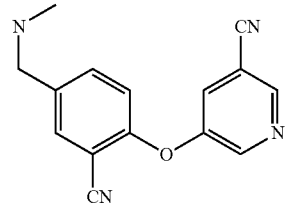 [SMILES: CNCc1ccc(Oc2cncc(C#N)c2)c(C#N)c1]

To a solution of 5-[(2-cyano-4-formylphenyl)oxy]-3-pyridinecarbonitrile (100 mg, 0.38 mmol) in dichloromethane were added methylamine hydrochloride (54.0 mg, 0.76 mmol) and sodium acetate (66 mg, 0.76 mmol). After 30 min, sodium triacetoxyborohydride (170 mg, 0.76 mmol) and 1 drop of acetic acid were added. The reaction mixture was stirred for 1 h, then quenched with saturated NaHCO$_3$ and extracted with dichloromethane (3*5 mL). Combined organic parts were dried over Na$_2$SO$_4$, filtered and concentrated. Purification via ISCO system (dichloromethane/methanol=10/1) afforded the title product.

LC-MS (ESI): m/z 265[M+H]$^+$; 1.64 min (ret time).

D125 5-(hydroxymethyl)-2-(pyridin-3-yloxy)benzonitrile

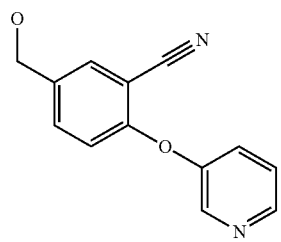 [SMILES: N#Cc1cc(CO)ccc1Oc1cccnc1]

The title compound was prepared by a procedure similar to that described for D91 and D92 starting from fluoro-5-formylbenzonitrile and 3-pyridinol.

D126 2-((5-(trifluoromethyl)pyridin-3-yl)oxy)-5-vinylbenzonitrile

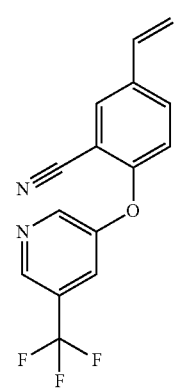 [SMILES: C=Cc1ccc(Oc2cncc(C(F)(F)F)c2)c(C#N)c1]

The title compound was prepared by a procedure similar to that described for D78 starting from 5-ethenyl-2-{[5-(trifluoromethyl)-3-pyridinyl]oxy}benzonitrile.

LC-MS (ESI): m/z 291[M+H]$^+$; 3.44 min (ret time).

D127 5-(2-hydroxyethyl)-2-((5-(trifluoromethyl)pyridin-3-yl)oxy)benzonitrile

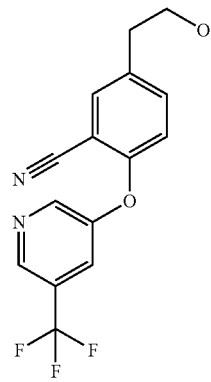 [SMILES: N#Cc1cc(CCO)ccc1Oc1cncc(C(F)(F)F)c1]

The title compound was prepared by a procedure similar to that described for D79 starting from 5-ethenyl-2-{[5-(trifluoromethyl)-3-pyridinyl]oxy}benzonitrile.

D128 5-formyl-2-(pyrimidin-5-yloxy)benzonitrile

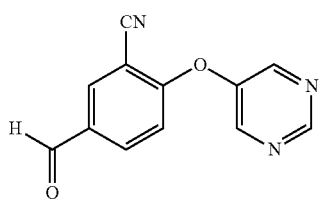 [SMILES: N#Cc1cc(C=O)ccc1Oc1cncnc1]

The title compound was prepared by a procedure similar to that described for D91 starting from 2-fluoro-5-formylbenzonitrile and 5-pyrimidinol.

LC-MS (ESI): m/z 226[M+H]$^+$; 1.93 min (ret time).

D129 5-(hydroxymethyl)-2-(pyrimidin-5-yloxy)benzonitrile

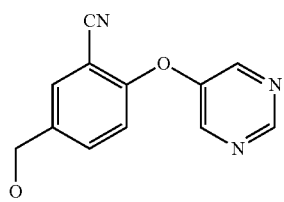 [SMILES: N#Cc1cc(CO)ccc1Oc1cncnc1]

The title compound was prepared by a procedure similar to that described for D92 starting from 5-formyl-2-(5-pyrimidinyloxy)benzonitrile.

LC-MS (ESI): m/z 228[M+H]$^+$; 1.71 min (ret time).

D130 5-hydroxynicotinonitrile

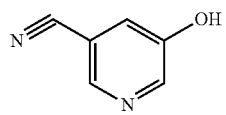

To a solution of 5-bromo-pyridin-3-ol (25.0 g, 144 mmol) in DMF (300 mL) was added CuCN (23.0 g, 259 mmol). The reaction mixture was refluxed for 24 h and concentrated. The crude product was used for the next step without further purification.

D131 5-(2-chloro-4-formylphenoxy)nicotinonitrile

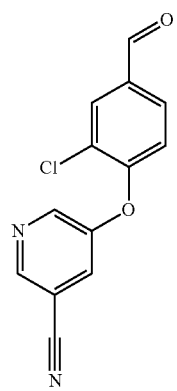 [SMILES: N#Cc1cncc(Oc2ccc(C=O)cc2Cl)c1]

The title compound was prepared by a procedure similar to that described for D91 starting from 3-chloro-4-fluorobenzaldehyde and 5-hydroxynicotinonitrile.

D132 5-(2-chloro-4-(hydroxymethyl)phenoxy)nicotinonitrile

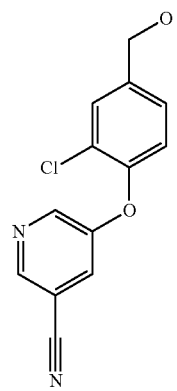 [SMILES: N#Cc1cncc(Oc2ccc(CO)cc2Cl)c1]

The title compound was prepared by a procedure similar to that described for D92 starting from 5-[(2-chloro-4-formylphenyl)oxy]-3-pyridinecarbonitrile.

LC-MS (ESI): m/z 261 [M+H]$^+$; 2.45 min (ret time).

D133 (6-(pyridin-4-yloxy)pyridin-3-yl)methanol

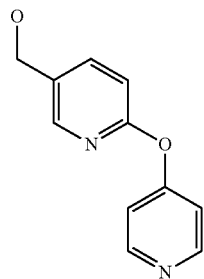 [SMILES: OCc1ccc(Oc2ccncc2)nc1]

The title compound was prepared by a procedure similar to that described for D91 and D92 starting from 6-chloro-3-pyridinecarbaldehyde and 4-pyridinol.
LC-MS (ESI): m/z 203 [M+H]$^+$; 0.98 min (ret time).

D134 3-fluoro-4-(pyrimidin-5-yloxy)benzaldehyde

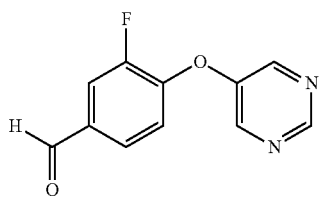 [SMILES: O=Cc1ccc(Oc2cncnc2)c(F)c1]

The title compound was prepared by a procedure similar to that described for D91 starting from 3,4-difluorobenzaldehyde and 5-pyrimidinol.
LC-MS (ESI): m/z 219 [M+H]$^+$; 2.20 min (ret time).

D135 5-(benzyloxy)pyrimidine

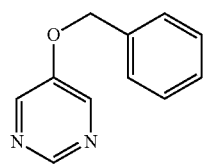 [SMILES: c1ccc(COc2cncnc2)cc1]

To a solution of 5-bromopyrimidine (3.0 g, 0.63 mmol) and phenylmethanol (20 g, 6.3 mmol) in toluene (20 mL) were added Cs$_2$CO$_3$ (9.2 g, 9.5 mmol) and CuI (0.36 g, 0.063 mmol) and 1,10-phenanthroline (0.68 g, 0.13 mmol). The reaction mixture was stirred at 110° C. overnight. Purification via ISCO system (petroleum ether/ethyl acetate=1/1) afforded the tilte product.
LC-MS (ESI): m/z 187 [M+H]$^+$; 2.49 min (ret time).

D136 pyrimidin-5-ol

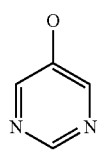

To a solution of 5-[(phenylmethyl)oxy]pyrimidine (2.43 g, 13.0 mmol) in methanol (20 mL) was added Pd/C (10% Pd/C, 10% on carbon). The reaction mixture was stirred at room temperature under H$_2$ atmosphere over weekend, then filtered and concentrated. The residue was used into next step without purification.

D137 (3-fluoro-4-(pyrimidin-5-yloxy)phenyl)methanol

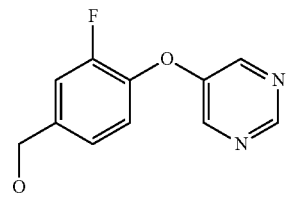 [SMILES: OCc1ccc(Oc2cncnc2)c(F)c1]

The title compound was prepared by a procedure similar to that described for D92 starting from 3-fluoro-4-(5-pyrimidinyloxy)benzaldehyde.
LC-MS (ESI): m/z 221 [M+H]$^+$; 1.91 min (ret time).

D138 5-(2-fluoro-4-formylphenoxy)nicotinonitrile

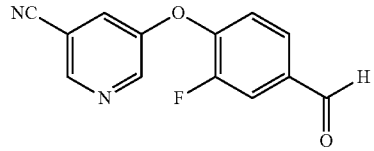 [SMILES: N#Cc1cncc(Oc2ccc(C=O)cc2F)c1]

The title compound was prepared by a procedure similar to that described for D91 starting from 5-hydroxy-nicotinonitrile and 3,4-difluoro-benzaldehyde.
$^1$H NMR (400 MHz, CDCl$_3$) δ: 9.98 (s, 1 H), 8.69 (s, 1 H), 8.64 (s, 1 H), 7.75 (m, 2 H), 7.52 (s, 1 H), 7.29 (m, 2 H).

D139 5-(2-fluoro-4-(hydroxymethyl)phenoxy)nicotinonitrile

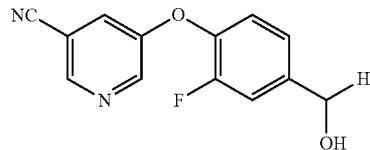 [SMILES: N#Cc1cncc(Oc2ccc(CO)cc2F)c1]

The title compound was prepared by a procedure similar to that described for D92 starting from 5-[(2-fluoro-4-formylphenyl)oxy]-3-pyridinecarbonitrile.

D140 5-(4-formylphenoxy)nicotinonitrile

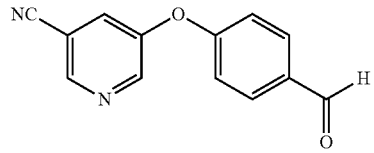 [SMILES: N#Cc1cncc(Oc2ccc(C=O)cc2)c1]

The title compound was prepared by a procedure similar to that described for D91 starting from 5-hydroxynicotinonitrile and 4-fluorobenzaldehyde.

D141 5-(4-(hydroxymethyl)phenoxy)nicotinonitrile

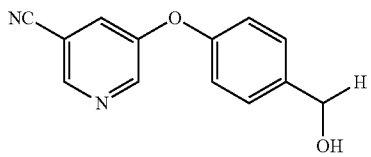 [SMILES: N#Cc1cncc(Oc2ccc(CO)cc2)c1]

The title compound was prepared by a procedure similar to that described for D92 starting from 5-[(4-formylphenyl)oxy]-3-pyridinecarbonitrile.

LC-MS (ESI): m/z 227 [M+H]$^+$; 2.17 min (ret time).

D142 2-((6-(trifluoromethyl)pyridin-3-yl)oxy)-5-vinylbenzonitrile

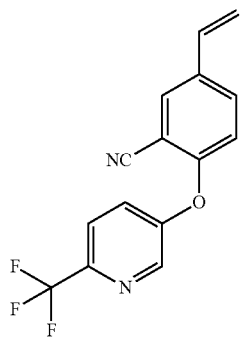 [SMILES: C=Cc1ccc(Oc2ccc(C(F)(F)F)nc2)c(C#N)c1]

The title compound was prepared by a procedure similar to that described for D78 starting from methyl(triphenyl)phosphonium bromide and 5-formyl-2-{[6-(trifluoromethyl)-3-pyridinyl]oxy}ben-zonitrile.

D143 5-(2-hydroxyethyl)-2-((6-(trifluoromethyl)pyridin-3-yl)oxy)benzonitrile

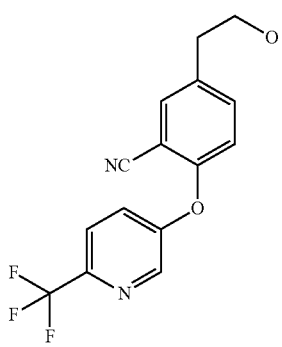 [SMILES: N#Cc1cc(CCO)ccc1Oc1ccc(C(F)(F)F)nc1]

The title compound was prepared by a procedure similar to that described for D79 starting from 5-ethenyl-2-{[6-(trifluoromethyl)-3-pyridinyl]oxy}benzonitrile.

D144 ethyl 5-chloro-6-(3-(trifluoromethyl)phenoxy)nicotinate

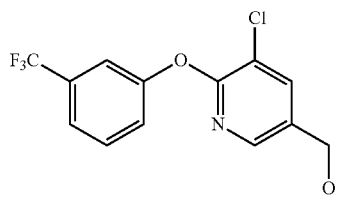 [SMILES: OCc1cnc(Oc2cccc(C(F)(F)F)c2)c(Cl)c1]

A mixture of 3-(trifluoromethyl)phenol (368 mg, 2.27 mmol), ethyl 5,6-dichloro-3-pyridinecarbo-xylate (500 mg, 2.27 mmol) and Na$_2$CO$_3$ (241 mg, 2.27 mmol) in acetonitrile (10 mL) was sealed in a microwave vial and irradiated with a microwave via Biotage microwave reactor at 160° C. for 4 h, then filtered and concentrated. The residue was used directly into next step.

LC-MS (ESI): m/z 293 [M+H]$^+$; 2.97 min (ret time).

D145 (5-chloro-6-(3-(trifluoromethyl)phenoxy)pyridin-3-yl)methanol

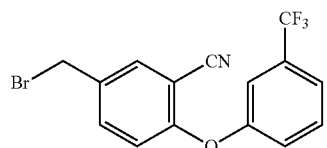

To a solution of ethyl 5-chloro-6-{[3-(trifluoromethyl)phenyl]oxy}-3-pyridinecarboxylate (0.785 g, 2.27 mmol) in ethanol (25 mL) was added calcium chloride (0.250 g, 2.27 mmol) at 0° C. After 15 min, NaBH$_4$ (860 mg, 2.27 mmol) was added. The reaction mixture was stirred at room temperature for 24 h, then quenched with saturated ammonium chloride solution, concentrated to remove ethanol and extracted with ethyl acetate. Combined organic parts were dried over anhydrous Na$_2$SO$_4$, filtered and concentrated. Purification via ISCO system (50% ethyl acetate in petroleum ether) afforded the title product.

LC-MS (ESI): m/z 346 [M+H]$^+$; 4.06 min (ret time).

D146 5-(bromomethyl)-2-(3-(trifluoromethyl)phenoxy)benzonitrile

To a solution of HBr in HOAc (40%) (10.0 mL, 73.7 mmol) was added 5-(hydroxymethyl)-2-{[3-(trifluoromethyl)phenyl]oxy}benzonitrile (0.580 g, 1.98 mmol). The reaction mixture was stirred at 80° C. for 1 h, then concentrated in vacuo, partitioned between ethyl acetate and wate. The organic part was dried over anhydrous sodium sulphate, filtered and concentrated. The residue was directly used into next step without further purification.

D147 2-((5-(trifluoromethyl)pyridin-2-yl)oxy)-5-vinylbenzonitrile

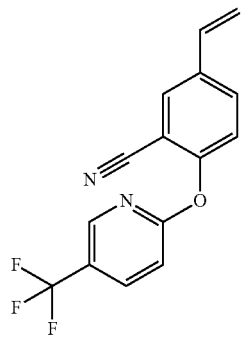 [SMILES: C=Cc1ccc(Oc2ccc(C(F)(F)F)cn2)c(C#N)c1]

The title compound was prepared by a procedure similar to that described for D78 starting from methyltriphenylphosphonium bromide and 5-formyl-2-{[5-(trifluoromethyl)-2-pyridinyl]oxy}benzo-nitrile.

LC-MS (ESI): m/z 291 [M+H]$^+$; 3.61 min (ret time).

D148 5-(2-hydroxyethyl)-2-((5-(trifluoromethyl)pyridin-2-yl)oxy)benzonitrile

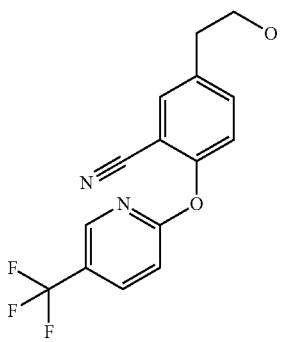 [SMILES: N#Cc1cc(CCO)ccc1Oc1ccc(C(F)(F)F)cn1]

The title compound was prepared by a procedure similar to that described for D79 starting from 5-ethenyl-2-{[5-(trifluoromethyl)-2-pyridinyl]oxy}benzonitrile.

D149 9-methoxy-6,7-dihydro-2H-pyrimido[6,1-a]isoquinoline-2,4(3H)-dione

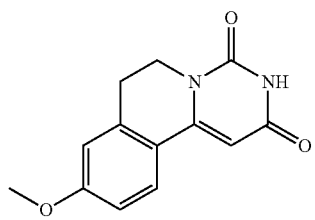 [SMILES: COc1ccc2c(c1)CCn1c-2cc(=O)[nH]c1=O]

To a solution of NaOH (0.800 g, 20.0 mmol) in water (20 mL) was added 2-chloro-9-(methyl-loxy)-6,7-dihydro-4H-pyrimido[6,1-a]isoquinolin-4-one (1.05 g, 4.00 mmol). The suspension was stirred at 110° C. for 2 h, then neutralized with HCl (3 M) around pH=7. The precipitation was collected by filteration, washed with water and dried in vacuum to give the title product as a yellow solid.

LC-MS (ESI): m/z 245 [M+H]$^+$; 2.03 min (ret time).

D150 4-(pyrimidin-5-yloxy)benzaldehyde

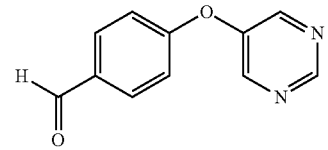 [SMILES: O=Cc1ccc(Oc2cncnc2)cc1]

The title compound was prepared by a procedure similar to that described for D91 starting from 4-fluorobenzaldehyde and 5-pyrimidinol.

LC-MS (ESI): m/z 201 [M+H]$^+$; 2.07 min (ret time).

D151 5-(4-(2-methoxyvinyl)phenoxy)pyrimidine

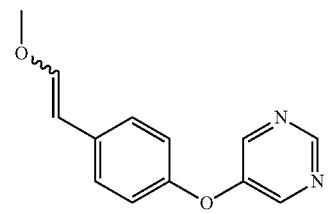 [SMILES: COC=Cc1ccc(Oc2cncnc2)cc1]

To a solution of [(methyloxy)methyl](triphenyl)phosphonium chloride (1.0 g, 3.0 mmol) in THF (8 mL) was added dropwise n-BuLi (2.0 mL, 1.6 M solution in THF) at −78° C. The reaction mixture was stirred at −78° C. for 20 min, then room temperature for 20 min, again cooled down to −78° C. A solution of 4-(pyrimidin-5-yloxy)benzaldehyde in tetrahydrofuran (3 mL) was added slowly. When the desired product was found, the reaction was quenched with saturated NH$_4$Cl (3 mL). Collected organic part was dried over Na$_2$SO$_4$, filtered and concentrated. Purification via ISCO system (petroleum ether/ethyl acetate=3/1) afforded the title product.

LC-MS (ESI): m/z 229 [M+H]$^+$; 2.88 min (ret time).

D152 2-(4-(pyrimidin-5-yloxy)phenyl) acetaldehyde

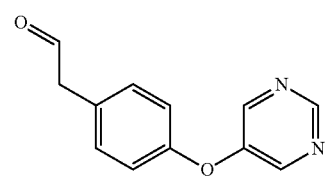 [SMILES: O=CCc1ccc(Oc2cncnc2)cc1]

To a solution of 5-({4-[(E)-2-(methyloxy)ethenyl]phenyl}oxy)pyrimidine (280 mg, 1.23 mmol) in acetonitrile (6 mL) were added NaI (368 mg, 2.45 mmol) and TMSCl (0.31 mL, 2.46 mmol). The reaction solution was stirred at room temperature for 20 min, then quenched with saturated Na$_2$S$_2$O$_3$ (5 mL) and partionated between ethyl acetate (5 mL*3) and water. Combined organic parts were dried over Na$_2$SO$_4$, filtered and concentrated. The residue was used into next step directly.

LC-MS (ESI): m/z 215 [M+H]$^+$; 2.01 min (ret time).

D153 2-(4-(pyrimidin-5-yloxy)phenyl)ethanol

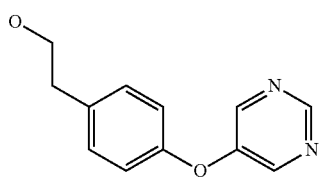 [SMILES: OCCc1ccc(Oc2cncnc2)cc1]

The title compound was prepared by a procedure similar to that described for D92 starting from [4-(5-pyrimidinyloxy)phenyl]acetaldehyde.
LC-MS (ESI): m/z 217 [M+H]$^+$; 1.98 min (ret time).

D154 3-fluoro-4-((6-(trifluoromethyl)pyridin-3-yl)oxy)benzaldehyde

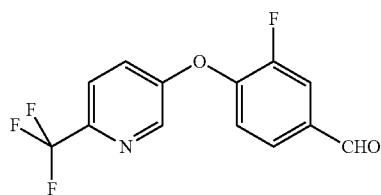 [SMILES: O=Cc1ccc(Oc2ccc(C(F)(F)F)nc2)c(F)c1]

The title compound was prepared by a procedure similar to that described for D91 starting from 6-(trifluoromethyl)-3-pyridinol and 3,4-difluorobenzaldehyde.

D155 (3-fluoro-4-((6-(trifluoromethyl)pyridin-3-yl)oxy)phenyl)methanol

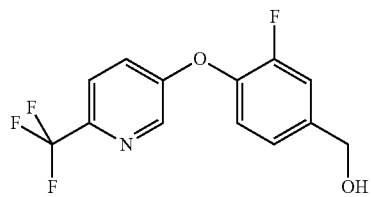 [SMILES: OCc1ccc(Oc2ccc(C(F)(F)F)nc2)c(F)c1]

The title compound was prepared by a procedure similar to that described for D92 starting from 3-fluoro-4-{[6-(trifluoromethyl)-3-pyridinyl]oxy}benzaldehyde.
LC-MS (ESI): m/z 288 [M+H]$^+$; 2.90 min (ret time).

D156 3-fluoro-4-((6-(trifluoromethyl)pyridin-2-yl)oxy)benzaldehyde

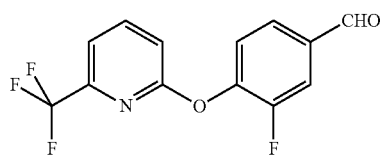 [SMILES: O=Cc1ccc(Oc2cccc(C(F)(F)F)n2)c(F)c1]

The title compound was prepared by a procedure similar to that described for D91 starting from 6-(trifluoromethyl)-2(1H)-pyridinone and 3,4-difluorobenzaldehyde.
LC-MS (ESI): m/z 286 [M+H]$^+$; 3.46 min (ret time).

D157 (3-fluoro-4-((6-(trifluoromethyl)pyridin-2-yl)oxy)phenyl)methanol

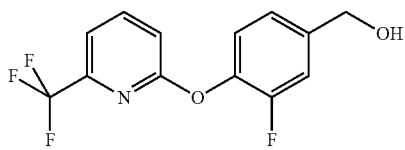 [SMILES: OCc1ccc(Oc2cccc(C(F)(F)F)n2)c(F)c1]

The title compound was prepared by a procedure similar to that described for D92 starting from 3-fluoro-4-{[6-(trifluoromethyl)-2-pyridinyl]oxy}benzaldehyde.
LC-MS (ESI): m/z 288 [M+H]$^+$; 3.06 min (ret time).

D158 5-(4-fluoro-3-(trifluoromethyl)phenoxy)picolinaldehyde

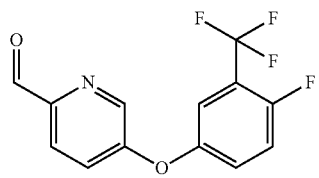 [SMILES: O=Cc1ccc(Oc2ccc(F)c(C(F)(F)F)c2)cn1]

The title compound was prepared by a procedure similar to that described for D91 starting from 5-fluoro-2-pyridinecarbaldehyde and 3-(trifluoromethyl)-4-fluorophenol.

D159 5-(4-fluoro-3-(trifluoromethyl)phenoxy)-2-vinylpyridine

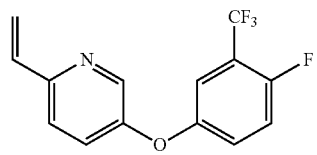 [SMILES: C=Cc1ccc(Oc2ccc(F)c(C(F)(F)F)c2)cn1]

The title compound was prepared by a procedure similar to that described for D78 starting from 5-(4-fluoro-3-(trifluoromethyl)phenoxy)picolinaldehyde D160 2-(5-(4-fluoro-3-(trifluoromethyl)phenoxy)pyridin-2-yl)ethanol

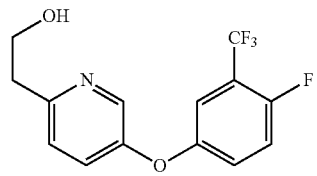 [SMILES: OCCc1ccc(Oc2ccc(F)c(C(F)(F)F)c2)cn1]

The title compound was prepared by a procedure similar to that described for D79 starting from 2-ethenyl-5-{[4-fluoro-3-(trifluoromethyl)phenyl]oxy}pyridine.
LC-MS (ESI): m/z 302 [M+H]$^+$; 2.33 min (ret time).

D161
5-(3-(trifluoromethyl)phenoxy)picolinaldehyde

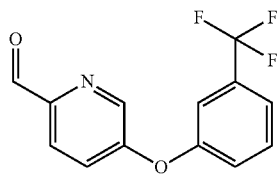 [SMILES: O=Cc1ccc(Oc2cccc(C(F)(F)F)c2)cn1]

The title compound was prepared by a procedure similar to that described for D91 starting from 5-fluoro-2-pyridinecarbaldehyde and 3-(trifluoromethyl)phenol.
LC-MS (ESI): m/z 268 [M+H]$^+$; 3.24 min (ret time).

D162
5-(3-(trifluoromethyl)phenoxy)-2-vinylpyridine

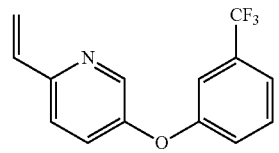 [SMILES: C=Cc1ccc(Oc2cccc(C(F)(F)F)c2)cn1]

The title compound was prepared by a procedure similar to that described for D78 starting from 5-{[3-(trifluoromethyl)phenyl]oxy}-2-pyridinecarbaldehyde.
LC-MS (ESI): m/z 266 [M+H]$^+$; 3.19 min (ret time).

D163 2-(5-(3-(trifluoromethyl)phenoxy)pyridin-2-yl)ethanol

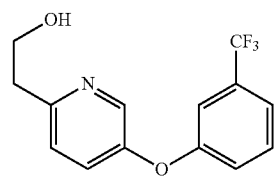 [SMILES: OCCc1ccc(Oc2cccc(C(F)(F)F)c2)cn1]

The title compound was prepared by a procedure similar to that described for D79 starting from 2-ethenyl-5-{[3-(trifluoromethyl)phenyl]oxy}pyridine.
LC-MS (ESI): m/z 284 [M+H]$^+$; 2.29 min (ret time).

D164 5-(4-chloro-3-(trifluoromethyl)phenoxy)-2-vinylpyridine

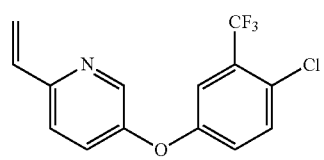 [SMILES: C=Cc1ccc(Oc2ccc(Cl)c(C(F)(F)F)c2)cn1]

The title compound was prepared by a procedure similar to that described for D78 starting from 5-{[4-fluoro-3-(trifluoromethyl)phenyl]oxy}-2-pyridinecarbaldehyde.
LC-MS (ESI): m/z 300 [M+H]$^+$; 3.47 min (ret time).

D165 2-(5-(4-chloro-3-(trifluoromethyl)phenoxy)pyridin-2-1ethanol

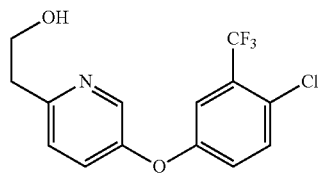 [SMILES: OCCc1ccc(Oc2ccc(Cl)c(C(F)(F)F)c2)cn1]

The title compound was prepared by a procedure similar to that described for D79 starting from 5-{[4-chloro-3-(trifluoromethyl)phenyl]oxy}-2-ethenylpyridine.
LC-MS (ESI): m/z 318 [M+H]$^+$; 2.50 min (ret time).

D166 (E)-5-(2-methoxyvinyl)-2-(3-(trifluoromethyl)phenoxy)benzonitrile and (Z)-5-(2-methoxyvinyl)-2-(3-(trifluoromethyl)phenoxy)benzonitrile

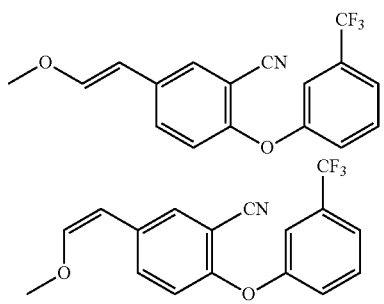

The title compound was prepared by a procedure similar to that described for D151 starting from 5-formyl-2-{[3-(trifluoromethyl)phenyl]oxy}benzonitrile.

D167 5-(2,2-dimethoxyethyl)-2-(3-(trifluoromethyl)phenoxy)benzonitrile

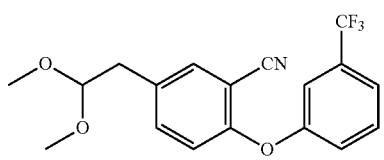 [SMILES: COC(Cc1ccc(Oc2cccc(C(F)(F)F)c2)c(C#N)c1)OC]

To a solution of 5-[(E)-2-(methyloxy)ethenyl]-2-{[3-(trifluoromethyl)phenyl]oxy}benzonitrile (443 mg, 1.39 mmol) and 5-[(Z)-2-(methyloxy)ethenyl]-2-{[3-(trifluoromethyl)phenyl]oxy}benzonitrile (443 mg, 1.39 mmol) in tetrahydrofuran (12 mL) was added a solution of HCl (1.50 mL, 18.0 mmol) in tetrahydrofuran (4 mL) at 0° C. The reaction mixture was stirred at 0° C. for 30 min, then was allowed to room temperature and stirred for 2 hr, then concentrated to give the residue which was directly used for next step. To a solution of the above intermediate in methanol (15 mL) was added NaBH$_4$ (52.5 mg, 1.39 mmol) at 0° C. The mixture was stirred at 0° C. for 30 min, then treated with HCl (1 M), concentrated and partitioned between ethyl acetate and water. Separated organic part was washed with brine, dried over sodium sulphate, filtered and concentrated. The residue was used into next step without purification

D168 5-(2-oxoethyl)-2-(3-(trifluoromethyl)phenoxy) benzonitrile

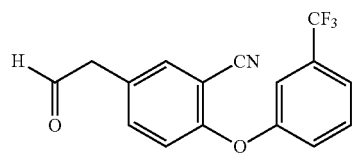 [SMILES: N#Cc1cc(CC=O)ccc1Oc1cccc(C(F)(F)F)c1]

To a solution of 5-[2,2-bis(methyloxy)ethyl]-2-{[3-(trifluoromethyl)phenyl]oxy}benzonitrile (955 mg, 2.72 mmol) in tetrahydrofuran (8 mL) was added water (8 mL) and HCl (1.50 mL, 49.4 mmol). The reaction mixture was stirred at 60° C. for 3 h, then concentrated to remove solvent, partitioned between ethyl acetate and water. Separated organic part was washed with brine, dried over sodium sulphate, filtered and concentrated. The crude product was directly used for next step without further purification.

D169 5-formyl-2-((6-(trifluoromethyl)pyridin-2-yl)oxy)benzonitrile

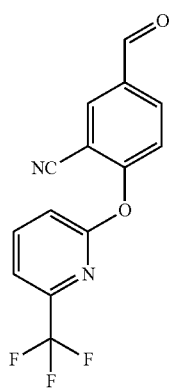

The title compound was prepared by a procedure similar to that described for D151 starting from 2-fluoro-5-formylbenzonitrile and 6-(trifluoromethyl)-2-pyridinol.
LC-MS (ESI): m/z 293 [M+H]$^+$; 3.11 min (ret time).

D170 5-(hydroxymethyl)-2-((6-(trifluoromethyl)pyridin-2-yl)oxy)benzonitrile

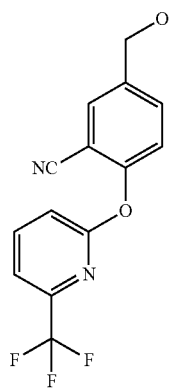 [SMILES: N#Cc1cc(CO)ccc1Oc1cccc(C(F)(F)F)n1]

The title compound was prepared by a procedure similar to that described for D92 starting from 5-formyl-2-{[6-(trifluoromethyl)-2-pyridinyl]oxy}benzonitrile.

D171 (E)-5-(2-methoxyvinyl)-2-((6-(trifluoromethyl)pyridin-3-yl)oxy)benzonitrile and (Z)-5-(2-methoxyvinyl)-2-((6-trifluoromethyl)pyridin-3-yl)oxy)benzonitrile

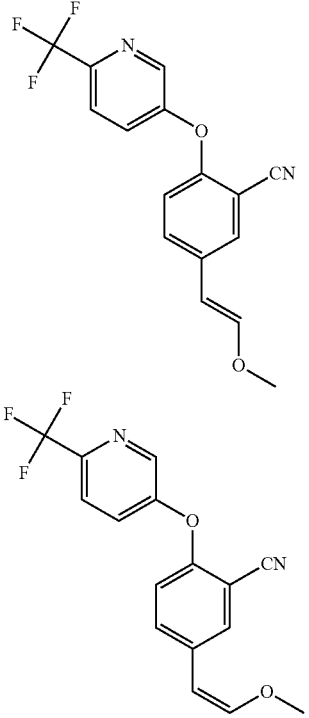

The title compound was prepared by a procedure similar to that described for D151 starting from 5-formyl-2-{[6-(trifluoromethyl)-3-pyridinyl]oxy}benzonitrile
LC-MS (ESI): m/z 321[M+H]$^+$; 3.80 min (ret time).

D172 5-(2-oxoethyl)-2-((6-(trifluoromethyl)pyridin-3-yl)oxy)benzonitrile

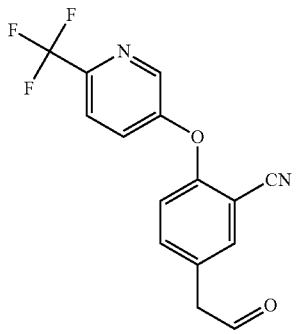 [SMILES: N#Cc1cc(CC=O)ccc1Oc1ccc(C(F)(F)F)nc1]

To a mixture of 5-[2-(methyloxy)ethenyl]-2-{[6-(trifluoromethyl)-3-pyridinyl]oxy}benzonitrile (400 mg, 1.25 mmol) and sodium iodide (225 mg, 1.50 mmol) in acetonitrile (20 mL) was added trimethylsilyl chloride (0.190 mL, 1.50 mmol) at −5° C. in ice/sodium chloride bath. After 2 h at −5° C., the reaction mixture was poured into aqueous Na$_2$S$_2$O$_3$, then extracted with ethyl acetate. Separated organic part was washed with brine, dried over Na$_2$SO$_4$, filtered and concentrated. The residue was used into next step directly without purification.
LC-MS (ESI): m/z 307 [M+H]$^+$; 2.83 min (ret time).

D173 5-(2-hydroxyethyl)-2-((6-(trifluoromethyl)pyridin-3-yl)oxy)benzonitrile

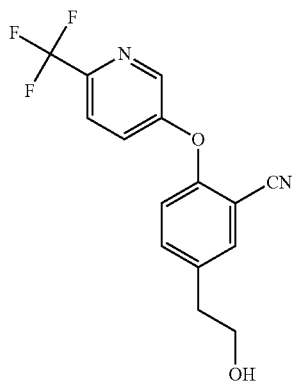 [SMILES: N#Cc1cc(CCO)ccc1Oc1ccc(C(F)(F)F)nc1]

The title compound was prepared by a procedure similar to that described for D92 starting from 5-(2-oxoethyl)-2-{[6-(trifluoromethyl)-3-pyridinyl]oxy}benzonitrile.
LC-MS (ESI): m/z 309 [M+H]$^+$; 3.27 min (ret time).

D174 3-fluoro-4-((6-(trifluoromethyl)pyridin-2-yl)oxy)benzaldehyde

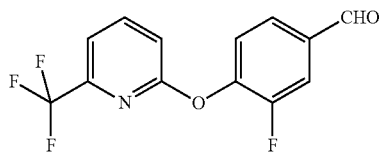 [SMILES: O=Cc1ccc(Oc2cccc(C(F)(F)F)n2)c(F)c1]

The title compound was prepared by a procedure similar to that described for D91 starting from 6-(trifluoromethyl)-2(1H)-pyridinone, 3,4-difluorobenzaldehyde and Cs$_2$CO$_3$ in N-Methyl-2-pyrrolidone.
LC-MS (ESI): m/z 286 [M+H]$^+$; 3.46 min (ret time).

D175 2-(2-fluoro-4-(2-methoxyvinyl)phenoxy)-6-(trifluoromethyl)pyridine

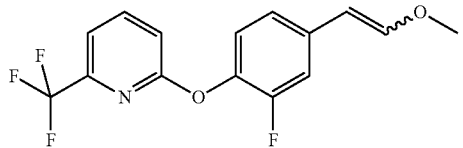 [SMILES: COC=Cc1ccc(Oc2cccc(C(F)(F)F)n2)c(F)c1]

The title compound was prepared by a procedure similar to that described for D151 starting from 3-fluoro-4-{[6-(trifluoromethyl)-2-pyridinyl]oxy}benzaldehyde.
LC-MS (ESI): m/z 314 [M+H]$^+$; 4.23 min (ret time).

D176 2-(3-fluoro-4-((6-(trifluoromethyl)pyridin-2-yl)oxy)phenyl)acetaldehyde

The title compound was prepared by a procedure similar to that described for D152 starting from 2-({2-fluoro-4-[2-(methyloxy)ethenyl]phenyl}oxy)-6-(trifluoromethyl)pyridine.
LC-MS (ESI): m/z 300 [M+H]$^+$; 3.18 min (ret time).

D177 2-(3-fluoro-4-((6-(trifluoromethyl)pyridin-2-yl)oxy)phenyl)ethanol

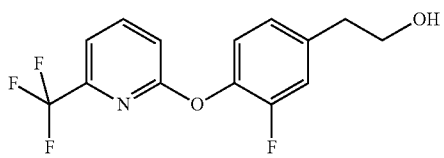 [SMILES: OCCc1ccc(Oc2cccc(C(F)(F)F)n2)c(F)c1]

The title compound was prepared by a procedure similar to that described for D92 starting from (3-fluoro-4-{[6-(trifluoromethyl)-2-pyridinyl]oxy}phenyl)acetaldehyde.
LC-MS (ESI): m/z 302 [M+H]$^+$; 3.04 min (ret time).

D178 4-(2-hydroxyethyl)phenol

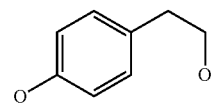

To a mixture of methyl (4-hydroxyphenyl)acetate (1.00 g, 6.02 mmol) and calcium chloride (1.34 g, 12.0 mmol) in ethanol (25 mL), which was stirred at room temperature for 30 min, was added NaBH$_4$ (0.911 g, 24.1 mmol) at 0° C. The reaction mixture was stirred at room temperature for 2 days, then quenched with saturated ammonium chloride solution, concentrated to remove and extracted with ethyl acetate. Separated organic part was dried over anhydrous Na$_2$SO$_4$, filtered and concentrated. The residue was used directly to the next step.

D179 2-(4-((5-(trifluoromethyl)pyridin-2-yl)oxy)phenyl)ethanol

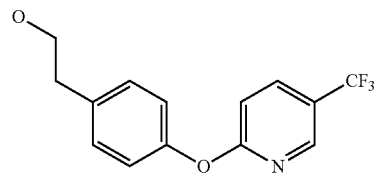 [SMILES: OCCc1ccc(Oc2ccc(C(F)(F)F)cn2)cc1]

The title compound was prepared by a procedure similar to that described for D91 starting from 4-(2-hydroxyethyl)phenol, 2-chloro-5-(trifluoromethyl)pyridine and Cs$_2$CO$_3$.
LC-MS (ESI): m/z 284 [M+H]$^+$; 2.97 min (ret time).

D180 3,5-difluoro-4-((6-(trifluoromethyl)pyridin-3-yl)oxy)benzaldehyde

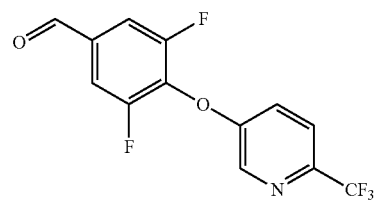 [SMILES: O=Cc1cc(F)c(Oc2ccc(C(F)(F)F)nc2)c(F)c1]

The title compound was prepared by a procedure similar to that described for D91 starting from 3,4,5-trifluorobenzaldehyde and 6-(trifluoromethyl)pyridin-3-ol.
LC-MS (ESI): m/z 304 [M+H]$^+$; 3.29 min (ret time).

D181 (3,5-difluoro-4-((6-(trifluoromethyl)pyridin-3-yl)oxy)phenyl)methanol

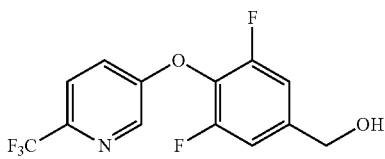 [SMILES: OCc1cc(F)c(Oc2ccc(C(F)(F)F)nc2)c(F)c1]

The title compound was prepared by a procedure similar to that described for D92 starting from 3,5-difluoro-4-((6-(trifluoromethyl)pyridin-3-yl)oxy)benzaldehyde.
LC-MS (ESI): m/z 306 [M+H]$^+$; 3.01 min (ret time).

D182 3-fluoro-4-((6-(trifluoromethyl)pyridin-3-yl)oxy)benzaldehyde

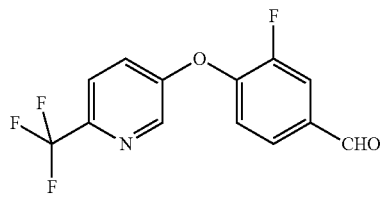 [SMILES: O=Cc1ccc(Oc2ccc(C(F)(F)F)nc2)c(F)c1]

The title compound was prepared by a procedure similar to that described for D91 starting from 6-(trifluoromethyl)-3-pyridinol, 3,4-difluorobenzaldehyde and Cs2CO3 in N-Methyl-2-pyrrolidone.
LC-MS (ESI): m/z 286 [M+H]$^+$; 3.26 min (ret time).

D183 2-(3-fluoro-4-((6-(trifluoromethyl)pyridin-3-yl)oxy)phenyl)acetaldehyde

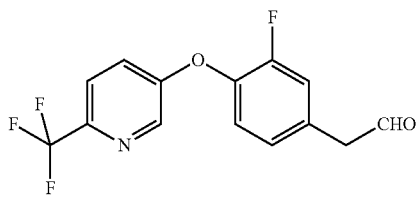 [SMILES: O=CCc1ccc(Oc2ccc(C(F)(F)F)nc2)c(F)c1]

The title compound was prepared by a procedure similar to that described for D152 starting from 5-({2-fluoro-4-[(2-(methyloxy)ethenyl]phenyl}oxy)-2-(trifluoromethyl)pyridine.
LC-MS (ESI): m/z 300 [M+H]$^+$; 3.08 min (ret time).

D184 2-(3-fluoro-4-((6-(trifluoromethyl)pyridin-3-yl)oxy)phenyl)ethanol

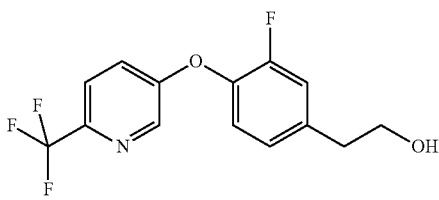 [SMILES: OCCc1ccc(Oc2ccc(C(F)(F)F)nc2)c(F)c1]

The title compound was prepared by a procedure similar to that described for D92 starting from (3-fluoro-4-{[6-(trifluoromethyl)-3-pyridinyl]oxy}phenyl)acetaldehyde.
LC-MS (ESI): m/z 302 [M+H]$^+$; 2.98 min (ret time).

D185 2-chloro-4-((6-(trifluoromethyl)pyridin-3-yl)oxy)benzaldehyde

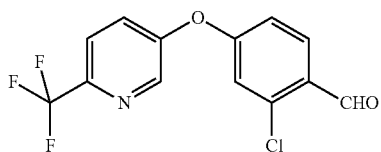 [SMILES: O=Cc1ccc(Oc2ccc(C(F)(F)F)nc2)cc1Cl]

The title compound was prepared by a procedure similar to that described for D91 starting from 6-(trifluoromethyl)-3-pyridinol and 2-chloro-4-fluorobenzaldehyde.
LC-MS (ESI): m/z 302 [M+H]$^+$; 3.46 min (ret time).

D186 (2-chloro-4-((6-(trifluoromethyl)pyridin-3-yl)oxy)phenyl)methanol

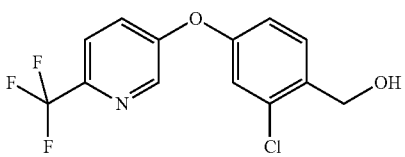 [SMILES: OCc1ccc(Oc2ccc(C(F)(F)F)nc2)cc1Cl]

The title compound was prepared by a procedure similar to that described for D92 starting from 2-chloro-4-{[6-(trifluoromethyl)-3-pyridinyl]oxy}benzaldehyde.
LC-MS (ESI): m/z 304 [M+H]$^+$; 3.10 min (ret time).

D187 3-fluoro-4-((6-methylpyridin-3-yl)oxy)benzaldehyde

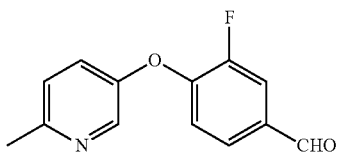 [SMILES: Cc1ccc(Oc2ccc(C=O)cc2F)cn1]

The title compound was prepared by a procedure similar to that described for D91 starting from 6-methyl-3-pyridinol and 3,4-difluorobenzaldehyde.
LC-MS (ESI): m/z 232 [M+H]$^+$; 1.79 min (ret time).

D188 (3-fluoro-4-((6-methylpyridin-3-yl)oxy)phenyl)methanol

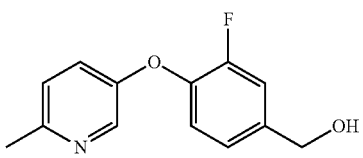 [SMILES: Cc1ccc(Oc2ccc(CO)cc2F)cn1]

The title compound was prepared by a procedure similar to that described for D92 starting from 3-fluoro-4-[(6-methyl-3-pyridinyl)oxy]benzaldehyde.
LC-MS (ESI): m/z 234 [M+H]$^+$; 1.49 min (ret time).

D189
5-formyl-2-((6-methylpyridin-3-yl)oxy)benzonitrile

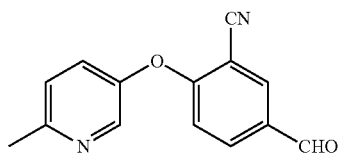 [SMILES: Cc1ccc(Oc2ccc(C=O)cc2C#N)cn1]

The title compound was prepared by a procedure similar to that described for D91 starting from 6-methyl-3-pyridinol and 2-fluoro-5-formylbenzonitrile.

LC-MS (ESI): m/z 239 [M+H]$^+$; 1.74 min (ret time).

D190 5-(hydroxymethyl)-2-((6-methylpyridin-3-yl)oxy)benzonitrile

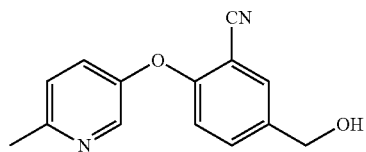 [SMILES: Cc1ccc(Oc2ccc(CO)cc2C#N)cn1]

The title compound was prepared by a procedure similar to that described for D92 starting from 5-formyl-2-[(6-methyl-3-pyridinyl)oxy]benzonitrile.

LC-MS (ESI): m/z 241 [M+H]$^+$; 1.745 min (ret time).

D191 2-chloro-5-(dibromomethyl)-3-fluoropyridine

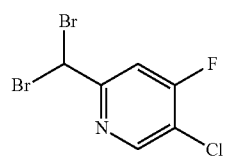 [SMILES: Fc1cc(C(Br)Br)ncc1Cl]

The title compound was prepared by a procedure similar to that described for D52 starting from 2-chloro-3-fluoro-5-methylpyridine.

LC-MS (ESI): m/z 304 [M+H]$^+$; 3.29 min (ret time).

D192 6-chloro-5-fluoronicotinaldehyde

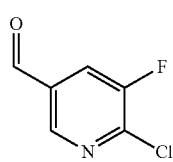

The title compound was prepared by a procedure similar to that described for D53 starting from 1-chloro-5-(dibromomethyl)-3-fluoropyridine.

D193 5-fluoro-6-(4-fluorophenoxy)nicotinaldehyde

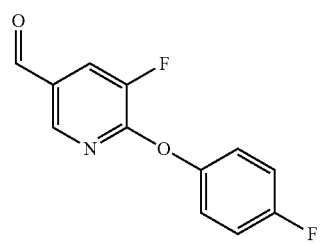 [SMILES: O=Cc1cnc(Oc2ccc(F)cc2)c(F)c1]

The title compound was prepared by a procedure similar to that described for D91 starting from 6-chloro-5-fluoronicotinaldehyde.

LC-MS (ESI): m/z 236 [M+H]$^+$; 3.67 min (ret time).

D194
(5-fluoro-6-(4-fluorophenoxy)pyridin-3-yl)methanol

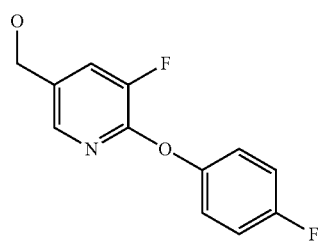 [SMILES: OCc1cnc(Oc2ccc(F)cc2)c(F)c1]

The title compound was prepared by a procedure similar to that described for D92 starting from 5-fluoro-6-(4-fluorophenoxy)nicotinaldehyde.

LC-MS (ESI): m/z 238 [M+H]$^+$; 2.57 min (ret time).

D195 5-formyl-2-((6-(trifluoromethyl)pyridin-2-yl)oxy)benzonitrile

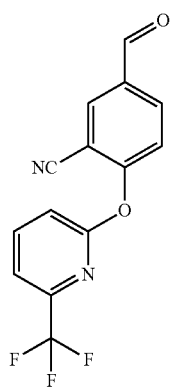 [SMILES: N#Cc1cc(C=O)ccc1Oc1cccc(C(F)(F)F)n1]

The title compound was prepared by a procedure similar to that described for D91 starting from 2-fluoro-5-formylbenzonitrile and 6-(trifluoromethyl)-2-pyridinol.

LC-MS (ESI): m/z 293 [M+H]$^+$; 3.11 min (ret time).

D196 2-((6-(trifluoromethyl)pyridin-2-yl)oxy)-5-vinylbenzonitrile

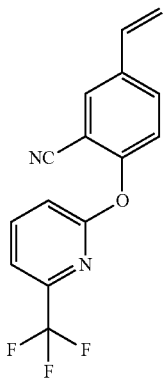

The title compound was prepared by a procedure similar to that described for D78 starting from 5-formyl-2-{[6-(trifluoromethyl)-2-pyridinyl]oxy}benzonitrile.
LC-MS (ESI): m/z 291 [M+H]$^+$; 3.54 min (ret time).

D197 5-(2-hydroxyethyl)-2-((6-(trifluoromethyl)pyridin-2-yl)oxy)benzonitrile

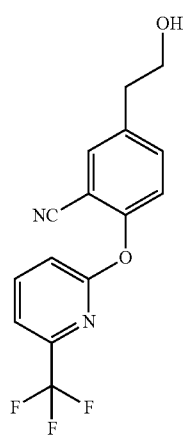

The title compound was prepared by a procedure similar to that described for D79 starting from 2-((6-(trifluoromethyl)pyridin-2-yl)oxy)-5-vinylbenzonitrile.

D198 5-(4-fluoro-3-(trifluoromethyl)phenoxy)picolinaldehyde

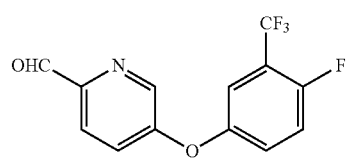 [SMILES: O=Cc1ccc(Oc2ccc(F)c(C(F)(F)F)c2)cn1]

The title compound was prepared by a procedure similar to that described for D91 starting from 5-chloropicolinaldehyde and 4-fluoro-3-(trifluoromethyl)phenol.

D199 (5-(4-fluoro-3-(trifluoromethyl)phenoxy)pyridin-2-yl)methanol

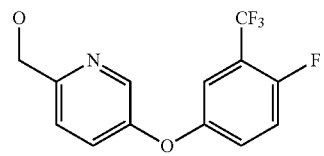 [SMILES: OCc1ccc(Oc2ccc(F)c(C(F)(F)F)c2)cn1]

The title compound was prepared by a procedure similar to that described for D92 starting from 5-(4-fluoro-3-(trifluoromethyl)phenoxy)picolinaldehyde.

D200 3-chloro-4-((6-methylpyridin-3-yl)oxy)benzaldehyde

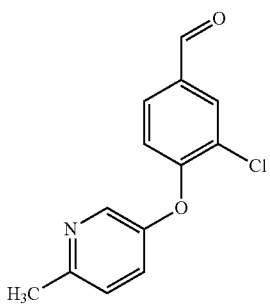 [SMILES: Cc1ccc(Oc2ccc(C=O)cc2Cl)cn1]

The title compound was prepared by a procedure similar to that described for D91 starting from 3-chloro-4-fluorobenzaldehyde and 6-methyl-3-pyridinol.
LC-MS (ESI): m/z 248 [M+H]$^+$; 2.01 min (ret time).

D201 (3-chloro-4-((6-methylpyridin-3-yl)oxy)phenyl)methanol

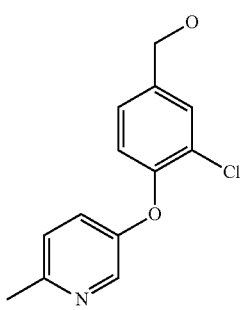 [SMILES: Cc1ccc(Oc2ccc(CO)cc2Cl)cn1]

The title compound was prepared by a procedure similar to that described for D92 starting from 3-chloro-4-((6-methylpyridin-3-yl)oxy)benzaldehyde
LC-MS (ESI): m/z 250 [M+H]$^+$; 1.66 min (ret time).

D202 3,5-difluoro-4-((6-(trifluoromethyl)pyridin-3-yl)oxy)benzaldehyde

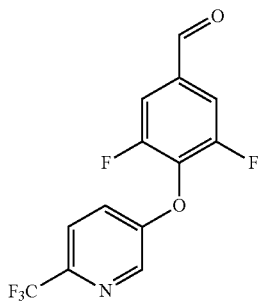 [SMILES: O=Cc1cc(F)c(Oc2ccc(C(F)(F)F)nc2)c(F)c1]

The title compound was prepared by a procedure similar to that described for D91 starting from 3,4,5-trifluorobenzaldehyde and 6-(trifluoromethyl)-3-pyridinol.

D203 (3,5-difluoro-4-((6-(trifluoromethyl)pyridin-3-yl)oxy)phenyl)methanol

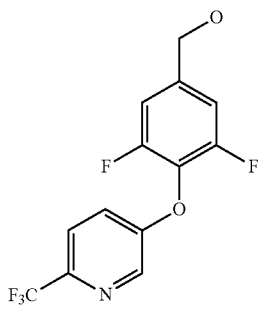 [SMILES: OCc1cc(F)c(Oc2ccc(C(F)(F)F)nc2)c(F)c1]

The title compound was prepared by a procedure similar to that described for D92 starting from 3,5-difluoro-4-((6-(trifluoromethyl)pyridin-3-yl)oxy)benzaldehyde.

LC-MS (ESI): m/z 306 [M+H]$^+$; 3.02 min (ret time).

D204 2-((5-chloropyridin-2-yl)oxy)-5-formylbenzonitrile

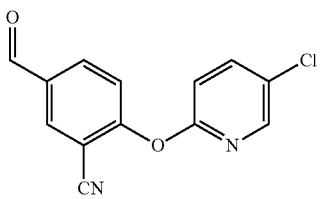 [SMILES: N#Cc1cc(C=O)ccc1Oc1ccc(Cl)cn1]

The title compound was prepared by a procedure similar to that described for D91 starting from 2-fluoro-5-formylbenzonitrile and 5-chloro-2-pyridinol.

LC-MS (ESI): m/z 259 [M+H]$^+$; 2.09 min (ret time).

D205 2-((5-chloropyridin-2-yl)oxy)-5-(hydroxymethyl)benzonitrile

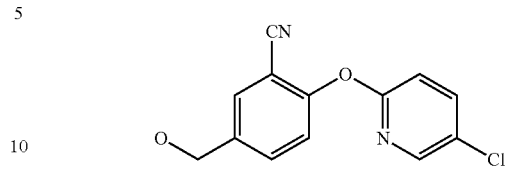

The title compound was prepared by a procedure similar to that described for D92 starting from 2-((5-chloropyridin-2-yl)oxy)-5-formylbenzonitrile.

LC-MS (ESI): m/z 306 [M+H]$^+$; 3.02 min (ret time).

D206 2-(trifluoromethyl)-1,4,5,6-tetrahydropyrimidin-5-ol

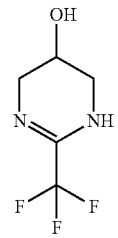

To a solution of ethyl trifluoroacetate (5.80 g, 40.8 mmol) in p-Xylene (30 mL) was added 1,3-diamino-2-propanol (3.60 g, 40.0 mmol). The reaction mixture was stirred at 160° C. for 4 h, then concentrated in vacuo to give the title product as a brown oil. The crude was used into next step without further purification.

LC-MS (ESI): m/z 169 [M+H]$^+$; 0.25 min (ret time).

D207 2-(trifluoromethyl)pyrimidin-5-ol

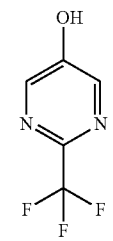 [SMILES: Oc1cnc(C(F)(F)F)nc1]

A mixture of 2-(trifluoromethyl)-1,4,5,6-tetrahydro-5-pyrimidinol (6.50 g, 38.7 mmol) and nitrobenzene (30 mL) was stirred at 90° C. to form a homogeneous solution. At this temperature, a solution of sodium methoxide (8.35 g, 155 mmol) in methanol (30 mL) was added portionwise, allowing the methanol to distill off before next addition (the whole process took about 3 hr). Then the reaction mixture was stirred at 120° C. for 1 h, then partitioned between ethyl acetate and water. Separated aqueous part was adjusted to pH=4.0 with 6 M hydrochloric acid solution and extracted with ethyl acetate. Combined organic parts were dried over sodium sulphate, filtered and concentrated. The residue was used directed into next step without further purification.

LC-MS (ESI): m/z 165 [M+H]$^+$; 1.78 min (ret time).

D208 5-formyl-2-((2-(trifluoromethyl)pyrimidin-5-yl)oxy)benzonitrile

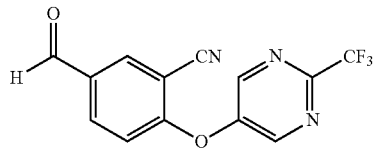 [SMILES: N#Cc1cc(C=O)ccc1Oc1cnc(C(F)(F)F)nc1]

The title compound was prepared by a procedure similar to that described for D91 starting from 2-fluoro-5-formylbenzonitrile and 2-(trifluoromethyl).pyrimidin-5-ol.

D209 5-(hydroxymethyl)-2-(trifluoromethyl)pyrimidin-5-yl)oxy)benzonitrile

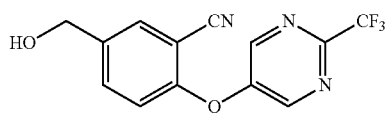 [SMILES: N#Cc1cc(CO)ccc1Oc1cnc(C(F)(F)F)nc1]

The title compound was prepared by a procedure similar to that described for D92 starting from 5-formyl-2-{[2-(trifluoromethyl)-5-pyrimidinyl]oxy}benzonitrile.

LC-MS (ESI): m/z 296 [M+H]$^+$; 2.63 min (ret time).

D210 3-fluoro-4-((2-(trifluoromethyl)pyrimidin-5-yl)oxy)benzaldehyde

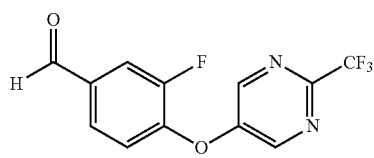 [SMILES: O=Cc1ccc(Oc2cnc(C(F)(F)F)nc2)c(F)c1]

The title compound was prepared by a procedure similar to that described for D91 starting from 3,4-difluorobenzaldehyde and 2-(trifluoromethyl)-5-pyrimidinol.

LC-MS (ESI): m/z 287 [M+H]$^+$; 3.10 min (ret time).

D211 (3-fluoro-4-((2-(trifluoromethyl)pyrimidin-5-yl)oxy)phenyl)methanol

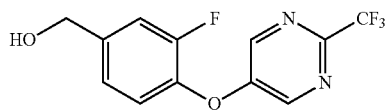 [SMILES: OCc1ccc(Oc2cnc(C(F)(F)F)nc2)c(F)c1]

The title compound was prepared by a procedure similar to that described for D92 starting from 3-fluoro-4-((2-(trifluoromethyl)pyrimidin-5-yl)oxy)benzaldehyde

D212 5-(2-methoxyvinyl)-2-((2-(trifluoromethyl)pyrimidin-5-yl)oxy)benzonitrile

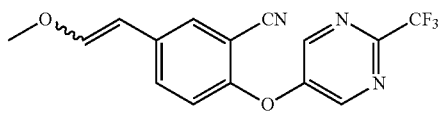 [SMILES: COC=Cc1ccc(Oc2cnc(C(F)(F)F)nc2)c(C#N)c1]

The title compound was prepared by a procedure similar to that described for D151 starting from 5-formyl-2-{[2-(trifluoromethyl)-5-pyrimidinyl]oxy}benzonitrile.

D213 5-(2-oxoethyl)-2-((2-(trifluoromethyl)pyrimidin-5-yl)oxy)benzonitrile

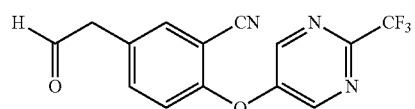

The title compound was prepared by a procedure similar to that described for D152 starting from 5-[2-(methyloxy)ethenyl]-2-{[2-(trifluoromethyl)-5-pyrimidinyl]oxy}benzonitrile.

D214 5-(2-hydroxyethyl)-2-((2-(trifluoromethyl)pyrimidin-5-yl)oxy)benzonitrile

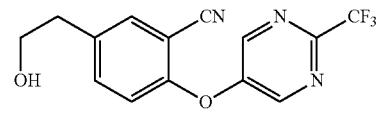 [SMILES: N#Cc1cc(CCO)ccc1Oc1cnc(C(F)(F)F)nc1]

The title compound was prepared by a procedure similar to that described for D92 starting from 5-(2-oxoethyl)-2-{[2-(trifluoromethyl)-5-pyrimidinyl]oxy}benzonitrile.

LC-MS (ESI): m/z 310 [M+H]$^+$; 2.70 min (ret time).

D215 4-((5-chloropyridin-2-yl)oxy)-3-fluorobenzaldehyde

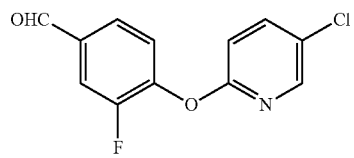 [SMILES: O=Cc1ccc(Oc2ccc(Cl)cn2)c(F)c1]

The title compound was prepared by a procedure similar to that described for D91 starting from 3,4-difluorobenzaldehyde and 5-chloro-2-pyridinol.

D216 (4-((5-chloropyridin-2-yl)oxy)-3-fluorophenyl)methanol

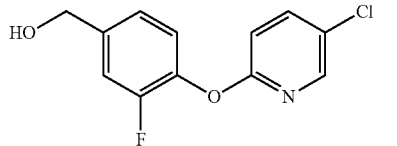 [SMILES: OCc1ccc(Oc2ccc(Cl)cn2)c(F)c1]

The title compound was prepared by a procedure similar to that described for D92 starting from 4-((5-chloropyridin-2-yl)oxy)-3-fluorobenzaldehyde.

D217 2-(4-chloro-3-(trifluoromethyl)phenoxy)-5-(2-methoxyvinyl)pyridine

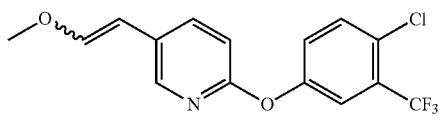 [SMILES: COC=Cc1ccc(Oc2ccc(Cl)c(C(F)(F)F)c2)nc1]

The title compound was prepared by a procedure similar to that described for D151 starting from 6-(4-chloro-3-(trifluoromethyl)phenoxy)nicotinaldehyde.

D218 2-(6-(4-chloro-3-(trifluoromethyl)phenoxy)pyridin-3-yl)acetaldehyde

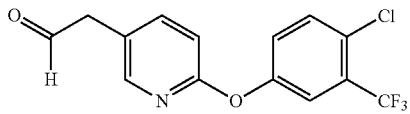 [SMILES: O=CCc1ccc(Oc2ccc(Cl)c(C(F)(F)F)c2)nc1]

The title compound was prepared by a procedure similar to that described for D152 starting from 2-{[4-chloro-3-(trifluoromethyl)phenyl]oxy}-5-[(E)-2-(methyloxy)ethenyl]pyridine.

D219 2-(6-(4-chloro-3-(trifluoromethyl)phenoxy)pyridin-3-yl)ethanol

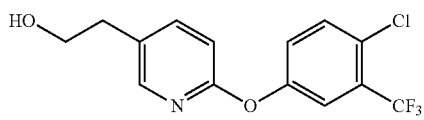 [SMILES: OCCc1ccc(Oc2ccc(Cl)c(C(F)(F)F)c2)nc1]

The title compound was prepared by a procedure similar to that described for D92 starting from (6-{[4-chloro-3-(trifluoromethyl)phenyl]oxy}-3-pyridinyl)acetaldehyde.
LC-MS (ESI): m/z 318 [M+H]$^+$; 3.19 min (ret time).

D220 5-(4-chloro-3-(trifluoromethyl)phenoxy)pyrimidine-2-carbonitrile

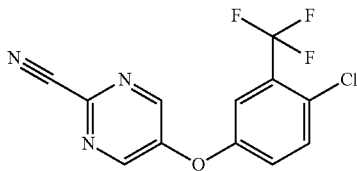 [SMILES: N#Cc1ncc(Oc2ccc(Cl)c(C(F)(F)F)c2)cn1]

The title compound was prepared by a procedure similar to that described for D91 starting from 5-bromo-2-pyrimidinecarbonitrile and 4-chloro-3-(trifluoromethyl)phenol.
LC-MS (ESI): m/z 300 [M+H]$^+$; 3.48 min (ret time).

D221 5-(4-chloro-3-(trifluoromethyl)phenoxy)pyrimidine-2-carbaldehyde

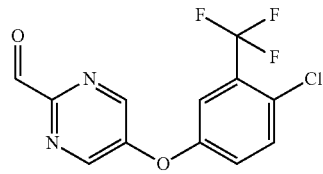 [SMILES: O=Cc1ncc(Oc2ccc(Cl)c(C(F)(F)F)c2)cn1]

To a solution of 5-{[4-chloro-3-(trifluoromethyl)phenyl]oxy}-2-pyrimidinecarbonitrile (150 mg, 0.500 mmol) in THF 10 ml at −78° C. was added dropwise DIBAL-H (2 mL, 1M solution in Toleuene, 1.00 mmol). The reaction mixture was stirred at −78° C. for 1 h, quenched with a saturated solution of potassium sodium tartrate tetrahydrate. Separated organic part was dried over Na$_2$SO$_4$, filtered and concentrated. The residue was used into next step without purification.

D222 (5-(4-chloro-3-(trifluoromethyl)phenoxy)pyrimidin-2-yl)methanol

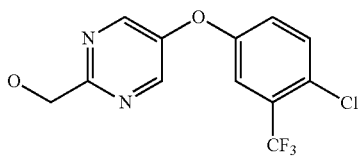 [SMILES: OCc1ncc(Oc2ccc(Cl)c(C(F)(F)F)c2)cn1]

The title compound was prepared by a procedure similar to that described for D92 starting from 5-{[4-chloro-3-(trifluoromethyl)phenyl]oxy}-2-pyrimidinecarbaldehyde.
LC-MS (ESI): m/z 305 [M+H]$^+$; 2.82 min (ret time).

D223 6-(2,4-difluorophenoxy)nicotinaldehyde

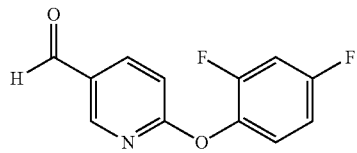 [SMILES: O=Cc1ccc(Oc2ccc(F)cc2F)nc1]

The title compound was prepared by a procedure similar to that described for D91 starting from 4-fluoro-3-pyridinecarbaldehyde and 2,4-difluorophenol.

D224
2-(2,4-difluorophenoxy)-5-(2-methoxyvinyl)pyridine

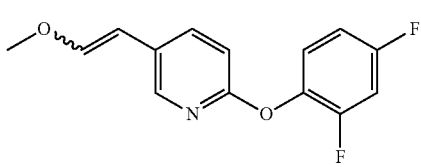 [SMILES: COC=Cc1ccc(Oc2ccc(F)cc2F)nc1]

The title compound was prepared by a procedure similar to that described for D151 starting from 6-[(2,4-difluorophenyl)oxy]-3-pyridinecarbaldehyde.

D225 2-(6-(2,4-difluorophenoxy)pyridin-3-yl)acetaldehyde

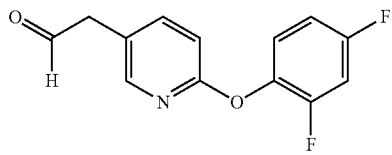 [SMILES: O=CCc1ccc(Oc2ccc(F)cc2F)nc1]

The title compound was prepared by a procedure similar to that described for D152 starting from 2-(2,4-difluorophenoxy)-5-(2-methoxyvinyl)pyridine

D226
2-(6-(2,4-difluorophenoxy)pyridin-3-yl)ethanol

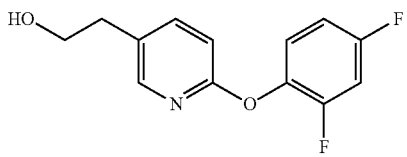 [SMILES: OCCc1ccc(Oc2ccc(F)cc2F)nc1]

The title compound was prepared by a procedure similar to that described for D92 starting from {6-[(2,4-difluorophenyl)oxy]-3-pyridinyl}acetaldehyde.

LC-MS (ESI): m/z 252 [M+H]$^+$; 2.60 min (ret time).

D227
3-fluoro-4-((6-methylpyridin-3-yl)oxy)benzaldehyde

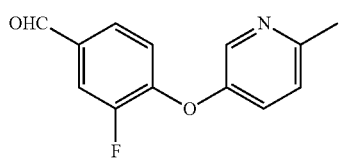 [SMILES: Cc1ccc(Oc2ccc(C=O)cc2F)cn1]

The title compound was prepared by a procedure similar to that described for D91 starting from 3,4-difluorobenzaldehyde and 6-methylpyridin-3-ol.

D228 5-(2-fluoro-4-vinylphenoxy)-2-methylpyridine

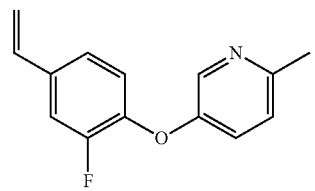 [SMILES: C=Cc1ccc(Oc2ccc(C)nc2)c(F)c1]

The title compound was prepared by a procedure similar to that described for D78 starting from 3-fluoro-4-[(6-methyl-3-pyridinyl)oxy]benzaldehyde.

LC-MS (ESI): m/z 230 [M+H]$^+$; 2.34 min (ret time).

D229 2-(3-fluoro-4-((6-methylpyridin-3-yl)oxy)phenyl)ethanol

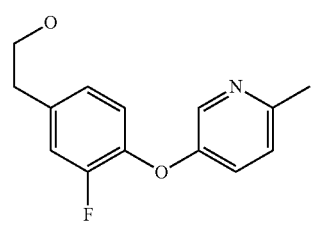 [SMILES: Cc1ccc(Oc2ccc(CCO)cc2F)cn1]

The title compound was prepared by a procedure similar to that described for D79 starting from 2-ethenyl-4-fluoro-5-[(4-methylphenyl)oxy]pyridine.

D230 2-(2-bromophenethoxy)tetrahydro-2H-pyran

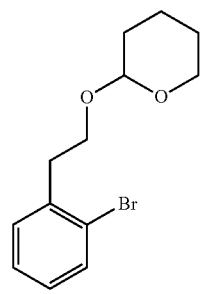 [SMILES: Brc1ccccc1CCOC1CCCCO1]

To a solution of 2-(2-bromophenyl)ethanol (15.0 g, 74.6 mmol) and TsOH (350 mg, 1.84 mmol) in chloroform (200 mL) was added carefully via syringe 3,4-dihydro-2H-pyran (7.5 mL, 82 mmol) at 0° C. The reaction mixture was stirred at room temperature for 3 h, then quenched with saturated solution of NaHCO$_3$. Separated organic part was dried over anhydrous Na$_2$SO$_4$, filtered and concentrated. Purification via ISCO system (10% ethyl acetate in petroleum ether) afforded the title product.

D231 4,4,5,5-tetramethyl-2-(2-(2-((tetrahydro-2H-pyran-2-yl)oxy)ethyl)phenyl)-1,3,2-dioxaborolane

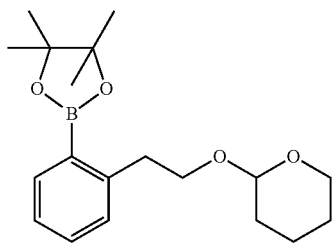

A mixture of 2-(2-bromophenethoxy)tetrahydro-2H-pyran (19.0 g, 66.6 mmol), 4,4,4',4',5,5,5',5'-octamethyl-2,2'-bi-1,3,2-dioxaborolane (22.0 g, 87.0 mmol), PdCl2 (dppf)-CH2Cl2 adduct (1.5 g, 1.837 mmol) and potassium acetate (8.50 g, 87.0 mmol) in 1,4-Dioxane (400 mL) was bubbled with nitrogen, then stirred at 100° C. overnight and concentrated. Purification via ISCO system (10% ethyl acetate in petroleum ether) afforded the title product.

D232 6-(2-(2-((tetrahydro-2H-pyran-2-yl)oxy)ethyl)phenyl)pyrimidine-2,4(1H,3H)-dione

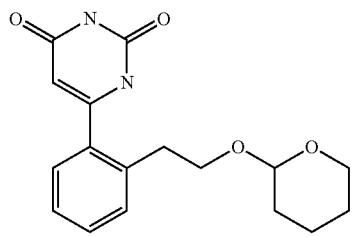 [SMILES: O=c1cc(-c2ccccc2CCOC2CCCCO2)[nH]c(=O)[nH]1]

A mixture of 4,4,5,5-tetramethyl-2-(2-(2-((tetrahydro-2H-pyran-2-yl)oxy)ethyl)phenyl)-1,3,2-dioxaborolane (12.0 g, 36.1 mmol), 6-chloro-2,4(1H,3H)-pyrimidinedione (5.29 g, 36.1 mmol), Na2CO3 (7.66 g, 72.2 mmol) and PdCl2 (dppf)-CH$_2$Cl$_2$ adduct (1.475 g, 1.806 mmol) in 1,4-Dioxane (150 mL) and Water (150 mL) was bubbled with nitrogen, stirred at 100° C. (oil bath) overnight and extracted with ethyl acetate. Separated organic part was dried over anhydrous Na$_2$SO$_4$, filtered and concentrated. Purification via ISCO system (80% ethyl acetate in petroleum ether) afforded the title product.

D233 6-(2-(2-hydroxyethyl)phenyl)pyrimidine-2,4(1H,3H)-dione

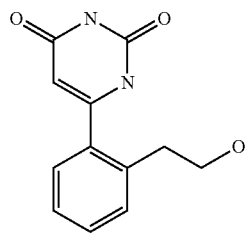 [SMILES: O=c1cc(-c2ccccc2CCO)[nH]c(=O)[nH]1]

To a solution of 6-(2-(2-((tetrahydro-2H-pyran-2-yl)oxy)ethyl)phenyl)pyrimidine-2,4(1H,3H)-dione (5 g, 15.81 mmol) in Methanol (20 mL) was added TsOH (100 mg, 0.526 mmol) at room temperatu-re. The reaction mixture was stirred at this temperature overnight, then concentrated. The residue was dissolved into methanol (5 mL) and the preticipate was collected, was washed with little amount of methanol afforded the title product.

LC-MS (ESI): m/z 233 [M+H]$^+$; 1.55 min (ret time).

D234 6,7-dihydro-2H-pyrimido[6,1-a]isoquinoline-2,4(3H)-dione

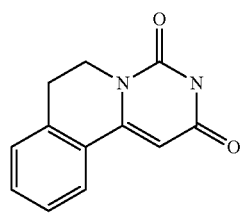 [SMILES: O=c1cc2n(c(=O)[nH]1)CCc1ccccc1-2]

To a solution of 6-(2-(2-hydroxyethyl)phenyl)pyrimidine-2,4(1H,3H)-dione (1.80 g, 7.75 mmol), DMAP (100 mg, 0.819 mmol) and Et$_3$N (5.00 mL, 35.9 mmol) in dichloromethane (300 mL) was added MsCl (1.20 mL, 15.4 mmol) at 0° C. The reaction mixture was stirred at room temperature overnight and concentrated. Purification via Biotage system with reversed phase column chromatography afforded the title product as a pale yellow solid.

LC-MS (ESI): m/z 215 [M+H]$^+$; 1.92 min (ret time).

D235 2-chloro-6,7-dihydro-4H-pyrimido[6,1-a]isoquinolin-4-one

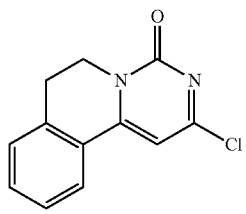 [SMILES: O=c1nc(Cl)cc2n1CCc1ccccc1-2]

A solution of 6,7-dihydro-2H-pyrimido[6,1-a]isoquinoline-2,4(3H)-dione (100 mg, 0.467 mmol) in POCl$_3$ (1.00 mL, 10.7 mmol) was stirred at 130° C. for 1 h, then concentrated. The residue was washed with cold brine and dried to give the title product

D236 1-bromo-4-fluoro-2-(2-methoxyvinyl)benzene

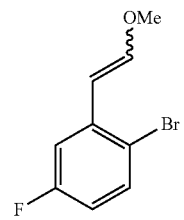 [SMILES: COC=Cc1cc(F)ccc1Br]

To a suspension of [(methyloxy)methyl](triphenyl)phosphonium chloride (6.68 g, 19.5 mmol) in Tetrahydrofuran (40 mL) at 0° C. was added KO$^t$Bu (2.19 g, 19.5 mmol). After 1 h, a solution of 2-bromo-5-fluorobenzaldehyde (3.05 g, 15.0 mmol) in tetrahydrofuran (10 mL) was added at same temperature. The reaction mixture was stirred at room tempertature for 3 h, then quenched with aqueous NH$_4$Cl solution, then extracted with ethyl acetate twice. Combined organic parts were washed with brine, dried over sodium sulphate and concentrated. Purification via ISCO system with petroleum ether afforded the title product as a colorless oil.

D237 2-(2-bromo-5-fluorophenyl)ethanol

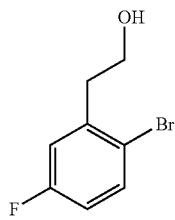

To a solution of (2-bromo-5-fluorophenyl)acetaldehyde (1.65 g, 7.60 mmol) in Methanol (30 mL) at 0° C. was added NaBH$_4$ (0.144 g, 3.80 mmol). The mixture was stirred at 0° C. for 30 min, then acidified with a solution of HCl (1 M) around pH=7 and concentrated to remove solvent. The residue was partitioned between ethyl acetate and water. Separated organic part was washed with brine, dried over sodium sulphate and concentrated. The crude product was used directly into next step without further purification.

D238
2-(2-bromo-5-fluorophenethoxy)tetrahydro-2H-pyran

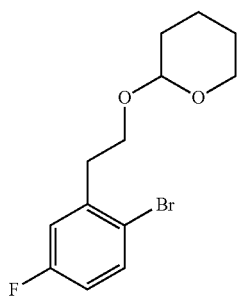 [SMILES: Fc1ccc(Br)c(CCOC2CCCCO2)c1]

The title compound was prepared by a procedure similar to that described for D230 starting from 2-(2-bromo-5-fluorophenyl)ethanol.

D239 2-(4-fluoro-2-(2-((tetrahydro-2H-pyran-2-yl)oxy)ethyl)phenyl)-4,4,5,5-tetramethyl-1,3,2-dioxaborolane

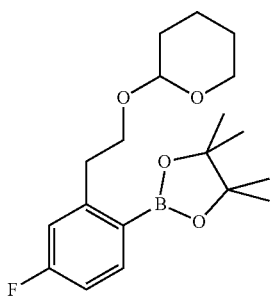 [SMILES: CC1(C)OB(c2ccc(F)cc2CCOC2CCCCO2)OC1(C)C]

The title compound was prepared by a procedure similar to that described for D231 starting from 2-{[2-(2-bromo-5-fluorophenyl)ethyl]oxy}tetrahydro-2H-pyran.

D240 6-(4-fluoro-2-(2-((tetrahydro-2H-pyran-2-yl)oxy)ethyl)phenyl)pyrimidine-2,4(1H,3H)-dione

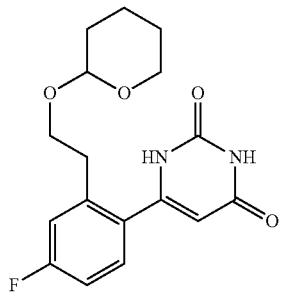 [SMILES: O=c1cc(-c2ccc(F)cc2CCOC2CCCCO2)[nH]c(=O)[nH]1]

The title compound was prepared by a procedure similar to that described for D232 starting from 2-(4-fluoro-2-(2-((tetrahydro-2H-pyran-2-yl)oxy)ethyl)phenyl)-4,4,5,5-tetramethyl-1,3,2-dioxaborolane.

D241 6-(4-fluoro-2-(2-hydroxyethyl)phenyl)pyrimidine-2,4(1H,3H)-dione

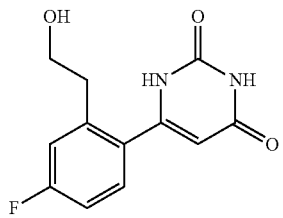 [SMILES: O=c1cc(-c2ccc(F)cc2CCO)[nH]c(=O)[nH]1]

The title compound was prepared by a procedure similar to that described for D233 starting from 6-(4-fluoro-2-(2-((tetrahydro-2H-pyran-2-yl)oxy)ethyl)phenyl)pyrimidine-2,4(1H,3H)-dione.

D242 9-fluoro-6,7-dihydro-2H-pyrimido[6,1-a]isoquinoline-2,4(3H)-dione

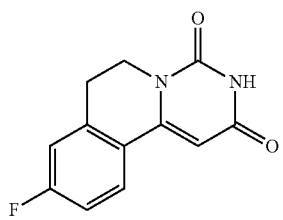 [SMILES: O=c1cc2n(c(=O)[nH]1)CCc1cc(F)ccc1-2]

The title compound was prepared by a procedure similar to that described for D234 starting from -(4-fluoro-2-(2-hydroxyethyl)phenyl)pyrimidine-2,4(1H,3H)-dione.

LC-MS (ESI): m/z 233 [M+H]$^+$; 2.01 min (ret time).

D243 2-chloro-9-fluoro-6,7-dihydro-4H-pyrimido[6,1-a]isoquinolin-4-one

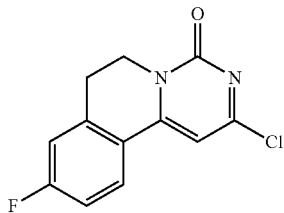 [SMILES: O=c1nc(Cl)cc2n1CCc1cc(F)ccc1-2]

The title compound was prepared by a procedure similar to that described for D235 starting from 9-fluoro-6,7-dihydro-2H-pyrimido[6,1-a]isoquinoline-2,4(3H)-dione.
LC-MS (ESI): m/z 251 [M+H]$^+$; 2.36 min (ret time).

D244 (4-((2-(trifluoromethyl)pyrimidin-5-yl)oxy)phenyl)methanol

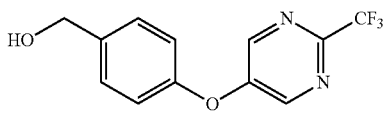 [SMILES: OCc1ccc(Oc2cnc(C(F)(F)F)nc2)cc1]

The title compound was prepared by a procedure similar to that described for D92 starting from 4-((2-(trifluoromethyl)pyrimidin-5-yl)oxy)benzaldehyde.
LC-MS (ESI): m/z 271 [M+H]$^+$; 2.67 min (ret time).

EXAMPLES

E3

2-{[(2-Chloro-4-{[4-chloro-3-(trifluoromethyl)phenyl]oxy}phenyl)methyl]oxy}-9-(methyloxy)-6,7-dihydro-4H-pyrimido[6,1-a]isoquinolin-4-one

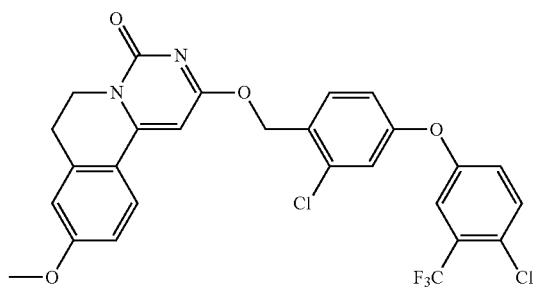 [SMILES: COc1ccc2c(c1)CCn1c-2cc(OCc2ccc(Oc3ccc(Cl)c(C(F)(F)F)c3)cc2Cl)nc1=O]

To a solution of (2-chloro-4-{[4-chloro-3-(trifluoromethyl)phenyl]oxy}phenyl)methanol (70.0 mg, 0.208 mmol) in anhydrous N,N-dimethylformamide (5 mL) was added sodium hydride (18.3 mg, 0.457 mmol) at 0° C. The reaction suspension was stirred at 0° C. for 15 min, then 2-chloro-9-(methyloxy)-6,7-dihydro-4H-pyrimido[6,1-a]isoquinolin-4-one (54.5 mg, 0.208 mmol) was added. After 30 min at 0° C., the reaction was quenched with water. Purification via reverse phase Biotage (acetonitrile/water) afforded the title product as a white solide of (20 mg, 16.2%).
LC-MS (ESI): m/z 563 [M+H]$^+$; 4.25 min (ret time).

E4

2-({[4-{[4-Chloro-3-(trifluoromethyl)phenyl]oxy}-2-(trifluoromethyl)phenyl]methyl}oxy)-9-(methyloxy)-6,7-dihydro-4H-pyrimido[6,1-a]isoquinolin-4-one

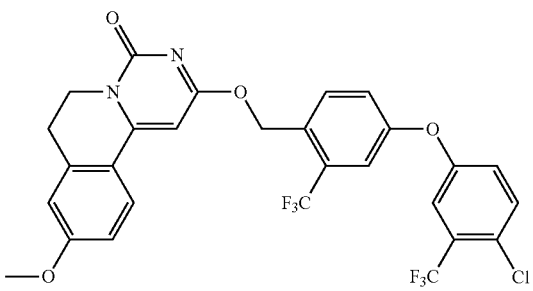 [SMILES: COc1ccc2c(c1)CCn1c-2cc(OCc2ccc(Oc3ccc(Cl)c(C(F)(F)F)c3)cc2C(F)(F)F)nc1=O]

The title compound was prepared by a procedure similar to that described for E1 starting from [4-{[4-chloro-3-(trifluoromethyl)phenyl]oxy}-2-(triflu-oromethyl)phenyl]methanol and 2-chloro-9-(methyloxy)-6,7-dihydro-4H-pyrimido[6,1-a]isoq-uinolin-4-one.
LC-MS (ESI): m/z 597 [M+H]$^+$; 4.26 min (ret time).

E5

9-(Methyloxy)-2-{[(2-(trifluoromethyl)-4-{[3-(trifluoromethyl)phenyl]oxy}phenyl)methyl]oxy}-6,7-dihydro-4H-pyrimido[6,1-a]isoquinolin-4-one

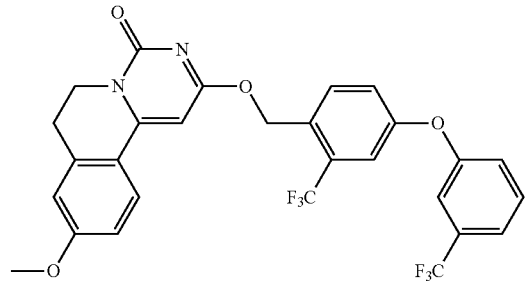 [SMILES: COc1ccc2c(c1)CCn1c-2cc(OCc2ccc(Oc3cccc(C(F)(F)F)c3)cc2C(F)(F)F)nc1=O]

The title compound was prepared by a procedure similar to that described for E1 starting from (2-(trifluoromethyl)-4-{[3-(trifluoromethyl)phenyl]oxy}phenyl)methanol and 2-chloro-9-(methyloxy)-6,7-dihydro-4H-pyrimido[6,1-a]isoquinolin-4-one.
LC-MS (ESI): m/z 563 [M+H]$^+$; 4.13 min (ret time).

E6

2-{[(2-Chloro-4-{[3-(trifluoromethyl)phenyl]oxy}phenyl)methyl]oxy}-9-(methyloxy)-6,7-dihydro-4H-pyrimido[6,1-a]isoquinolin-4-one

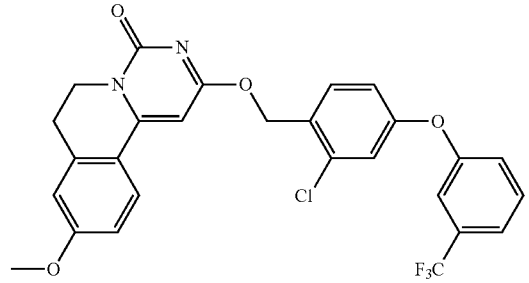 [SMILES: COc1ccc2c(c1)CCn1c-2cc(OCc2ccc(Oc3cccc(C(F)(F)F)c3)cc2Cl)nc1=O]

The title compound was prepared by a procedure similar to that described for E1 starting from (2-chloro-4-{[3-(trifluoromethyl)phenyl]oxy}phenyl)methanol and 2-chloro-9-(methyloxy)-6,7-dihydro-4H-pyrimido[6,1-a]isoquinolin-4-one.

LC-MS (ESI): m/z 529 [M+H]$^+$; 4.15 min (ret time).

E7

4-(((9-Methoxy-4-oxo-6,7-dihydro-4H-pyrimido[6,1-a]isoquinolin-2-yl)oxy)methyl)-2-(3-(trifluoromethyl)phenoxy)benzonitrile

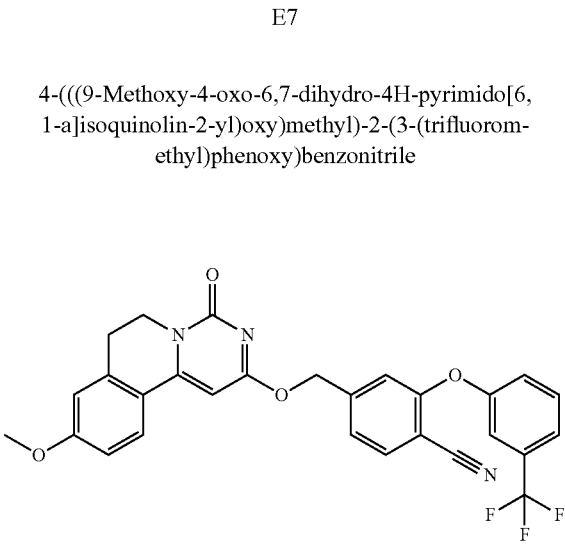

The title compound was prepared by a procedure similar to that described for E1 starting from 4-(hydroxymethyl)-2-{[3-(trifluoromethyl)phenyl]oxy}benzonitrile and 2-chloro-9-(methyloxy)-6,7-dihydro-4H-pyrimido[6,1-a]isoquinolin-4-one.

LC-MS (ESI): m/z 520 [M+H]$^+$; 3.66 min (ret time).

E9

2-({[9-(Methyloxy)-4-oxo-6,7-dihydro-4H-pyrimido[6,1-a]isoquinolin-2-yl]oxy}methyl)-5-{[3-(trifluoromethyl)phenyl]oxy}benzonitrile

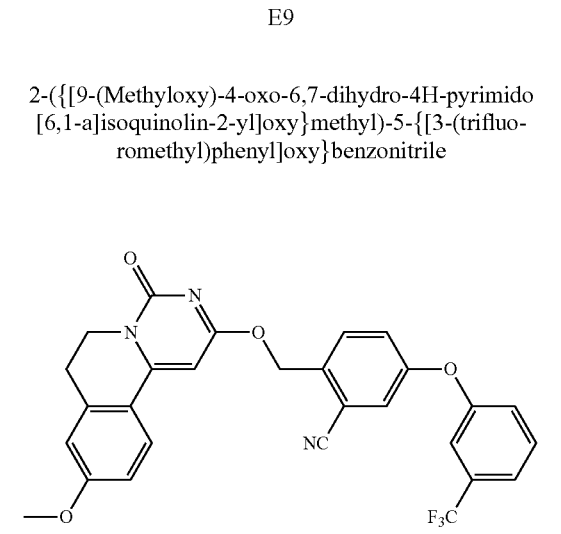

The title compound was prepared by a procedure similar to that described for E1 starting from 5-(2-hydroxyethyl)-2-{[3-(trifluoromethyl)phenyl]oxy}benzonitrile and 2-chloro-9-(methyloxy)-6,7-dihydro-4H-pyrimido[6,1-a]isoquinolin-4-one.

LC-MS (ESI): m/z 534 [M+H]$^+$; 3.76 min (ret time).

E10

9-(Methyloxy)-2-{[(6-{[3-(trifluoromethyl)phenyl]oxy}-3-pyridinyl)methyl]oxy}-6,7-dihydro-4H-pyrimido[6,1-a]isoquinolin-4-one

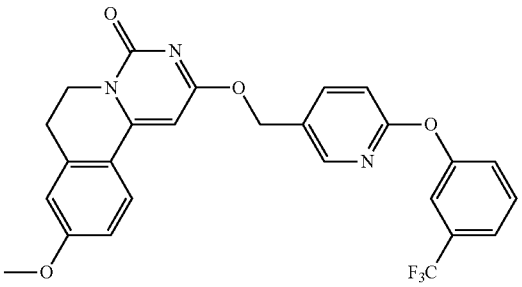

The title compound was prepared by a procedure similar to that described for E1 starting from (6-{[3-(trifluoromethyl)phenyl]oxy}-3-pyridinyl)methanol and 2-chloro-9-(methyloxy)-6,7-dihydro-4H-pyrimido[6,1-a]isoquinolin-4-one.

LC-MS (ESI): m/z 496 [M+H]$^+$; 3.69 min (ret time).

E11

5-({[9-(Methyloxy)-4-oxo-6,7-dihydro-4H-pyrimido[6,1-a]isoquinolin-2-yl]thio}methyl)-2-{[3-(trifluoromethyl)phenyl]oxy}benzonitrile

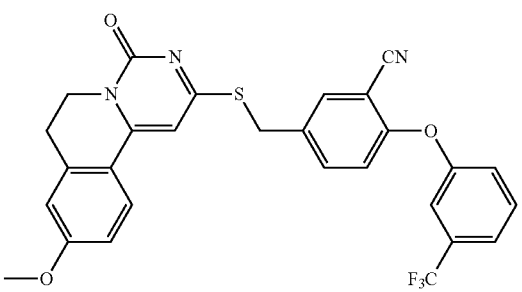 [SMILES: COc1ccc2c(c1)CCn1c-2cc(SCc2ccc(Oc3cccc(C(F)(F)F)c3)c(C#N)c2)nc1=O]

The title compound was prepared by a procedure similar to that described for E1 starting from 5-(mercaptomethyl)-2-{[3-(trifluoromethyl)phenyl]oxy}benzonitrile and 2-chloro-9-(methyloxy)-6,7-dihydro-4H-pyrimido[6,1-a]isoquinolin-4-one.

LC-MS (ESI): m/z 536 [M+H]$^+$; 3.80 min (ret time).

E12

2-{[2-(4-{[4-Chloro-3-(trifluoromethyl)phenyl]oxy}phenyl)ethyl]oxy}-9-(methyloxy)-6,7-dihydro-4H-pyrimido[6,1-a]isoquinolin-4-one

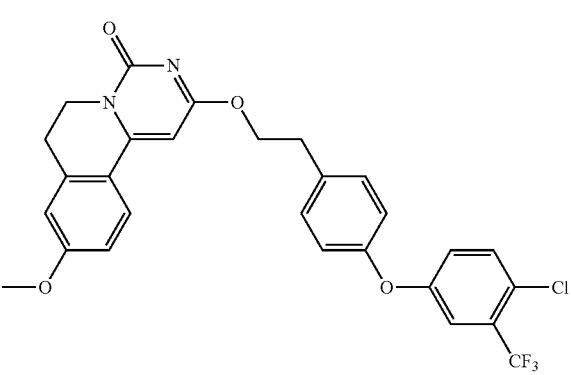 [SMILES: COc1ccc2c(c1)CCn1c-2cc(OCCc2ccc(Oc3ccc(Cl)c(C(F)(F)F)c3)cc2)nc1=O]

The title compound was prepared by a procedure similar to that described for E1 starting from 2-(4-{[4-chloro-3-(trifluoromethyl)phenyl]oxy}phenyl)ethanol and 2-chloro-9-(methyloxy)-6,7-dihydro-4H-pyrimido[6,1-a]isoquinolin-4-one.

LC-MS (ESI): m/z 543 [M+H]$^+$; 4.18 min (ret time).

E13

9-(Methyloxy)-2-{[(3-(methyloxy)-4-{[3-(trifluoromethyl)phenyl]oxy}phenyl)methyl]oxy}-6,7-dihydro-4H-pyrimido[6,1-a]isoquinolin-4-one

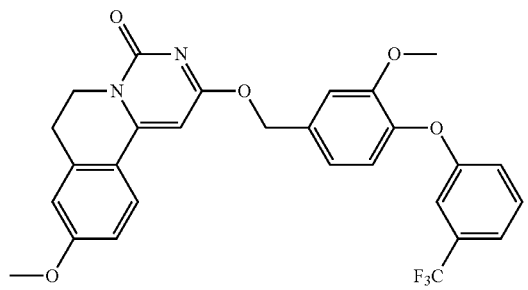 [SMILES: COc1ccc2c(c1)CCn1c-2cc(OCc2ccc(Oc3cccc(C(F)(F)F)c3)c(OC)c2)nc1=O]

The title compound was prepared by a procedure similar to that described for E1 starting from (3-(methyloxy)-4-{[3-(trifluoromethyl)phenyl]oxy}phenyl)methanol and 2-chloro-9-(methyloxy)-6,7-dihydro-4H-pyrimido[6,1-a]isoquinolin-4-one.

LC-MS (ESI): m/z 525 [M+H]$^+$; 4.50 min (ret time).

E14

9-(Methyloxy)-2-{[(3-methyl-4-{[3-(trifluoromethyl)phenyl]oxy}phenyl)methyl]oxy}-6,7-dihydro-4H-pyrimido[6,1-a]isoquinolin-4-one

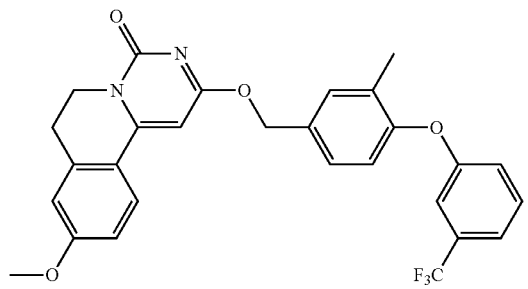 [SMILES: COc1ccc2c(c1)CCn1c-2cc(OCc2ccc(Oc3cccc(C(F)(F)F)c3)c(C)c2)nc1=O]

The title compound was prepared by a procedure similar to that described for E1 starting from (3-methyl-4-{[3-(trifluoromethyl)phenyl]oxy}phenyl)methanol and 2-chloro-9-(methyloxy)-6,7-dihydro-4H-pyrimido[6,1-a]isoquinolin-4-one.

LC-MS (ESI): m/z 509 [M+H]$^+$; 4.74 min (ret time).

E15

9-(Methyloxy)-2-{[(3-(trifluoromethyl)-4-{[3-(trifluoromethyl)phenyl]oxy}phenyl)methyl]oxy}-6,7-dihydro-4H-pyrimido[6,1-a]isoquinolin-4-one

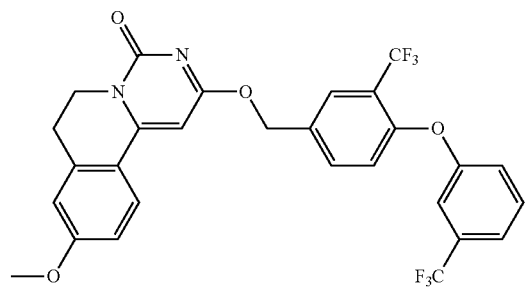

The title compound was prepared by a procedure similar to that described for E1 starting from 3-(trifluoromethyl)-4-{[3-(trifluoromethyl)phenyl]oxy}phenyl)methanol and 2-chloro-9-(methyloxy)-6,7-dihydro-4H-pyrimido[6,1-a]isoquinolin-4-one.

LC-MS (ESI): m/z 563 [M+H]$^+$; 4.75 min (ret time).

E16

2-{[4-Fluoro-3-(trifluoromethyl)phenyl]oxy}-5-({[9-(methyloxy)-4-oxo-6,7-dihydro-4H-pyrimido[6,1-a]isoquinolin-2-yl]oxy}methyl)benzonitrile

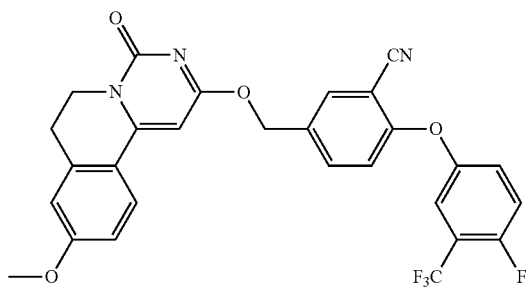 [SMILES: COc1ccc2c(c1)CCn1c-2cc(OCc2ccc(Oc3ccc(F)c(C(F)(F)F)c3)c(C#N)c2)nc1=O]

The title compound was prepared by a procedure similar to that described for E1 starting from 2-{[4-fluoro-3-(trifluoromethyl)phenyl]oxy}-5-(hydroxymethyl)benzonitrile and 2-chloro-9-(methyloxy)-6,7-dihydro-4H-pyrimido[6,1-a] isoquinolin-4-one.

LC-MS (ESI): m/z 538 [M+H]$^+$; 3.75 min (ret time).

E17

2-{[4-Chloro-3-(trifluoromethyl)phenyl]oxy}-5-({[9-(methyloxy)-4-oxo-6,7-dihydro-4H-pyrimido[6,1-a]isoquinolin-2-yl]oxy}methyl)benzonitrile

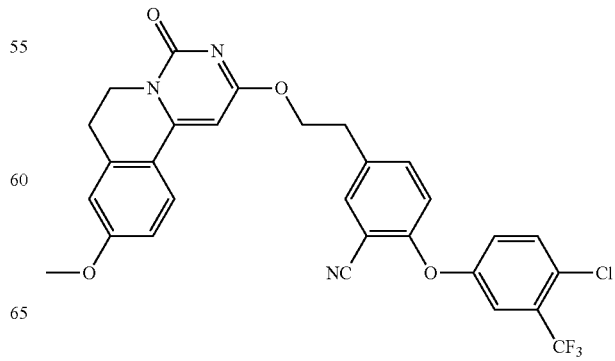

The title compound was prepared by a procedure similar to that described for E1 starting from 2-{[4-chloro-3-(trifluoromethyl)phenyl]oxy}-5-(2-hydroxyethyl)benzonitrile and 2-chloro-9-(methyloxy)-6,7-dihydro-4H-pyrimido[6,1-a]isoquinolin-4-one.

LC-MS (ESI): m/z 568 [M+H]+; 3.91 min (ret time).

E18

2-((3-Bromo-4-(3-(trifluoromethyl)phenoxy)benzyl)oxy)-9-methoxy-6,7-dihydro-4H-pyrimido[6,1-a]isoquinolin-4-one

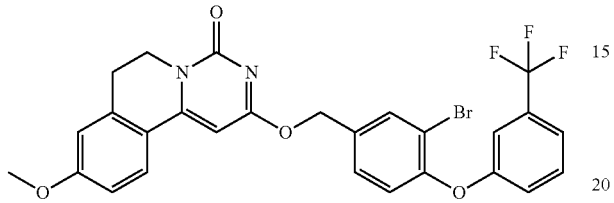

The title compound was prepared by a procedure similar to that described for E1 starting from the (3-bromo-4-{[3-(trifluoromethyl)phenyl]oxy}phenyl)methanol and 2-chloro-9-(methyloxy)-6,7-dihydro-4H-pyrimido[6,1-a]isoquinolin-4-one.

LC-MS (ESI): m/z 573 [M+H]+; 4.74 min (ret time).

E19

2-((3-Chloro-4-(3-(trifluoromethyl)phenoxy)benzyl)oxy)-9-methoxy-6,7-dihydro-4H-pyrimido[6,1-a]isoquinolin-4-one

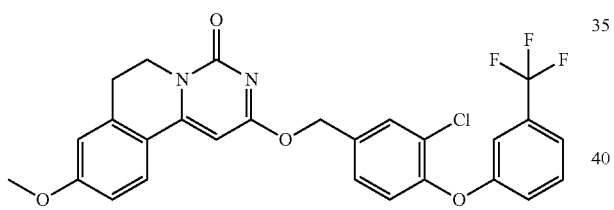

The title compound was prepared by a procedure similar to that described for E1 starting from (3-chloro-4-{[3-(trifluoromethyl)phenyl]oxy}pyridinyl)methanol and 2-chloro-9-(methyloxy)-6,7-dihydro-4H-pyrimido[6,1-a]isoquinolin-4-one.

LC-MS (ESI): m/z 529 [M+H]+; 4.06 min (ret time).

E20

9-(Methyloxy)-2-{[(5-{[3-(trifluoromethyl)phenyl]oxy}-2-pyridinyl)met-hyl]oxy}-6,7-dihydro-4H-pyrimido[6,1-a]isoquinolin-4-one

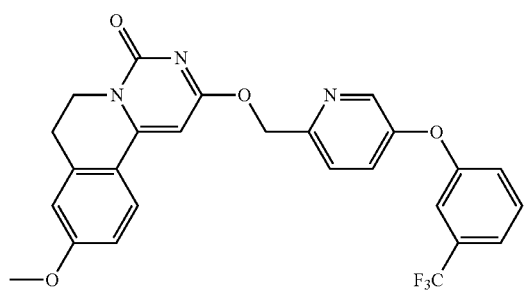

The title compound was prepared by a procedure similar to that described for E1 starting from (5-{[3-(trifluoromethyl)phenyl]oxy}-2-pyridinyl)methanol and 2-chloro-9-(methyloxy)-6,7-dihydro-4H-pyrimido[6,1-a]isoquinolin-4-one.

LC-MS (ESI): m/z 496 [M+H]+; 4.20 min (ret time).

E21

2-{[6-{[4-Chloro-3-(trifluoromethyl)phenyl]oxy}-3-pyridinyl)methyl]oxy}-9-(methyloxy)-6,7-dihydro-4H-pyrimido[6,1-a]isoquinolin-4-one

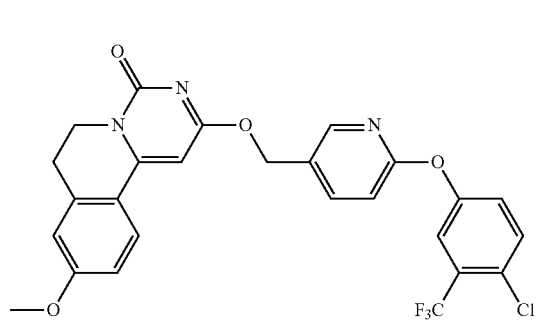 [SMILES: COc1ccc2c(c1)CCn1c-2cc(OCc2ccc(Oc3ccc(Cl)c(C(F)(F)F)c3)nc2)nc1=O]

The title compound was prepared by a procedure similar to that described for E1 starting from 2-chloro-9-(methyloxy)-6,7-dihydro-4H-pyrimido[6,1-a]isoquinolin-4-one and (6-{[4-chloro-3-(trifluoromethyl)phenyl]oxy}-3-pyridinyl)methanol.

LC-MS (ESI): m/z 530 [M+H]+; 4.50 min (ret time).

E22

5-(((9-Methoxy-4-oxo-6,7-dihydro-4H-pyrimido[6,1-a]isoquinolin-2-yl)oxy)methyl)-2-((5-(trifluoromethyl)pyridin-2-yl)oxy)benzonitrile

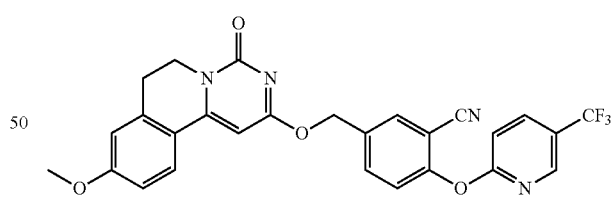

To a solution of 5-(hydroxymethyl)-2-{[5-(trifluoromethyl)-2-pyridinyl]oxy}benzonitrile (202 mg, 0.685 mmol) in anhydrous DMF (5 mL) was added sodium hydride (34.3 mg, 1.428 mmol) at 0° C. The resultant solution was stirred for 5 min, then 2-chloro-9-(methyloxy)-6,7-dihydro-4H-pyrimido[6,1-a]isoquinolin-4-one (150 mg, 0.571 mmol) was added at 0° C. This mixture was stirred at rt for 1 h, quenched by addition of water, extracted with EtOAc (200 mL), washed with water (60 mL×3) and concentrated. The residue was purified via MDAP to afford the title product as a white solid (35 mg).

LC-MS (ESI): m/z 521[M+H]+, 3.57 min (ret time).

¹HNMR (400 MHZ, DMSO): δ 8.60 (s, 1H), δ 8.35 (dd, J=2.6, 8.8 Hz, 1H), δ 8.06 (d, J=2.0 Hz, 1H), δ 7.94 (d, J=8.7 Hz, 1H), δ 7.88 (dd, J=2.0, 8.6 Hz, 1H), δ 7.54 (d, J=8.5, 1H), δ 7.48 (d, J=8.7 Hz, 1H), δ 6.92 (d, J=2.4 Hz, 1H), δ 6.90 (dd, J=2.6, 8.7 Hz, 1H), δ 6.62 (s, 1H), δ 5.42 (s, 2H), δ 4.03 (t, J=6.0 Hz, 2H), δ3.83 (s, 3H), δ2.99 (t, J=6.6 Hz, 2H).

E23

2-((5-(4-Chloro-3-(trifluoromethyl)phenoxy)pyridin-2-yl)methoxy)-9-methoxy-6,7-dihydro-4H-pyrimido[6,1-a]isoquinolin-4-one

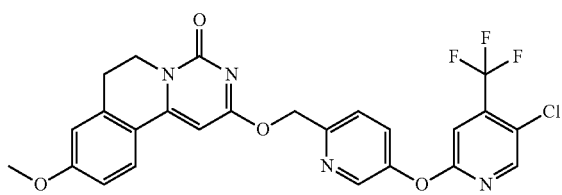 [SMILES: COc1ccc2c(c1)CCn1c-2cc(OCc2ccc(Oc3cc(C(F)(F)F)c(Cl)cn3)cn2)nc1=O]

The title compound was prepared by a procedure similar to that described for E1 starting from (5-{[4-chloro-3-(trifluoromethyl)phenyl]oxy}-2-pyridinyl)methanol and 2-chloro-9-(methyloxy)-6,7-dihydro-4H-pyrimido[6,1-a]isoquinolin-4-one.

LC-MS (ESI): m/z 530 [M+H]⁺; 3.70 min (ret time).

E24

2-((6-(4-Chloro-3-(trifluoromethyl)phenoxy)-5-fluoropyridin-3-yl)methoxy)-9-methoxy-6,7-dihydro-4H-pyrimido[6,1-a]isoquinolin-4-one

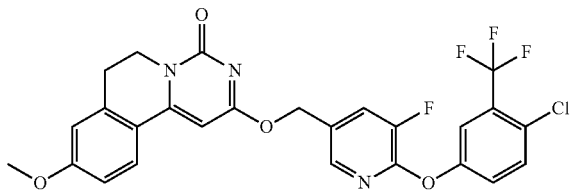 [SMILES: COc1ccc2c(c1)CCn1c-2cc(OCc2cnc(Oc3ccc(Cl)c(C(F)(F)F)c3)c(F)c2)nc1=O]

The title compound was prepared by a procedure similar to that described for E1 starting from (6-{[4-chloro-3-(trifluoromethyl)phenyl]oxy}-5-fluoro-3-pyridinyl)methanol and 2-chloro-9-(methyloxy)-6,7-dihydro-4H-pyrimido[6,1-a]isoqui-nolin-4-one.

LC-MS (ESI): m/z 548 [M+H]⁺; 4.61 min (ret time).

E25

2-((5-Fluoro-6-(3-(trifluoromethyl)phenoxy)pyridin-3-yl)methoxy)-9-methoxy-6,7-dihydro-4H-pyrimido[6,1-a]isoquinolin-4-one

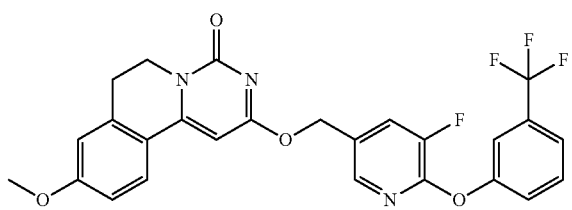 [SMILES: COc1ccc2c(c1)CCn1c-2cc(OCc2cnc(Oc3cccc(C(F)(F)F)c3)c(F)c2)nc1=O]

The title compound was prepared by a procedure similar to that described for E1 starting from (5-fluoro-6-{[3-(trifluoromethyl)phenyl]oxy}-3-pyridinyl)methanol and 2-chloro-9-(methyloxy)-6,7-dihydro-4H-pyrimido[6,1-a]isoquinolin-4-one.

LC-MS (ESI): m/z 514 [M+H]⁺; 4.40 min (ret time).

E26

2-((5-Fluoro-6-(4-fluoro-3-(trifluoromethyl)phenoxy)pyridin-3-yl)methoxy)-9-methoxy-6,7-dihydro-4H-pyrimido[6,1-a]isoquinolin-4-one

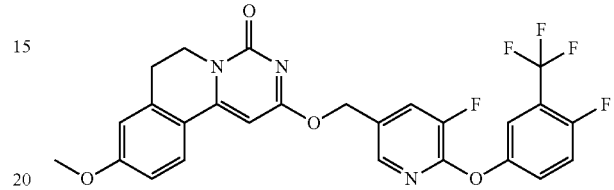

The title compound was prepared by a procedure similar to that described for E1 starting from (5-fluoro-6-{[4-fluoro-3-(trifluoromethyl)phenyl]oxy}-3-pyridinyl)methanol and 2-chloro-9-(methyloxy)-6,7-dihydro-4H-pyrimido[6,1-a]isoquin-olin-4-one.

LC-MS (ESI): m/z 532 [M+H]⁺; 4.44 min (ret time).

E27

2-((5-Chloropyridin-3-yl)oxy)-5-(((9-methoxy-4-oxo-6,7-dihydro-4H-pyrimido[6,1-a]isoquinolin-2-yl)oxy)methyl)benzonitrile

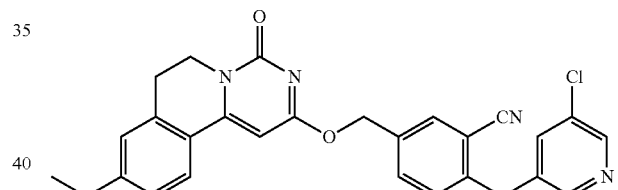

The title compound was prepared by a procedure similar to that described for E1 starting from 2-[(5-chloro-3-pyridinyl)oxy]-5-(hydroxymethyl)benzo-nitrile and 2-chloro-9-(methyloxy)-6,7-dihydro-4H-pyrimido[6,1-a]isoquinolin-4-one.

LC-MS (ESI): m/z 487 [M+H]⁺; 3.36 min (ret time).

E28

2-((5-Chloropyridin-3-yl)oxy)-5-(((9-methoxy-4-oxo-6,7-dihydro-4H-pyrimido[6,1-a]isoquinolin-2-yl)amino)methyl)benzonitrile

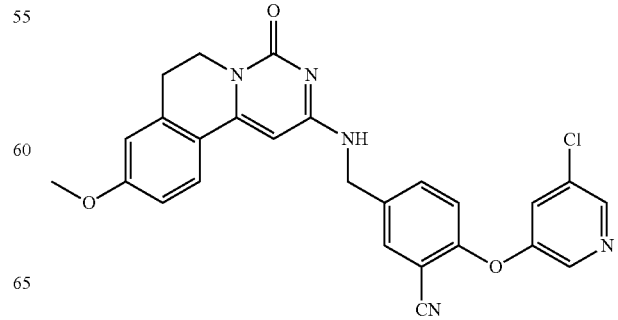

To a solution of 5-(aminomethyl)-2-[(5-chloro-3-pyridinyl)oxy]benzonitrile (113 mg, 0.435 mmol) in CH₃CN (5 mL) were added 2-chloro-9-(methyloxy)-6,7-dihydro-4H-pyrimido[6,1-a]isoquinolin-4-one (137 mg, 0.522 mmol) and K₂CO₃ (180 mg). The reaction mixture was sealed in a microwave vial and irradiated with a microwave at 50° C. for 20 min. Purification via mass-directed autopreparation afforded the title product (24 mg).

LC-MS (ESI): m/z 486 [M+H]⁺; 2.71 min (ret time).

E29

2-((4-((5-Chloropyridin-3-yl)oxy)benzyl)amino)-9-methoxy-6,7-dihydro-4H-pyrimido[6,1-a]isoquinolin-4-one

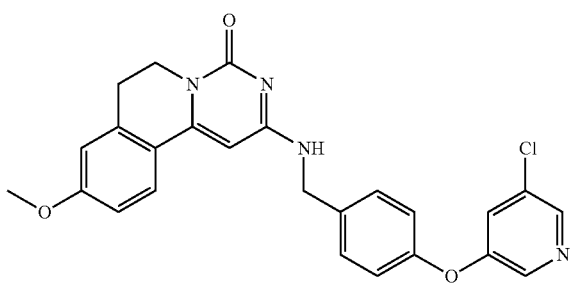 [SMILES: COc1ccc2c(c1)CCn1c-2cc(NCc2ccc(Oc3cncc(Cl)c3)cc2)nc1=O]

To a solution of ({4-[(5-chloro-3-pyridinyl)oxy]phenyl}methyl)amine (15 mg, 0.064 mmol) and 2-chloro-9-(methyloxy)-6,7-dihydro-4H-pyrimido[6,1-a]isoquinolin-4-one (50 mg, 3 eq) in DMF (1 mL) added K₂CO₃ (27 mg, 3 eq) and NaI (10 mg, 1 eq). The reaction mixture was stirred at room temperature until the starting material was consumed up, then filtered off the solid. Purification via mass-directed autopreparation afforded the title product (16 mg).

LC-MS (ESI): m/z 461 [M+H]⁺; 2.79 min (ret time).

E30

5-(2-((9-Methoxy-4-oxo-6,7-dihydro-4H-pyrimido[6,1-a]isoquinolin-2-yl)oxy)ethyl)-2-((5-(trifluoromethyl)pyridin-2-yl)oxy)benzonitrile

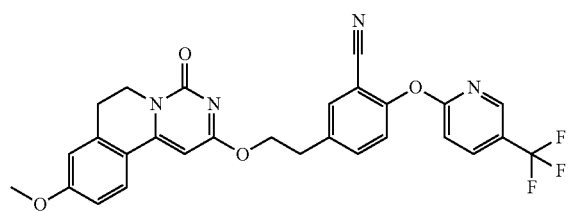 [SMILES: COc1ccc2c(c1)CCn1c-2cc(OCCc2ccc(Oc3ccc(C(F)(F)F)cn3)c(C#N)c2)nc1=O]

The title compound was prepared by a procedure similar to that described for E1 starting from 5-(2-hydroxyethyl)-2-{[5-(trifluoromethyl)-2-pyridinyl]oxy}benzonitrile and 2-chloro-9-(methyloxy)-6,7-dihydro-4H-pyrimido[6,1-a]isoquino-lin-4-one.

LC-MS (ESI): m/z 535 [M+H]⁺; 4.20 min (ret time).

E31

2-(4-Chloro-3-(trifluoromethyl)phenoxy)-5-(((9-methoxy-4-oxo-6,7-dihy-dro-4H-pyrimido[6,1-a]isoquinolin-2-yl)amino)methyl)benzonitrile

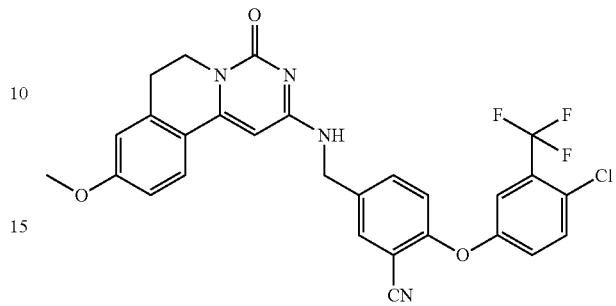

To a solution of [(4-{[4-chloro-3-(trifluoromethyl)phenyl]oxy}phenyl)methyl]amine (75 mg, 0.25 mmol) and 2-chloro-9-(methyloxy)-6,7-dihydro-4H-pyrimido[6,1-a]isoquinolin-4-one (121 mg, 2 eq) in DMF (1 mL) were added K₂CO₃ (63 mg, 2 eq) and NaI (35 mg, 1 eq). The reation solution was stirred at room temperature overnight. Then purification via mass-directed autopreparation afforded the title product (54 mg).

LC-MS (ESI): m/z 553 [M+H]⁺; 3.26 min (ret time).

E32

5-(2-Cyano-4-(((9-methoxy-4-oxo-6,7-dihydro-4H-pyrimido[6,1-a]isoqui-nolin-2-yl)oxy)methyl)phenoxy)nicotinonitrile

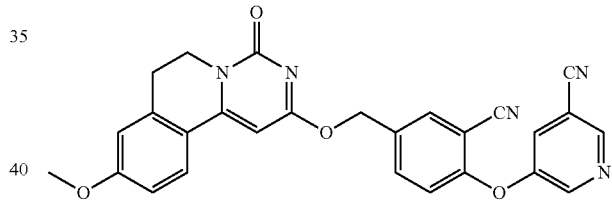

The title compound was prepared by a procedure similar to that described for E1 starting from 5-({[2-cyano-4-(hydroxymethyl)phenyl]oxy})-3-pyridine-carbonitrile and 2-chloro-9-(methyloxy)-6,7-dihydro-4H-pyrimido[6,1-a]isoquinolin-4-one.

LC-MS (ESI): m/z 479 [M+H]⁺; 3.08 min (ret time)

E33

2-((5-Chloropyridin-3-yl)oxy)-5-(((9-methoxy-4-oxo-6,7-dihydro-4H-pyr-imido[6,1-a]isoquinolin-2-yl)(methyl)amino)methyl)benzonitrile

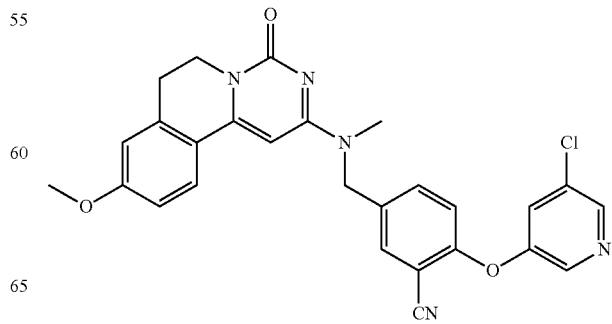

The title compound was prepared by a procedure similar to that described for E31 starting from 2-[(5-chloro-3-pyridinyl)oxy]-5-[(methylamino)methyl]benzonitrile and 2-chloro-9-(methyloxy)-6,7-dihydro-4H-pyrimido[6,1-a]isoquinolin-4-one.

LC-MS (ESI): m/z 500 [M+H]$^+$; 2.77 min (ret time).

E34

5-(((9-Methoxy-4-oxo-6,7-dihydro-4H-pyrimido[6,1-a]isoquinolin-2-yl)oxy)methyl)-2-((5-(trifluoromethyl)pyridin-3-yl)oxy)benzonitrile

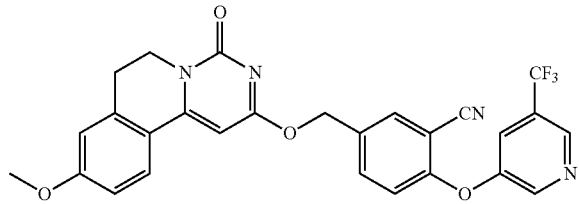 [SMILES: COc1ccc2c(c1)CCn1c-2cc(OCc2ccc(Oc3cncc(C#N)c3)c(C#N)c2)nc1=O]

The title compound was prepared by a procedure similar to that described for E1 starting from 5-(hydroxymethyl)-2-({[5-(trifluoromethyl)-3-pyridinyl]oxy}benzonitrile and 2-chloro-9-(methyloxy)-6,7-dihydro-4H-pyrimido[6,1-a]isoquinolin-4-one.

LC-MS (ESI): m/z 521 [M+H]$^+$; 3.45 min (ret time).

E35

2-(3-Chloro-4-(trifluoromethyl)phenoxy)-5-(((9-methoxy-4-oxo-6,7-dihydro-4H-pyrimido[6,1-a]isoquinolin-2-yl)(methyl)amino)methyl)benzonitrile

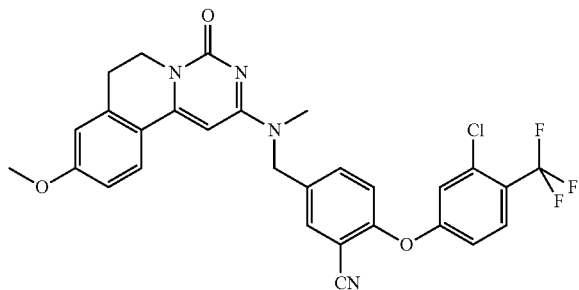 [SMILES: COc1ccc2c(c1)CCn1c-2cc(N(C)Cc2ccc(Oc3ccc(C(F)(F)F)c(Cl)c3)c(C#N)c2)nc1=O]

The title compound was prepared by a procedure similar to that described for E31 starting from 2-{[3-chloro-4-(trifluoromethyl)phenyl]oxy}-5-[(methyl-amino)methyl]benzonitrile and 2-chloro-9-(methyloxy)-6,7-dihydro-4H-pyrimido[6,1-a]isoquinolin-4-one.

LC-MS (ESI): m/z 567 [M+H]$^+$; 3.24 min (ret time).

E36

5-({[9-(Methyloxy)-4-oxo-6,7-dihydro-4H-pyrimido[6,1-a]isoquinolin-2-yl]oxy}methyl)-2-{[6-(trifluoromethyl)-3-pyridinyl]oxy}benzonitrile

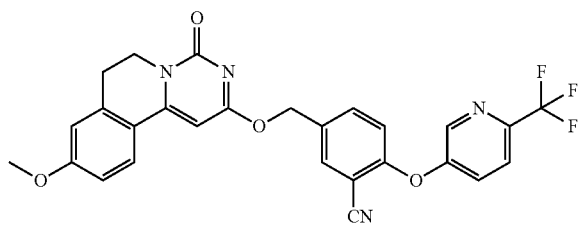 [SMILES: COc1ccc2c(c1)CCn1c-2cc(OCc2ccc(Oc3ccc(C(F)(F)F)nc3)c(C#N)c2)nc1=O]

To a solution of 5-(hydroxymethyl)-2-{[6-(trifluoromethyl)-3-pyridinyl]oxy}benzonitrile (90 mg, 0.306 mmol) in anhydrous DMF (5 mL) was added sodium hydride (73.4 mg, 1.835 mmol) at 0° C. The resultant solution was stirred for 15 min, then 2-chloro-9-(methyloxy)-6,7-dihydro-4H-pyrimido[6,1-a]isoquinolin-4-one (96 mg, 0.367 mmol) was added at 0° C. This mixture was stirred at rt for 30 min, quenched by addition of water and filtered. The filtrate was purified via MDAP to afford the title product as a white solid (50 mg).

LC-MS (ESI): m/z 521[M+H], 3.47 min (ret time).
$^1$H-NMR (400 MHZ, DMSO): δ 8.73 (d, J=2.8 Hz, 1H), δ 8.09 (d, J=2.0 Hz, 1H), δ 7.99 (d, J=8.8 Hz, 1H), δ 7.94 (d, J=8.8 Hz, 1H), δ 7.83 (m, 2H), δ 7.33 (d, J=8.8 Hz, 1H), δ 6.98 (d, J=2.4 Hz, 1H), δ 6.95 (dd, J=2.6, 8.7 Hz, 1H), δ 6.59 (s, 1H), δ 5.39 (s, 2H), δ4.03(d, J=6.8 Hz, 2H), δ3.93(s, 3H), δ2.98(d, J=6.8 Hz, 2H).

E37

9-methoxy-2-((4-(3-(trifluoromethyl)phenoxy)benzyl)oxy)-6,7-dihydro-4H-pyrimido[6,1-a]isoquinolin-4-one

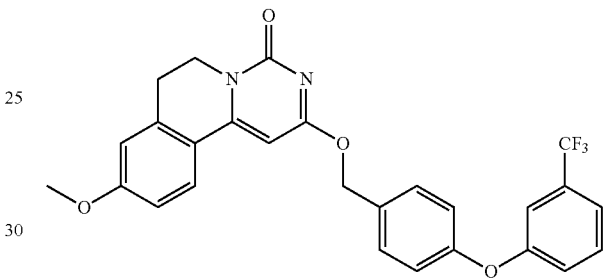

To a solution of 5-(hydroxymethyl)-2-{[3-(trifluoromethyl)phenyl]oxy}benzonitrile (380 mg, 1.20 mmol) in DMF (10 mL) was added NaH (206 mg, 60% dispersed in mineral oil at) at 0° C., After 30 min, 2-chloro-9-(methyloxy)-6,7-dihydro-4H-pyrimido[6,1-a]isoquinolin-4-one (551 mg, 1.94 mmol) was added. The reaction solution was stirred for 30 min at room temperature, then quenched with ice water (10 mL) and extracted with ethyl acetate (3*20 mL). Combined organic parts were layer dried over anhydrous Na$_2$SO$_4$, filtered and concentrated. Purification via Mass-Directed autopreparation afforded the desired product (118 mg).

LC-MS (ESI): m/z 495 [M+H]$^+$; 3.93 min (ret time).

E38

2-((3,5-difluoro-4-(3-(trifluoromethyl)phenoxy)benzyl)amino)-9-methoxy-6,7-dihydro-4H-pyrimido[6,1-a]isoquinolin-4-one

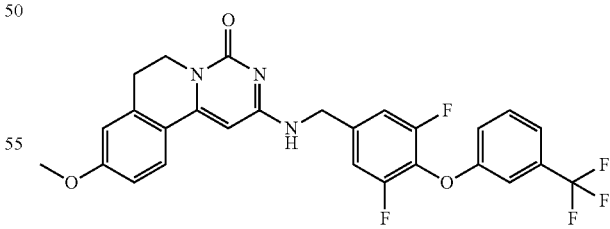

A mixture of [(3,5-difluoro-4-{[3-(trifluoromethyl)phenyl]oxy}phenyl)methyl]amine (200 mg, 0.660 mmol), 2-Chloro-9-(methyloxy)-6,7-dihydro-4H-pyrimido[6,1-a]isoquinolin-4-one (150 mg, 0.571 mmol), and Potassium carbonate (240 mg, 1.74 mmol) in Acetonitrile (5 mL) was refluxed for 6 h, then filtered through silica pad and concentrated. Purification via flash chromatography yielded the desired product as a white solid.

LC-MS (ESI): m/z 530 [M+H]$^+$; 3.27 min (ret time).

E39

2-((3-fluoro-4-(3-(trifluoromethyl)phenoxy)benzyl)
amino)-9-methoxy-6,7-dihydro-4H-pyrimido[6,1-a]
isoquinolin-4-one

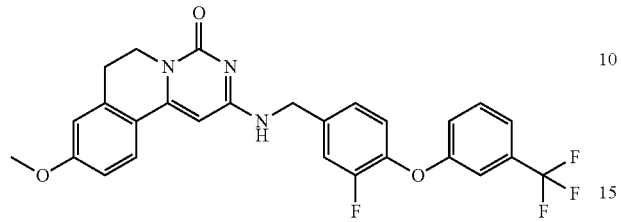

The title compound was prepared by a procedure similar to that described for E38 starting from [(3-Fluoro-4-{[3-(trifluoromethyl)phenyl]oxy}phenyl)methyl]amin, 2-chloro-9-(methyloxy)-6,7-dihydro-4H-pyrimido[6,1-a]isoquinolin-4-one and Potassium carbonate.

LC-MS (ESI): m/z 512 [M+H]$^+$; 3.25 min (ret time).

E40

2-((3-fluoro-4-(3-(trifluoromethyl)phenoxy)benzyl)
oxy)-9-methoxy-6,7-dihydro-4H-pyrimido[6,1-a]
isoquinolin-4-one

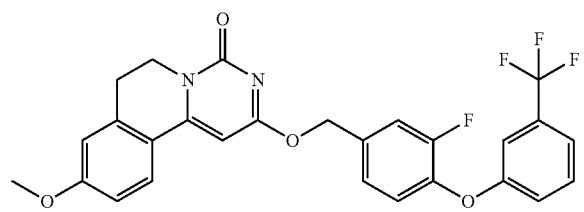 [SMILES: COc1ccc2c(c1)CCn1c-2cc(OCc2ccc(Oc3cccc(C(F)(F)F)c3)c(F)c2)nc1=O]

The title compound was prepared by a procedure similar to that described for E37 starting from (3-Fluoro-4-{[3-(trifluoromethyl)phenyl]oxy}) phenyl)methanol and 2-Chloro-9-(methyloxy)-6,7-dihydro-4H-pyrimido[6,1-a]isoquinolin-4-one.

LC-MS (ESI): m/z 513 [M+H]$^+$; 3.94 min (ret time).

E41

5-((9-methoxy-4-oxo-6,7-dihydro-4H-pyrimido[6,1-a]isoquinolin-2-yl)oxy)-2-(3-(trifluoro-methyl)phenoxy)benzonitrile

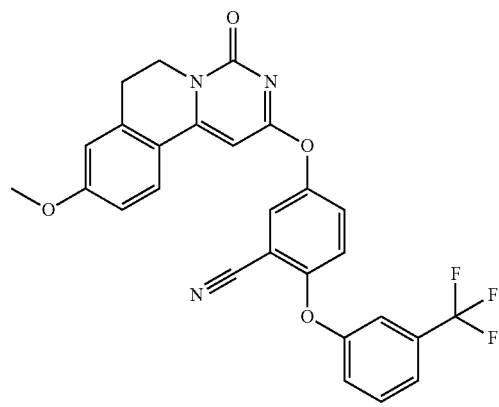 [SMILES: COc1ccc2c(c1)CCn1c-2cc(Oc2ccc(Oc3cccc(C(F)(F)F)c3)c(C#N)c2)nc1=O]

A mixture of 5-hydroxy-2-{[3-(trifluoromethyl)phenyl]oxy}benzonitrile (75 mg, 0.27 mmol), 2-chloro-9-(methyloxy)-6,7-dihydro-4H-pyrimido[6,1-a]isoquinolin-4-one (85 mg, 0.32 mmol), potassium carbonate (148 mg, 1.07 mmol) in N,N-dimethylformamide (DMF) (3 mL) was heated at 80° C. for 30 min. Purification via Biotage (C-18) system afforded the desired product (60 mg) as a white solid.

LC-MS (ESI): m/z 506 [M+H]$^+$; 3.69 min (ret time).

E42

2-(4-(4-chloro-3-(trifluoromethyl)phenoxy)phenoxy)-9-methoxy-6,7-dihydro-4H-pyrimi-do[6,1-a]
isoquinolin-4-one

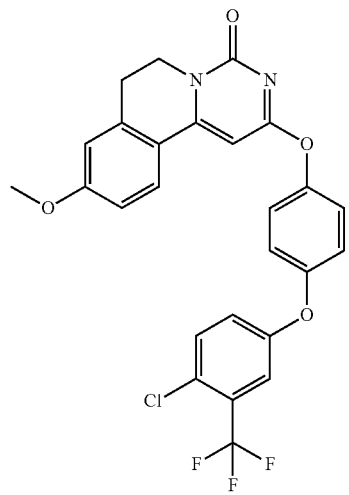 [SMILES: COc1ccc2c(c1)CCn1c-2cc(Oc2ccc(Oc3ccc(Cl)c(C(F)(F)F)c3)cc2)nc1=O]

The title compound was prepared by a procedure similar to that described for E41 starting from 4-{[4-chloro-3-(trifluoromethyl)phenyl]oxy}phenol, 2-chloro-9-(methyloxy)-6,7-dihydro-4H-pyrimido[6,1-a]isoquinolin-4-one and potassium carbonate in dimethyl sulfoxide (DMSO).

E43

2-(4-chloro-3-(trifluoromethyl)phenoxy)-5-(((9-methoxy-4-oxo-6,7-dihydro-4H-pyrimido[6,1-a]
isoquinolin-2-yl)oxy)methyl)benzonitrile

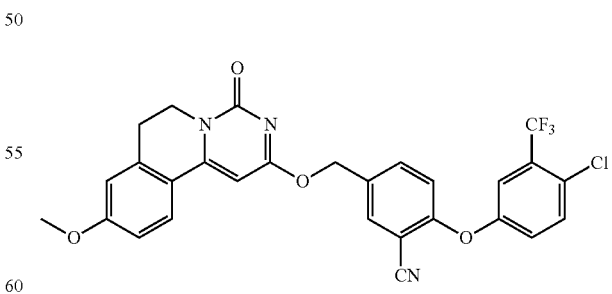

The title compound was prepared by a procedure similar to that described for E37 starting from 2-{[4-chloro-3-(trifluoromethyl)phenyl]oxy}-5-(hydroxymethyl)benzonitrile and 2-chloro-9-(methyloxy)-6,7-dihydro-4H-pyrimido[6,1-a]isoquinolin-4-one.

LC-MS (ESI): m/z 554 [M+H]$^+$; 3.83 min (ret time).

E44

5-(2-((9-methoxy-4-oxo-6,7-dihydro-4H-pyrimido[6,1-a]isoquinolin-2-yl)oxy)ethyl)-2-(3-(trifluoromethyl)phenoxy)benzonitrile

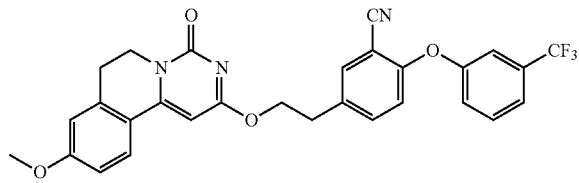 [SMILES: COc1ccc2c(c1)CCn1c-2cc(OCCc2ccc(Oc3cccc(C(F)(F)F)c3)c(C#N)c2)nc1=O]

The title compound was prepared by a procedure similar to that described for E37, starting from 5-(2-hydroxyethyl)-2-{[3-(trifluoromethyl)phenyl]oxy}benzonitrile and 2-chloro-9-(methyloxy)-6,7-dihydro-4H-pyrimido[6,1-a]isoquinolin-4-one.

LC-MS (ESI): m/z 534 [M+H]$^+$; 3.75 min (ret time).

E45

5-(2-cyano-4-(((9-methoxy-4-oxo-6,7-dihydro-4H-pyrimido[6,1-a]isoquinolin-2-yl)(methyl)amino)methyl)phenoxy)nicotinonitrile

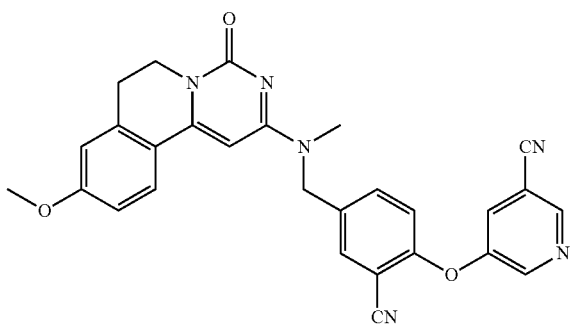 [SMILES: COc1ccc2c(c1)CCn1c-2cc(N(C)Cc2ccc(Oc3cncc(C#N)c3)c(C#N)c2)nc1=O]

To a solution of 5-({2-cyano-4-[(methylamino)methyl]phenyl}oxy)-3-pyridinecarbonitrile (56.0 mg, 0.212 mmol) and 2-chloro-9-(methyloxy)-6,7-dihydro-4H-pyrimido[6,1-a]isoquinolin-4-one (167 mg) in DMF (5 mL) was added K$_2$CO$_3$ (88.0 mg), NaI (32.0 mg). The reaction mixture was stirred at 40° C. overnight. Purification via Mass-Directed Autopreparation afforded the title product (46 mg).

LC-MS (ESI): m/z 491 [M+H]$^+$; 2.59 min (ret time).

E46

5-(((9-methoxy-4-oxo-6,7-dihydro-4H-pyrimido[6,1-a]isoquinolin-2-yl)oxy)methyl)-2-(pyridin-3-yloxy)benzonitrile

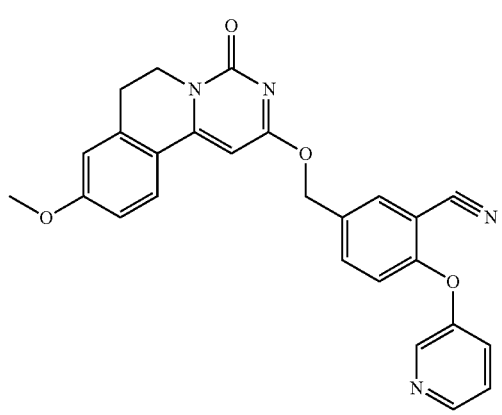 [SMILES: COc1ccc2c(c1)CCn1c-2cc(OCc2ccc(Oc3cccnc3)c(C#N)c2)nc1=O]

The title compound was prepared by a procedure similar to that described for E37 starting from 5-(hydroxymethyl)-2-(3-pyridinyloxy)benzonitrile and 2-chloro-9-(methyloxy)-6,7-dihydro-4H-pyrimido[6,1-a]isoquinolin-4-one.

LC-MS (ESI): m/z 453 [M+H]$^+$; 2.70 min (ret time).

E47

5-(2-((9-methoxy-4-oxo-6,7-dihydro-4H-pyrimido[6,1-a]isoquinolin-2-yl)oxy)ethyl)-2-((5-(trifluoromethyl)pyridin-3-yl)oxy)benzonitrile

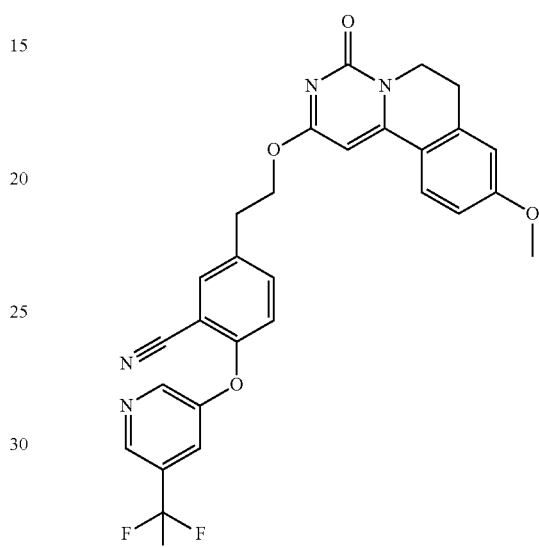

The title compound was prepared by a procedure similar to that described for E37 starting from 5-(2-hydroxyethyl)-2-{[5-(trifluoromethyl)-3-pyridinyl]oxy}benzonitrile and 2-chloro-9-(methyloxy)-6,7-dihydro-4H-pyrimido[6,1-a]isoquinolin-4-one.

LC-MS (ESI): m/z 535 [M+H]$^+$; 3.44 min (ret time).

E48

5-(((9-methoxy-4-oxo-6,7-dihydro-4H-pyrimido[6,1-a]isoquinolin-2-yl)oxy)methyl)-2-(pyrimidin-5-yloxy)benzonitrile

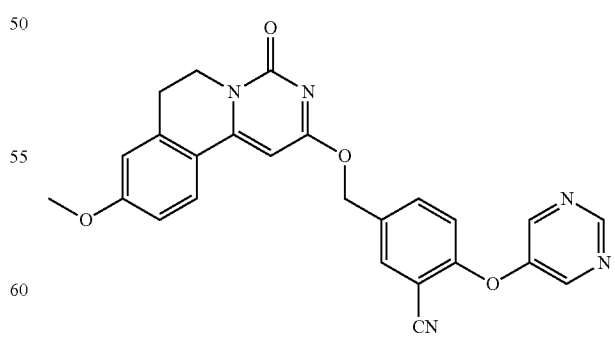

The title compound was prepared by a procedure similar to that described for E37 starting from 5-(hydroxymethyl)-2-(5-pyrimidinyloxy)benzonitrile and 2-chloro-9-(methyloxy)-6,7-dihydro-4H-pyrimido[6,1-a]isoquinolin-4-one.

LC-MS (ESI): m/z 454 [M+H]$^+$; 2.84 min (ret time).

E49

5-(2-chloro-4-(((9-methoxy-4-oxo-6,7-dihydro-4H-pyrimido[6,1-a]isoquinolin-2-yl)oxy)methyl)phenoxy)nicotinonitrile

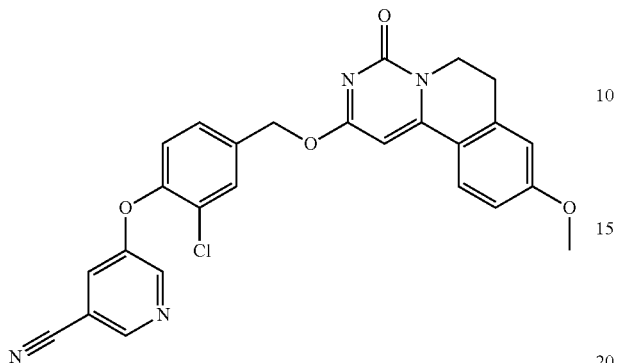

The title compound was prepared by a procedure similar to that described for E37 starting from 5-{[2-chloro-4-(hydroxymethyl)phenyl]oxy}-3-pyridinecarbonitrile and 2-chloro-9-(methyloxy)-6,7-dihydro-4H-pyrimido[6,1-a]isoquinolin-4-one LC-MS (ESI): m/z 487 [M+H]$^+$; 3.95 min (ret time).

E50

9-methoxy-2-((6-(pyridin-4-yloxy)pyridin-3-yl)methoxy)-6,7-dihydro-4H-pyrimido[6,1-a]isoquinolin-4-one

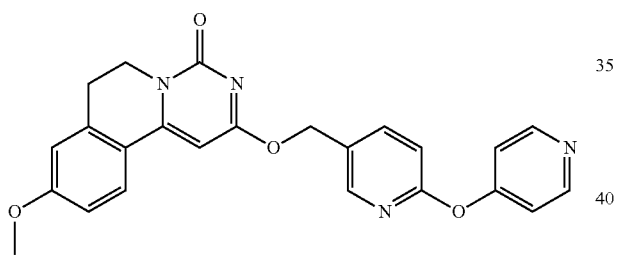

The title compound was prepared by a procedure similar to that described for E37 starting from [6-(4-pyridinyloxy)-3-pyridinyl]methanol and 2-chloro-9-(methyloxy)-6,7-dihydro-4H-pyrimido[6,1-a]isoquinolin-4-one LC-MS (ESI): m/z 429 [M+H]$^+$; 2.49 min (ret time).

E51

2-((3-fluoro-4-(pyrimidin-5-yloxy)benzyl)oxy)-9-methoxy-6,7-dihydro-4H-pyrimido[6,1-a]isoquinolin-4-one

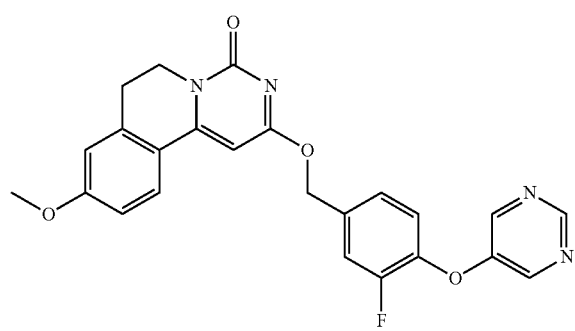 [SMILES: COc1ccc2c(c1)CCn1c-2cc(OCc2ccc(Oc3cncnc3)c(F)c2)nc1=O]

The title compound was prepared by a procedure similar to that described for E37 starting from 3-fluoro-4-(5-pyrimidinyloxy)phenyl]methanol and 2-chloro-9-(methyloxy)-6,7-dihydro-4H-pyrimido[6,1-a]isoquinolin-4-one.

LC-MS (ESI): m/z 447 [M+H]$^+$; 3.04 min (ret time).

E52

5-(2-fluoro-4-(((9-methoxy-4-oxo-6,7-dihydro-4H-pyrimido[6,1-a]isoquinolin-2-yl)oxy)me-thyl)phenoxy)nicotinonitrile

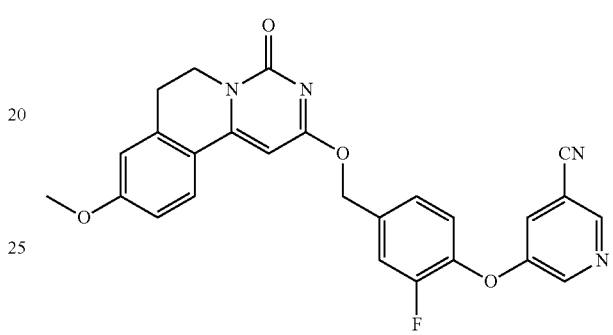

The title compound was prepared by a procedure similar to that described for E37 starting from 5-{[2-fluoro-4-(hydroxymethyl)phenyl]oxy}-3-pyridinecarbonitrile and 2-chloro-9-(methyloxy)-6,7-dihydro-4H-pyrimido[6,1-a]isoquinolin-4-one.

LC-MS (ESI): m/z 471 [M+H]$^+$; 3.26 min (ret time).

E54

2-((5-chloro-6-(3-(trifluoromethyl)phenoxy)pyridin-3-yl)methoxy)-9-methoxy-6,7-dihydro-4H-pyrimido[6,1-a]isoquinolin-4-one

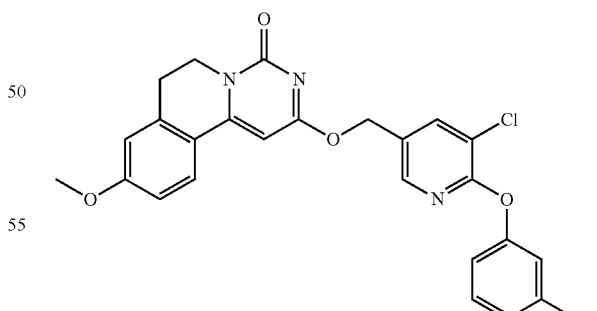

The title compound was prepared by a procedure similar to that described for E37, starting from (5-chloro-6-{[3-(trifluoromethyl)phenyl]oxy}-3-pyridinyl)methanol and 2-chloro-9-(methyloxy)-6,7-dihydro-4H-pyrimido[6,1-a]isoquinolin-4-one.

LC-MS (ESI): m/z 530 [M+H]$^+$; 3.92 min (ret time).

E55

5-(2-((9-methoxy-4-oxo-6,7-dihydro-4H-pyrimido[6,
1-a]isoquinolin-2-yl)oxy)ethyl)-2-((6-(trifluorom-
ethyl)pyridin-3-yl)oxy)benzonitrile

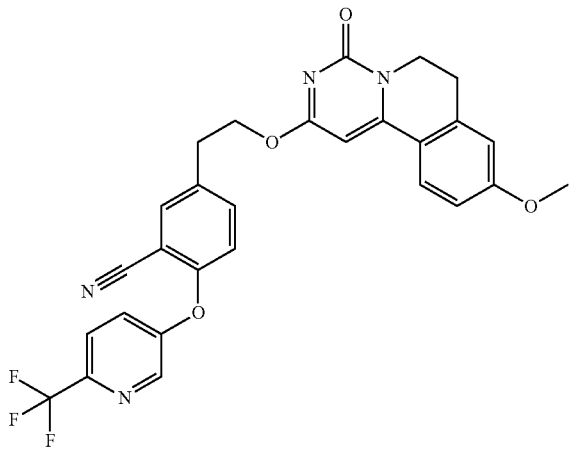 [SMILES: COc1ccc2c(c1)CCn1c-2cc(OCCc2ccc(Oc3ccc(C(F)(F)F)nc3)c(C#N)c2)nc1=O]

The title compound was prepared by a procedure similar to that described for E37, starting from 5-(2-hydroxyethyl)-2-{[6-(trifluoromethyl)-3-pyridinyl]oxy}benzonitrile and 2-chloro-9-(methyloxy)-6,7-dihydro-4H-pyrimido[6,1-a]isoquinolin-4-one.

LC-MS (ESI): m/z 535 [M+H]$^+$; 3.56 min (ret time).

E56

5-(2-((9-methoxy-4-oxo-6,7-dihydro-4H-pyrimido[6,
1-a]isoquinolin-2-yl)oxy)ethyl)-2-((5-(trifluorom-
ethyl)pyridin-2-yl)oxy)benzonitrile

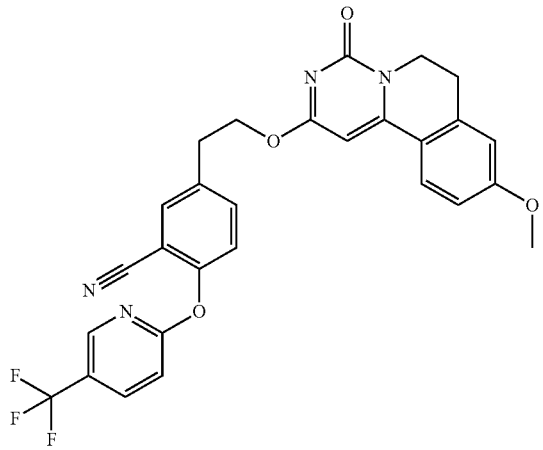 [SMILES: COc1ccc2c(c1)CCn1c-2cc(OCCc2ccc(Oc3ccc(C(F)(F)F)cn3)c(C#N)c2)nc1=O]

The title compound was prepared by a procedure similar to that described for E37, starting from 5-(2-hydroxyethyl)-2-{[5-(trifluoromethyl)-2-pyridinyl]oxy}benzonitrile and 2-chloro-9-(methyloxy)-6,7-dihydro-4H-pyrimido[6,1-a]isoquinolin-4-one.

LC-MS (ESI): m/z 535 [M+H]$^+$; 4.19 min (ret time).

E57

9-methoxy-2-(4-(pyrimidin-5-yloxy)phenethoxy)-6,
7-dihydro-4H-pyrimido[6,1-a]isoquino-lin-4-one

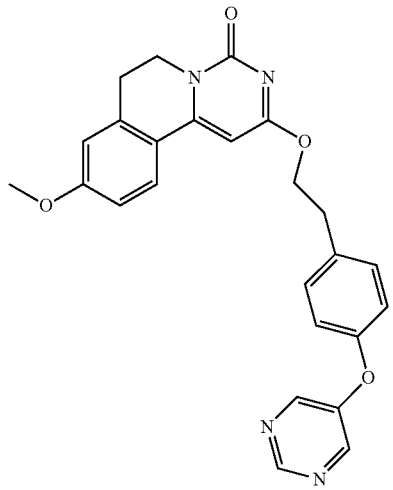 [SMILES: COc1ccc2c(c1)CCn1c-2cc(OCCc2ccc(Oc3cncnc3)cc2)nc1=O]

The title compound was prepared by a procedure similar to that described for E37, starting from 2-[4-(5-pyrimidinyloxy)phenyl]ethanol and 2-chloro-9-(methyloxy)-6,7-dihydro-4H-pyrimido[6,1-a]isoquinolin-4-one.

LC-MS (ESI): m/z 443 [M+H]$^+$; 3.04 min (ret time).

E58

2-((3-fluoro-4-((6-(trifluoromethyl)pyridin-3-yl)oxy)
benzyl)oxy)-9-methoxy-6,7-dihydro-4H-pyrimido[6,
1-a]isoquinolin-4-one

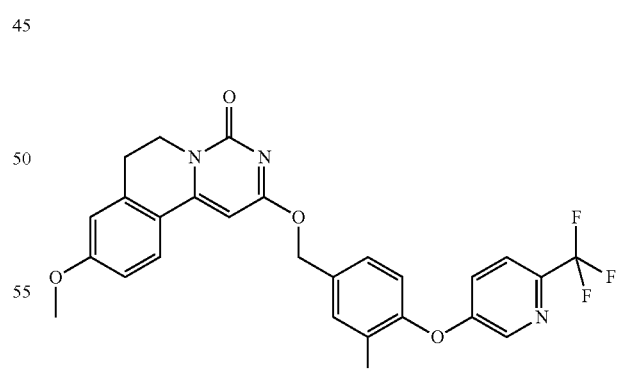

The title compound was prepared by a procedure similar to that described for E37, starting from (3-fluoro-4-{[6-(trifluoromethyl)-3-pyridinyl]oxy}phenyl)methanol and 2-chloro-9-(methyloxy)-6,7-dihydro-4H-pyrimido[6,1-a]isoquinolin-4-one.

LC-MS (ESI): m/z 514 [M+H]$^+$; 3.64 min (ret time).

E59

2-((3-fluoro-4-((6-(trifluoromethyl)pyridin-2-yl)oxy)benzyl)oxy)-9-methoxy-6,7-dihydro-4H-pyrimido[6,1-a]isoquinolin-4-one

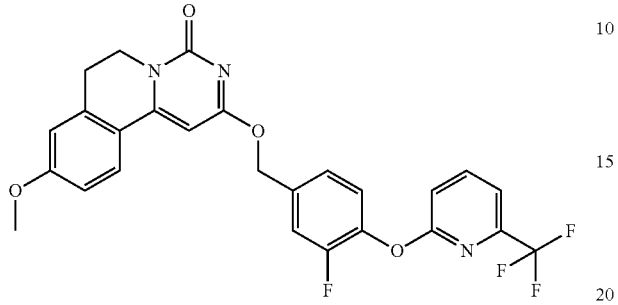

The title compound was prepared by a procedure similar to that described for E37, starting from (3-fluoro-4-{[6-(trifluoromethyl)-2-pyridinyl]oxy}phenyl)methanol and 2-chloro-9-(methyloxy)-6,7-dihydro-4H-pyrimido[6,1-a]isoquinolin-4-one LC-MS (ESI): m/z 514 [M+H]$^+$; 3.98 min (ret time).

E60

2-(2-(5-(4-fluoro-3-(trifluoromethyl)phenoxy)pyridin-2-yl)ethoxy)-9-methoxy-6,7-dihydro-4H-pyrimido[6,1-a]isoquinolin-4-one

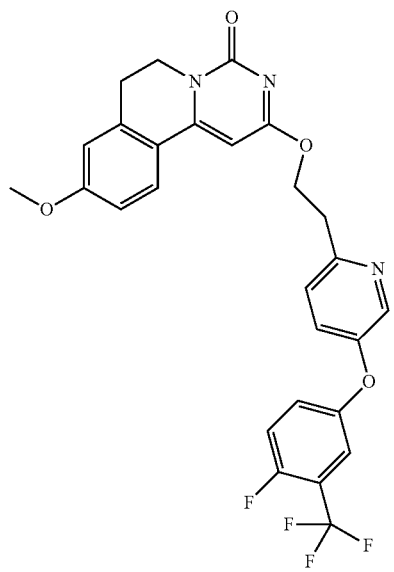 [SMILES: COc1ccc2c(c1)CCn1c-2cc(OCCc2ccc(Oc3ccc(F)c(C(F)(F)F)c3)cn2)nc1=O]

The title compound was prepared by a procedure similar to that described for E37, starting from 2-(5-{[4-fluoro-3-(trifluoromethyl)phenyl]oxy}-2-pyridinyl)ethanol and 2-chloro-9-(methyloxy)-6,7-dihydro-4H-pyrimido[6,1-a]isoquinolin-4-one.

LC-MS (ESI): m/z 528 [M+H]$^+$; 3.25 min (ret time).

E61

9-methoxy-2-(2-(5-(3-(trifluoromethyl)phenoxy)pyridin-2-yl)ethoxy)-6,7-dihydro-4H-pyrimido[6,1-a]isoquinolin-4-one

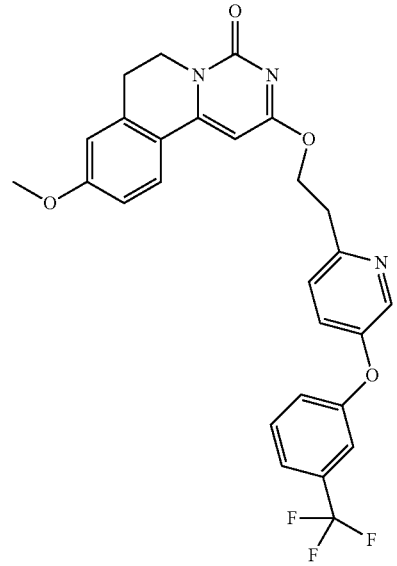 [SMILES: COc1ccc2c(c1)CCn1c-2cc(OCCc2ccc(Oc3cccc(C(F)(F)F)c3)cn2)nc1=O]

The title compound was prepared by a procedure similar to that described for E37, starting from 2-(5-{[3-(trifluoromethyl)phenyl]oxy}-2-pyridinyl)ethanol and 2-chloro-9-(methyloxy)-6,7-dihydro-4H-pyrimido[6,1-a]isoquinolin-4-one.

LC-MS (ESI): m/z 510 [M+H]$^+$; 3.22 min (ret time).

E62

2-(2-(5-(4-chloro-3-(trifluoromethyl)phenoxy)pyridin-2-yl)ethoxy)-9-methoxy-6,7-dihydro-4H-pyrimido[6,1-a]isoquinolin-4-one

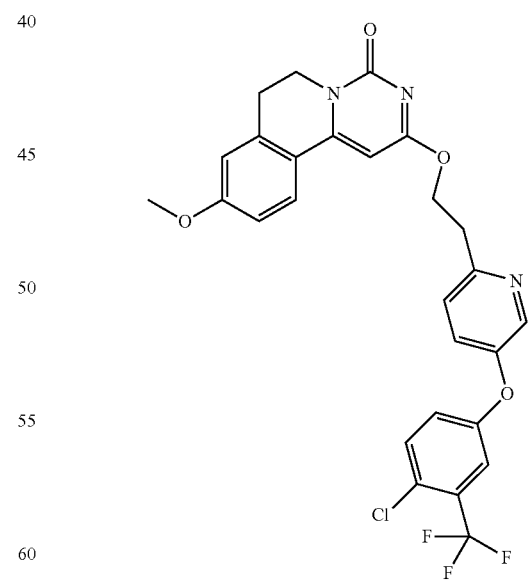

The title compound was prepared by a procedure similar to that described for E37, starting from 2-(5-{[4-chloro-3-(trifluoromethyl)phenyl]oxy}-2-pyridinyl)ethanol and 2-chloro-9-(methyloxy)-6,7-dihydro-4H-pyrimido[6,1-a]isoquinolin-4-one.

LC-MS (ESI): m/z 544 [M+H]$^+$; 3.43 min (ret time).

E63

5-(((9-methoxy-4-oxo-6,7-dihydro-4H-pyrimido[6,1-a]isoquinolin-2-yl)oxy)methyl)-2-((6-(trifluoromethyl)pyridin-2-yl)oxy)benzonitrile

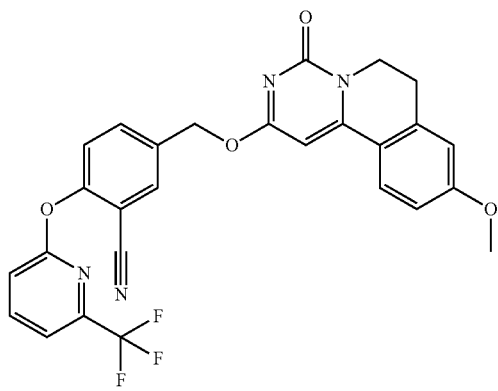 [SMILES: COc1ccc2c(c1)CCn1c-2cc(OCc2ccc(Oc3cccc(C(F)(F)F)n3)c(C#N)c2)nc1=O]

The title compound was prepared by a procedure similar to that described for E37, starting from 5-(hydroxymethyl)-2-{[6-(trifluoromethyl)-2-pyridinyl]oxy}benzonitrile and 2-chloro-9-(methyloxy)-6,7-dihydro-4H-pyrimido[6,1-a]isoquinolin-4-one.

LC-MS (ESI): m/z 521 [M+H]⁺; 3.49 min (ret time).

E64

5-(2-((9-methoxy-4-oxo-6,7-dihydro-4H-pyrimido[6,1-a]isoquinolin-2-yl)oxy)ethyl)-2-((6-(trifluoromethyl)pyridin-3-yl)oxy)benzonitrile

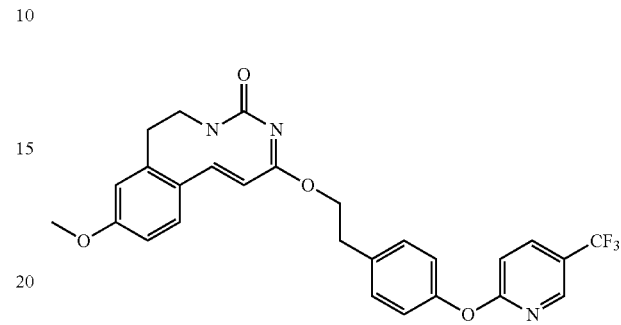

The title compound was prepared by a procedure similar to that described for E37, starting from 5-(2-hydroxyethyl)-2-{[6-(trifluoromethyl)-3-pyridinyl]oxy}benzonitrile and 2-chloro-9-(methyloxy)-6,7-dihydro-4H-pyrimido[6,1-a]isoquinolin-4-one.

LC-MS (ESI): m/z 535 [M+H]⁺; 3.48 min (ret time).

E65

2-(3-fluoro-4-((6-(trifluoromethyl)pyridin-2-yl)oxy)phenethoxy)-9-methoxy-6,7-dihydro-4H-pyrimido[6,1-a]isoquinolin-4-one

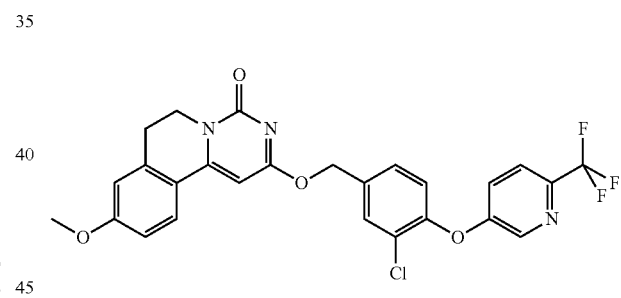

The title compound was prepared by a procedure similar to that described for E37, starting from 2-(3-fluoro-4-{[6-(trifluoromethyl)-2-pyridinyl]oxy}phenyl)ethanol and 2-chloro-9-(methyloxy)-6,7-dihydro-4H-pyrimido[6,1-a]isoquinolin-4-one LC-MS (ESI): m/z 528 [M+H]⁺; 3.68 min (ret time).

E66

9-methoxy-2-(4-((5-(trifluoromethyl)pyridin-2-yl)oxy)phenethoxy)-6,7-dihydro-4H-pyrimido[6,1-a]isoquinolin-4-one

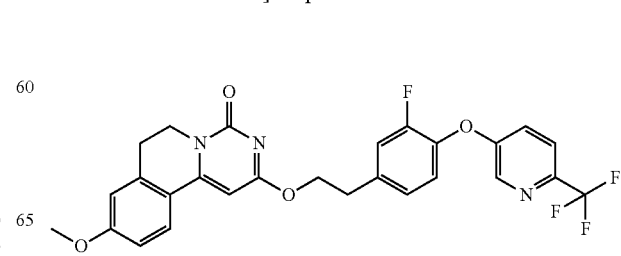

The title compound was prepared by a procedure similar to that described for E37, starting from 2-(4-{[5-(trifluoromethyl)-2-pyridinyl]oxy}phenyl)ethanol and then 2-chloro-9-(methyloxy)-6,7-dihydro-4H-pyrimido[6,1-a]isoquinolin-4-one.

LC-MS (ESI): m/z 510 [M+H]⁺; 3.71 min (ret time).

E67

2-((3-chloro-4-((6-(trifluoromethyl)pyridin-3-yl)oxy)benzyl)oxy)-9-methoxy-6,7-dihydro-4H-pyrimido[6,1-a]isoquinolin-4-one The title compound was prepared by a procedure similar to that described for E37, starting from (3-chloro-4-{[6-(trifluoromethyl)-3-pyridinyl]oxy}phenyl)methanol and 2-chloro-9-(methyloxy)-6,7-dihydro-4H-pyrimido[6,1-a]isoquinolin-4-one.

LC-MS (ESI): m/z 530 [M+H]⁺; 3.77 min (ret time).

E68

2-(3-fluoro-4-((6-(trifluoromethyl)pyridin-3-yl)oxy)phenethoxy)-9-methoxy-6,7-dihydro-4H-pyrimido[6,1-a]isoquinolin-4-one The title compound was prepared by a procedure similar to that described for E37, starting from 2-(3-fluoro-4-{[6-(trifluoromethyl)-3-pyridinyl]oxy}phenyl)ethanol and 2-chloro-9-(methyloxy)-6,7-dihydro-4H-pyrimido[6,1-a]isoquinolin-4-one.
LC-MS (ESI): m/z 528 [M+H]+; 3.69 min (ret time).

E69

2-((2-chloro-4-((6-(trifluoromethyl)pyridin-3-yl)oxy)benzyl)oxy)-9-methoxy-6,7-dihydro-4H-pyrimido[6,1-a]isoquinolin-4-one

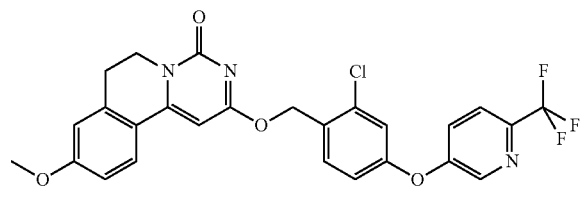 [SMILES: COc1ccc2c(c1)CCn1c-2cc(OCc2ccc(Oc3ccc(C(F)(F)F)nc3)cc2Cl)nc1=O]

The title compound was prepared by a procedure similar to that described for E37, starting from (2-chloro-4-{[6-(trifluoromethyl)-3-pyridinyl]oxy}phenyl)methanol and 2-chloro-9-(methyloxy)-6,7-dihydro-4H-pyrimido[6,1-a]isoquinolin-4-one.
LC-MS (ESI): m/z 530 [M+H]+; 3.79 min (ret time).

E70

2-((2-chloro-4-((6-(trifluoromethyl)pyridin-3-yl)oxy)benzyl)oxy)-9-methoxy-6,7-dihydro-4H-pyrimido[6,1-a]isoquinolin-4-one

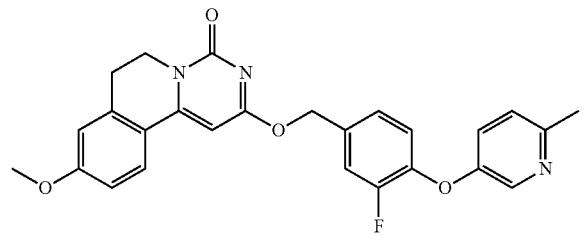

The title compound was prepared by a procedure similar to that described for E37, starting from {3-fluoro-4-[(6-methyl-3-pyridinyl)oxy]phenyl}methanol and 2-chloro-9-(methyloxy)-6,7-dihydro-4H-pyrimido[6,1-a]isoquinolin-4-one.
LC-MS (ESI): m/z 460 [M+H]+; 2.57 min (ret time).

E71

5-(((9-methoxy-4-oxo-6,7-dihydro-4H-pyrimido[6,1-a]isoquinolin-2-yl)oxy)methyl)-2-((6-methylpyridin-3-yl)oxy)benzonitrile

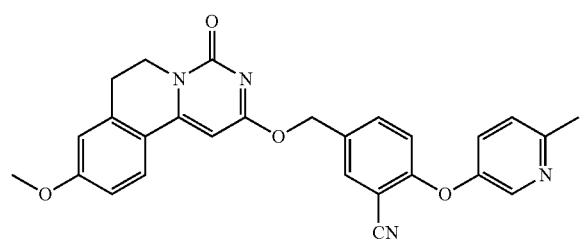

The title compound was prepared by a procedure similar to that described for E37, starting from 5-(hydroxymethyl)-2-[(6-methyl-3-pyridinyl)oxy]benzonitrile and 2-chloro-9-(methyloxy)-6,7-dihydro-4H-pyrimido[6,1-a]isoquinolin-4-one.
LC-MS (ESI): m/z 467 [M+H]+; 2.58 min (ret time).

E72

2-((5-fluoro-6-(4-fluorophenoxy)pyridin-3-yl)methoxy)-9-methoxy-6,7-dihydro-4H-pyrimido[6,1-a]isoquinolin-4-one

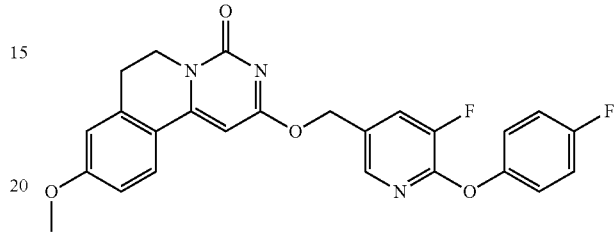

The title compound was prepared by a procedure similar to that described for E37, starting from {5-fluoro-6-[(4-fluorophenyl)oxy]-3-pyridinyl}methanol and 2-chloro-9-(methyloxy)-6,7-dihydro-4H-pyrimido[6,1-a]isoquinolin-4-one.
LC-MS (ESI): m/z 464 [M+H]+; 3.49 min (ret time).

E74

2-((5-(4-fluoro-3-(trifluoromethyl)phenoxy)pyridin-2-yl)methoxy)-9-methoxy-6,7-dihydro-4H-pyrimido-[6,1-a]isoquinolin-4-one

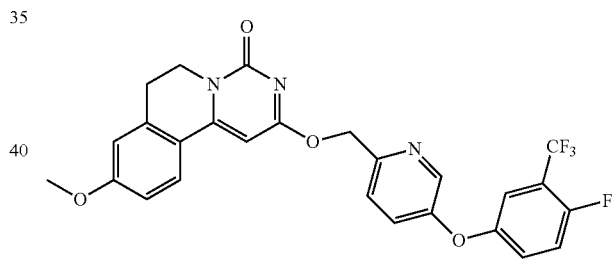

The title compound was prepared by a procedure similar to that described for E37, starting from (5-{[4-fluoro-3-(trifluoromethyl)phenyl]oxy}-2-pyridinyl)methanol and 2-chloro-9-(methyloxy)-6,7-dihydro-4H-pyrimido[6,1-a]isoquinolin-4-one.
LC-MS (ESI): m/z 514 [M+H]+; 3.54 min (ret time).

E75

2-((3-chloro-4-((6-methylpyridin-3-yl)oxy)benzyl)oxy)-9-methoxy-6,7-dihydro-4H-pyrimido[6,1-a]isoquinolin-4-one

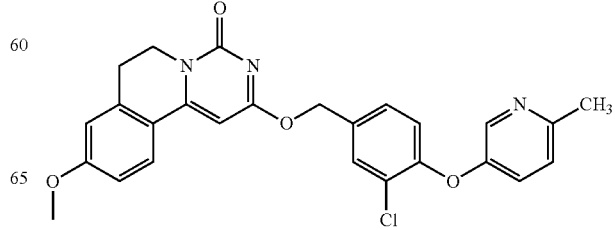

The title compound was prepared by a procedure similar to that described for E37, starting from {3-chloro-4-[(6-methyl-3-pyridinyl)oxy]phenyl}methanol and 2-chloro-9-(methyloxy)-6,7-dihydro-4H-pyrimido[6,1-a]isoquinolin-4-one.
LC-MS (ESI): m/z 476 [M+H]$^+$; 2.70 min (ret time).

E76

2-((3,5-difluoro-4-((6-(trifluoromethyl)pyridin-3-yl)oxy)benzyl)oxy)-9-methoxy-6,7-dihydro-4H-pyrimido[6,1-a]isoquinolin-4-one

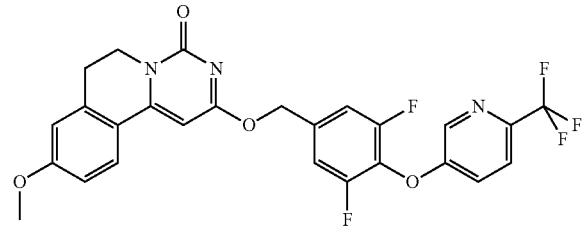 [SMILES: COc1ccc2c(c1)CCn1c-2cc(OCc2cc(F)c(Oc3ccc(C(F)(F)F)nc3)c(F)c2)nc1=O]

The title compound was prepared by a procedure similar to that described for E37, starting from (3,5-difluoro-4-{[6-(trifluoromethyl)-3-pyridinyl]oxy}phenyl)methanol and 2-chloro-9-(methyloxy)-6,7-dihydro-4H-pyrimido[6,1-a]isoquinolin-4-one.
LC-MS (ESI): m/z 476 [M+H]$^+$; 2.70 min (ret time).

E77

2-((5-chloropyridin-2-yl)oxy)-5-(((9-methoxy-4-oxo-6,7-dihydro-4H-pyrimido[6,1-a]isoquinolin-2-yl)oxy)methyl)benzonitrile

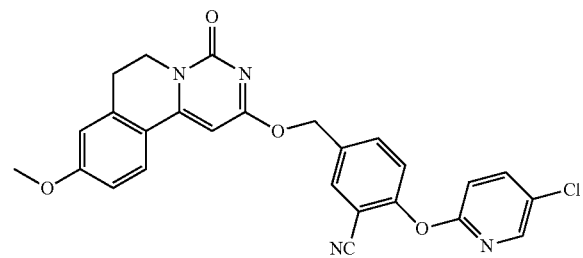 [SMILES: COc1ccc2c(c1)CCn1c-2cc(OCc2ccc(Oc3ccc(Cl)cn3)c(C#N)c2)nc1=O]

The title compound was prepared by a procedure similar to that described for E37, starting from 2-[(5-chloro-2-pyridinyl)oxy]-5-(hydroxymethyl)benzonitrile and 2-chloro-9-(methyloxy)-6,7-dihydro-4H-pyrimido[6,1-a]isoquinolin-4-one.
LC-MS (ESI): m/z 487 [M+H]$^+$; 3.39 min (ret time).

E78

5-(((9-methoxy-4-oxo-6,7-dihydro-4H-pyrimido[6,1-a]isoquinolin-2-yl)oxy)methyl)-2-((2-(trifluoromethyl)pyrimidin-5-yl)oxy)benzonitrile

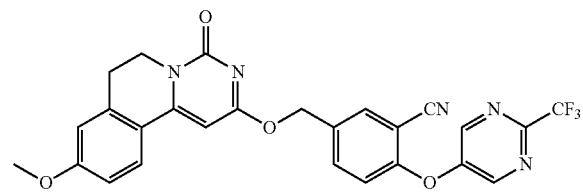 [SMILES: COc1ccc2c(c1)CCn1c-2cc(OCc2ccc(Oc3cnc(C(F)(F)F)nc3)c(C#N)c2)nc1=O]

The title compound was prepared by a procedure similar to that described for E37, starting from 5-(hydroxymethyl)-2-{[2-(trifluoromethyl)-5-pyrimidinyl]oxy}benzonitrile and 2-chloro-9-(methyloxy)-6,7-dihydro-4H-pyrimido[6,1-a]isoquinolin-4-one.
LC-MS (ESI): m/z 522 [M+H]$^+$; 3.41 min (ret time).

E80

5-(((9-methoxy-4-oxo-6,7-dihydro-4H-pyrimido[6,1-a]isoquinolin-2-yl)oxy)methyl)-2-((2-(trifluoromethyl)pyrimidin-5-yl)oxy)benzonitrile

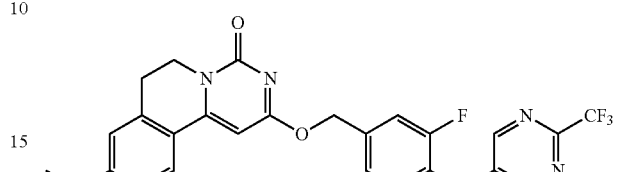

The title compound was prepared by a procedure similar to that described for E37, starting from (3-fluoro-4-{[2-(trifluoromethyl)-5-pyrimidinyl]oxy}phenyl)methanol and 2-chloro-9-(methyloxy)-6,7-dihydro-4H-pyrimido[6,1-a]isoquinolin-4-one.
LC-MS (ESI): m/z 515 [M+H]$^+$; 3.56 min (ret time).

E81

2-((4-((5-chloropyridin-2-yl)oxy)-3-fluorobenzyl)oxy)-9-methoxy-6,7-dihydro-4H-pyrimido[6,1-a]isoquinolin-4-one

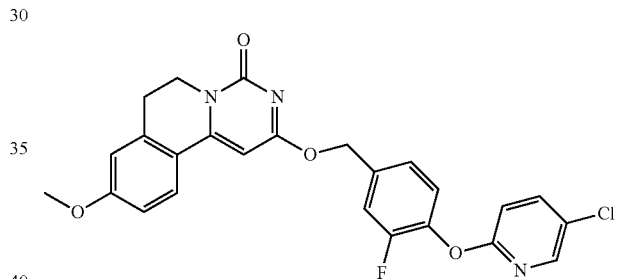

The title compound was prepared by a procedure similar to that described for E37, starting from {4-[(5-chloro-2-pyridinyl)oxy]-3-fluorophenyl}methanol and 2-chloro-9-(methyloxy)-6,7-dihydro-4H-pyrimido[6,1-a]isoquinolin-4-one.
LC-MS (ESI): m/z 480 [M+H]$^+$; 2.94 min (ret time).

E82

2-((3-((5-chloropyridin-2-yl)oxy)-4-fluorobenzyl)oxy)-9-methoxy-6,7-dihydro-4H-pyrimido[-6,1-a]isoquinolin-4-one

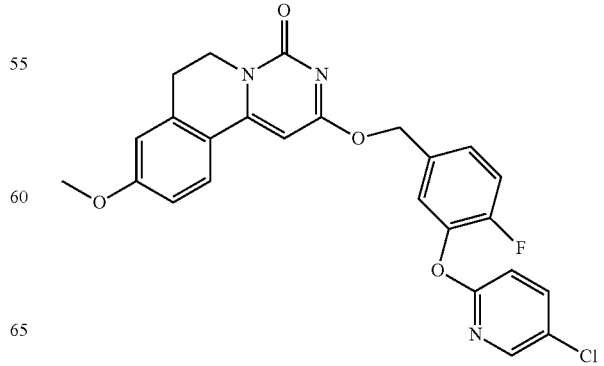

The title compound was prepared by a procedure similar to that described for E37, starting from 2-chloro-9-(methyloxy)-6,7-dihydro-4H-pyrimido[6,1-a]isoquinolin-4-one and from {3-[(5-chloro-2-pyridinyl)oxy]-4-fluorophenyl}methanol.
LC-MS (ESI): m/z 480 [M+H]+; 3.66 min (ret time).

E83

5-(2-((9-methoxy-4-oxo-6,7-dihydro-4H-pyrimido[6,1-a]isoquinolin-2-yl)oxy)ethyl)-2-((2-(trifluoromethyl)pyrimidin-5-yl)oxy)benzonitrile

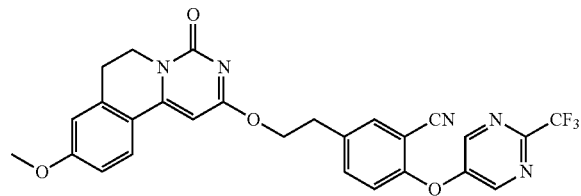 [SMILES: COc1ccc2c(c1)CCn1c-2cc(OCCc2ccc(Oc3cnc(C(F)(F)F)nc3)c(C#N)c2)nc1=O]

The title compound was prepared by a procedure similar to that described for E37, starting from 5-(2-hydroxyethyl)-2-{[2-(trifluoromethyl)-5-pyrimidinyl]oxy}benzonitrile and 2-chloro-9-(methyloxy)-6,7-dihydro-4H-pyrimido[6,1-a]isoquinolin-4-one.
LC-MS (ESI): m/z 536 [M+H]+; 3.43 min (ret time).

E84

2-(2-(6-(4-chloro-3-(trifluoromethyl)phenoxy)pyridin-3-yl)ethoxy)-9-methoxy-6,7-dihydro-4H-pyrimido[6,1-a]isoquinolin-4-one

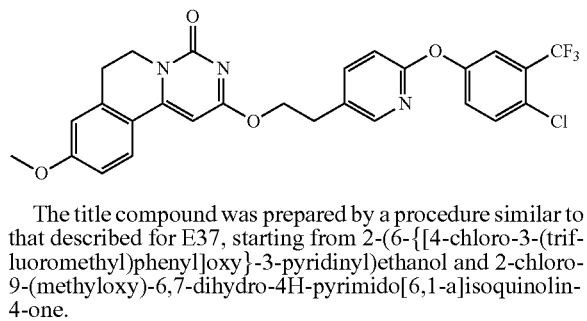

The title compound was prepared by a procedure similar to that described for E37, starting from 2-(6-{[4-chloro-3-(trifluoromethyl)phenyl]oxy}-3-pyridinyl)ethanol and 2-chloro-9-(methyloxy)-6,7-dihydro-4H-pyrimido[6,1-a]isoquinolin-4-one.
LC-MS (ESI): m/z 544 [M+H]+; 3.87 min (ret time).

E85

2-((5-(4-chloro-3-(trifluoromethyl)phenoxy)pyrimidin-2-yl)methoxy)-9-methoxy-6,7-dihydro-4H-pyrimido[6,1-a]isoquinolin-4-one

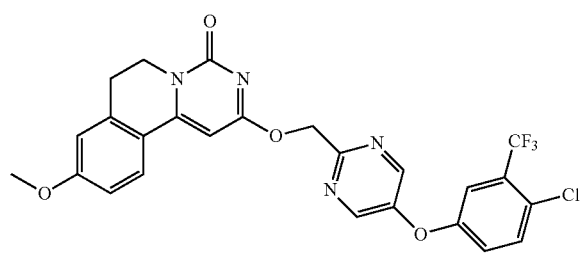 [SMILES: COc1ccc2c(c1)CCn1c-2cc(OCc2ncc(Oc3ccc(Cl)c(C(F)(F)F)c3)cn2)nc1=O]

The title compound was prepared by a procedure similar to that described for E37, starting from (5-{[4-chloro-3-(trifluoromethyl)phenyl]oxy}-2-pyrimidinyl)methanol and 2-chloro-9-(methyloxy)-6,7-dihydro-4H-pyrimido[6,1-a]isoquinolin-4-one.
LC-MS (ESI): m/z 531 [M+H]+; 3.54 min (ret time).

E86

2-(2-(6-(2,4-difluorophenoxy)pyridin-3-yl)ethoxy)-9-methoxy-6,7-dihydro-4H-pyrimido[6,1-a]isoquinolin-4-one

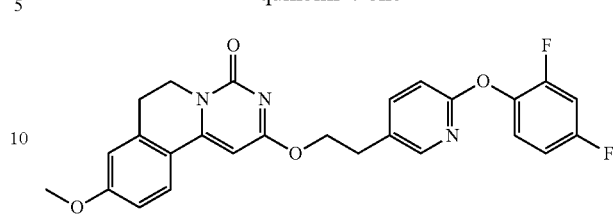

The title compound was prepared by a procedure similar to that described for E37, starting from 2-{6-[(2,4-difluorophenyl)oxy]-3-pyridinyl}ethanol and 2-chloro-9-(methyloxy)-6,7-dihydro-4H-pyrimido[6,1-a]isoquinolin-4-one.
LC-MS (ESI): m/z 478 [M+H]+; 3.45 min (ret time).

E87

2-(3-fluoro-4-((6-methylpyridin-3-yl)oxy)phenethoxy)-9-methoxy-6,7-dihydro-4H-pyrimido[6,1-a]isoquinolin-4-one

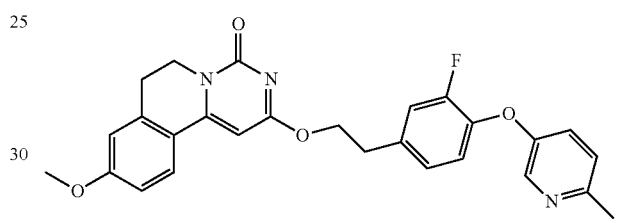

The title compound was prepared by a procedure similar to that described for E37, starting from 2-{3-fluoro-4-[(6-methyl-3-pyridinyl)oxy]phenyl}ethanol and 2-chloro-9-(methyloxy)-6,7-dihydro-4H-pyrimido[6,1-a]isoquinolin-4-one.
LC-MS (ESI): m/z 474 [M+H]+; 2.65 min (ret time).

E88

2-(4-chloro-3-(trifluoromethyl)phenoxy)-5-(((4-oxo-6,7-dihydro-4H-pyrimido[6,1-a]isoquinolin-2-yl)oxy)methyl)benzonitrile

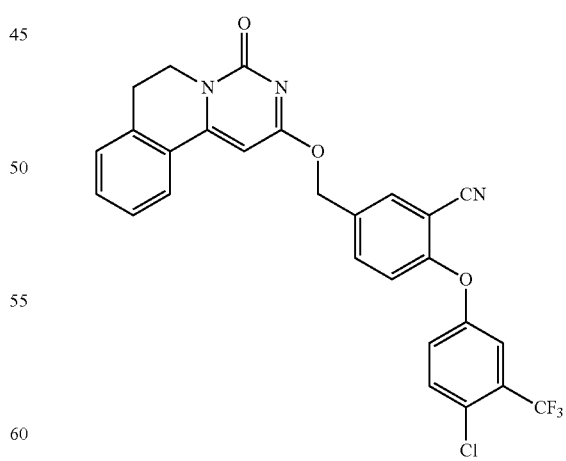

The title compound was prepared by a procedure similar to that described for E37, starting from 2-{[4-chloro-3-(trifluoromethyl)phenyl]oxy}-5-(hydroxymethyl)benzonitrile and 2-chloro-6,7-dihydro-4H-pyrimido[6,1-a]isoquinolin-4-one.
LC-MS (ESI): m/z 524 [M+H]+; 3.87 min (ret time).

E89

5-(((9-fluoro-4-oxo-6,7-dihydro-4H-pyrimido[6,1-a]isoquinolin-2-yl)oxy)methyl)-2-(3-(trifluoromethyl)phenoxy)benzonitrile

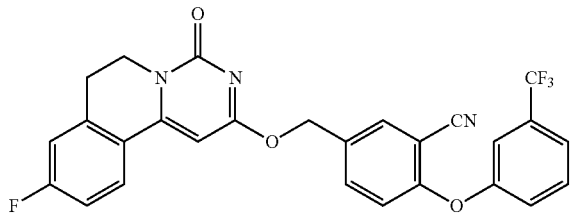 [SMILES: N#Cc1cc(COc2cc3n(c(=O)n2)CCc2cc(F)ccc2-3)ccc1Oc1cccc(C(F)(F)F)c1]

The title compound was prepared by a procedure similar to that described for E37, starting from 2-chloro-9-fluoro-6,7-dihydro-4H-pyrimido[6,1-a]isoquinolin-4-one and 5-(hydroxymethyl)-2-{[3-(trifluoromethyl)phenyl]oxy}benzonitrile.

LC-MS (ESI): m/z 508 [M+H]$^+$; 3.75 min (ret time).

E90

2-(4-(4-chloro-3-(trifluoromethyl)phenoxy)phenethoxy)-9-fluoro-6,7-dihydro-4H-pyri-mido[6,1-a]isoquinolin-4-one

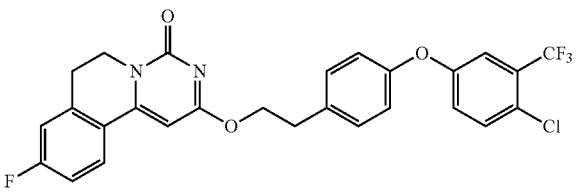 [SMILES: O=c1nc(OCCc2ccc(Oc3ccc(Cl)c(C(F)(F)F)c3)cc2)cc2n1CCc1cc(F)ccc1-2]

The title compound was prepared by a procedure similar to that described for E37, starting from 2-chloro-9-fluoro-6,7-dihydro-4H-pyrimido[6,1-a]isoquinolin-4-one and 2-(4-{[4-chloro-3-(trifluoromethyl)phenyl]oxy}phenyl)ethanol.

LC-MS (ESI): m/z 531 [M+H]$^+$; 4.19 min (ret time).

E91

5-(((4-oxo-6,7-dihydro-4H-pyrimido[6,1-a]isoquinolin-2-yl)oxy)methyl)-2-((6-(trifluoro-methyl)pyridin-3-yl)oxy)benzonitrile

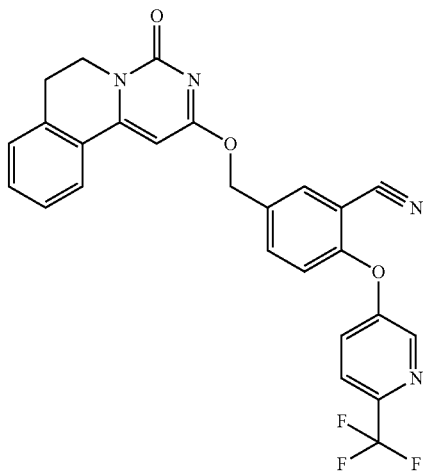 [SMILES: N#Cc1cc(COc2cc3n(c(=O)n2)CCc2ccccc2-3)ccc1Oc1ccc(C(F)(F)F)nc1]

The title compound was prepared by a procedure similar to that described for E37, starting from 5-(hydroxymethyl)-2-{[6-(trifluoromethyl)-3-pyridinyl]oxy}benzonitrile and 2-chloro-6,7-dihydro-4H-pyrimido[6,1-a]isoquinolin-4-one.

LC-MS (ESI): m/z 491 [M+H]$^+$; 3.46 min (ret time).

E92

2-(4-chloro-3-(trifluoromethyl)phenoxy)-5-(((9-fluoro-4-oxo-6,7-dihydro-4H-pyrimido[6,1-a]isoquinolin-2-yl)oxy)methyl)benzonitrile

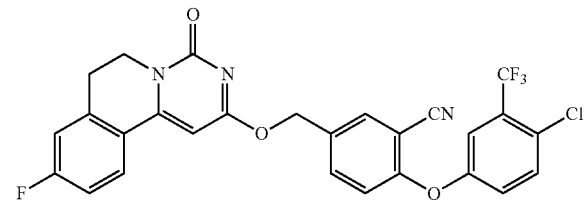 [SMILES: N#Cc1cc(COc2cc3n(c(=O)n2)CCc2cc(F)ccc2-3)ccc1Oc1ccc(Cl)c(C(F)(F)F)c1]

The title compound was prepared by a procedure similar to that described for E37, starting from 2-chloro-9-fluoro-6,7-dihydro-4H-pyrimido[6,1-a]isoquinolin-4-one and 2-{[4-chloro-3-(trifluoromethyl)phenyl]oxy}-5-(hydroxymethyl)benzonitrile.

LC-MS (ESI): m/z 542 [M+H]$^+$; 3.89 min (ret time).

E93

5-(((9-fluoro-4-oxo-6,7-dihydro-4H-pyrimido[6,1-a]isoquinolin-2-yl)oxy)methyl)-2-((5-(trifluoromethyl)pyridin-2-yl)oxy)benzonitrile

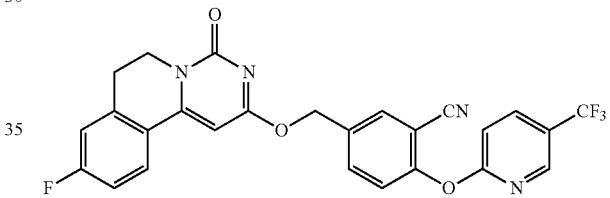

The title compound was prepared by a procedure similar to that described for E37, starting from 2-chloro-9-fluoro-6,7-dihydro-4H-pyrimido[6,1-a]isoquinolin-4-one and 5-(hydro-xymethyl)-2-{[5-(trifluoromethyl)-2-pyridinyl]oxy}benzonitrile.

LC-MS (ESI): m/z 509 [M+H]$^+$; 3.59 min (ret time).

E94

2-((3,5-difluoro-4-((6-(trifluoromethyl)pyridin-3-yl)oxy)benzyl)oxy)-6,7-dihydro-4H-pyrimido[6,1-a]isoquinolin-4-one

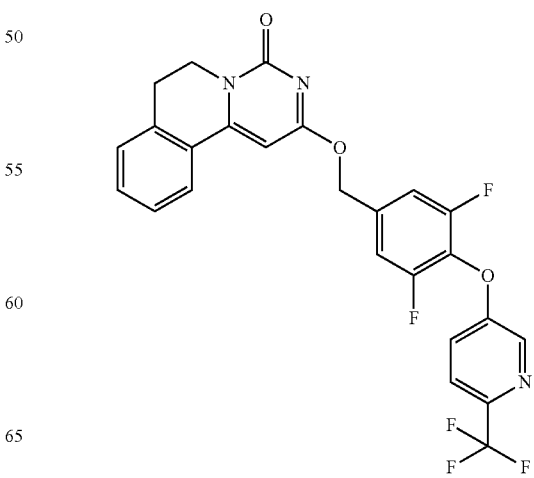

The title compound was prepared by a procedure similar to that described for E37, starting from (3,5-difluoro-4-{[6-(trifluoromethyl)-3-pyridinyl]oxy}phenyl)methanol and 2-chloro-6,7-dihydro-4H-pyrimido[6,1-a]isoquinolin-4-one.
LC-MS (ESI): m/z 502 [M+H]$^+$; 3.71 min (ret time).

E95

2-((3-fluoro-4-((6-(trifluoromethyl)pyridin-2-yl)oxy)benzyl)oxy)-6,7-dihydro-4H-pyri-mido[6,1-a]isoquinolin-4-one

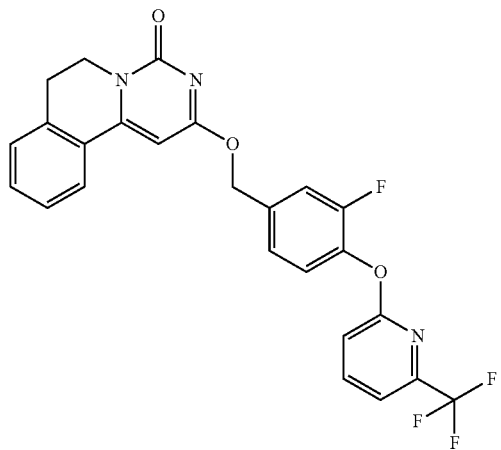 [SMILES: O=c1nc(OCc2ccc(Oc3cccc(C(F)(F)F)n3)c(F)c2)cc2n1CCc1ccccc1-2]

The title compound was prepared by a procedure similar to that described for E37, starting from (3-fluoro-4-{[6-(trifluoromethyl)-2-pyridinyl]oxy}phenyl)methanol and 2-chloro-6,7-dihydro-4H-pyrimido[6,1-a]isoquinolin-4-one.
LC-MS (ESI): m/z 484 [M+H]$^+$; 3.66 min (ret time).

E96

5-(((4-oxo-6,7-dihydro-4H-pyrimido[6,1-a]isoquinolin-2-yl)oxy)methyl)-2-((6-(trifluoro-methyl)pyridin-2-yl)oxy)benzonitrile

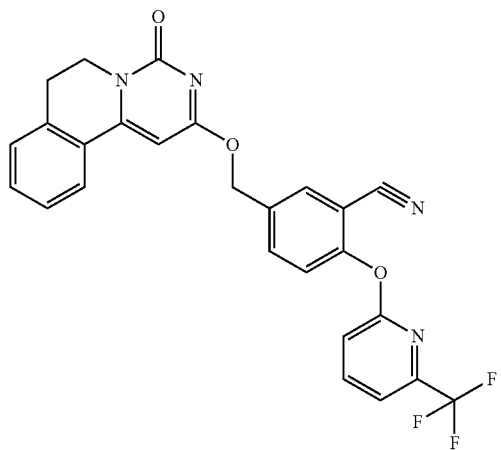 [SMILES: N#Cc1cc(COc2cc3n(c(=O)n2)CCc2ccccc2-3)ccc1Oc1cccc(C(F)(F)F)n1]

The title compound was prepared by a procedure similar to that described for E37, starting from 5-(hydroxymethyl)-2-{[6-(trifluoromethyl)-2-pyridinyl]oxy}benzonitrile and 2-chloro-6,7-dihydro-4H-pyrimido[6,1-a]isoquinolin-4-one.
LC-MS (ESI): m/z 491 [M+H]$^+$; 3.54 min (ret time).

E97

5-(((4-oxo-6,7-dihydro-4H-pyrimido[6,1-a]isoquinolin-2-yl)oxy)methyl)-2-(3-(trifluoro-methyl)phenoxy)benzonitrile

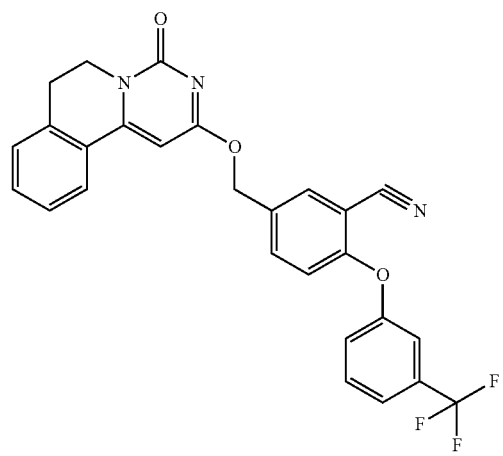 [SMILES: N#Cc1cc(COc2cc3n(c(=O)n2)CCc2ccccc2-3)ccc1Oc1cccc(C(F)(F)F)c1]

The title compound was prepared by a procedure similar to that described for E37, starting from 5-(hydroxymethyl)-2-{[3-(trifluoromethyl)phenyl]oxy}benzonitrile and 2-chloro-6,7-dihydro-4H-pyrimido[6,1-a]isoquinolin-4-one.
LC-MS (ESI): m/z 490 [M+H]$^+$; 3.73 min (ret time).

E98

9-fluoro-2-((3-fluoro-4-((2-(trifluoromethyl)pyrimidin-5-yl)oxy)benzyl)oxy)-6,7-dihydro-4H-pyrimido[6,1-a]isoquinolin-4-one

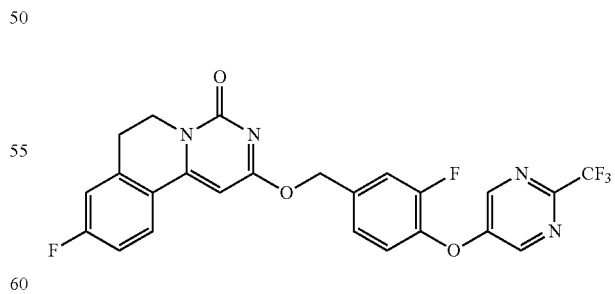

The title compound was prepared by a procedure similar to that described for E37, starting from 2-chloro-9-fluoro-6,7-dihydro-4H-pyrimido[6,1-a]isoquinolin-4-one and (3-fluoro-4-((2-(trifluoromethyl)pyrimidin-5-yl)oxy)phenyl)methanol.
LC-MS (ESI): m/z 503 [M+H]$^+$; 3.59 min (ret time).

E99

2-((3-fluoro-4-((6-(trifluoromethyl)pyridin-3-yl)oxy)benzyl)oxy)-6,7-dihydro-4H-pyrimido[6,1-a]isoquinolin-4-one

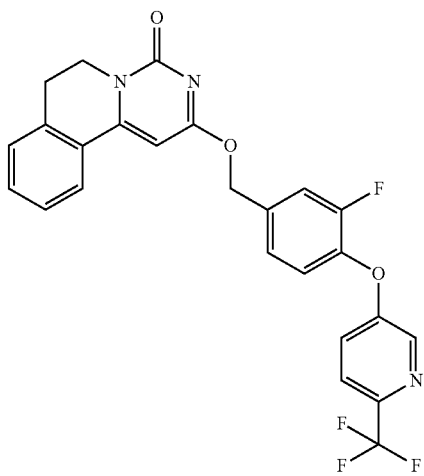 [SMILES: O=c1nc(OCc2ccc(Oc3ccc(C(F)(F)F)nc3)c(F)c2)cc2n1CCc1ccccc1-2]

The title compound was prepared by a procedure similar to that described for E37, starting from 2-chloro-6,7-dihydro-4H-pyrimido[6,1-a]isoquinolin-4-one and (3-fluoro-4-((6-(trifluoromethyl)pyridin-3-yl)oxy)phenyl)methanol.

LC-MS (ESI): m/z 484 [M+H]$^+$; 3.68 min (ret time).

E100

2-((3-fluoro-4-((5-(trifluoromethyl)pyridin-2-yl)oxy)benzyl)oxy)-9-methoxy-6,7-dihydro-4H-pyrimido[6,1-a]isoquinolin-4-one

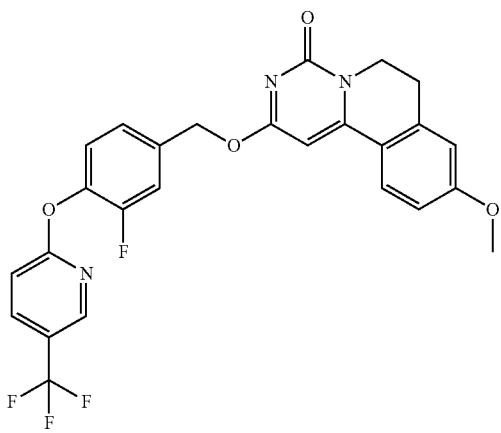 [SMILES: COc1ccc2c(c1)CCn1c-2cc(OCc2ccc(Oc3ccc(C(F)(F)F)cn3)c(F)c2)nc1=O]

The title compound was prepared by a procedure similar to that described for E37, starting from (3-fluoro-4-{[5-(trifluoromethyl)-2-pyridinyl]oxy}phenyl)methanol and 2-chloro-9-(methyloxy)-6,7-dihydro-4H-pyrimido[6,1-a]isoquinolin-4-one.

LC-MS (ESI): m/z 514 [M+H]$^+$; 3.70 min (ret time).

E101

5-(((4-oxo-6,7-dihydro-4H-pyrimido[6,1-a]isoquinolin-2-yl)oxy)methyl)-2-((2-(trifluoromethyl)pyrimidin-5-yl)oxy)benzonitrile

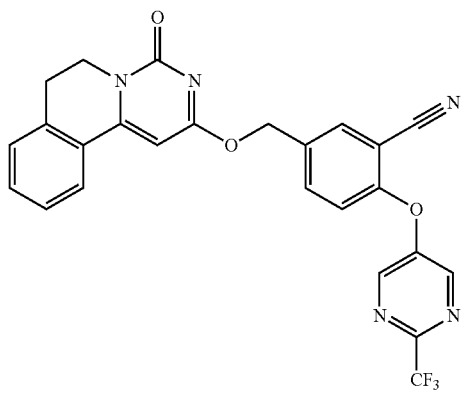 [SMILES: N#Cc1cc(COc2cc3n(c(=O)n2)CCc2ccccc2-3)ccc1Oc1cnc(C(F)(F)F)nc1]

The title compound was prepared by a procedure similar to that described for E37, starting from 2-chloro-6,7-dihydro-4H-pyrimido[6,1-a]isoquinolin-4-one and 5-(hydroxymethyl)-2-((2-(trifluoromethyl)pyrimidin-5-yl)oxy)benzonitrile.

LC-MS (ESI): m/z 492 [M+H]$^+$; 3.39 min (ret time).

E102

9-fluoro-2-((3-fluoro-4-((6-(trifluoromethyl)pyridin-2-yl)oxy)benzyl)oxy)-6,7-dihydro-4H-pyrimido[6,1-a]isoquinolin-4-one The title compound was prepared by a procedure similar to that described for E37, starting from 2-chloro-9-fluoro-6,7-dihydro-4H-pyrimido[6,1-a]isoquinolin-4-one and (3-fluoro-4-((6-(trifluoromethyl)pyridin-2-yl)oxy)phenyl)methanol.

LC-MS (ESI): m/z 502 [M+H]$^+$; 3.69 min (ret time).

E103

9-fluoro-2-((4-((2-(trifluoromethyl)pyrimidin-5-yl)oxy)benzyl)oxy)-6,7-dihydro-4H-pyrimido[6,1-a]isoquinolin-4-one The title compound was prepared by a procedure similar to that described for E37, starting from 2-chloro-9-fluoro-6,7-dihydro-4H-pyrimido[6,1-a]isoquinolin-4-one and (4-((2-(trifluoromethyl)pyrimidin-5-yl)oxy)phenyl)methanol.
LC-MS (ESI): m/z 485 [M+H]⁺; 3.53 min (ret time).

E104

2-((3-fluoro-4-((2-(trifluoromethyl)pyrimidin-5-yl)oxy)benzyl)oxy)-6,7-dihydro-4H-pyrimido[6,1-a]isoquinolin-4-one

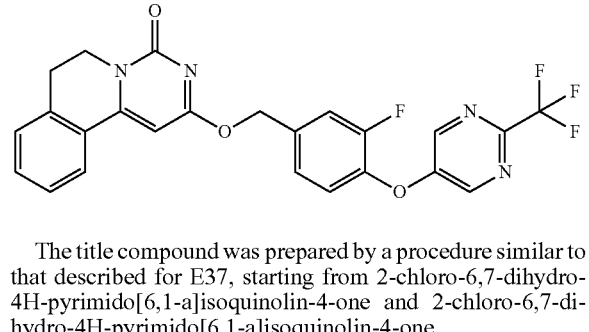

The title compound was prepared by a procedure similar to that described for E37, starting from 2-chloro-6,7-dihydro-4H-pyrimido[6,1-a]isoquinolin-4-one and 2-chloro-6,7-dihydro-4H-pyrimido[6,1-a]isoquinolin-4-one.
LC-MS (ESI): m/z 485 [M+H]⁺; 3.59 min (ret time).

E105

2-((5-(4-chloro-3-(trifluoromethyl)phenoxy)pyridin-2-yl)methoxy)-6,7-dihydro-4H-pyrim-ido[6,1-a]isoquinolin-4-one

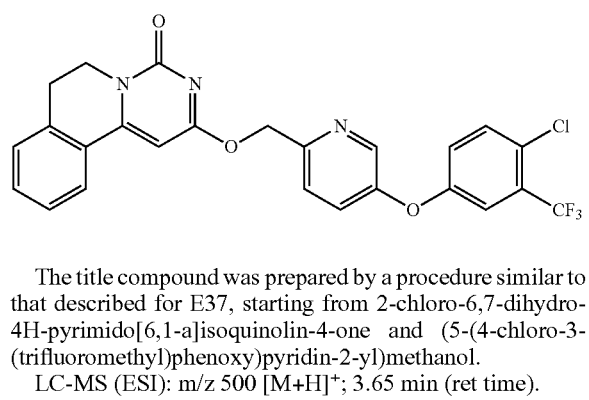

The title compound was prepared by a procedure similar to that described for E37, starting from 2-chloro-6,7-dihydro-4H-pyrimido[6,1-a]isoquinolin-4-one and (5-(4-chloro-3-(trifluoromethyl)phenoxy)pyridin-2-yl)methanol.
LC-MS (ESI): m/z 500 [M+H]⁺; 3.65 min (ret time).

E106

2-((5-(4-fluoro-3-(trifluoromethyl)phenoxy)pyridin-2-yl)methoxy)-6,7-dihydro-4H-pyri-mido[6,1-a]isoquinolin-4-one

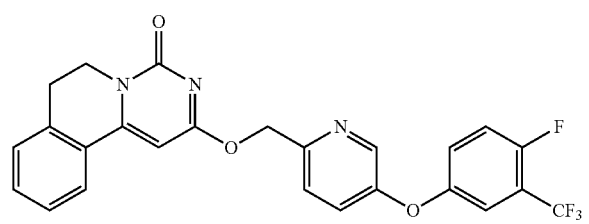 [SMILES: O=c1nc(OCc2ccc(Oc3ccc(F)c(C(F)(F)F)c3)cn2)cc2n1CCc1ccccc1-2]

The title compound was prepared by a procedure similar to that described for E37, starting from 2-chloro-6,7-dihydro-4H-pyrimido[6,1-a]isoquinolin-4-one and (5-(4-fluoro-3-(trifluoromethyl)phenoxy)pyridin-2-yl)methanol.
LC-MS (ESI): m/z 484 [M+H]⁺; 3.48 min (ret time).

E107

2-((3-fluoro-4-((5-(trifluoromethyl)pyridin-2-yl)oxy)benzyl)oxy)-6,7-dihydro-4H-pyrimi-do[6,1-a]isoquinolin-4-one

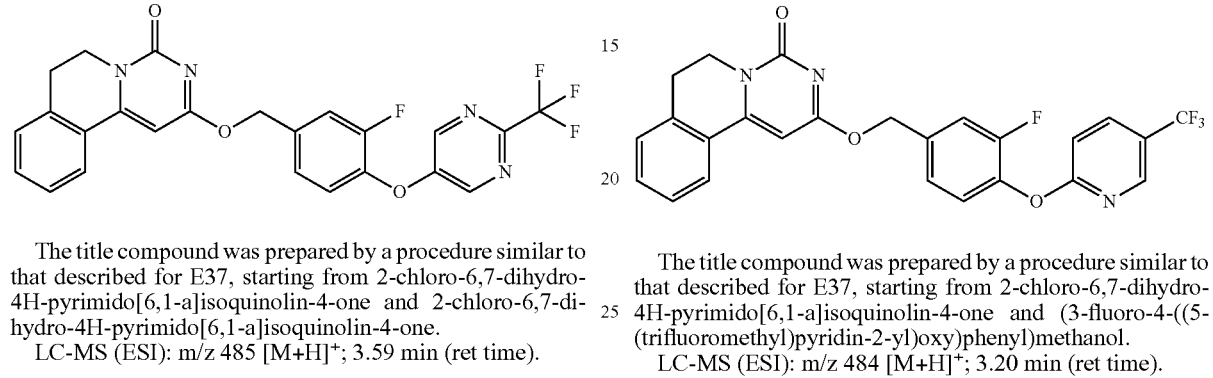

The title compound was prepared by a procedure similar to that described for E37, starting from 2-chloro-6,7-dihydro-4H-pyrimido[6,1-a]isoquinolin-4-one and (3-fluoro-4-((5-(trifluoromethyl)pyridin-2-yl)oxy)phenyl)methanol.
LC-MS (ESI): m/z 484 [M+H]⁺; 3.20 min (ret time).

E108

2-(4-(3-(trifluoromethyl)phenoxy)phenethoxy)-6,7-dihydro-4H-pyrimido[6,1-a]isoquinolin-4-one

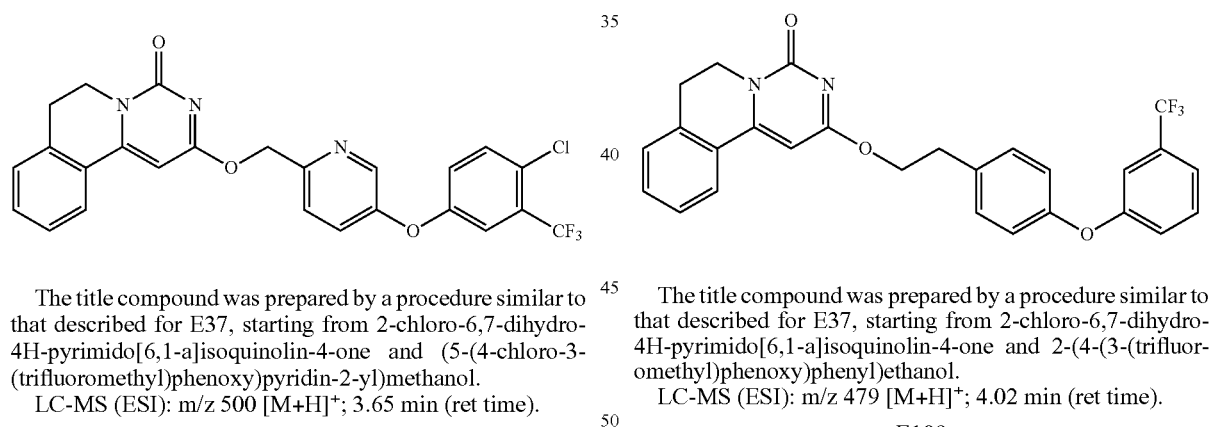

The title compound was prepared by a procedure similar to that described for E37, starting from 2-chloro-6,7-dihydro-4H-pyrimido[6,1-a]isoquinolin-4-one and 2-(4-(3-(trifluoromethyl)phenoxy)phenyl)ethanol.
LC-MS (ESI): m/z 479 [M+H]⁺; 4.02 min (ret time).

E109

2-((3,5-difluoro-4-((6-(trifluoromethyl)pyridin-3-yl)oxy)benzyl)oxy)-9-fluoro-6,7-dihydro-4H-pyrimido[6,1-a]isoquinolin-4-one

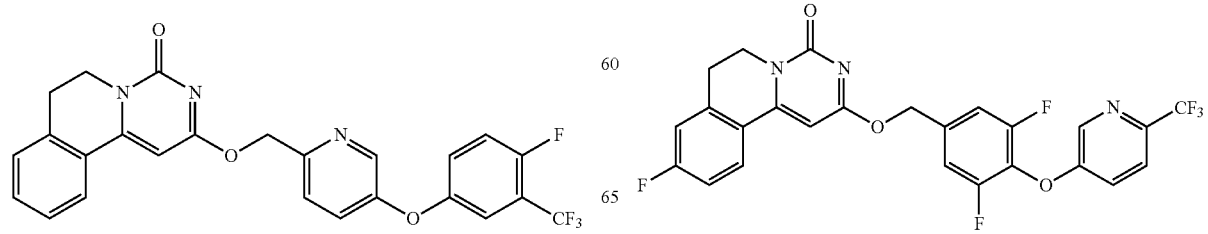

The title compound was prepared by a procedure similar to that described for E37, starting from 2-chloro-9-fluoro-6,7-dihydro-4H-pyrimido[6,1-a]isoquinolin-4-one and (3,5-difluoro-4-((6-(trifluoromethyl)pyridin-3-yl)oxy)phenyl)methanol.
LC-MS (ESI): m/z 520 [M+H]⁺; 3.71 min (ret time).

E110

5-(2-((9-fluoro-4-oxo-6,7-dihydro-4H-pyrimido[6,1-a]isoquinolin-2-yl)oxy)ethyl)-2-((5-(trifluoromethyl)pyridin-2-yl)oxy)benzonitrile

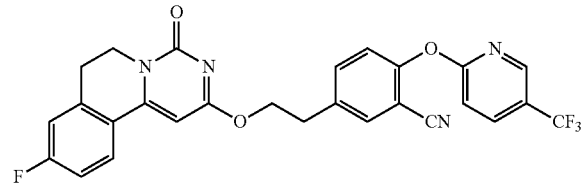 [SMILES: N#Cc1cc(CCOc2cc3n(c(=O)n2)CCc2cc(F)ccc2-3)ccc1Oc1ccc(C(F)(F)F)cn1]

The title compound was prepared by a procedure similar to that described for E37, starting from 2-chloro-9-fluoro-6,7-dihydro-4H-pyrimido[6,1-a]isoquinolin-4-one and 5-(2-hydroxyethyl)-2-((5-(trifluoromethyl)pyridin-2-yl)oxy)benzonitrile.
LC-MS (ESI): m/z 523 [M+H]⁺; 3.58 min (ret time).

E111

5-(((9-fluoro-4-oxo-6,7-dihydro-4H-pyrimido[6,1-a]isoquinolin-2-yl)oxy)methyl)-2-((6-(trifluoromethyl)pyridin-3-yl)oxy)benzonitrile

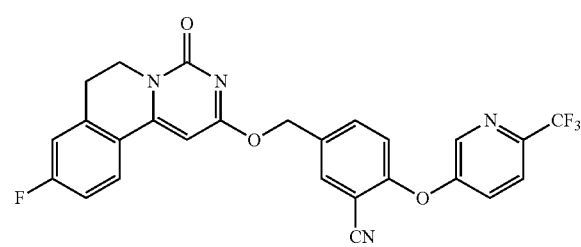 [SMILES: N#Cc1cc(COc2cc3n(c(=O)n2)CCc2cc(F)ccc2-3)ccc1Oc1ccc(C(F)(F)F)nc1]

The title compound was prepared by a procedure similar to that described for E37, starting from 2-chloro-9-fluoro-6,7-dihydro-4H-pyrimido[6,1-a]isoquinolin-4-one and 5-(hydroxymethyl)-2-((6-(trifluoromethyl)pyridin-3-yl)oxy)benzonitrile.
LC-MS (ESI): m/z 509 [M+H]⁺; 3.46 min (ret time).

E112

5-(((9-fluoro-4-oxo-6,7-dihydro-4H-pyrimido[6,1-a]isoquinolin-2-yl)oxy)methyl)-2-((6-(trifluoromethyl)pyridin-2-yl)oxy)benzonitrile

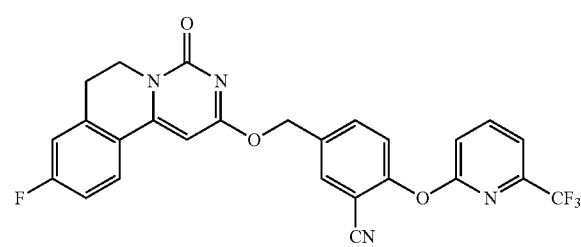 [SMILES: N#Cc1cc(COc2cc3n(c(=O)n2)CCc2cc(F)ccc2-3)ccc1Oc1cccc(C(F)(F)F)n1]

The title compound was prepared by a procedure similar to that described for E37, starting from 2-chloro-9-fluoro-6,7-dihydro-4H-pyrimido[6,1-a]isoquinolin-4-one and 5-(hydroxymethyl)-2-((6-(trifluoromethyl)pyridin-2-yl)oxy)benzonitrile.
LC-MS (ESI): m/z 509 [M+H]⁺; 3.55 min (ret time).

E113

2-(4-chloro-3-(trifluoromethyl)phenoxy)-5-(((9-methyl-4-oxo-6,7-dihydro-4H-pyrimido[6,1-a]isoquinolin-2-yl)oxy)methyl)benzonitrile

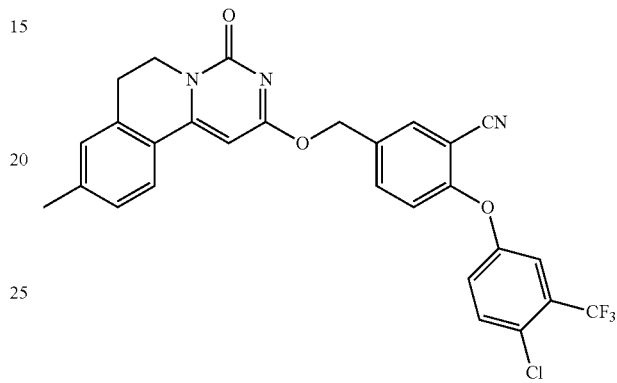

The title compound was prepared by a procedure similar to that described for E37, starting from 2-chloro-9-methyl-6,7-dihydro-4H-pyrimido[6,1-a]isoquinolin-4-one and 2-(4-chloro-3-(trifluoromethyl)phenoxy)-5-(hydroxymethyl)benzonitrile.
LC-MS (ESI): m/z 538 [M+H]⁺; 4.02 min (ret time).

E114

2-((3,5-difluoro-4-((6-(trifluoromethyl)pyridin-3-yl)oxy)benzyl)oxy)-9-methyl-6,7-dihydro-4H-pyrimido[6,1-a]isoquinolin-4-one

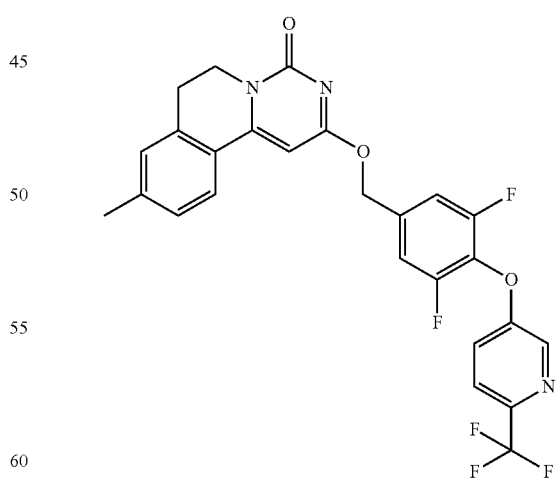

The title compound was prepared by a procedure similar to that described for E37, starting from (3,5-difluoro-4-{[6-(trifluoromethyl)-3-pyridinyl]oxy}phenyl)methanol and 2-chloro-9-methyl-6,7-dihydro-4H-pyrimido[6,1-a]isoquinolin-4-one.
LC-MS (ESI): m/z 516 [M+H]⁺; 3.86 min (ret time)

E115

5-(((9-methyl-4-oxo-6,7-dihydro-4H-pyrimido[6,1-a]isoquinolin-2-yl)oxy)methyl)-2-((2-(trifluoromethyl)pyrimidin-5-yl)oxy)benzonitrile

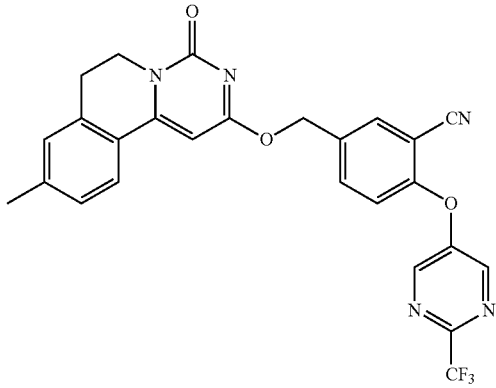 [SMILES: Cc1ccc2c(c1)CCn1c-2cc(OCc2ccc(Oc3cnc(C(F)(F)F)nc3)c(C#N)c2)nc1=O]

The title compound was prepared by a procedure similar to that described for E37, starting from 2-chloro-9-methyl-6,7-dihydro-4H-pyrimido[6,1-a]isoquinolin-4-one and 5-(hydroxymethyl)-2-((2-(trifluoromethyl)pyrimidin-5-yl)oxy)benzonitrile.

LC-MS (ESI): m/z 506 [M+H]$^+$; 3.54 min (ret time)

E116

2-((3-fluoro-4-((2-(trifluoromethyl)pyrimidin-5-yl)oxy)benzyl)oxy)-9-methyl-6,7-dihydro-4H-pyrimido[6,1-a]isoquinolin-4-one

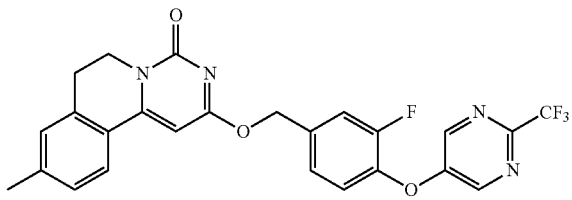 [SMILES: Cc1ccc2c(c1)CCn1c-2cc(OCc2ccc(Oc3cnc(C(F)(F)F)nc3)c(F)c2)nc1=O]

The title compound was prepared by a procedure similar to that described for E37, starting from 2-chloro-9-methyl-6,7-dihydro-4H-pyrimido[6,1-a]isoquinolin-4-one and (3-fluoro-4-((2-(trifluoromethyl)pyrimidin-5-yl)oxy)phenyl)methanol.

LC-MS (ESI): m/z 499 [M+H]$^+$; 3.71 min (ret time)

E117

5-(((9-methyl-4-oxo-6,7-dihydro-4H-pyrimido[6,1-a]isoquinolin-2-yl)oxy)methyl)-2-((6-(trifluoromethyl)pyridin-3-yl)oxy)benzonitrile

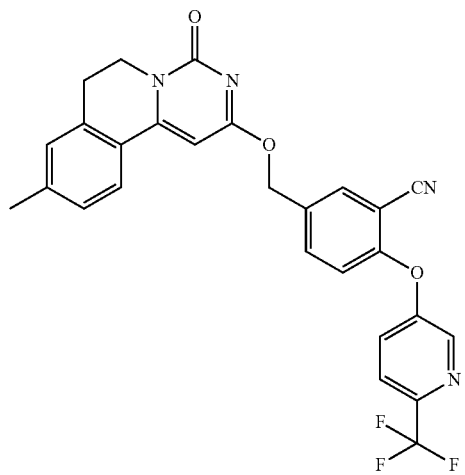

The title compound was prepared by a procedure similar to that described for E37, starting from 2-chloro-9-methyl-6,7-dihydro-4H-pyrimido[6,1-a]isoquinolin-4-one and 5-(hydroxymethyl)-2-((6-(trifluoromethyl)pyridin-3-yl)oxy)benzonitrile.

LC-MS (ESI): m/z 505 [M+H]$^+$; 3.59 min (ret time)

E118

2-((3-fluoro-4-((6-(trifluoromethyl)pyridin-3-yl)oxy)benzyl)oxy)-9-methyl-6,7-dihydro-4H-pyrimido[6,1-a]isoquinolin-4-one

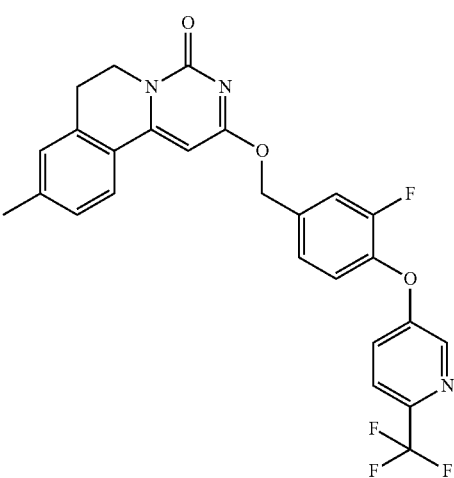 [SMILES: Cc1ccc2c(c1)CCn1c-2cc(OCc2ccc(Oc3ccc(C(F)(F)F)nc3)c(F)c2)nc1=O]

The title compound was prepared by a procedure similar to that described for E37, starting from 2-chloro-9-methyl-6,7-dihydro-4H-pyrimido[6,1-a]isoquinolin-4-one and (3-fluoro-4-((6-(trifluoromethyl)pyridin-3-yl)oxy)phenyl)methanol.

LC-MS (ESI): m/z 498 [M+H]$^+$; 3.78 min (ret time)

E119

5-(((9-methyl-4-oxo-6,7-dihydro-4H-pyrimido[6,1-a]isoquinolin-2-yl)oxy)methyl)-2-(3-(trifluoromethyl)phenoxy)benzonitrile

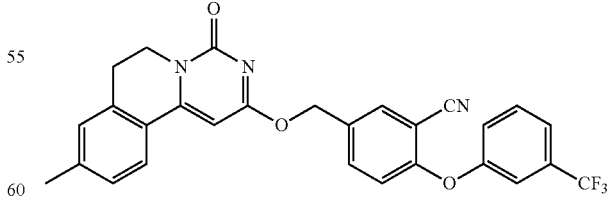

The title compound was prepared by a procedure similar to that described for E37, starting from 2-chloro-9-methyl-6,7-dihydro-4H-pyrimido[6,1-a]isoquinolin-4-one and 5-(hydroxymethyl)-2-(3-(trifluoromethyl)phenoxy)benzonitrile.

LC-MS (ESI): m/z 504 [M+H]$^+$; 3.85 min (ret time)

E120

9-fluoro-2-((3-fluoro-4-(4-fluoro-3-(trifluoromethyl)phenoxy)benzyl)oxy)-6,7-dihydro-4H-pyrimido[6,1-a]isoquinolin-4-one

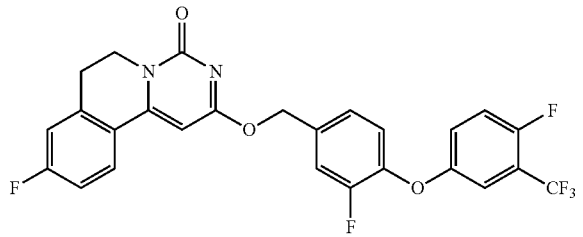 [SMILES: O=c1nc(OCc2ccc(Oc3ccc(F)c(C(F)(F)F)c3)c(F)c2)cc2n1CCc1cc(F)ccc1-2]

The title compound was prepared by a procedure similar to that described for E37, starting from 2-chloro-9-fluoro-6,7-dihydro-4H-pyrimido[6,1-a]isoquinolin-4-one and (3-fluoro-4-(4-fluoro-3-(trifluoromethyl)phenoxy)phenyl)methanol.

LC-MS (ESI): m/z 504 [M+H]$^+$; 3.85 min (ret time)

E121

2-((3,5-difluoro-4-((5-(trifluoromethyl)pyridin-2-yl)oxy)benzyl)oxy)-9-fluoro-6,7-dihydro-4H-pyrimido[6,1-a]isoquinolin-4-one

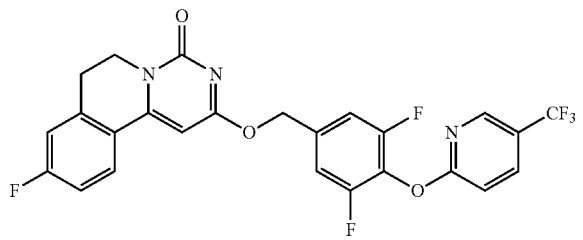 [SMILES: O=c1nc(OCc2cc(F)c(Oc3ccc(C(F)(F)F)cn3)c(F)c2)cc2n1CCc1cc(F)ccc1-2]

The title compound was prepared by a procedure similar to that described for E37, starting from 2-chloro-9-fluoro-6,7-dihydro-4H-pyrimido[6,1-a]isoquinolin-4-one and (3,5-difluoro-4-((5-(trifluoromethyl)pyridin-2-yl)oxy)phenyl)methanol.

LC-MS (ESI): m/z 520 [M+H]$^+$; 3.70 min (ret time)

E122

9-fluoro-2-((3-fluoro-4-((6-(trifluoromethyl)pyridin-3-yl)oxy)benzyl)oxy)-6,7-dihydro-4H-pyrimido[6,1-a]isoquinolin-4-one

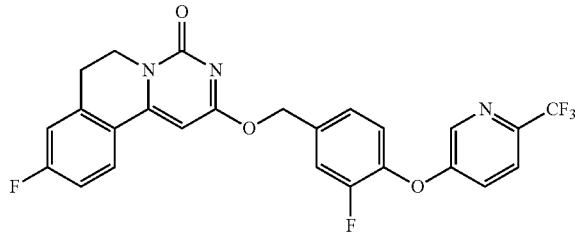 [SMILES: O=c1nc(OCc2ccc(Oc3ccc(C(F)(F)F)nc3)c(F)c2)cc2n1CCc1cc(F)ccc1-2]

The title compound was prepared by a procedure similar to that described for E37, starting from 2-chloro-9-fluoro-6,7-dihydro-4H-pyrimido[6,1-a]isoquinolin-4-one and (3-fluoro-4-((6-(trifluoromethyl)pyridin-3-yl)oxy)phenyl)methanol.

LC-MS (ESI): m/z 502 [M+H]$^+$; 3.63 min (ret time)

E123

5-(((9-methyl-4-oxo-6,7-dihydro-4H-pyrimido[6,1-a]isoquinolin-2-yl)oxy)methyl)-2-((5-(trifluoromethyl)pyridin-2-yl)oxy)benzonitrile

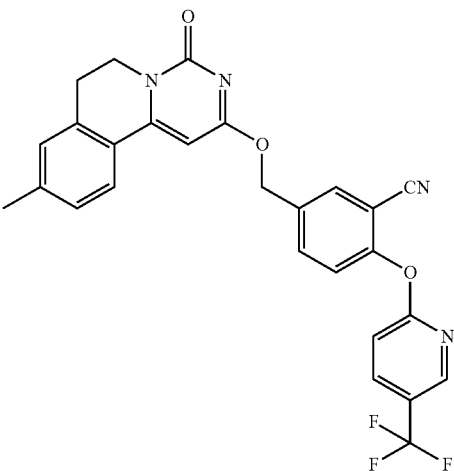 [SMILES: Cc1ccc2c(c1)CCn1c-2cc(OCc2ccc(Oc3ccc(C(F)(F)F)cn3)c(C#N)c2)nc1=O]

The title compound was prepared by a procedure similar to that described for E37, starting from 2-chloro-9-methyl-6,7-dihydro-4H-pyrimido[6,1-a]isoquinolin-4-one and 5-(hydroxymethyl)-2-((5-(trifluoromethyl)pyridin-2-yl)oxy)benzonitrile.

LC-MS (ESI): m/z 505 [M+H]$^+$; 3.70 min (ret time)

E124

2-((5-(4-chloro-3-(trifluoromethyl)phenoxy)pyridin-2-yl)methoxy)-9-methyl-6,7-dihydro-4H-pyrimido[6,1-a]isoquinolin-4-one

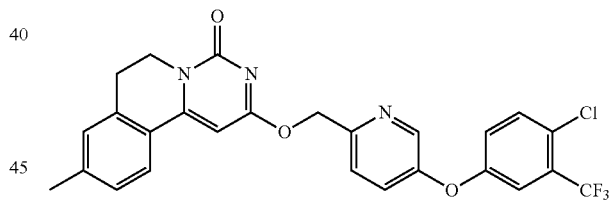

The title compound was prepared by a procedure similar to that described for E37, starting from 2-chloro-9-methyl-6,7-dihydro-4H-pyrimido[6,1-a]isoquinolin-4-one and (5-(4-chloro-3-(trifluoromethyl)phenoxy)pyridin-2-yl)methanol.

LC-MS (ESI): m/z 514 [M+H]$^+$; 3.82 min (ret time)

E125

2-((3-fluoro-4-((5-(trifluoromethyl)pyridin-2-yl)oxy)benzyl)oxy)-9-methyl-6,7-dihydro-4H-pyrimido[6,1-a]isoquinolin-4-one

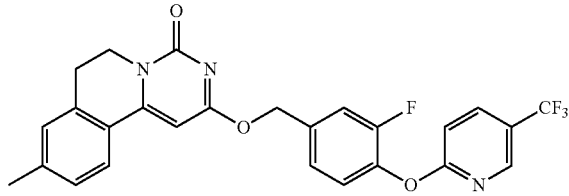 [SMILES: Cc1ccc2c(c1)CCn1c-2cc(OCc2ccc(Oc3ccc(C(F)(F)F)cn3)c(F)c2)nc1=O]

The title compound was prepared by a procedure similar to that described for E37, starting from 2-chloro-9-methyl-6,7-dihydro-4H-pyrimido[6,1-a]isoquinolin-4-one and (3-fluoro-4-((5-(trifluoromethyl)pyridin-2-yl)oxy)phenyl)methanol.

LC-MS (ESI): m/z 498 [M+H]+; 3.36 min (ret time)

E126

2-((3,5-difluoro-4-((2-(trifluoromethyl)pyrimidin-5-yl)oxy)benzyl)oxy)-9-methyl-6,7-dihydro-4H-pyrimido[6,1-a]isoquinolin-4-one

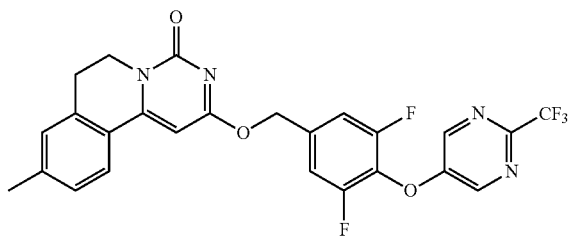 [SMILES: Cc1ccc2c(c1)CCn1c-2cc(OCc2cc(F)c(Oc3cnc(C(F)(F)F)nc3)c(F)c2)nc1=O]

The title compound was prepared by a procedure similar to that described for E37, starting from 2-chloro-9-methyl-6,7-dihydro-4H-pyrimido[6,1-a]isoquinolin-4-one and (3,5-difluoro-4-((2-(trifluoromethyl)pyrimidin-5-yl)oxy)phenyl)methanol.

LC-MS (ESI): m/z 517 [M+H]+; 3.77 min (ret time).

E127

5-(((9-methyl-4-oxo-6,7-dihydro-4H-pyrimido[6,1-a]isoquinolin-2-yl)oxy)methyl)-2-((6-(trifluoromethyl)pyridin-2-yl)oxy)benzonitrile

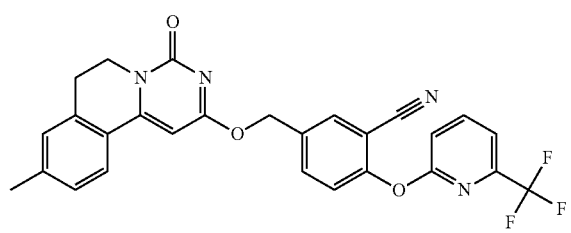 [SMILES: Cc1ccc2c(c1)CCn1c-2cc(OCc2ccc(Oc3cccc(C(F)(F)F)n3)c(C#N)c2)nc1=O]

The title compound was prepared by a procedure similar to that described for E37, starting from 2-chloro-9-methyl-6,7-dihydro-4H-pyrimido[6,1-a]isoquinolin-4-one and 5-(hydroxymethyl)-2-((6-(trifluoromethyl)pyridin-2-yl)oxy)benzonitrile.

LC-MS (ESI): m/z 505 [M+H]+; 3.64 min (ret time)

E128

2-((3-fluoro-4-((6-(trifluoromethyl)pyridin-2-yl)oxy)benzyl)oxy)-9-methyl-6,7-dihydro-4H-pyrimido[6,1-a]isoquinolin-4-one

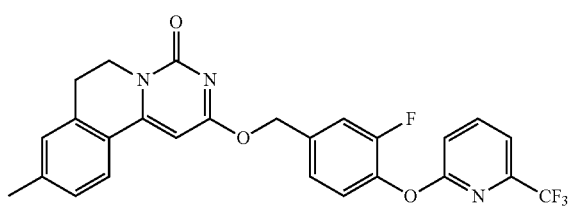 [SMILES: Cc1ccc2c(c1)CCn1c-2cc(OCc2ccc(Oc3cccc(C(F)(F)F)n3)c(F)c2)nc1=O]

The title compound was prepared by a procedure similar to that described for E37, starting from 2-chloro-9-methyl-6,7-dihydro-4H-pyrimido[6,1-a]isoquinolin-4-one and (3-fluoro-4-((6-(trifluoromethyl)pyridin-2-yl)oxy)phenyl)methanol.

LC-MS (ESI): m/z 498 [M+H]+; 3.80 min (ret time)

E129

2-(4-chloro-3-(trifluoromethyl)phenoxy)-5-(2-((9-fluoro-4-oxo-6,7-dihydro-4H-pyrimi-do[6,1-a]isoquinolin-2-yl)oxy)ethyl)benzonitrile

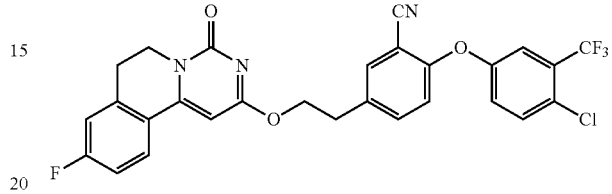

The title compound was prepared by a procedure similar to that described for E37, starting from 2-chloro-9-fluoro-6,7-dihydro-4H-pyrimido[6,1-a]isoquinolin-4-one and 2-(4-chloro-3-(trifluoromethyl)phenoxy)-5-(2-hydroxyethyl)benzonitrile.

LC-MS (ESI): m/z 556 [M+H]+; 3.87 min (ret time)

E130

5-(((9-fluoro-4-oxo-6,7-dihydro-4H-pyrimido[6,1-a]isoquinolin-2-yl)oxy)methyl)-2-((6-met-hylpyridin-3-yl)oxy)benzonitrile

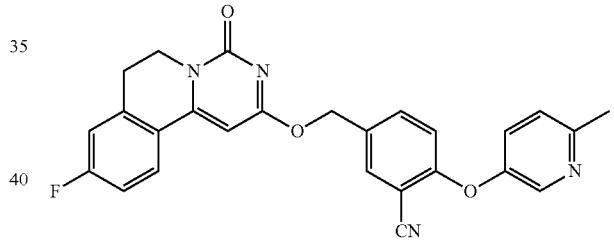

The title compound was prepared by a procedure similar to that described for E37, starting from 5-(((9-fluoro-4-oxo-6,7-dihydro-4H-pyrimido[6,1-a]isoquinolin-2-yl)oxy)methyl)-2-((6-methylpyridin-3-yl)oxyl)benzonitrile.

LC-MS (ESI): m/z 455 [M+H]+; 2.62 min (ret time)

E131

5-(2-((9-fluoro-4-oxo-6,7-dihydro-4H-pyrimido[6,1-a]isoquinolin-2-yl)oxy)ethyl)-2-((6-(trifluoromethyl)pyridin-3-yl)oxy)benzonitrile

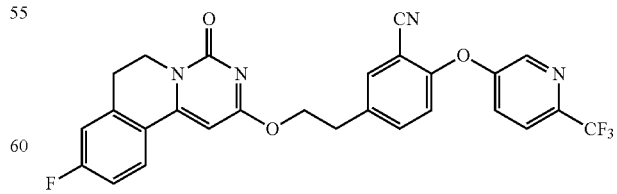

The title compound was prepared by a procedure similar to that described for E37, starting from 2-(4-chloro-3-(trifluoromethyl)phenoxy)-5-(2-((9-fluoro-4-oxo-6,7-dihydro-4H-pyrimido[6,1-a]isoquinolin-2-yl)oxy)ethyl)benzonitrile.

LC-MS (ESI): m/z 523 [M+H]+; 3.49 min (ret time)

E132

5-(((9-chloro-4-oxo-6,7-dihydro-4H-pyrimido[6,1-a]isoquinolin-2-yl)oxy)methyl)-2-((6-(trifluoromethyl)pyridin-2-yl)oxy)benzonitrile

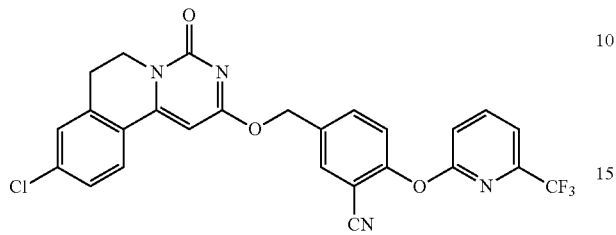

The title compound was prepared by a procedure similar to that described for E37, starting from 2,9-dichloro-6,7-dihydro-4H-pyrimido[6,1-a]isoquinolin-4-one and 5-(hydroxym-ethyl)-2-((6-(trifluoromethyl)pyridin-2-yl)oxy)benzonitrile.

LC-MS (ESI): m/z 525 [M+H]$^+$; 3.71 min (ret time)

E133

5-(((9-chloro-4-oxo-6,7-dihydro-4H-pyrimido[6,1-a]isoquinolin-2-yl)oxy)methyl)-2-(3-(trifluoromethyl)phenoxy)benzonitrile

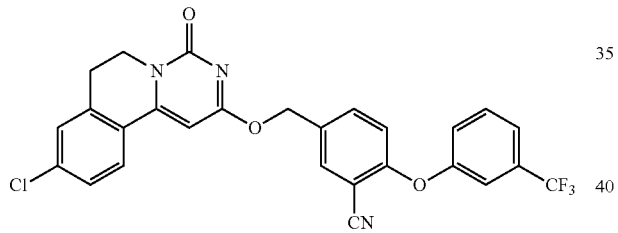

The title compound was prepared by a procedure similar to that described for E37, starting from 2,9-dichloro-6,7-dihydro-4H-pyrimido[6,1-a]isoquinolin-4-one and 5-(hydroxym-ethyl)-2-(3-(trifluoromethyl)phenoxy)benzonitrile.

LC-MS (ESI): m/z 524 [M+H]$^+$; 3.92 min (ret time)

E134

9-chloro-2-((3,5-difluoro-4-((6-(trifluoromethyl)pyridin-3-yl)oxy)benzyl)oxy)-6,7-dihydro-4H-pyrimido[6,1-a]isoquinolin-4-one

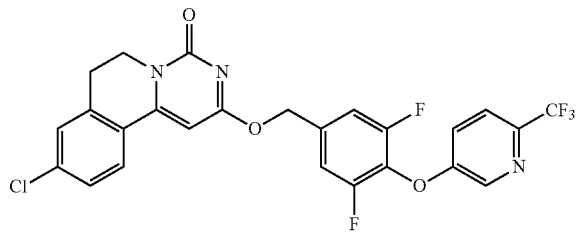 [SMILES: O=c1nc(OCc2cc(F)c(Oc3ccc(C(F)(F)F)nc3)c(F)c2)cc2n1CCc1cc(Cl)ccc1-2]

The title compound was prepared by a procedure similar to that described for E37, starting from 2,9-dichloro-6,7-dihydro-4H-pyrimido[6,1-a]isoquinolin-4-one and (3,5-difluoro-4-((6-(trifluoromethyl)pyridin-3-yl)oxy)phenyl)methanol.

LC-MS (ESI): m/z 536 [M+H]$^+$; 3.91 min (ret time)

E135

5-(((9-chloro-4-oxo-6,7-dihydro-4H-pyrimido[6,1-a]isoquinolin-2-yl)oxy)methyl)-2-((6-(trifluoromethyl)pyridin-3-yl)oxy)benzonitrile

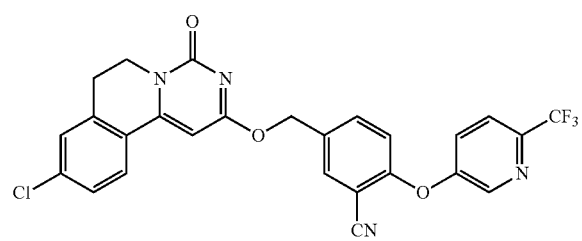 [SMILES: N#Cc1cc(COc2cc3n(c(=O)n2)CCc2cc(Cl)ccc2-3)ccc1Oc1ccc(C(F)(F)F)nc1]

The title compound was prepared by a procedure similar to that described for E37, starting from 2,9-dichloro-6,7-dihydro-4H-pyrimido[6,1-a]isoquinolin-4-one and 5-(hydroxymethyl)-2-((6-(trifluoromethyl)pyridin-3-yl)oxy)benzonitrile.

LC-MS (ESI): m/z 525 [M+H]$^+$; 3.66 min (ret time)

D. Biological Assay and Data

The compounds of present invention are Lp-PLA$_2$ inhibitors, and are useful in the treatment of diseases mediated by Lp-PLA$_2$. The biological activities of the compounds of present invention can be determined by using any suitable assay for determining the activity of a candidate compound as a Lp-PLA$_2$ inhibitor, as well as tissue and in vivo models.

Lipoprotein-Associated Phospholipase A2 (Lp-PLA$_2$) Biochemical Assay (1) Recombinant Human Lp-PLA$_2$ Assay (rhLp-PLA$_2$) (Also Referred to as "PED6" Assay)

N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Molecular Probes. There is a quenching para-nitro phenyl (PNP) group in the sn3 position and a Bodipy fluorescein (FL) group in the sn2 position. Upon cleavage with LpPLA$_2$, the Bodipy Fl group is liberated and then may result in an increase in fluorescence. Inhibitors of LpPLA$_2$ therefore prevent this cleavage and no fluorescent increase is observed.

The PED6 assay is run as an unquenched 10 µL assay. Compounds source plate is prepared by making 1:3 (by volume) serial dilution of the compounds into pure DMSO on 384-well microplate. Then 0.01 µL of compounds on compound source plate are transferred into 384 well Greiner 784076 (black) plates by ECHO liquid dispenser. 5 µL of recombinant human Lp-PLA$_2$ enzyme (2 nM rhLp-PLA$_2$ in assay buffer of 50 mM HEPES, pH7.4, 150 mM NaCl, 1 mM CHAPS) is added to each well of the plate with compounds. Plates are centrifuged for 10 sec at 500 rpm. After 30 minutes preincubation, 5 µL of substrate (4 µM PED6 [from 5 mM DMSO stock] in assay buffer of 50 mM HEPES, pH7.4, 150 mM NaCl, 1 mM CHAPS) is added to 384 well Greiner 784076 (black) plates. Plates are centrifuged for 10 sec at 500 rpm. Plate is covered to protect from light and incubated for 20 min at room temperature. Plates are read for Fluorescence intensity at ex: 480/em: 540 using ViewLux microplate imager. PIC50 data, curve and QC analysis is conducted by using XL fit module in Excel.

(2) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, it liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds.

The PLA2 VIIB assay is applied as an unquenched 10 µL assay. Compounds source plate is prepared by making 1:3 (by volume) serial dilution of the compounds into pure DMSO on 384-well microplate. 0.01 µL of compounds on compound source plate are transferred into 384 well Greiner 784076 (black) plates-by ECHO liquid dispenser. 5 µL of Novel Serine Dependent Lipase (NSDL) enzyme (5 nM NSDL in assay buffer of 50 mM HEPES, pH 7.4, 150 mM NaCl, 1 mM CHAPS) is added to each well with compounds. Plates are centrifuged for 10 sec at 500 rpm. After 30 minutes preincubation, 5 µL of substrate (5 µM PED6 [from 5 mM DMSO stock] in assay buffer of 50 mM HEPES, pH7.4, 150 mM NaCl, 1 mM CHAPS) is added to 384 well Greiner 784076 (black) low-volume plates by BRAVO liquid handling station. Plates are kinetic read by starting read immediately after PED6 addition at ex: 480/em: 540 using ViewLux microplate reader. pIC50 data, curve and QC analysis is conducted using XLfit module in Excel.

(3) Lipoprotein-Associated Phospholipase A2 (Lp-PLA$_2$) Human Plasma Assay

The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluoresence after Michael addition of thiols. This assay may detect the activity of Lp-PLA$_2$ from plasma, as determined by specific inhibition by Lp-PLA$_2$ inhibitors.

The thio-PAF assay is run as a quenched 15 µL assay. Compounds source plate is prepared by making 1:3 (by volune) serial dilution of the compounds into pure DMSO on 384-well microplate. 0.01 µL of compounds on compound source plate are transferred to 384 well Greiner 784076 (black) low-volume plates by ECHO liquid dispenser. 8 µL pooled human plasma, which was previously aliquoted and frozen, is added. Plates are centrifuged for 10 sec at 500 rpm. After minutes preincubation, 2 µL of substrate (2.5 mM thio-PAF, 3.2 mM NEM (N-ethylmaleimide) [made fresh daily in DMSO], and 32 µM CPM [from a DMSO stock] in assay buffer of 50 mM HEPES, pH7.4, 150 mM NaCl, 1 mM CHAPS is added to 384 well Greiner 784076 (black) low-volume plates by BRAVO liquid handling station. Plates are centrifuged for 10 sec at 500 rpm. Plate is covered to protect from light and incubated for 2 min at room temperature. Reaction is quenched with 5 µL of 5% aqueous trifluoroacetic acid (TFA). Plates are covered to protect from light and incubated for 40 min at room temperature. Plates are read at ex: 380/em: 485 using Envision microplate reader. PIC50 data, curve and QC analysis is conducted by using XLFit module in Excel.

Results

All exemplified compounds of the present invention were tested according to the above assays or similar assay as described above and were found to demonstrate inhition activity to Lp-PLA$_2$. The compounds described below were tested generally according to the PED6 assay described above. The pIC$_{50}$ value for each compound was either reported in at least one experiment or the average of multiple experiments. It is understood that the data illustrated below may have reasonable variations depending on the specific conditions and procedures used by the person conducting the experiments. It is noted that the upper limit for pIC$_{50}$ obtained in the PED6 assay described above is 9.3. If a refined assay is used, compounds that exhibit pIC$_{50}$ equal to 9.3 in the PED6 assay described above may demonstrate pIC$_{50}$ higher than 9.3.

The pIC$_{50}$ values in the PED6 assay for compounds of all Examples except example 7, 14, 18, 19, 41, 42, 50, 54 and 123 were at least 5.0.

The pIC$_{50}$ values in the PED6 assay for examples 11, 12, 16, 21, 22, 23, 24, 27, 28-32, 34, 36, 37, 40, 43, 44, 46-49, 52, 55, 56, 58-60, 62, 64, 66-68, 70, 71, 72, 74- 77, 79, 80, 82- 84, 87- 91, 106, 108-122, 124, and 126-135 were at least 8.0.

The pIC$_{50}$ values in the PED6 assay for examples 22, 27, 36, 46, 47, 58, 70, 71, 88, 91-94, 96-98, 104, 111-113, 117, 119-121, 129-131, 133 were at least 9.0.

Table 1 below provides the pIC50 for some exemplified compounds.

| Example No. | rhLp-PLA$_2$ (PED6 assay) (pIC50) |
|---|---|
| 22 | 9.2 |
| 36 | 9.0 |
| 58 | 9.0 |
| 88 | 9.1 |
| 89 | 8.5 |
| 91 | 9.0 |
| 92 | 9.1 |
| 93 | 9.0 |
| 94 | 9.0 |
| 96 | 9.1 |
| 98 | 9.3 |

E. Methods of Use

The compounds of this invention are inhibitors of Lp-PLA$_2$. Therefore, these compounds may be used in therapy, for example, in the treatment of disorders associated with the activity of Lp-PLA$_2$. Accordingly, another aspect of the invention is directed to methods of treating conditions associated with the activity of Lp-PLA$_2$.

In one embodiment, the compounds of this invention may be used to treat any disease that involves endothelial dysfunction, for example, atherosclerosis, diabetes, hypertension, angina pectoris and after ischaemia and reperfusion. In certain embodiment, the compounds of the present invention may be used to treat any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, myocardial infarction, ischaemia, reperfusion injury, sepsis, and acute and chronic inflammation. In one embodiment, the compounds of the present invention may be used to treat disease that involves activated monocytes, macrophages or lymphocytes, as all of these cell types express Lp-PLA$_2$ and exemplary disorder includes, but is not limited to, psoriasis, rheumatoid arthritis, wound healing and chronic obstructive pulmonary disease (COPD).

In one embodiment, the present invention provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

In certain embodiment, the compounds of the present invention may be used to treat the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312.

In one embodiment, the compounds of the present invention may be used with statin. The statins are a well-known class of cholesterol lowering agents and include atorvastatin, simvarstatin, pravastatin, cerivastatin, fluvastatin, lovastatin and rosuvastatin. The two agents may be administered at substantially the same time or at different times, according to the discretion of the physician.

In certain embodiment, the compounds of the present invention may be used with an anti-diabetic agent or an insulin sensitizer. In one embodiment, a compound of the present invention may be used with PPAR gamma activators, for instance GI262570 (GlaxoSmithKline) and the glitazone class of compounds such as rosiglitazone, troglitazone and pioglitazone.

In one embodiment, the compounds of the present invention may be used to treat a neurodegeneration disease in a subject. The methods comprise administering to a subject in need thereof a pharmaceutical composition comprising an agent that inhibits the activity of Lp-PLA$_2$. Exemplary neurodegeneration diseases include, but are not limited to, Alzheimer's disease, vascular dementia, Parkinson's disease and Huntington's disease. In certain embodiment, the neurodegeneration disease described herein is associated with an abnormal blood brain barrier. In one embodiment, the subject administered an agent that inhibits the activity of Lp-PLA$_2$ is a human.

In one embodiment, the present invention provides methods of treating a subject with or at risk of vascular dementia. The methods comprise administering to the subject a pharmaceutical composition comprising a safe and effective amount of a compound of present invention. In certain embodiment, the vascular dementia is associated with Alzheimer's disease.

In one embodiment, the present invention provides methods of treating a neurological disorder associated with an abnormal blood brain barrier (BBB) function, inflammation, and/or microglia activation in a subject in need thereof. The methods comprise administering to the subject a safe and effective amount of a compound of present invention. In certain embodiment, the abnormal blood-brain barrier is a permeable blood brain barrier. In one embodiment, the disease is a neurodegeneration disease. Such neurodegeneration diseases are, for example, but are not limited to, vascular dementia, Alzheimer's disease, Parkinson's disease and Huntington's disease. In certain embodiment, the present invention provides methods of treating disease associated with a subject with blood brain barrier (BBB) leakage. Exemplary disease include, but is not limited to, brain hemorrhage, cerebral amyloid angiopathy. In one embodiment, the neurodegeneration disease is Alzheimer's disease. In certain embodiment, the neurodegeneration disease is vascular dementia. In one embodiment, the neurodegeneration disease is Multiple Sclerosis (MS).

In one embodiment, the present invention provides methods of decreasing beta amyloid, referred to as "Aβ" accumulation in the brain of a subject. The methods comprise administering to a subject in need thereof a pharmaceutical composition comprising a safe and effective amount of a compound of the present invention. In certain embodiment, the beta amyloid is Abeta-42.

In one embodiment, the present invention provides methods of decreasing tau hyperphosphorylation in the brain of a subject. The methods comprise administering to the subject a safe and effective amount of a compound of the present invention.

In certain embodiment, when a subject is administered a safe and effective amount of a compound of the present invention, the methods may further comprise administering to the subject another therapeutic agent that may be useful in treating the neurodegenerative disease for which the subject is being treated, or that may be a co-morbidity. For example, when the neurodegenerative disease is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation.

In one embodiment, the present invention relates to methods of treating metabolic bone diseases by administering to the subject in need thereof a safe and effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diseases, metabolic syndrome, insulin resistance, hyperparathyroidism and related diseases. In certain embodiment, the subject in need thereof is a human.

It is believed that methods of preventing osteoporosis and/or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In one embodiment, methods for inhibiting Lp-PLA$_2$ by reducing and/or down-regulating the expression of Lp-PLA$_2$ RNA are provided. In certain embodiment, preventing and/or reducing loss of bone mass and/or loss of bone density leads to preventing or reducing symptoms associated with metabolic bone diseases such as osteoporosis and/or osteopenic diseases.

In one embodiment, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene, a selective estrogen modulator (SERM), estrogen therapy, hormone replacement therapy (ET/HRT) and teriparatide) may be used.

One aspect of the present invention provides methods for treating eye diseases by administering a safe and effective amount of a compound of present invention. Eye diseases applicable in the present invention may be associated with the breakdown of the inner blood-retinal barrier (iBRB). Exemplary eye diseases relate to diabetic eye diseases and disorders include macular edema, diabetic retinopathy, and the like. Further, in one embodiment, the present invention relates to methods for treatment eye diseases by administering a compound of the present invention to inhibit $Lp-PLA_2$. Exemplary eye diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like.

Further, some embodiments of the present invention provide methods for treating diabetic macular edema in a subject. The method comprises administering to a subject in need thereof a safe and effective amount of a compound of present invention.

In one embodiment, the present invention provides methods of treating a subject with or at risk of macular edema. The methods comprise administering to the subject a safe and effective amount of a compound of the present invention. In certain embodiment, the macular edema is associated with diabetic eye disease, for example, diabetic retinopathy. In one embodiment, the macular edema is associated with posterior uveitis.

In one embodiment, the present invention provides methods of treating glaucoma or macular degeneration. The methods comprise administering to the subject a safe and effective amount of a compound of the present invention.

In one embodiment, the present invention provides methods of treating a disease associated with the breakdown of the inner blood-retinal barrier in a subject in need thereof. The methods comprise administering to the subject a safe and effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating posterior uveitis by administering a safe and effective amount of a compound of the present invention.

One aspect of the present invention provides the use of a compound of the present invention for the preparation of a medicament for carrying out a method described herein. Another aspect of the present invention provides a compound of the present invention for use in carrying out methods of treatment described herein is provided.

F. Composition

The compounds of the present invention may be formulated into pharmaceutical compositions prior to administration to a subject. Accordingly, one aspect of the invention is directed to pharmaceutical compositions comprising a compound of the invention and one or more pharmaceutically-acceptable excipients. In accordance with another aspect of the invention, a process for the preparation of a pharmaceutical composition including admixing a compound of the Formula (I), Formula (IA), Formula (II) or salts thereof, solvates etc thereof, with one or more pharmaceutically acceptable excipients.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the condition being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A safe and effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a safe and effective amount of a compound of present invention for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A safe and effective amount of a salt or solvate, etc., may be determined as a proportion of the effective amount of the compound of Formula (I), Formula (IA), or Formula (II) per se. It is envisaged that similar dosages would be appropriate for treatment of the other conditions referred to above.

The pharmaceutical compositions of the invention may contain one compound of the invention. In one embodiment, the pharmaceutical compositions may contain more than one compound of the invention. For example, in certain embodiment, the pharmaceutical compositions may contain two compounds of the invention. In addition, the pharmaceutical compositions may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate carrying or transporting of the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

What is claimed is:

1. A compound of Formula (I) or a pharmaceutically acceptable salt thereof,

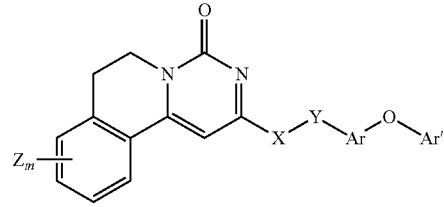

wherein:

Z is selected from the group consisting of $C_1$-$C_3$alkyl, —O—($C_1$-$C_3$alkyl) and halo;

m is 0, 1, 2 or 3;

X is O;

Y is —$(CH_2)_n$—, wherein n is 0, 1, 2, or 3;

Ar is phenyl or heteroaryl, either of which is optionally substituted with one or more substituents selected from the group consisting of CN, halo, $C_1$-$C_3$alkyl, $C_1$-$C_3$alkoxy and $C_1$-$C_3$haloalkyl; and Ar' is phenyl or heteroaryl, either of which is optionally substituted with one or more substituents selected from the group consisting of CN, halo, $C_1$-$C_3$alkyl, $C_1$-$C_3$alkoxy and $C_1$-$C_3$haloalkyl.

2. A compound of claim 1, wherein Z is —$OCH_3$.

3. A compound of claim 1, wherein Z is F or Cl.

4. A compound of claim 1, wherein m is 0 or 1.

5. A compound of claim 1, wherein Y is —$CH_2$— or —$CH_2$—$CH_2$—.

6. A compound of claim 1, wherein Ar is phenyl, which is optionally substituted with one or more substituents selected from the groups consisting of CN, $CF_3$ and halo.

7. A compound of claim 1, wherein Ar is pyridinyl which is optionally substituted with one or more substituents selected from the groups consisting of CN and halo.

8. A compound of claim 1, wherein Ar' is phenyl, pyridinyl or pyrimidinyl, which is optionally substituted with one or more substituents selected from the group consisting of $CH_3$, halo and $CF_3$.

9. A compound of claim 1, wherein the compounds of Formula (I) has the structure of formula (IA), Formula (IA)

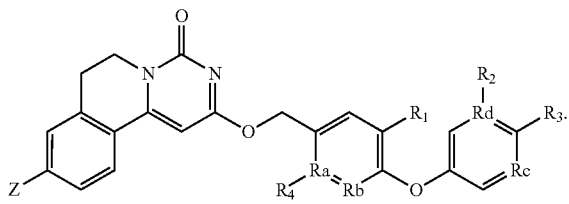

wherein.

Z is OCH₃, Me or F;

each occurrence of $R_a$ and $R_d$ is independently C or N;

each occurrence of $R_b$, and $R_c$ is independently CH or N;

each occurrence of $R_1$, $R_2$, $R_3$, and $R_4$ is independently selected from the group consisting of H, CN, CF₃ and halo; and when $R_a$ is N, $R_4$ is absent; and when $R_d$ is N, $R_2$ is absent.

10. A compound of claim 9, wherein Z is —OCH₃.

11. A compound of claim 9, wherein $R_a$ and $R_d$ are C and $R_b$ and $R_c$ are CH.

12. A compound of claim 9, wherein at least one of $R_1$ and $R_4$ is CN or F.

13. A compound of Formula (I), according to claim 1, wherein the compound is selected from a group consisting of:

2-{[2-Chloro-4-{[4-chloro-3-(trifluoromethyl)phenyl]oxy}phenyl)methyl]oxy}-9-(methyloxy)-6,7-dihydro-4H-pryimido[6,1-a]isoquinolin-4-one;

2-({[4-{[4-Chloro-3-(trifluoromethyl)phenyl]oxy}-2-(trifluoromethyl)phenyl]methyl}oxy)-9-(methyloxy)-6,7-dihydro-4H-pryimido[6,1-a]isoquinolin-4-one;

9-(Methyloxy)-2-{[2-(trifluoromethyl)-4-{[3-(trifluoromethyl)phenyl]oxy}phenyl]methyl]oxy}-6,7-dihydro-4H-pyrimido[6,1-a]isoquinolin-4-one;

2-{[(2-Chloro-4-{[3-(trifluoromethyl)phenyl]oxy}phenyl)methyl]oxy}-9-(methyloxy)-6,7-dihydro-4H-pyrimido[6,1-a]isoquinolin-4-one;

4-(((9-Methoxy-4-oxo-6,7-dihydro-4H-pryimido[6,1-a]isoquinolin-2-yl)oxy)methyl)-2-(3-(trifluoromethyl)phenyoxy)benzonitrile;

2({[9-Methyloxy)-4-oxo-6,7-dihydro-4H-pyrimido[6,1-a]isoquinolin-2-yl]oxy}methyl)-5-{[3-(trifluoromethyl)phenyl]oxy}benzonitrile;

9-(Methyloxy)-2-{[(6-{[3-(trifluoromethyl)phenyl]oxy}-3-pyridinyl)methyl]oxy}-6,7-dihydro-4H-pyrimido[6,1-a]isoquinolin-4-one;

2-{[2-(4-{[4-Chloro-3-(trifluoromethyl)phenyl]oxy}phenyl)ethyl]oxy}-9-(methyloxy)-6,7-dihydro-4H-pyrimido[6,1-a]isoquinolin-4-one;

9-(Methyloxy)-2-{[(3-(methyloxy)-4-{[3-(trifluoromethyl)phenyl]oxy}phenyl)methyl]oxy}-6,7-dihydro-4H-pyrimido[6,1-a]isoquinolin-4-one;

9-(Methyloxy)-2-{[(3-methyl-4-{[3-(trifluoromethyl)phenyl]oxy}phenyl)methyl]oxy}-6,7-dihydro-4H-pyrimido[6,1-a]isoquinolin-4-one;

9-Methyloxy)-2-{[(3-(trifluoromethyl)-4-{[3-(trifluoromethyl)phenyl]oxy}phenyl)methyl]oxy}-6,7-dihydro-4H-pyrimido[6,1-a]isoquinolin-4-one;

2-{[4-Fluoro-3-(triofluoromethyl)phenyl]oxy}-5-({[9-(methyloxy)-4-oxo-6,7-dihydro-4H-pyrimido[6,1-a]isoquinolin-2-yl]oxy}methyl)benzonitrile;

2-{[4-Chloro-3-(trifluoromethyl)phenyl]oxy}-5-({[9-(methyloxy)-4-oxo-6,7-dihydro-4H-pyrimido[6,1-a]isoquinolin-2-yl]oxy}methyl)benzonitrile;

2-((3-Bromo-4-(3-(triofluoromethyl)phenoxy)benzyl)oxy)-9-methoxy-6,7-dihydro-4H-pyrimido[6,1-a]isoquinolin-4-one;

2-((3-Chloro-4-(3-(trifluoromethyl)phenoxy)benzyl)oxy)-9-methoxy-6,7-dihydro-4H-pyrimido[6,1-a]isoquinolin-4-one;

9-(Methyloxy)-2-{[(5-{[3-(trifluoromethyl)phenyl]oxy}-2-pyridinyl)methyl]oxy}-6,7-dihydro-4H-pyrimido[6,1-a]isoquinolin-4-one;

2-{[(6-{[4-Chloro-3-(trifluoromethyl)phenyl]oxy}-3-pyridinyl)methyl]oxy}-9-(methyloxy) -6,7-dihydro-4H-pyrimido[6,1-a]isoquinolin-4-one;

5-(((9-Methoxy-4-oxo-6,7-dihydro-4H-pyrimido[6,1-a]isoquinolin-2-yl)oxy)methyl)-2-((5-(trifluoromethyl)pyridin-2-yl)oxy)benzonitrile;

2-((5-(4-Chloro-3-(trifluoromethyl)phenoxy)pyridin-2-yl)methoxy)-9-methoxy-6,7-dihydro-4H-pyrimido[6,1-a]isoquinolin-4-one;

2-((6-(4-Chloro-3-(trifluoromethyl)phenoxy)-5-fluoropyridin-3-yl)methoxy)-9-methoxy-6,7-dihydro-4H-pyrimido[6,1-a]isoquinolin-4-one;

2-((5-Fluoro-6-(3-(trifluoromethyl)phenoxy)pyridin-3-yl)methoxy)-9-methoxy-6,7-dihydro-4H-pyrimido[6,1-a]isoquinolin-4-one;

2-((5-Fluoro-6-(4-fluoro-3-(trifluoromethyl)phenoxy)pyridin-3-yl)methoxy)-9-methoxy-6,7-dihydro-4H-pyrimido[6,1-a]isoquinolin-4-one;

2-((5-Chloropyridin-3yl)oxy)-5-(((9-methoxy-4-oxo-6,7-dihydro-4H-pyrimido[6,1-a]isoquinolin-2-yl)oxy)methyl)benzonitrile;

5-(2-((9-Methoxy-4-oxo-6,7-dihydro-4H-pyrimido[6,1-a]isoquinolin-2-yl)oxy)ethyl)-2-((5-(trifluoromethyl)pyridin-2-yl)oxy)benzonitrile;

5-(2-Cyano-4-(((9-methoxy-4-oxo-6,7-dihydro-4H-pyrimido[6,1-a]isoquinolin-2-yl)oxy)methyl)phenoxy)nicotinonitrile;

5-(((9-Methoxy-4-oxo-6,7-dihydro-4H-pyrimido[6,1-a]isoquinolin-2-yl)oxy)methyl)-2-((5-(trifluoromethyl)pyridin-3-yl)oxy)benzonitrile;

5-({[9-(Methyloxy)-4-oxo-6,7-dihydro-4H-pyrimido[6,1-a]isoquinolin-2-yl]oxy}methyl)-2-{[6-(trifluoromethyl)-3-pryidinyl]oxy}benzonitrile;

9-methoxy-2-((4-(3-(trifluoromethyl)phenoxy)benzyl)oxy)-6,7-dihydro-4H-pyrimido[6,1-a]isoquinolin-4-one;

2-((3-fluoro-4-(3-(trifluoromethyl)phenoxy)benzyl)oxy)-9-methoxy-6,7-dihydro-4H-pyrimido[6,1-a]isoquinolin-4-one;

5-((9-methoxy-4-oxo-6,7-dihydro-4H-pyrimido[6,1-a]isoquinolin-2-yl)oxy)-2-(3-(trifluoro-methyl)phenoxy)benzonitrile;

2-(4-(4-chloro-3-(trifluoromethyl)phenoxy)phenoxy)-9-methoxy-6,7-dihydro-4H-pyrimido[6,1-a]isoquinolin-4-one;

2-(4-chloro-3-(trifluoromethyl)phenoxy)-5-(((9-methoxy-4-oxo-6,7-dihydro-4H-pyrimido[6,1-a]isoquinolin-2-yl)oxy)methyl)benzonitrile;

5-(2-((9-methoxy-4-oxo-6,7-dihydro-4H-pyrimido[6,1-a]isoquinolin-2-yl)oxy)ethyl)-2-(3-(trifluoromethyl)phenoxy)benzonitrile;

5-(((9-methoxy-4-oxo-6,7-dihydro-4H-pyrimido[6,1-a]isoquinolin-2-yl)oxy)methyl)-2-(pyridin-3-yloxy)benzonitrile;

5-(2-((9-methoxy-4-oxo-6,7-dihydro-4H-pyrimido[6,1-a]isoquinolin-2-yl)oxy)ethyl)-2-((5-(trifluoromethyl)pyridin-3-yl)oxy)benzonitrile;

5-(((9-methoxy-4-oxo-6,7-dihydro-4H-pyrimido[6,1-a]isoquinolin-2-yl)oxy)methyl)-2-(pyrimidin-5-yloxy)benzonitrile;

5-(2-chloro-4-(((9-methoxy-4-oxo-6,7-dihydro-4H-pyrimido[6,1-a]isoquinolin-2-yl)oxy)methyl)phenoxy)nicotinonitrile;

9-methoxy-2-((6-(pyridin-4-yloxy)pyridin-3-yl)methoxy)-6,7-dihydro-4H-pyrimido[6,1-a]isoquinolin-4-one;

2-((3-fluoro-4-(pyrimidin-5-yloxy)benzyl)oxy)-9-methoxy-6,7-dihydro-4H-pyrimido[6,1-a]isoquinolin-4-one;

5-(2-fluoro-4-(((9-methoxy-4-oxo-6,7-dihydro-4H-pyrimido[6,1-a]isoquinolin-2-yl)oxy)methyl)phenoxy)nicotinonitrile;

2-((5-chloro-6-(3-(trifluoromethyl)phenoxy)pyridin-3-yl)methoxy)-9-methoxy-6,7-dihydro-4H-pyrimido[6,1-a]isoquinolin-4-one;

5-(2-((9-methoxy-4-oxo-6,7-dihydro-4H-pyrimido[6,1-a]isoquinolin-2-yl)oxy)ethyl)-2-((6-(trifluoromethyl)pyridin-3-yl)oxy)benzonitrile;

5-(2-((9-methoxy-4-oxo-6,7-dihydro-4H-pyrimido[6,1-a]isoquinolin-2-yl)oxy)ethyl)-2-((5-(trifluoromethyl)pyridin-2-yl)oxy)benzonitrile;

9-methoxy-2-(4-(pyrimidin-5-yloxy)phenethoxy)-6,7-dihydro-4H-pyrimido[6,1-a]isoquinolin-4-one;

2-((3-fluoro-4-((6-(trifluoromethyl)pyridin-3-yl)oxy)benzyl)oxy)-9-methoxy-6,7-dihydro-4H-pyrimido[6,1-a]isoquinolin-4-one;

2-((3-fluoro-4-((6-(trifluoromethyl)pyridin-2-yl)oxy)benzyl)oxy)-9-methoxy-6,7-dihydro-4H-pyrimido[6,1-a]isoquinolin-4-one;

2-(2-(5-(4-fluoro-3-(trifluoromethyl)phenoxy)pyridin-2-yl)ethoxy)-9-methoxy-6,7-dihydro-4H-pyrimido[6,1-a]isoquinolin-4-one;

9-methoxy-2-(2-(5-(3-(trifluoromethyl)phenoxy)pyridin-2-yl)ethoxy)-6,7-dihydro-4H-pyrimido[6,1-a]isoquinolin-4-one;

2-(2-(5-(4-chloro-3-(trifluoromethyl)phenoxy)pyridin-2-yl)ethoxy)-9-methoxy-6,7-dihydro-4H-pyrimido[6,1-a]isoquinolin-4-one;

5-(((9-methoxy-4-oxo-6,7-dihydro-4H-pyrimido[6,1-a]isoquinolin-2-yl)oxy)methyl)-2-((6-(trifluoromethyl)pyridin-2-yl)oxy)benzonitrile;

5-(2-((9-methoxy-4-oxo-6,7-dihydro-4H-pyrimido[6,1-a]isoquinolin-2-yl)oxy)ethyl)-2-((6-(trifluoromethyl)pyridin-3-yl)oxy)benzonitrile;

2-(3-fluoro-4-((6-(trifluoromethyl)pyridin-2-yl)oxy)phenethoxy)-9-methoxy-6,7-dihydro-4H-pyrimido[6,1-a]isoquinolin-4-one;

9-methoxy-2-(4-((5-(trifluoromethyl)pyridin-2-yl)oxy)phenethoxy)-6,7-dihydro-4H-pyrimido[6,1-a]isoquinolin-4-one;

2-((3-chloro-4-((6-(trifluoromethyl)pyridin-3-yl)oxy)benzyl)oxy)-9-methoxy-6,7-dihydro-4H-pyrimido[6,1-a]isoquinolin-4-one;

2-((3-fluoro-4-((6-(trifluoromethyl)pyridin-3-yl)oxy)phenethoxy)-9-methoxy-6,7-dihydro-4H-pyrimido[6,1-a]isoquinolin-4-one;

2-((2-chloro-4-((6-trifluoromethyl)pyridin-3-yl)oxy)benzyl)oxy)-9-methoxy-6,7-dihydro-4H-pyrimido[6,1-a]isoquinolin-4-one;

2-((2-chloro-4-((6-trifluoromethyl)pyridin-3-yl)oxy)benzyl)oxy)-9-methoxy-6,7-dihydro-4H-pyrimido[6,1-a]isoquinolin-4-one;

5-(((9-methoxy-4-oxo-6,7-dihydro-4H-pyrimido[6,1-a]isoquinolin-2-yl)oxy)methyl)-2-((6-methylpyridin-3-yl)oxy)benzonitrile;

2-((5-fluoro-6-(4-fluorophenoxy)pyridin-3-yl)methoxy)-9-methoxy-6,7-dihydro-4H-pyrimido[6,1-a]isoquinolin-4-one;

2-((5-(4-fluoro-3-(trifluoromethyl)phenoxy)pyridin-2-yl)methoxy)-9-methoxy-6,7-dihydro-4H-pyrimido[6,1-a]isoquinolin-4-one;

2-((3-chloro-4-((6-methylpyridin-3-yl)oxy)benzyl)oxy)-9-methoxy-6,7-dihydro-4H-pyrimido[6,1-a]isoquinolin-4-one;

2-((3,5-difluoro-4-((6-(trifluoromethyl)pyridin-3-yl)oxy)benzyl)oxy)-9-methoxy-6,7-dihydro-4H-pyrimido[6,1-a]isoquinolin-4-one;

2-((5-chloropyridin-2-yl)oxy)-5-(((9-methoxy-4-oxo-6,7-dihydro-4H-pyrimido[6,1-a]isoquinolin-2-yl)oxy)methyl)benzonitrile;

5-(((9-methoxy-4-oxo-6,7-dihydro-4H-pyrimido[6,1-a]isoquinolin-2-yl)oxy)methyl)-2-((2-(trifluoromethyl)pyrimidin-5-yl)oxy)benzonitrile;

5-(((9-methoxy-4-oxo-6,7-dihydro-4H-pyrimido[6,1-a]isoquinolin-2-yl)oxy)methyl)-2-((2-(trifluoromethyl)pyrimidin-5-yl)oxy)benzonitrile;

2-((4-((5-chloropyridin-2-yl)oxy)-3-fluorobenzyl)oxy)-9-methoxy-6,7-dihydro-4H-pyrimido[6,1-a]isoquinolin-4-one;

2-((3-((5-chloropyridin-2-yl)oxy)-4-fluorobenzyl)oxy)-9-methoxy-6,7-dihydro-4H-pyrimido[6,1-a]isoquinolin-4-one;

5-(2-((9-methoxy-4-oxo-6,7-dihydro-4H-pyrimido[6,1-a]isoquinolin-2-yl)oxy)ethyl)-2-((2-(trifluoromethyl)pyrimidin-5-yl)oxy)benzonitrile;

2-(2-(6-(4-chloro-3-(trifluoromethyl)phenoxy)pyridin-3-yl)ethoxy)-9-methoxy-6,7-dihydro-4H-pyrimido[6,1-a]isoquinolin-4-one;

2-((5-(4-chloro-3-(trifluoromethyl)phenoxy)pyridin-2-yl)methoxy)-9-methoxy-6,7-dihydro-4H-pyrimido[6,1-a]isoquinolin-4-one;

2-(2-(6-(2,4-difluorophenoxy)pyridin-3-yl)ethoxy)-9-methoxy-6,7-dihydro-4H-pyrimido[6,1-a]isoquinolin-4-one;

2-(3-fluoro-4-((6-methylpyridin-3-yl)oxy)phenethoxy)-9-methoxy-6,7-dihydro-4H-pyrimido[6,1-a]isoquinolin-4-one;

2-(4-chloro-3-(trifluoromethyl)phenoxy)-5-(((4-oxo-6,7-dihydro-4H-pyrimido[6,1-a]isoquinolin-2-yl)oxy)methyl)benzonitrile;

5-(((9-fluoro-4-oxo-6,7-dihydro-4H-pyrimido[6,1-a]isoquinolin-2-yl)oxy)methyl)-2-(3-(trifluormethyl)phenoxy)benzonitrile;

2-(4-(4-chloro-3-(trifluoromethyl)phenoxy)phenethoxy)-9-fluoro-6,7-dihydro-4H-pyrimido[6,1-a]isoquinolin-4-one;

5-(((4-oxo-6,7-dihydro-4H-pyrimido[6,1-a]isoquinolin-2-yl)oxy)methyl)-2-((6-(trifluoro-methyl)pyridin-3-yl)oxy)benzonitrile;

2-(4-chloro-3-(trifluoromethyl)phenoxy)-5-(((9-fluoro-4-oxo-6,7-dihydro-4H-pyrimido[6,1-a]isoquinolin-3-yl)oxy)methyl)benzonitrile;

5-(((9-fluoro-4-oxo-6,7-dihydro-4H-pyrimido[6,1-a]isoquinolin-2-yl)oxy)methyl)-2-((5-(trifluoromethyl)pyridin-2-yl)oxy)benzonitrile;

2-((3,5-difluoro-4-((6-(trifluormethyl)pyridin-3-yl)oxy)benzyl)oxy)-6,7-dihydro-4H-pyrimido[6,1-a]isoquinolin-4-one;

2-((3-fluoro-4-((6-(trifluoromethyl)pyridin-2-yl)oxy)benzyl)oxy) -6,7-dihydro-4H-pyrimido[6,1-a]isoquinolin-4-one;

5-(((4-oxo-6,7-dihydro-4H-pyrimido[6,1-a]isoquinolin-2-yl)oxy)methyl)-2-((6-(trifluoro-methyl)pyridin-2-yl)oxy)benzonitrile;

5-(((4-oxo-6,7-dihydro-4H-pyrimido[6,1-a]isoquinolin-2-yl)oxy)methyl)-2-(3-(trifluoro-methyl)phenoxy)benzonitrile;

9-fluoro-2-((3-fluoro-4-((2-(trifluoromethyl)pyrimidin-5-yl)oxy)benzyl)oxy)- 6,7-dihydro-4H-pyrimido[6,1-a]isoquinolin-4-one;

2-((3-fluoro-4-((6-(trifluoromethyl)pyridin-3-yl)oxy)benzyl)oxy)benzyl)oxy) -6,7-dihydro-4H-pyrimido[6,1-a]isoquinolin-4-one;

2-((3-fluoro-4-((5-(trifluoromethyl)pyridin-2-yl)oxy)benzyl)oxy)-9-methoxy- 6,7-dihydro-4H-pyrimido[6,1-a]isoquinolin-4-one;

5-(((4-oxo- 6,7-dihydro-4H-pyrimido[6,1-a]isoquinolin-2-yl)oxy)methyl)-2-((2-(trifluoromethyl)pyrimidin-5-yl)oxy)benzonitrile;

9-fluoro-2-((3-fluoro-4-((6-(trifluoromethyl)pyridin-2-yl)oxy)benzyl)oxy)-6,7-dihydro-4H-pyrimido[6,1-a]isoquinolin-4-one;

9-fluoro-2-((4-((2-(trifluoromethyl)pyrimidin-5-yl)oxy)benzyl)oxy)-6,7-dihydro-4H-pyrimido[6,1-a]isoquinolin-4-one;

2-((3-fluoro-4-((2-(trifluoromethyl)pyrimidin-5-yl)oxy)benzyl)oxy)-6,7-dihydro-4H-pyrimido[6,1-a]isoquinolin-4-one;

2-((5-(4-chloro-3-(trifluoromethyl)phenoxy)pyridin-2-yl)methoxy)-6,7-dihydro-4H-pyrimido[6,1-a]isoquinolin-4-one;

2-((5-(4-fluoro-3-(trifluoromethyl)phenoxy)pyridin-2-yl)methoxy)-6,7-dihydro-4H-pyrimido[6,1-a]isoquinolin-4-one;

2-((3-fluoro-4-((5-(trifluoromethyl)pyridin-2-yl)oxy)benzyl)oxy)-6,7-dihydro-4H-pyrimido[6,1-a]isoquinolin-4-one;

2-(4-(3-(trifluoromethyl)phenoxy)phenethoxy)-6,7-dihydro-4H-pyrimido[6,1-a]isoquinolin-4-one;

2-((3,5-difluoro-4-((6-(trifluoromethyl)pyridin-3-yl)oxy)benzyl)oxy)-9-fluoro-6,7-dihydro-4H-pyrimido[6,1-a]isoquinolin-4-one;

5-(2-((9-fluoro-4-oxo-6,7-dihydro-4H-pyrimido[6,1-a]isoquinolin-2-yl)oxy)ethyl)-2-((5-(trifluoromethyl)pyridin-2-yl)oxy)benzonitrile;

5-(((9-fluoro-4-oxo-6,7-dihydro-4H-pyrimido[6,1-a]isoquinolin-2-yl)oxy)methyl)-2-((6-(trifluoromethyl)pyridin-3-yl)oxy)benzonitrile;

5-(((9-fluoro-4-oxo-6,7-dihydro-4H-pyrimido[6,1-a]isoquinolin-2-yl)oxy)methyl)-2-((6-(trifluoromethyl)pyridin-2-yl)oxy)benzonitrile;

2-(4-chloro-3-(trifluoromethyl)phenoxy)-5-(((9-methyl-4-oxo-6,7-dihydro-4H-pyrimido[6,1-a]isoquinolin-2-yl)oxy)methyl)benzonitrile;

2-((3,5-difluoro-4-((6-(trifluoromethyl)pyridin-3-yl)oxy)benzyl)oxy)-9-methyl- 6,7-dihydro-4H-pyrimido[6,1-a]isoquinolin-4-one;

5-(((9-methyl-4-oxo-6,7-dihydro-4H-pyrimido[6,1-a]isoquinolin-2-yl)oxy)methyl)-2-((2-(trifluoromethyl)pyrimidin-5-yl)oxy)benzonitrile;

2-((3-fluoro-4-((2-(trifluoromethyl)pyrimidin-5-yl)oxy)benzyl)oxy)-9-methyl-6,7-dihydro-4H-pyrimido[6,1-a]isoquinolin-4-one;

5-(((9-methyl-4-oxo-6,7-dihydro-4H-pyrimido[6,1-a]isoquinolin-2-yl)oxy)methyl)-2-((6-(trifluoromethyl)pyridin-3-yl)oxy)benzonitrile;

2-((3-fluoro-4-((6-(trifluoromethyl)pyridin-3-yl)oxy)benzyl)oxy)-9-methyl-6,7-dihydro-4H-pyrimido[6,1-a]isoquinolin-4-one;

5-(((9-methyl-4-oxo-6,7-dihydro-4H-pyrimido[6,1-a]isoquinolin-2-yl)oxy)methyl)-2-(3-(trifluoromethyl)phenoxy)benzonitrile;

9-fluoro-2-((3-fluoro-4-(4-fluoro-3-(trifluoromethyl)phenoxy)benzyl)oxy)-6,7-dihydro-4H-pyrimido[6,1-a]isoquinolin-4-one;

2-((3,5-difluoro-4-((5-(trifluoromethyl)pyridin-2-yl)oxy)benzyl)oxy)-9-fluoro-6,7-dihydro-4H-pyrimido[6,1-a]isoquinolin-4-one;

9-fluoro-2-((3-fluoro-4-((6-(trifluoromethyl)pyridin-3-yl)oxy)benzyl)oxy)-6,7-dihydro-4H-pyrimido[6,1-a]isoquinolin-4-one;

5-(((9-methyl-4-oxo-6,7-dihydro-4H-pyrimido[6,1-a]isoquinolin-2-yl)oxy)methyl)-2-((5-(trifluoromethyl)pyridin-2-yl)oxy)benzonitrile;

2-((5-(4-chloro-3-(trifluoromethyl)phenoxy)pyridin-2-yl)methoxy)-9-methyl- 6,7-dihydro-4H-pyrimido[6,1-a]isoquinolin-4-one;

2-((3-fluoro-4-((5-(trifluoromethyl)pyridin-2-yl)oxy)benzyl)oxy)-9-methyl-6,7-dihydro-4H-pyrimido[6,1-a]isoquinolin-4-one;

2-((3,5-difluoro-4-((2-(trifluoromethyl)pyridin-5-yl)oxy)benzyl)oxy)-9-methyl-6,7-dihydro-4H-pyrimido[6,1-a]isoquinolin-4-one;

5-(((9-methyl-4-oxo-6,7-dihydro-4H-pyrimido[6,1-a]isoquinolin-2-yl)oxy)methyl)-2-((6-(trifluoromethyl)pyridin-2-yl)oxy)benzonitrile;

2-((3-fluoro-4-((6-(trifluoromethyl)pyridin-2-yl)oxy)benzyl)oxy)-9-methyl-6,7-dihydro-4H-pyrimido[6,1-a]isoquinolin-4-one;

2-(4-chloro-3-(trifluoromethyl)phenoxy)-5-(2-((9-fluoro-4-oxo-6,7-dihydro-4H-pyrimido[6,1-a]isoquinolin-2-yl)ethyl)benzonitrile;

5-(((9-fluoro-4-oxo-6,7-dihydro-4H-pyrimido[6,1-a]isoquinolin-2-yl)oxy)methyl)-2-((6-methylpyridin-3-yl)oxy)benzonitrile;

5-(2-((9-fluoro-4-oxo-6,7-dihydro-4H-pyrimido[6,1-a]isoquinolin-2-yl)oxy)ethyl)-2-((6-(trifluoromethyl)pyridin-3-yl)oxy)benzonitrile;

5-(((9-chloro-4-oxo-6,7-dihydro-4H-pyrimido[6,1-a]isoquinolin-2-yl)oxy)methyl)-2-((6-(trifluoromethyl)pyridin-2-yl)oxy)benzonitrile;

5-(((9-chloro-4-oxo-6,7-dihydro-4H-pyrimido[6,1-a]isoquinolin-2-yl)oxy)methyl)-2-(3-(trifluoromethyl)phenoxy)benzonitrile;

9-chloro-2-((3,5-difluoro-4-((6-(trifluoromethyl)pyridin-3-yl)oxy)benzyl)oxy)-6,7-dihydro-4H-pyrimido[6,1-a]isoquinolin-4-one;

5-(((9-chloro-4-oxo-6,7-dihydro-4H-pyrimido[6,1-a]isoquinolin-2-yl)oxy)methyl)-2-((6-(trifluoromethyl)pyridin-3-yl)oxy)benzonitrile;

or a pharmaceutically acceptable salt thereof.

14. A compound of Formula (I) or a pharmaceutically acceptable salt thereof according to claim 1 has the structure of 4-(((9-Methoxy-4-oxo-6,7-dihydro-4H-pyrimido[6,1-a]isoquinolin-2-yl)oxy)methyl)-2-(3-trifluoromethyl)phenoxy)benzonitrile

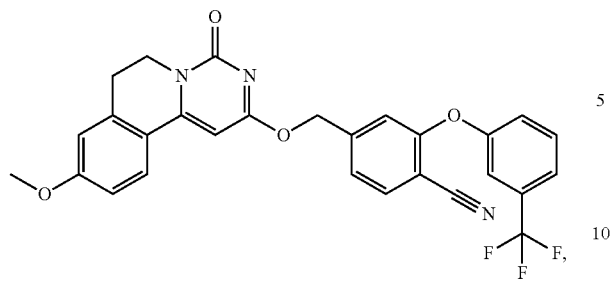
15. A pharmaceutical composition comprising a compound of Formula (I) according to claim 1 and one or more pharmaceutically acceptable excipents.
* * * * *